(12) United States Patent
Finney et al.

(10) Patent No.: US 10,774,152 B2
(45) Date of Patent: Sep. 15, 2020

(54) MOLECULES WITH SPECIFICITY FOR CD45 AND CD79

(71) Applicant: UCB BIOPHARMA SPRL, Brussels (BE)

(72) Inventors: Helene Margaret Finney, Slough (GB); Stephen Edward Rapecki, Slough (GB); Michael John Wright, Slough (GB); Kerry Louise Tyson, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/326,499

(22) PCT Filed: Jul. 16, 2015

(86) PCT No.: PCT/EP2015/066368
§ 371 (c)(1),
(2) Date: Jan. 16, 2017

(87) PCT Pub. No.: WO2016/009029
PCT Pub. Date: Jan. 21, 2016

(65) Prior Publication Data
US 2017/0204183 A1 Jul. 20, 2017

(30) Foreign Application Priority Data
Jul. 16, 2014 (GB) .................................. 1412659.3

(51) Int. Cl.
| | | |
|---|---|---|
| A61K 39/00 | (2006.01) | |
| C07K 16/28 | (2006.01) | |
| C07K 16/18 | (2006.01) | |
| C07K 16/46 | (2006.01) | |

(52) U.S. Cl.
CPC ............ *C07K 16/289* (2013.01); *C07K 16/18* (2013.01); *C07K 16/2803* (2013.01); *C07K 16/468* (2013.01); *A61K 2039/505* (2013.01); *C07K 2317/24* (2013.01); *C07K 2317/31* (2013.01); *C07K 2317/55* (2013.01); *C07K 2317/622* (2013.01); *C07K 2317/76* (2013.01)

(58) Field of Classification Search
CPC .............................................. A61K 2039/505
See application file for complete search history.

(56) References Cited

U.S. PATENT DOCUMENTS

| | | | |
|---|---|---|---|
| 4,741,900 A | 5/1988 | Alvarez et al. | |
| 5,223,409 A | 6/1993 | Ladner et al. | |
| 5,403,484 A | 4/1995 | Ladner et al. | |
| 5,427,908 A | 6/1995 | Dower et al. | |
| 5,516,637 A | 5/1996 | Huang et al. | |
| 5,545,806 A | 8/1996 | Lonberg et al. | |
| 5,569,825 A | 10/1996 | Lonberg et al. | |
| 5,571,698 A | 11/1996 | Ladner et al. | |
| 5,580,717 A | 12/1996 | Dower et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,658,727 A | 8/1997 | Barbas et al. | |
| 5,661,016 A | 8/1997 | Lonberg et al. | |
| 5,698,426 A | 12/1997 | Huse | |
| 5,731,168 A | 3/1998 | Carter et al. | |
| 5,733,743 A | 3/1998 | Johnson et al. | |
| 5,750,753 A | 5/1998 | Kimae et al. | |
| 5,770,429 A | 6/1998 | Lonberg et al. | |
| 5,780,225 A | 7/1998 | Wigler et al. | |
| 5,798,229 A | 8/1998 | Strittmatter et al. | |
| 5,821,047 A | 10/1998 | Garrard et al. | |
| 5,969,108 A | 10/1999 | McCafferty et al. | |
| 6,010,902 A | 1/2000 | Ledbetter et al. | |
| 6,106,834 A | 8/2000 | Lazarovits et al. | |
| 6,809,185 B1 | 10/2004 | Schoonjans et al. | |
| 7,183,076 B2 | 2/2007 | Arathoon et al. | |
| 7,825,224 B2 | 11/2010 | Vilen et al. | |
| 8,088,378 B2 | 1/2012 | Chen et al. | |
| 8,409,577 B2 | 4/2013 | Thompson et al. | |
| 8,545,850 B2 | 10/2013 | Chen et al. | |
| 8,669,349 B2 | 3/2014 | Johnson et al. | |
| 8,691,531 B2 | 4/2014 | Chen et al. | |
| 8,722,857 B2 | 5/2014 | Chen et al. | |
| 9,695,236 B2 | 7/2017 | Johnson et al. | |
| 9,845,355 B2 | 12/2017 | Chen et al. | |
| 9,896,506 B2 | 2/2018 | Chen et al. | |

(Continued)

FOREIGN PATENT DOCUMENTS

| | | |
|---|---|---|
| EP | 0392745 A2 | 10/1990 |
| EP | 0438474 A1 | 7/1991 |

(Continued)

OTHER PUBLICATIONS

Dennis et al. (J. Biol. Chem. Sep. 20, 2002; 277 (38): 35035-43).*
Holt et al. (Protein Eng. Des. Sel. May 2008; 21 (5): 283-8).*
Schoonjans et al. (Biomol. Eng. Jun. 2001; 17 (6): 193-202).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Innnnunol. May 2003; 39 (15): 941-952).*
Vajdos et al. (J. Mol. Biol. Jul. 5, 2002; 320 (2): 415-428).*

(Continued)

*Primary Examiner* — Stephen L Rawlings
(74) *Attorney, Agent, or Firm* — Medler Ferro Woodhouse & Mills PLLC

(57) ABSTRACT

The present disclosure relates to a multispecific molecule comprising a binding domain specific to the antigen CD45 and a binding domain specific to the antigen CD79a and/or CD79b, compositions comprising same and use of each in treatment, for example treatment of autoimmune disease.

12 Claims, 17 Drawing Sheets
Specification includes a Sequence Listing.

(56) References Cited

U.S. PATENT DOCUMENTS

| | | | |
|---|---|---|---|
| 9,975,949 B2 | 5/2018 | Sun et al. | |
| 10,358,493 B2 | 7/2019 | Finney et al. | |
| 10,370,447 B2 | 8/2019 | Finney et al. | |
| 2003/0027247 A1 | 2/2003 | Wang et al. | |
| 2003/0202975 A1 | 10/2003 | Tedder | |
| 2005/0033031 A1 | 2/2005 | Couto | |
| 2005/0048578 A1 | 3/2005 | Zhang | |
| 2006/0252130 A1 | 11/2006 | Boehm et al. | |
| 2007/0141672 A1 | 6/2007 | Shin | |
| 2011/0076270 A1 | 3/2011 | Aversa et al. | |
| 2013/0142787 A1 | 6/2013 | Chang et al. | |
| 2013/0209463 A1 | 8/2013 | Rotman et al. | |
| 2013/0336977 A1 | 12/2013 | Thompson et al. | |
| 2014/0099254 A1* | 4/2014 | Chang | A61K 38/21 424/1.11 |
| 2014/0212425 A1 | 7/2014 | Chang et al. | |
| 2015/0239974 A1 | 8/2015 | Chang et al. | |
| 2017/0081404 A1 | 3/2017 | Finney et al. | |
| 2017/0204178 A1 | 7/2017 | Finney et al. | |
| 2017/0226207 A1 | 8/2017 | Yamajuku et al. | |
| 2018/0201678 A1 | 7/2018 | Finney et al. | |
| 2018/0201679 A1 | 7/2018 | Chen et al. | |
| 2018/0237521 A1 | 8/2018 | Finney et al. | |
| 2018/0273620 A1 | 9/2018 | Finney et al. | |
| 2018/0334513 A1 | 11/2018 | Wright | |
| 2018/0334514 A1 | 11/2018 | Wright | |
| 2018/0346603 A1 | 12/2018 | Bhatta et al. | |
| 2018/0346604 A1 | 12/2018 | Rapecki | |
| 2018/0355063 A1 | 12/2018 | Finney | |
| 2019/0322739 A1 | 10/2019 | Finney et al. | |

FOREIGN PATENT DOCUMENTS

| | | |
|---|---|---|
| EP | 0463151 A1 | 1/1992 |
| EP | 0546073 A1 | 6/1993 |
| EP | 1049787 A1 | 11/2000 |
| EP | 1156826 A1 | 11/2001 |
| EP | 1242457 A1 | 9/2002 |
| EP | 1570267 A1 | 9/2005 |
| EP | 2176295 A1 | 4/2010 |
| EP | 2176296 A1 | 4/2010 |
| EP | 2247620 A1 | 11/2010 |
| EP | 2252631 A2 | 11/2010 |
| EP | 2474557 A2 | 7/2012 |
| EP | 2502937 A2 | 9/2012 |
| EP | 2657253 A2 | 10/2013 |
| EP | 2706069 A1 | 3/2014 |
| EP | 2869850 A1 | 5/2015 |
| EP | 3045475 A1 | 7/2016 |
| EP | 3178929 A1 | 6/2017 |
| EP | 3227336 A1 | 10/2017 |
| EP | 3269737 A1 | 1/2018 |
| WO | WO86/01533 A1 | 3/1986 |
| WO | WO89/00195 A1 | 1/1989 |
| WO | WO89/01476 A1 | 2/1989 |
| WO | WO90/02809 A1 | 3/1990 |
| WO | WO91/09967 A1 | 7/1991 |
| WO | WO91/10737 A1 | 7/1991 |
| WO | WO92/01047 A1 | 1/1992 |
| WO | WO92/02551 A1 | 2/1992 |
| WO | WO92/18619 A1 | 10/1992 |
| WO | WO92/22583 A1 | 12/1992 |
| WO | WO93/06231 A1 | 4/1993 |
| WO | WO 93/11162 | 6/1993 |
| WO | WO93/11236 A1 | 6/1993 |
| WO | WO95/15982 A1 | 6/1995 |
| WO | WO95/20401 A1 | 8/1995 |
| WO | WO96/26964 A1 | 9/1996 |
| WO | WO98/20734 A1 | 5/1998 |
| WO | WO 02/072832 | 9/2002 |
| WO | WO 03/012069 | 2/2003 |
| WO | WO03/031581 A2 | 4/2003 |
| WO | WO03/048327 A2 | 6/2003 |
| WO | WO 03/093320 | 11/2003 |
| WO | WO2004/039840 A1 | 5/2004 |
| WO | WO2004/051268 A1 | 6/2004 |
| WO | WO 2004/081051 | 9/2004 |
| WO | WO2004/106377 A1 | 12/2004 |
| WO | WO2005/003169 A2 | 1/2005 |
| WO | WO2005/003170 A2 | 1/2005 |
| WO | WO2005/003171 A2 | 1/2005 |
| WO | WO 2005/006210 | 1/2005 |
| WO | 2005/016950 A1 | 2/2005 |
| WO | WO2005/026210 A2 | 3/2005 |
| WO | WO2005/113605 A1 | 12/2005 |
| WO | WO2005/117984 A2 | 12/2005 |
| WO | WO2005/118642 A2 | 12/2005 |
| WO | WO2006/004910 A2 | 1/2006 |
| WO | WO2006/119897 A2 | 11/2006 |
| WO | WO2007/060406 A1 | 5/2007 |
| WO | WO2007/085837 A1 | 8/2007 |
| WO | WO2007/087453 A2 | 8/2007 |
| WO | WO 2007/146968 | 12/2007 |
| WO | WO 2008/070569 | 6/2008 |
| WO | WO 2008/119353 | 10/2008 |
| WO | WO2009/012268 A1 | 1/2009 |
| WO | WO2009/040562 A1 | 4/2009 |
| WO | 2009/099728 A1 | 8/2009 |
| WO | WO2010/035012 A1 | 4/2010 |
| WO | WO 2011/025904 | 3/2011 |
| WO | WO2011/061492 A2 | 5/2011 |
| WO | WO2011/086091 A1 | 7/2011 |
| WO | WO2011/130305 A2 | 10/2011 |
| WO | WO2011/131746 A2 | 10/2011 |
| WO | WO2012/023053 A2 | 2/2012 |
| WO | WO 2012/116453 | 9/2012 |
| WO | WO2012/151199 A1 | 11/2012 |
| WO | WO 2012/162561 | 11/2012 |
| WO | WO2013/060867 A2 | 5/2013 |
| WO | WO 2013/078455 | 5/2013 |
| WO | WO 2013/085893 | 6/2013 |
| WO | WO 2014/001326 | 1/2014 |
| WO | WO2014/011518 A1 | 1/2014 |
| WO | WO 2014/011519 | 1/2014 |
| WO | WO2014/011520 A1 | 1/2014 |
| WO | WO 2014/011521 | 1/2014 |
| WO | 2014/066271 A1 | 5/2014 |
| WO | WO2014/096390 A1 | 6/2014 |
| WO | WO2014/131694 A1 | 9/2014 |
| WO | WO2015/021089 A1 | 2/2015 |
| WO | WO 2015/057834 | 4/2015 |
| WO | WO 2015/181282 | 12/2015 |
| WO | WO2015/197772 A1 | 12/2015 |
| WO | WO2015/197789 A1 | 12/2015 |
| WO | WO 2016/009030 | 1/2016 |
| WO | WO 2016/168773 | 10/2016 |
| WO | WO2017/009473 A1 | 1/2017 |
| WO | WO2017/009476 A1 | 1/2017 |
| WO | WO2017/093402 A1 | 6/2017 |
| WO | WO2017/093404 A1 | 6/2017 |
| WO | WO2017/093406 A1 | 6/2017 |
| WO | WO2017/093408 A1 | 6/2017 |
| WO | WO2017/093410 A1 | 6/2017 |

OTHER PUBLICATIONS

De Pascalis et al. (J. Innnnunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Arndt, C. et al. "Costimulation improves the killing capability of T cells redirected to tumor cells expressing low levels of CD33: description of a novel modular targeting system" *Leukemia*, 2014, pp. 59-69, vol. 28, No. 1.
Campbell, J. D. M. et al. "Rapid detection, enrichment and propagation of specific T cell subsets based on cytokine secretion" *Clinical and Experimental Immunology*, 2010, pp. 1-10, vol. 163, No. 1.

(56) References Cited

OTHER PUBLICATIONS

Carnahan, J. et al. "Epratuzumab, a CD22-targeting recombinant humanized antibody with a different mode of action from rituximab" *Molecular Immunology*, 2007, pp. 1331-1341, vol. 44, No. 6.

Doerner, A. et al. "Therapeutic antibody engineering by high efficiency cell screening" *FEBS Letters*, 2014, pp. 278-287, vol. 588, No. 2.

Goldenberg, D. M. et al. "Multifunctional Antibodies by the Dock-and-Lock Method for Improved Cancer Imaging and Therapy by Pretargeting" *The Journal of Nuclear Medicine*, Jan. 2008, pp. 158-163, vol. 49, No. 1.

Hanes, J. et al. "Ribosome display efficiently selects and evolves high-affinity antibodies in vitro from immune libraries" *Proc. Natl. Acad. Sci.*, Nov. 1998, pp. 14130-14135, vol. 95, No. 24.

Ko, S. et al. "Engineering Antibodies for Dual Specificity and Enhanced Potency" *Biotechnology and Bioprocess Engineering*, 2015, pp. 201-210, vol. 20, No. 2.

Kontermann, R. E. "Dual targeting strategies with bispecific antibodies" *mAbs*, Mar./Apr. 2012, pp. 182-197, vol. 4, No. 2.

Luo, H. et al. "Design and Applications of Bispecific Heterodimers: Molecular Imaging and beyond" *Molecular Pharmaceutics*, Apr. 16, 2014, pp. 1750-1761, vol. 11, No. 6.

Pfeifer, M. et al. "Anti-CD22 and anti-CD79B antibody drug conjugates are active in different molecular diffuse large B-cell lymphoma subtypes" *Leukemia*, May 8, 2015, pp. 1578-1586, vol. 29, No. 7.

Zahnd, C. et al. "Directed in Vitro Evolution and Crystallographic Analysis of a Peptide-binding Single Chain Antibody Fragment (scFv) with Low Picomolar Affinity" *The Journal of Biological Chemistry*, Apr. 30, 2004, pp. 18870-18877, vol. 279, No. 18.

Written Opinion in International Application No. PCT/EP2015/066368, dated Oct. 9, 2015, pp. 1-5.

Gold, M. R. et al. "The B Cell Antigen Receptor Activates the Akt (Protein Kinase B)/Glycogen Synthase Kinase-3 Signaling Pathway via Phosphatidylinositol 3-Kinase" *The Journal of Immunology*, 1999, pp. 1894-1905, vol. 163.

Hernández-Molina et al., "The meaning of anti-Ro and anti-La antibodies in primary Sjögren's syndrome," Autoimmunity Reviews 10:123-125 (2011).

Adair et al., "Therapeutic Antibodies," Drug Design Reviews Online 2(3):209-217 (2005).

Altschul et al., "Basic local alignment search tool," J Mol Biol 215(3):403-410 (1990).

Altschul et al., "Gapped BLAST and PSI-BLAST: a new generation of protein database search programs," Nucleic Acids Res 25(17):3389-3402 (1997).

Ames et al., "Conversion of murine Fabs isolated from a combinatorial phage display library to full length immunoglobulins," J Immunol Methods 184(2):177-186 (1995).

Angal et al., "A single amino acid substitution abolishes the heterogeneity of chimeric mouse/human (IgG4) antibody," Mol Immunol 30(1):105-108 (1993).

Armour et al., "Recombinant human IgG molecules lacking Fcgamma receptor I binding and monocyte triggering activities," Eur J Immunol 29(8):2613-2624 (1999).

Babcook et al., "A novel strategy for generating monoclonal antibodies from single, isolated lymphocytes producing antibodies of defined specificities," Proc Natl Acad Sci USA 93(15):7843-7848 (1996).

Bartalena et al., "Thyroid hormone transport proteins," Clin Lab Med 13(3):583-598 (1993).

Berger et al., "Antigen recognition by conformational selection," FEBS Lett 450:149-153 (1999).

Bradshaw et al., "Concurrent detection of secreted products from human lymphocytes by microengraving: cytokines and antigen-reactive antibodies," Clin Immunol 129(1):10-18 (2008).

Bree et al., "Pharmacokinetics of intravenously administered 125I-labelled human alpha 1-acid glycoprotein," Clin Pharmacokinet 11(4):336-342 (1986).

Brinkmann et al., "Phage display of disulfide-stabilized Fv fragments," J Immunol Methods 182(1):41-50 (1995).

Brosterhus et al., "Enrichment and detection of live antigen-specific CD4(+) and CD8(+) T cells based on cytokine secretion," Eur J Immunol 29(12):4053-4059 (1999).

Bruhns et al., "Specificity and affinity of human Fcgamma receptors and their polymorphic variants for human IgG subclasses," Blood 113(16):3716-3725 (2009).

Burton et al., "Human antibodies from combinatorial libraries," Adv Immunol 57:191-280 (1994).

Chan et al., "Therapeutic antibodies for autoimmunity and inflammation," Nat Rev Immunol 10(5):301-316 (2010).

Chen et al., "Enhancement and destruction of antibody function by somatic mutation: unequal occurrence is controlled by V gene combinatorial associations," EMBO J 14(12):2784-2794 (1995).

Chothia et al., "Canonical structures for the hypervariable regions of immunoglobulins," J Mol Biol 196(4):901-917 (1987).

Chu et al., "Suppression of rheumatoid arthritis B cells by XmAb5871, an anti-CD19 antibody that coengages B cell antigen receptor complex and Fcγ receptor IIb inhibitory receptor," Arthritis Rheumatol 66:1153-1164 (2014).

Clargo et al., "The rapid generation of recombinant functional monoclonal antibodies from individual, antigen-specific bone marrow-derived plasma cells isolated using a novel fluorescence-based method," MAbs 6(1):143-159 (2014).

Crameri et al., "DNA shuffling of a family of genes from diverse species accelerates directed evolution," Nature 391:288-291 (1998).

Czerwinski et al., "Construction of dimeric F(ab) useful in blood group serology," Transfusion 42(2):257-264 (2002).

Datta-Mannan et al., "Humanized IgG1 variants with differential binding properties to the neonatal Fc receptor: relationship to pharmacokinetics in mice and primates," Drug Metab Dispos 35(1):86-94 (2007).

Dmitrova et al., "A new LexA-based genetic system for monitoring and analyzing protein heterodimerization in *Escherichia coli*," Mol Gen Genet 257:205-212 (1998).

Dubowchik et al., "Receptor-mediated and enzyme-dependent targeting of cytotoxic anticancer drugs," Pharmacol Ther 83(2):67-123 (1999).

Dunkin et al., "Immune cell therapy in IBD," Dig Dis 32:61-66 (2014).

Feldman et al. "Adoptive Cell Therapy—Tumor-Infiltrating Lymphocytes, T-Cell Receptors, and Chimeric Antigen Receptors," Semin Oncol 42(4):626-639 (2015).

Finney et al., "Chimeric receptors providing both primary and costimulatory signaling in T cells from a single gene product," J Immunol 161:2791-2797 (1998).

Gish et al., "Identification of protein coding regions by database similarity search," Nat Genet 3(3):266-272 (1993).

Gitlin et al., "The selectivity of the human placenta in the transer of plasma proteins from mother to fetus," J Clin Invest 43:1938-1951 (1964).

Glockshuber et al., "A comparison of strategies to stabilize immunoglobulin Fv-fragments," Biochemistry 29(6):1362-1367 (1990).

Harris, "Processing of C-terminal lysine and arginine residues of proteins isolated from mammalian cell culture," J Chromatogr A 705(1):129-134 (1995).

Hermiston et al., "CD45: A Critical Regulator of Signaling Thresholds in Immune Cells," Ann Rev Immunol 21:107-137 (2003).

Hinnebusch, "Evidence for translational regulation of the activator of general amino acid control in yeast," Proc Natl Acad Sci USA 81:6442-6446 (1984).

Hinton et al., "Engineered human IgG antibodies with longer serum half-lives in primates," J Biol Chem 279(8):6213-6216 (2004).

Hollinger et al., "Engineered antibody fragments and the rise of single domains," Nat Biotechnol 23(9):1126-1136 (2005).

Holmes, "Buy buy bispecific antibodies," Nat Rev Drug Discov 10(11):798-800 (2011).

Hope et al., "GCN4 protein, synthesized in vitro, binds HIS3 regulatory sequences: implications for general control of amino acid biosynthetic genes in yeast," Cell 43(1):177-188 (1985).

(56) References Cited

OTHER PUBLICATIONS

Idusogie et al., "Mapping of the C1q binding site on rituxan, a chimeric antibody with a human IgG1 Fc," J Immunol 164(8):4178-1484 (2000).
Idusogie et al., "Engineered antibodies with increased activity to recruit complement," J Immunol 166(4):2571-2575 (2001).
Jourdan et al., "An in vitro model of differentiation of memory B cells into plasmablasts and plasma cells including detailed phenotypic and molecular characterization," Blood 114(25):5173-5181 (2009).
Jung et al., "Design of interchain disulfide bonds in the framework region of the Fv fragment of the monoclonal antibody B3," Proteins 19(1):35-47 (1994).
Karnell et al., "CD19 and CD32b Differentially Regulate Human B Cell Responsiveness," J Immunol 192(4):1480-1490 (2014).
Kashmiri et al., "SDR grafting—a new approach to antibody humanization," Methods 36(1):25-34 (2005).
Keller et al., "Independent Metalloregulation of Ace1 and Mac1 in *Saccharomyces cerevisiae*," Eukaryot Cell 4(11):1863-1871 (2005).
Kettleborough et al., "Isolation of tumor cell-specific single-chain Fv from immunized mice using phage-antibody libraries and the re-construction of whole antibodies from these antibody fragments," Eur J Immunol 24(4):952-958 (1994).
Kohler et al., "Continuous cultures of fused cells secreting antibody of predefined specificity," Nature 256:495-497 (1975).
Kozbor et al., "The production of monoclonal antibodies from human lymphocytes," Immunol Today 4(3):72-79 (1983).
Kudo et al., "T lymphocytes expressing a CD16 signaling receptor exert antibody-dependent cancer cell killing," Cancer Res 74(1):93-103 (2014).
Labrijn et al., "Therapeutic IgG4 antibodies engage in Fab-arm exchange with endogenous human IgG4 in vivo," Nat Biotechnol 27(8):767-771 (2009).
Lazar et al., "Engineered antibody Fc variants with enhanced effector function," Proc Natl Acad Sci USA 103(11):4005-4010 (2006).
Love et al.' "A microengraving method for rapid selection of single cells producing antigen-specific antibodies," Nat Biotechnol 24(6):703-707 (2006).
Low et al., "Mimicking Somatic Hypermutation: Affinity Maturation of Antibodies Displayed on Bacteriophage Using a Bacterial Mutator Strain," J Mol Biol 260(3):359-368 (1996).
Luo et al., "Vl-linker-Vh orientation-dependent expression of single chain Fv-containing an engineered disulfide-stabilized bond in the framework regions," J Biochem 118(4):825-831 (1995).
Madden et al., "Applications of network BLAST server," Methods Enzymol 266:131-141 (1996).
Mahoney et al., "Combination cancer immunotherapy and new immunomodulatory targets," Nat Rev Drug Discov 14:561-584 (2015).
Marks et al., "By-passing immunization: building high affinity human antibodies by chain shuffling," Bio/Technology 10(7):779-783 (1992).
Merchant et al., "An efficient route to human bispecific IgG," Nat Biotechnol 16(7):677-681 (1998).
Moore et al., "Application of dual affinity retargeting molecules to achieve optimal redirected T-cell killing of B-cell lymphoma," Blood 117(17):4542-4551 (2011).
Muller et al., "Bispecific antibodies for cancer immunotherapy: Current perspectives," BioDrugs 24:89-98 (2010).
Nunez-Prado et al., "The coming of age of engineered multivalent antibodies," Drug Discov Today 20(5):588-594 (2015).
Nygren et al., "Scaffolds for engineering novel binding sites in proteins," Curr Opin Struct Biol 7(4):463-469 (1997).
Patten et al., "Applications of DNA shuffling to pharmaceuticals and vaccines," Curr Opin Biotechnol 8(6):724-733 (1997).
Persic et al., "An integrated vector system for the eukaryotic expression of antibodies or their fragments after selection from phage display libraries," Gene 187(1):9-18 (1997).
Peters, "Serum albumin," Adv Protein Chem 37:161-245 (1985).
Pule et al., "Artificial T-cell receptors," Cytotherapy 5(3):211-226 (2003).
Rajagopal et al., "A form of anti-Tac(Fv) which is both single-chain and disulfide stabilized: comparison with its single-chain and disulfide-stabilized homologs," Protein Eng 10(12):1453-1459 (1997).
Reiter et al., "Stabilization of the Fv fragments in recombinant immunotoxins by disulfide bonds engineered into conserved framework regions," Biochemistry 33(18):5451-5159 (1994).
Reiter et al., "Improved binding and antitumor activity of a recombinant anti-erbB2 immunotoxin by disulfide stabilization of the Fv fragment," J Biol Chem 269(28):18327-18331 (1994).
Richards et al., "Optimization of antibody binding to FcgammaRIIa enhances macrophage phagocytosis of tumor cells," Mol Cancer Ther 7(8):2517-2527 (2008).
Ridgway et al., "'Knobs-into-holes' engineering of antibody CH3 domains for heavy chain heterodimerization," Protein Eng 9:617-621 (1996).
Rodgers et al., "Switch-mediated activation and retargeting of CAR-T cells for B-cell malignancies," *Proc Natl Acad Sci USA* 113(4):E459-E468 (2016).
Rudikoff et al., "Single amino acid substitution altering antigen-binding specificity," *Proc Natl Acad Sci USA* 79:1979-1983 (1982).
Ryan et al., "Antibody targeting of B-cell maturation antigen on malignant plasma cells," Mol Cancer Ther 6(11):3009-3018 (2007).
Schoonjans et al., "A new model for intermediate molecular weight recombinant bispecific and trispecific antibodies by efficient heterodimerization of single chain variable domains through fusion to a Fab-chain," *Biomol Eng* 17:193-202 (2001).
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276(9):6591-6604 (2001).
Spang et al., "Heterodimeric Barnase-Barstar Vaccine Molecules: Influence of One versus Two Targeting Units Specific for Antigen Presenting Cells," *PLoS One* 7(9):e45393 (2012).
Stavenhagen et al., "Enhancing the potency of therapeutic monoclonal antibodies via Fc optimization," Adv Enzyme Regul 48:152-164 (2008).
Stavenhagen et al., "Fc optimization of therapeutic antibodies enhances their ability to kill tumor cells in vitro and controls tumor expansion in vivo via low-affinity activating Fcgamma receptors," Cancer Res 16(18):8882-8890 (2007).
Steurer et al., "Ex vivo coating of islet cell allografts with murine CTLA4/Fc promotes graft tolerance," J Immunol 155(3):1165-1174 (1995).
Thireos et al., "5' untranslated sequences are required for the translational control of a yeast regulatory gene," Proc Natl Acad Sci USA 81:5096-5100 (1984).
Thompson et al., "Affinity maturation of a high-affinity human monoclonal antibody against the third hypervariable loop of human immunodeficiency virus: use of phage display to improve affinity and broaden strain reactivity," J Mol Biol 256(1):77-88 (1996).
Thorpe et al., "The preparation and cytotoxic properties of antibody-toxin conjugates," Immunol Rev 62:119-158 (1982).
Vaccaro et al., "Engineering the Fc region of immunoglobulin G to modulate in vivo antibody levels," Nat Biotechnol 23(10):1283-1288 (2005).
Van Der Stegen et al., "The pharmacology of second-generation chimeric antigen receptors," Nat Rev Drug Discov 14:499-509 (2015).
Vaughan et al., "Human antibodies by design," Nat Biotechnol 16(6):535-539 (1998).
Veri et al., "Therapeutic Control of B Cell Activation via a Recruitment of FcCγ Receptor IIB (CD32B) Inhibitory Function with a Novel Bispecific Antibody Scaffold," *Arthritis Rheum* 62(7):1933-1943 (2010).
Verma et al., "Antibody engineering: comparison of bacterial, yeast, insect and mammalian expression systems," J Immunol Methods 216:165-181 (1998).
Waldemann et al, "Metabolism of immunoglobulins," Prog Allergy 13:1-110 (1969).
Walker et al., "CD22: an inhibitory enigma," Immunology 123(3):314-325 (2008).

(56) References Cited

OTHER PUBLICATIONS

Wang et al., "Antibody Engineering Using Phage Display with a Coiled-Coil Heterodimeric Fv Antibody Fragment," *PLoS ONE* 6(4):e19023 (2011).
Wienands, "The B-cell antigen receptor: formation of signaling complexes and the function of adaptor proteins," Curr Top Microbiol Immunol 245:53-76 (2000).
Willcox et al., "Production of soluble α⊕ T-cell receptor heterodimers suitable for biophysical analysis of ligand binding," *Protein Sci* 8:2418-2423 (1999).
Yang et al., "CDR walking mutagenesis for the affinity maturation of a potent human anti-HIV-1 antibody into the picomolar range," J Mol Biol 254(3):392-403 (1995).
Young et al., "Thermal stabilization of a single-chain Fv antibody fragment by introduction of a disulphide bond," FEBS Lett 377(2):135-139 (1995).
Yu et al., "Interaction between Bevacizumab and Murine VEGF-A: A Reassessment," Invest Ophthalmol Vis Sci 49(2):522-527 (2008).
Zhang et al., "PowerBLAST: a new network BLAST application for interactive or automated sequence analysis and annotation," Genome Res 7(6):649-656 (1997).
Zhu et al., "Remodeling domain interfaces to enhance heterodimer formation," Protein Sci 6(4):781-788 (1997).
Kussie et al., "A single engineered amino acid substitution changes antibody fine specificity" The Journal of Immunology 152:146-152 (1994).
Ward et al., "Binding activities of a repertoire of single immunoglobulin variable domains secreted from *Escherichia coli*," Nature 341:544-546 (1989).

Non-final Office Action issued in U.S. Appl. No. 15/743,764, dated May 30, 2019.
Edwards et al., "The Remarkable Flexibility of the Human Antibody Repertoire; Isolation of Over One Thousand Different Antibodies to a Single Protein, BLys," J. Mol. Biol. 334:103-118 (2003).
Lloyd et al., "Modelling the Human Immune Response: Performance of a 10E11 Human Antibody Repertoire Against a Broad Panel of Therapeutically Relevant Antigens," Protein Engineering, Design & Selection 22(3):159-168 (2009).
Final Office Action issued in co-pending U.S. Appl. No. 15/743,764, dated Oct. 23, 2019.
Chang et al., "The Dock and Lock Method: A Novel Platform Technology for Building Multivalent, Multifunctional Structures of Defined Composition with Retained Bioactivity," Clin Cancer Res 13 (18 Suppl): 5586s-5591s (2007).
Kumar et al., "Molecular Cloning and Expression of the Fabs of Human Autoantibodies in *Escherichia coli*," J Biol. Chem. 275(45): 35129-35136 (2000).
Smith-Gill et al., "Contributions of Immunoglobulin Heavy and Light Chains to Antibody Specificity for Lysozyme and Two Haptens," the Journal of Immunology 139(12): 4135-4144 (1987).
Snyder et al., "Overview of Monoclonal Antibodies and Small Molecules Targeting the Epidermal Growth Factor Receptor Pathway in Colorectal Cancer," Clin Colorec Canc 5 (Suppl.2): S71-S80 (2005).
Song et al., "Light Chain of Natural Antibody Plays a Dominant Role in Protein Antigen Binding," Biochem. Biophys Res. Comm. 268: 390-394 (2000).
Polson et al., "Antibody-drug Conjugates Targeted to CD79 for the Treatment of Non-Hodgkin Lymphoma," Blood 110(2): 616-623 (2007).

\* cited by examiner

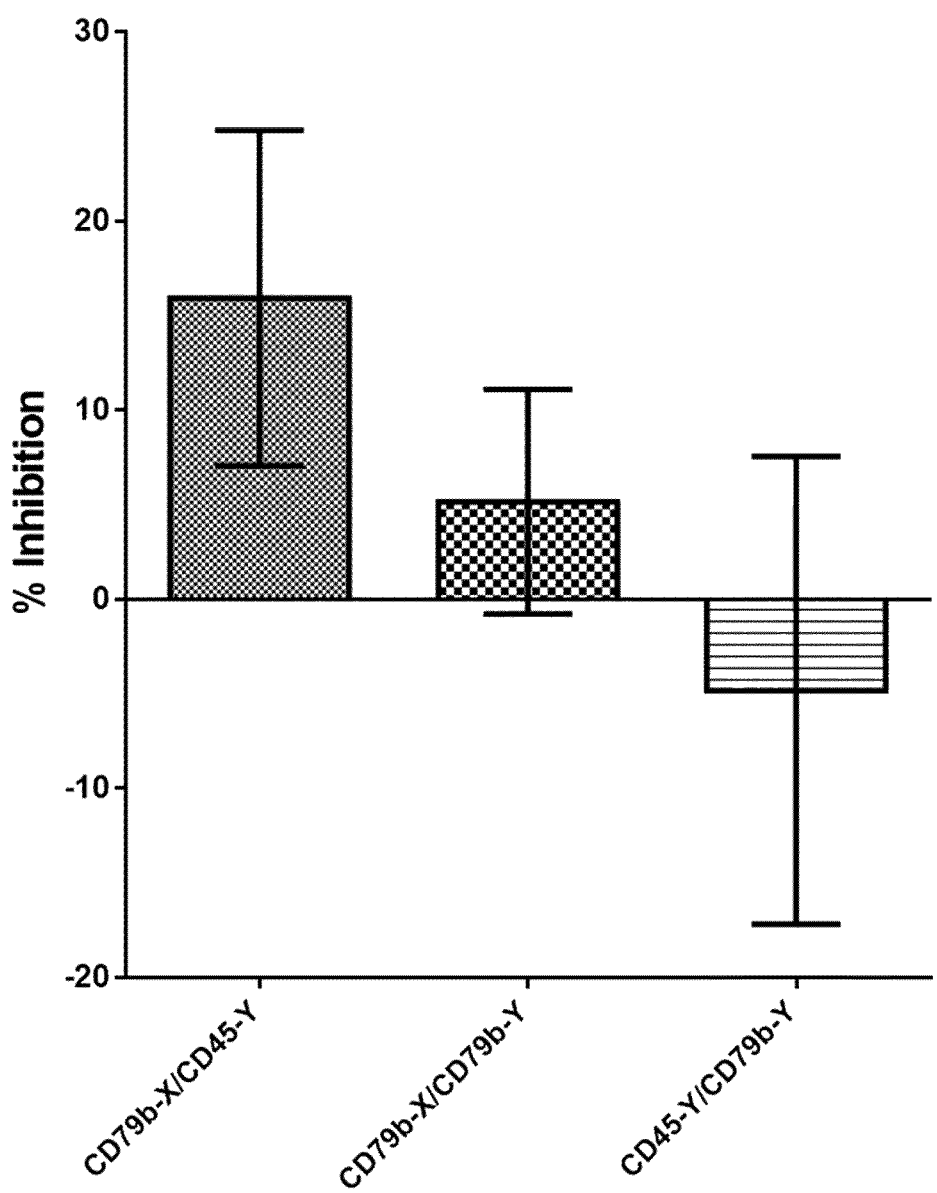

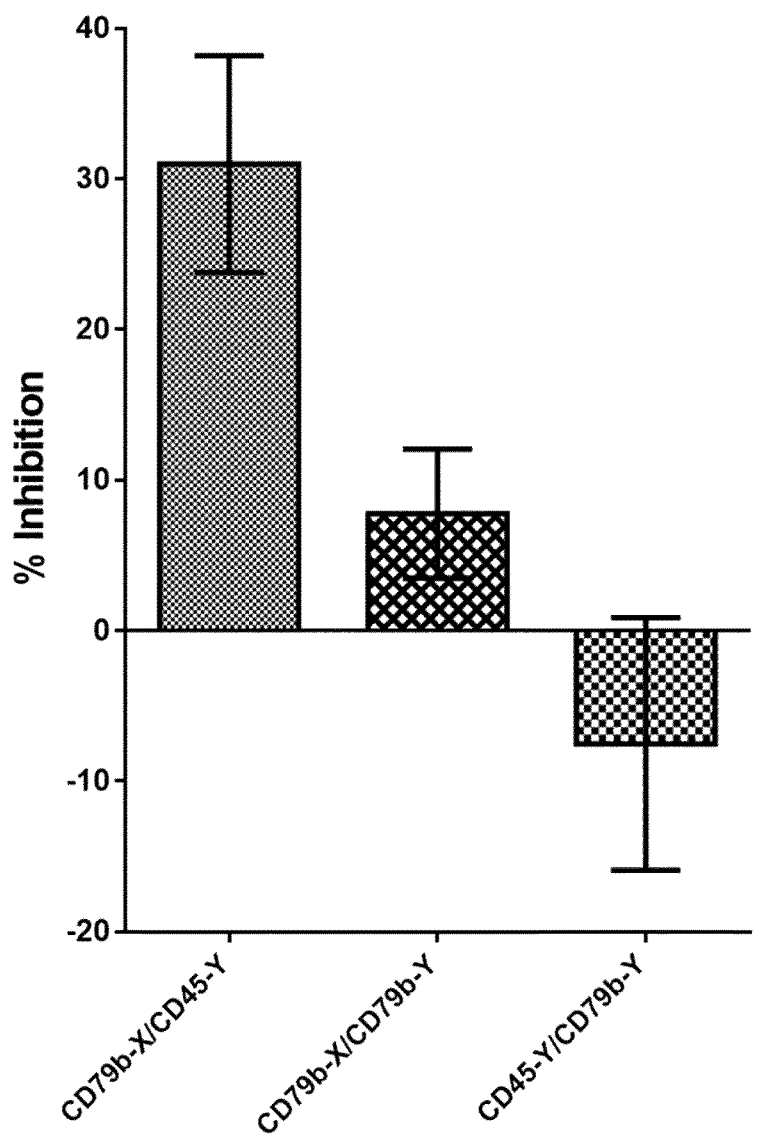
Figure 2 pPLCg2 Y759 on B cells

Figure 3 CD86 Titration –CD45/CD79b
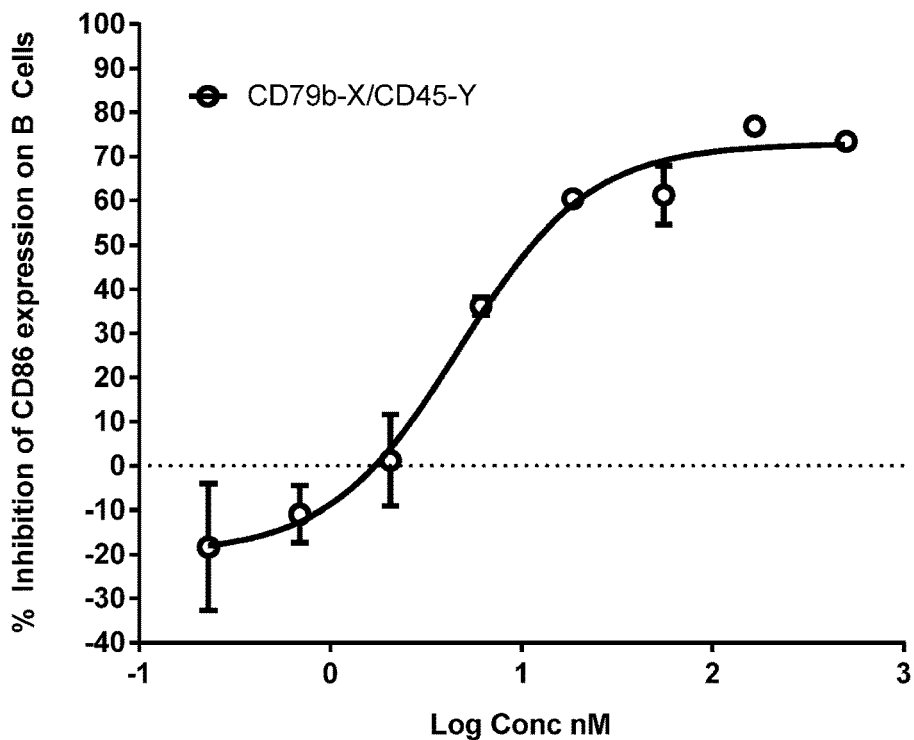
Figure 4 CD79b-Y Combination Inhibition of Anti-IgM Stimulation Induced by PLC-γ2 Phosphorylation
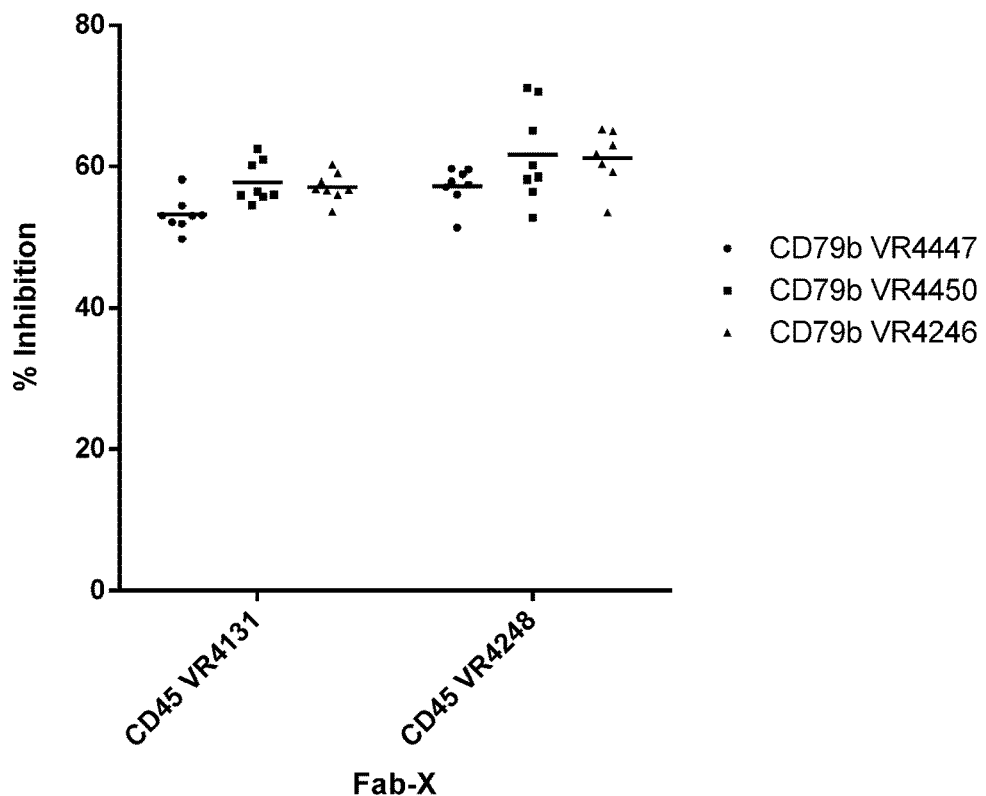

Figure 5A
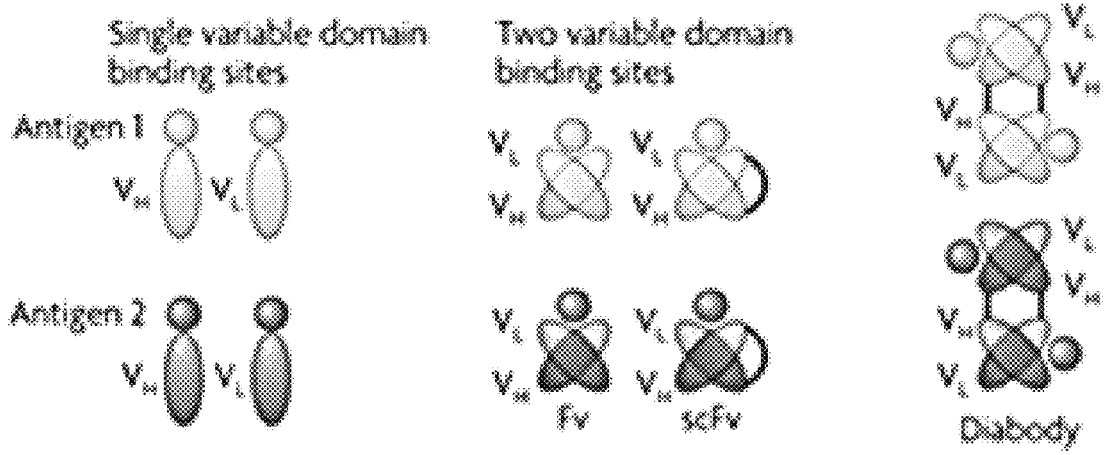
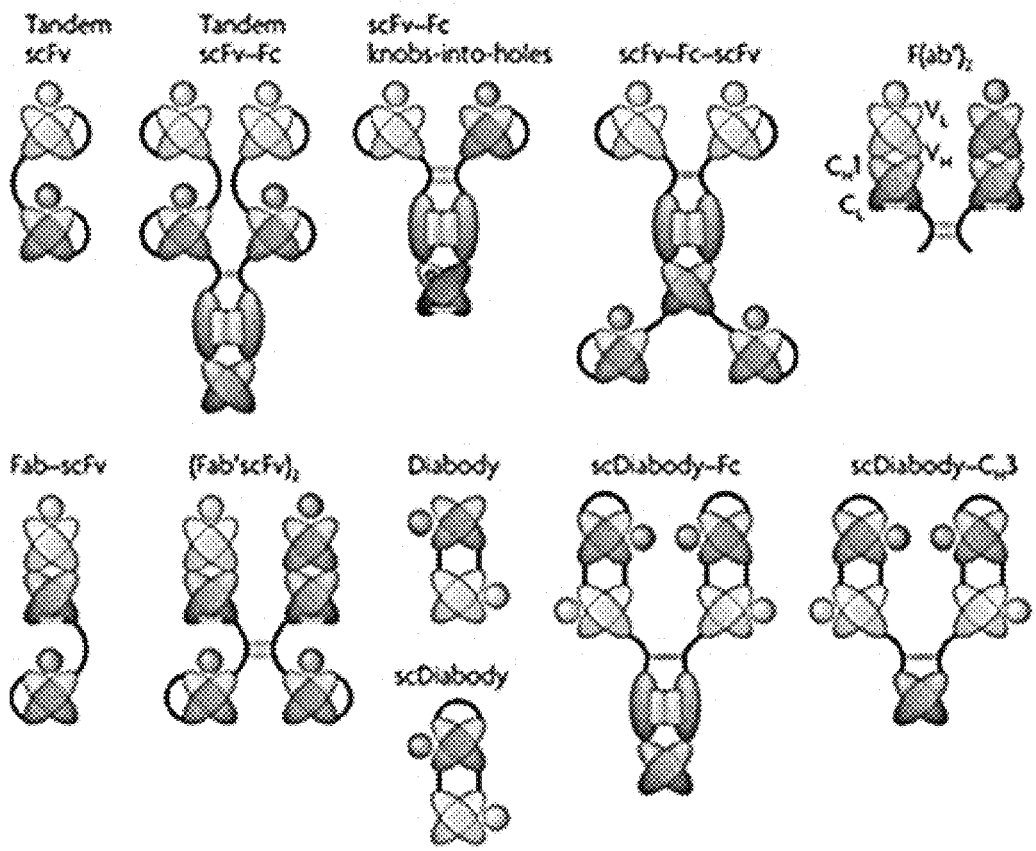

Figure 6

Fab-X specificity antigen 1 - 15

Fab-Y specificity antigen 1 - 23

% Inhibition Syk

| SP_Y | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | -4.37 | 33.57 | 10.45 | 13.99 | 3.81 | 4.26 | 8.34 | 21.07 | 4.10 | 13.98 | 6.07 | 16.03 | 7.39 | 9.00 | 23.01 |
| 2 | 27.22 | 25.26 | 52.32 | 63.81 | 30.98 | 19.94 | 26.90 | 29.48 | 20.58 | 30.61 | 9.05 | 4.18 | 14.73 | 36.56 | 33.04 |
| 3 | 17.62 | 69.66 | 3.88 | 16.35 | 7.81 | -5.45 | 6.94 | 12.43 | 6.90 | 7.41 | 15.55 | 18.23 | 8.31 | 7.13 | 15.98 |
| 4 | 13.81 | 70.47 | -9.21 | 11.98 | 2.91 | -0.27 | 7.92 | 9.85 | 0.93 | 4.02 | 8.95 | 40.06 | 10.33 | 6.02 | 15.96 |
| 5 | 5.05 | 36.09 | -1.78 | -0.25 | 10.55 | -14.55 | 11.68 | 6.91 | -0.32 | -2.82 | 9.14 | 12.00 | 3.48 | 7.99 | 9.03 |
| 6 | --- | 21.62 | 7.24 | 15.78 | 16.88 | 2.69 | 2.50 | 14.67 | 9.48 | 4.44 | 11.14 | 20.93 | 12.37 | --- | --- |
| 7 | 10.54 | 35.72 | 2.40 | 16.16 | 14.92 | 1.39 | 2.23 | 14.14 | 5.64 | 10.62 | 8.02 | 17.58 | 9.49 | 10.65 | 10.80 |
| 8 | 6.03 | 26.05 | -7.89 | 3.46 | 7.85 | -18.33 | 0.26 | -5.98 | -2.08 | 0.09 | 7.83 | 5.13 | 2.60 | 9.59 | 9.47 |
| 9 | 13.56 | 32.14 | -4.74 | 2.87 | 9.63 | -7.13 | 5.17 | 10.72 | 0.79 | 1.69 | 9.22 | 13.53 | 2.49 | 15.70 | 10.52 |
| 10 | 15.35 | 54.98 | 13.21 | 17.70 | -2.07 | 6.11 | 21.65 | 23.25 | 9.94 | 10.33 | 16.30 | 41.50 | 13.23 | 6.52 | 16.72 |
| 11 | --- | -0.28 | -50.76 | -5.43 | -0.23 | -118.10 | -4.78 | -9.59 | 0.08 | -4.95 | 6.09 | 2.91 | -9.06 | --- | --- |
| 12 | 5.85 | 8.47 | 19.70 | 42.01 | 20.13 | 12.42 | 15.14 | 26.89 | 20.69 | 24.69 | 18.86 | 36.32 | 18.07 | 20.28 | 38.97 |
| 13 | --- | 31.56 | 22.19 | 28.34 | 15.50 | 13.12 | 14.23 | 27.59 | 22.46 | 14.25 | 16.00 | 26.84 | 16.21 | --- | --- |
| 14 | 9.13 | 40.70 | 10.80 | 14.56 | 5.88 | 8.89 | 7.52 | 22.68 | 6.27 | 9.04 | 7.34 | 33.39 | 11.20 | 7.01 | 14.84 |
| 15 | 9.38 | 33.18 | 7.13 | 11.20 | 15.92 | 11.35 | 9.90 | 19.61 | 9.90 | 10.62 | 13.98 | 28.99 | 15.26 | 13.77 | 25.64 |
| 16 | --- | 26.46 | -7.59 | 19.38 | 15.65 | -24.93 | 12.05 | 14.00 | 15.27 | 11.98 | 13.29 | 20.57 | 11.99 | --- | --- |
| 17 | --- | 22.79 | -4.70 | 19.07 | 17.98 | -37.56 | 10.99 | 11.71 | 15.83 | 8.61 | 10.98 | 21.28 | 9.71 | --- | --- |
| 18 | --- | 28.91 | 29.09 | 33.25 | 23.16 | 10.61 | 13.85 | 26.28 | 21.37 | 18.39 | 18.45 | 32.78 | 18.27 | --- | --- |
| 19 | --- | 33.63 | -15.93 | 2.00 | 15.54 | -24.55 | 11.73 | 10.55 | 7.32 | 4.45 | 15.19 | 20.98 | 10.61 | --- | --- |
| 20 | --- | 24.94 | -13.88 | 20.88 | 10.53 | -21.56 | 8.43 | 6.69 | 8.81 | 7.57 | 10.73 | 17.52 | 13.55 | --- | --- |
| 21 | --- | 23.94 | 6.69 | 22.70 | 22.45 | -3.18 | 13.33 | 21.28 | 15.88 | 10.81 | 15.92 | 25.96 | 17.22 | --- | --- |
| 22 | 13.93 | 20.55 | -18.75 | -4.96 | 6.90 | -17.32 | 4.12 | -3.15 | -4.19 | -6.48 | 11.71 | 2.48 | -0.84 | 9.14 | 11.68 |
| 23 | --- | 24.25 | -9.45 | 22.83 | 24.63 | -26.70 | 9.65 | 13.79 | 10.74 | 7.96 | 13.02 | 24.43 | 18.33 | --- | --- |

Figure 7

Fab-X specificity antigen 1-15

| SP_Y... | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | 0.81 | 22.29 | 11.45 | 10.78 | 5.39 | 1.60 | 7.43 | 5.90 | 2.24 | 3.29 | -2.71 | 10.80 | 0.99 | 6.90 | -4.08 |
| 2 | 19.70 | 18.61 | 44.00 | 50.83 | 23.17 | 19.01 | 24.57 | 21.47 | 25.89 | 39.80 | 12.35 | 0.52 | 18.91 | 28.55 | 25.89 |
| 3 | 17.93 | 61.18 | 3.00 | 15.38 | 5.38 | -0.12 | 4.05 | 3.77 | 6.84 | 12.78 | 11.01 | 16.71 | 2.97 | 9.17 | 4.69 |
| 4 | 13.34 | 55.83 | -3.82 | 7.24 | 1.41 | -1.39 | 6.75 | 0.89 | 3.12 | 3.12 | 4.16 | 40.49 | 1.71 | 5.13 | 1.10 |
| 5 | 0.34 | 25.16 | 0.51 | -0.63 | 7.36 | -1.41 | 11.49 | 4.08 | 5.59 | 2.99 | 5.76 | 11.67 | 2.84 | 5.90 | -2.06 |
| 6 | --- | 20.71 | -0.85 | 6.04 | 0.40 | 3.49 | -2.60 | -0.87 | 3.41 | 0.22 | 1.34 | 12.34 | 3.36 | --- | --- |
| 7 | 10.95 | 27.95 | 1.38 | 15.66 | 11.27 | 2.40 | 2.48 | 4.45 | 6.13 | 16.07 | 3.18 | 12.77 | 3.92 | 5.85 | 0.37 |
| 8 | 7.73 | 24.86 | 4.02 | 5.23 | 3.56 | 0.49 | 2.68 | -1.16 | 2.39 | 1.45 | 4.10 | 8.50 | -0.64 | 3.01 | 0.97 |
| 9 | 7.37 | 28.27 | -0.02 | 3.22 | 6.39 | 1.35 | 4.75 | 4.06 | 4.92 | 4.09 | 3.10 | 10.50 | 0.62 | 5.62 | 1.50 |
| 10 | 17.08 | 47.69 | 7.72 | 5.65 | -5.55 | 1.40 | 21.89 | 6.66 | 5.90 | 5.11 | 7.61 | 35.77 | 1.50 | 4.32 | -0.06 |
| 11 | --- | 11.76 | -10.93 | 1.38 | -0.56 | -24.94 | -1.36 | 0.83 | 3.58 | 3.88 | 5.92 | 11.18 | -4.57 | --- | --- |
| 12 | 6.05 | -3.88 | 9.02 | 29.48 | 4.92 | 1.15 | 1.89 | 5.75 | 7.23 | 20.95 | 5.44 | 17.92 | 3.37 | 16.34 | 8.67 |
| 13 | --- | 23.78 | -0.99 | 7.30 | 0.43 | -1.40 | 1.83 | 6.41 | 8.91 | 3.25 | 2.76 | 11.64 | 5.41 | --- | --- |
| 14 | 4.40 | 28.11 | 1.77 | 5.61 | 4.01 | 1.73 | 5.95 | 2.45 | 4.05 | 6.85 | -0.60 | 20.60 | 5.45 | 4.11 | 0.05 |
| 15 | 4.96 | 25.60 | 0.87 | 3.43 | 5.41 | 1.77 | 1.89 | 1.80 | 3.72 | 1.96 | 2.29 | 14.57 | 5.26 | 2.36 | 0.11 |
| 16 | --- | 22.39 | -5.77 | 4.50 | 2.41 | -6.86 | 4.89 | 2.52 | 5.19 | 3.07 | 3.38 | 9.47 | 1.17 | --- | --- |
| 17 | --- | 19.53 | -6.98 | 6.73 | 2.99 | -10.27 | 2.35 | 2.13 | 6.02 | 2.08 | 3.10 | 10.86 | 2.03 | --- | --- |
| 18 | --- | 19.90 | 2.43 | 12.38 | 2.08 | -1.05 | 1.09 | 4.25 | 6.70 | 4.90 | 4.40 | 12.49 | 4.34 | --- | --- |
| 19 | --- | 35.50 | -12.22 | -2.38 | -1.61 | -9.05 | 5.97 | 1.78 | 5.27 | 4.63 | 5.92 | 15.60 | 3.16 | --- | --- |
| 20 | --- | 21.53 | -9.67 | 2.95 | -0.16 | -6.71 | -3.46 | -4.81 | 4.13 | 2.31 | 6.52 | 10.96 | 4.25 | --- | --- |
| 21 | --- | 19.03 | -6.66 | 2.36 | 1.10 | -6.49 | -0.95 | 5.09 | 4.96 | 3.55 | 3.97 | 10.89 | 3.63 | --- | --- |
| 22 | 14.73 | 26.47 | -5.00 | 0.58 | 3.97 | -0.08 | 3.70 | -1.25 | 1.72 | 0.99 | 11.40 | 7.99 | 2.80 | 8.39 | 4.58 |
| 23 | --- | 19.72 | -16.22 | 0.75 | -1.16 | -11.03 | -3.57 | 3.30 | 3.57 | 1.23 | 4.90 | 8.22 | 4.20 | --- | --- |

Fab-Y specificity antigen 1-23

% Inhibition PLCγ2

Figure 8

Fab-X specificity antigen 1-15

| SP_Y... | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| 1 | -11.06 | 53.06 | -1.56 | 6.02 | -8.08 | -12.41 | 3.84 | -12.93 | -8.22 | -8.88 | -11.49 | -3.34 | -17.29 | -4.43 | -6.28 |
| 2 | 40.41 | 37.15 | 48.29 | 48.35 | 39.50 | 30.66 | 40.36 | 25.61 | 42.23 | 42.64 | 32.59 | 37.11 | 26.58 | 35.70 | 38.11 |
| 3 | 13.19 | 70.81 | 2.37 | 15.53 | 8.68 | 7.93 | 12.32 | 3.78 | 10.56 | 14.18 | 8.76 | -1.58 | 6.61 | 10.75 | 10.83 |
| 4 | 8.35 | 55.50 | -6.07 | 17.80 | 7.97 | 7.14 | 8.49 | 6.54 | 6.98 | 9.67 | 12.96 | 41.04 | 5.99 | 9.28 | 7.89 |
| 5 | -3.80 | 40.21 | -0.85 | 13.54 | 2.05 | -2.13 | 3.01 | -6.86 | 0.91 | 2.02 | 0.76 | 4.48 | -3.42 | 4.06 | 0.15 |
| 6 | --- | 40.39 | 6.67 | 19.26 | -4.86 | 12.95 | 3.52 | 2.59 | 6.73 | 5.65 | 5.28 | 4.77 | -1.03 | --- | --- |
| 7 | 0.53 | 45.36 | 4.87 | 18.76 | 4.08 | 0.72 | -1.43 | 5.07 | 4.69 | 11.49 | 6.48 | 5.72 | 4.78 | 0.73 | -3.71 |
| 8 | 6.61 | 37.54 | 5.72 | 16.25 | -1.45 | 2.38 | 0.64 | 0.17 | 1.10 | 2.08 | 6.50 | 7.58 | 2.18 | -4.37 | -4.53 |
| 9 | 0.51 | 42.34 | 0.95 | 9.41 | -0.30 | 1.07 | 2.86 | -2.56 | 0.51 | -0.55 | 2.07 | 2.49 | -2.84 | 4.54 | 0.16 |
| 10 | 11.13 | 52.32 | 3.75 | 12.67 | -4.41 | 3.82 | 15.78 | -3.15 | 5.70 | 4.26 | 1.77 | 22.73 | -4.68 | 7.65 | 8.05 |
| 11 | --- | 33.40 | -3.95 | 18.04 | 7.48 | 6.00 | 3.13 | 4.24 | 5.66 | 13.11 | 9.85 | 11.24 | 2.04 | --- | --- |
| 12 | 0.69 | 29.50 | -7.93 | 38.94 | 2.68 | 4.95 | -0.13 | -2.53 | 2.52 | 15.03 | -0.82 | 3.63 | -5.61 | 25.99 | 12.57 |
| 13 | --- | 35.33 | -4.80 | 10.35 | -4.98 | -7.45 | -7.91 | -6.47 | 3.78 | -0.83 | -4.68 | -3.84 | -9.54 | --- | --- |
| 14 | 1.62 | 44.02 | 0.91 | 16.05 | 1.80 | -2.56 | 1.09 | -4.49 | 3.94 | 5.30 | -0.19 | 8.15 | -5.85 | 5.21 | 0.66 |
| 15 | 2.25 | 36.02 | -2.44 | 10.00 | -0.22 | 0.37 | -2.20 | -2.11 | 2.41 | 1.84 | 3.23 | 2.78 | 2.51 | -2.19 | -4.62 |
| 16 | --- | 33.56 | -3.12 | 15.33 | 0.19 | -5.46 | -0.71 | -5.67 | 1.83 | 1.35 | -0.24 | -1.99 | -8.53 | --- | --- |
| 17 | --- | 35.02 | -4.92 | 16.87 | 1.78 | -2.20 | 0.34 | -2.12 | 3.07 | 1.17 | 0.98 | 0.80 | -2.14 | --- | --- |
| 18 | --- | 31.31 | -1.77 | 19.71 | -6.19 | -4.39 | -3.72 | -3.91 | 2.70 | 3.44 | -0.42 | -1.65 | -5.72 | --- | --- |
| 19 | --- | 50.00 | -2.93 | 9.92 | 2.01 | 9.54 | 10.19 | 2.60 | 11.44 | 9.84 | 7.96 | 9.17 | 3.37 | --- | --- |
| 20 | --- | 38.56 | -1.83 | 18.96 | 1.40 | 5.57 | 0.37 | 1.23 | 4.23 | 6.85 | 10.48 | 6.54 | 2.60 | --- | --- |
| 21 | --- | 36.74 | 1.67 | 11.59 | -5.60 | 6.23 | 0.59 | 6.00 | 6.99 | 5.11 | 3.12 | 3.73 | 3.44 | --- | --- |
| 22 | -2.71 | 40.50 | -2.45 | 12.91 | -1.39 | 6.77 | 1.56 | 4.97 | 1.68 | 2.93 | 18.10 | 8.41 | 8.06 | -2.35 | -4.93 |
| 23 | --- | 33.54 | -1.68 | 5.45 | -2.46 | 7.13 | 0.05 | -3.14 | 2.99 | 3.34 | 6.02 | 4.97 | -4.12 | --- | --- |

Fab-Y specificity antigen 1-23

% Inhibition AKT

Figure 11 Inhibition of PLCγ2 (+/- SD) by purified CD79b-CD45 transient on IgM stimulated B-cells from donor 129

Figure 12 Inhibition of PLCγ2 (+/- SD) by purified CD79b-CD45 transient on IgM stimulated B-cells from donor 130

Figure 13 Inhibition of p38 (+/- SD) by purified CD79b-CD45 transient on IgM stimulated B-cells from donor 129

Figure 14 Inhibition of p38 (+/- SD) by purified CD79b-CD45 transient on IgM stimulated B-cells from donor 130

Figure 15 Inhibition of Akt (+/- SD) by purified CD79b-CD45 transient on IgM stimulated B-cells from donor 129

Figure 16 Inhibition of Akt (+/- SD) by purified CD79b-CD45 transient on IgM stimulated B-cells from donor 130

MOLECULES WITH SPECIFICITY FOR CD45 AND CD79

CROSS-REFERENCE TO RELATED APPLICATION

This application is the U.S. national stage application of International Patent Application No. PCT/EP2015/066368, filed Jul. 16, 2015.

The Sequence Listing for this application is labelled "Seq-List-replace.txt" which was created on Feb. 7, 2017 and is 70 KB. The entire content of the sequence listing is incorporated herein by reference in its entirety.

FIELD OF INVENTION

The present disclosure relates to a molecule which is at least bispecific to the antigens CD45 and CD79, a formulation comprising said molecule and use of any one of the same in treatment. The present disclosure also extends to methods of preparing said molecules and said formulations. In an independent aspect the disclosure also extends to novel antibody sequences and fragments described herein.

Background of Invention

Biological mechanisms in vivo are extremely complicated cascades of signals, which are difficult to deconvolute and understand. An example of such signalling is that required to activate B-cells. The B cell antigen receptor (BCR) is composed of membrane immunoglobulin (mIg) molecules and associated Igα/Igβ (CD79a/CD79b) heterodimers (α/β). The mIg subunits bind antigen, resulting in receptor aggregation, while the α/β subunits transduce signals to the cell interior. BCR aggregation rapidly activates the Src family kinases Lyn, Blk, and Fyn as well as the Syk and Btk tyrosine kinases. This initiates the formation of a 'signalosome' composed of the BCR, the aforementioned tyrosine kinases, adaptor proteins such as CD19 and BLNK, and signaling enzymes such as PLCγ2, PI3K, and Vav.

Signals emanating from the signalosome activate multiple signaling cascades that involve kinases, GTPases, and transcription factors. This results in changes in cell metabolism, gene expression, and cytoskeletal organization. The complexity of BCR signaling permits many distinct outcomes, including survival, tolerance (anergy) or apoptosis, proliferation, and differentiation into antibody-producing cells or memory B cells. The outcome of the response is determined by the maturation state of the cell, the nature of the antigen, the magnitude and duration of BCR signaling, and signals from other receptors such as CD40, the IL-21 receptor, and BAFF-R.

Many other transmembrane proteins, some of which are receptors, modulate specific elements of BCR signaling. A few of these, including CD45, CD19, CD22, PIR-B, and FcγRIIB1 (CD32). The magnitude and duration of BCR signaling are limited by negative feedback loops including those involving the Lyn/CD22/SHP-1 pathway, the Cbp/Csk pathway, SHIP, Cbl, Dok-1, Dok-3, FcγRIIB1, PIR-B, and internalization of the BCR.

In vivo, B cells are often activated by antigen-presenting cells that capture antigens and display them on their cell surface. Activation of B cells by such membrane-associated antigens requires BCR-induced cytoskeletal reorganization.

Autoreactive B cells are responsible for the production of pathogenic autoantibodies which can either directly or indirectly cause or exacerbate autoimmune conditions. Depletion of CD20 positive B cells has been used to successfully treat a number of autoimmune conditions and thus established conclusively that B cells play an important role in causing or maintaining a number of autoimmune diseases. Although B cell depletion has been a successful therapeutic option evidence also exists that control of B cell growth and activation status can also be an effective way to modulate B cell function. Alternative strategies that do not deplete B cells and offer the flexibility of controlling B cells without long term suppression of B cell immunity which has been shown to be associated with some side effects would therefore be desirable. In addition not all B cell responses or activities are harmful and evidence suggests that maintenance of regulatory B cell populations can be protective. Such an approach should be effective in diseases which have abnormal B cell function caused by inappropriate or excessive BcR signalling. Examples include, but are not limited to, inflammation, autoimmunity and cancer. Of particular interest are diseases that either have a direct requirement for BcR signalling or require inhibition or stimulation of humoral immune responses.

Bispecific antibodies are widely expected to play a major role in the next generation of biotherapeutics (D. Holmes, Nature Rev Drug Disc November 2011:10; 798). They have the potential to deliver superior, long term, broad efficacy in a greater proportion of patients. This can be achieved by either co-engaging different antigens simultaneously within a common disease pathway, thereby reducing redundancy; or by targeting antigens from independent pathways to provide an additive or synergistic effect.

To date strategies to inhibit B cell function without deleting the B cell have focused on exploiting the natural mechanism of regulation by CD32b (FcgRIIB). These include bispecific antibodies to CD79b/CD32b (Veri et al., Arthritis & Rheumatism 2010 62 1933-1943), CD19/CD32b (Karnell et al., J.Immunol 2014 192 1430-1490) and an antibody to CD19 with an Fc with enhanced CD32b binding (Chu et al., Arthritis & Rheumatology 2014 66 1153-1164).

Bispecific antibodies are widely expected to play a major role in the next generation of biotherapeutics (D. Holmes, Nature Rev Drug Disc November 2011:10; 798). They have the potential to deliver superior, long term, broad efficacy in a greater proportion of patients. This can be achieved by either co-engaging different antigens simultaneously within a common disease pathway, thereby reducing redundancy; or by targeting antigens from independent pathways to provide an additive or synergistic effect.

To date strategies to inhibit B cell function without deleting the B cell have focused on exploiting the natural mechanism of regulation by CD32b (FcgRIIB). These include bispecific antibodies to CD79b/CD32b (Arthritis & Rheumatism 2010 62 1933-1943), CD19/CD32b (J.Immunol 2014 192 1430-1490) and an antibody to CD19 with an Fc with enhanced CD32b binding (Arthritis & Rheumatology 2014 66 1153-1164).

Co-ligation of Fc gamma receptor IIb (CD32b) with the B cell receptor occurs to naturally regulate signalling, in particular when antigen is bound to antibody in small immune complexes. CD32b then recruits the phophatases SHP-1 and SHIP-1 which antagonise BcR activation. Although this natural regulatory mechanism can control B cell function, disruption of CD32b function caused by variation in the protein sequence of CD32b can lead to autoimmune disease and this receptor can be down regulated in autoimmune disease—e.g. as in the case of SLE. Alternative ways of blocking B cell activity are thus desirable as they offer alternative, non-natural, ways of regulating BcR function. These alternative mechanisms are likely to be particularly important when natural mechanisms are disfunctional in the given disease.

Bispecific antibodies facilitate access to novel biology such as:
1) cross-linking receptors on a cell, if appropriate,
2) inducing cell mediated effects,
3) localizing a cytokine to a cell to regulate signaling or locally block cytokine function,
4) engaging multiple epitopes simultaneously to generate "new activity", increase function or specificity, which may not be exhibited by a single monoclonal antibody or indeed mixtures of un-linked antibodies (polymonoclonals), including mixtures directed to different antigens.

Under normal physiological conditions upon antigen binding CD45 is excluded from the BcR complex. The present inventors have surprisingly found that using a bispecific antibody to couple the BcR (CD79) to the molecule CD45, BCR signalling can be inhibited. Thus by physically linking the BcR with CD45 through use of a bispecific antibody the inventors have found that activation in B cells can be inhibited.

The present inventors have therefore identified a synergistic function for molecules which are at least bispecific for CD45 and CD79. This function seems to be detectable primarily when binding regions with the combination of specificities are provided in a bispecific (multispecific) format, as opposed to simply being provided as a mixture of, for example monoclonal antibodies or binding fragments thereof.

The multispecific molecules of the invention are therefore useful in controlling aberrant B cell functions associated with certain diseases such as autoimmunity and cancer.

SUMMARY OF THE DISCLOSURE

Thus provided is a multispecific molecule comprising a binding domain specific to the antigen CD45 and a binding domain specific to the antigen CD79.

The combination according to the present disclosure in a bispecific format shows interesting biological activity in functional in vitro assays, for example inhibition of B cell signalling as measured by any one of the following: inhibition of phosphorylation of Akt S473, inhibition of phosphorylation of P38 and PLCγ2 Y759 inhibition of IkB, in addition to the inhibition of expression of CD86, CD71 and/or CD40 on B cells. The same level of activity is not apparent for individual components alone or the components provided in admixture. However, the activity is apparent when a bispecific construct with specificity for CD45 and CD79 is provided.

The inhibition of certain B cell functions observed in these assays is indicative that a multispecific molecule of the invention, comprising a binding domain specific to CD45 and a binding domain specific to CD79, may be used to alter B cell function and, for example to provide a therapeutic alternative to depletion of B cells.

B cell receptor signalling is a critical function of the B cell and a requirement for antigen specific activation of B cells. BcR signalling is critical from early stages of B cell development through to the activation and development of memory B cell responses. The B cell receptor is composed of a surface immunoglobulin (Ig) molecule which associates with heterodimeric complex of CD79a and CD79b. When surface Ig recognises antigen it is thought that this results in a clustering of the CD79a/b complex which results in downstream activation of the immediate signalling cascade, which includes Src family kinases as well as Syk and Btk tyrosine kinases. This signalling complex then can recruit adaptor proteins such as CD19 and BLNK and results in activation of PLCγ2 and PI3K which in turn can activate further downstream pathways such as those that control B cell growth, survival and differentiation. This signalling complex can be further regulated by other second signals via signalling through BAFF-R, IL-21R and CD40 and can also be regulated by other signalling molecules such as CD19, CD21, CD83, CD22, CD32b and CD45 amongst others. Upon recognition of antigen by the BcR one of the first responses activated is the up-regulation of surface receptors such as the co-stimulatory molecules CD80 and CD86. These molecules bind to corresponding receptors on T cells which deliver further survival and activation signals that allow survival and expansion of T cells that recognise antigen in the context of MHC class II. This response is further amplified by the ability of B cells to present antigen in the context of MHC class II back to the T cell, which releases factors such as IL-2 and IL-21. These cytokines in turn expand B cell number greatly.

Furthermore, inhibition of B cell receptor signalling can lead to inhibition of downstream functions. One such outcome would be the inhibition of co-stimulatory molecules such as CD86 (or reduced expression of the same) which will lead to the inhibition of T cell function, survival and differentiation.

Thus inhibition of B cell receptor signalling can be beneficial in controlling aberrant B cell functions associated with autoimmunity and cancer. B cell receptor signalling is required for B cell proliferation, differentiation, antigen presentation and cytokine release in autoimmune disease. Thus inhibiting BcR activity can regulate B cell functions such as immunoglobulin secretion, T cell activation and control inappropriate B cell activity associated with, for example autoimmune conditions. In addition there are some B cell leukaemias and lymphomas that require B cell receptor signalling for survival and growth which may be controlled by inhibitors of B cell receptor activation.

In one embodiment the binding domain or binding domains of the multi-specific molecules of the present invention each independently comprise one or two (such as two) antibody variable domains specific to a relevant antigen (such as CD45 or CD79 or a further antigen if the molecule is at least trispecific).

CD79 as used herein refers to the complex composed of CD79a and CD79b. Accordingly, antibodies which bind CD79 may bind to CD79a and/or CD79b. Binds to CD79a and/or CD79b as employed herein refers to: specific to CD79a, specific to CD79b, specific to both CD79a and b (i.e. recognises an epitope on CD79a and also recognises an epitope on CD79b—i.e. pan specific) or is specific to the complex of CD79a and CD79b (i.e. recognises an epitope formed from the interaction of CD79a and CD79b in the complex form).

In one embodiment an antibody or binding fragment thereof employed in the molecules of the present disclosure is specific to CD79a.

In one embodiment an antibody or binding fragment thereof employed in the molecules of the present disclosure is specific to CD79b.

In one embodiment an antibody or binding fragment thereof employed in the molecules of the present disclosure is specific to CD79 complex, i.e. it recognises an epitope present in the complex and is specific thereto, for example an epitope comprising an interaction between CD79a and CD79b.

In one embodiment even where the binding domain is specific to CD79a or CD79b it will be appreciated that the binding domain will still bind to CD79a or CD79b when in the complex form.

Where there are two variable regions in a binding domain or in each binding domain then the two variable regions will generally work co-operatively to provide specificity for the relevant antigen, for example they are a cognate pair or affinity matured to provide adequate affinity such that the domain is specific to a particular antigen. Typically they are a heavy and light chain variable region pair (VH/VL pair).

In one embodiment the molecule of the present disclosure is bispecific.

In one embodiment the molecule of the present disclosure is trispecific, for example where the third binding domain is specific to serum albumin, for example human serum albumin.

In one embodiment the molecule of the present disclosure is monospecific for CD79 and CD45 i.e. the molecule only comprises one binding domain which binds CD79 and one binding domain which binds CD45.

In one embodiment the multispecific molecule of the present disclosure is a single chain.

In one embodiment the multispecific molecule of the present disclosure comprises a heavy chain and also a light chain. In one example, as employed herein a heavy and light chain pairing is not referred to as a dimer, particularly where in one embodiment the molecule of the present disclosure does not comprise multimers, such as dimers of the antibody, unit/fragment or components.

In one aspect, there is provided a multi-specific antibody molecule comprising or consisting of:

a) a polypeptide chain of formula (I):

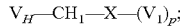

$V_H$—$CH_1$—X—$(V_1)_p$;

b) a polypeptide chain of formula (II):

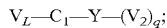

$V_L$—$C_1$—Y—$(V_2)_q$;

wherein:
$V_H$ represents a heavy chain variable domain;
$CH_1$ represents a domain of a heavy chain constant region, for example domain 1 thereof;
X represents a bond or linker, for example an amino acid linker;
Y represents a bond or linker, for example an amino acid linker;
$V_1$ represents a dab, scFv, dsscFv or dsFv;
$V_L$ represents a variable domain, for example a light chain variable domain;
$C_L$ represents a domain from a constant region, for example a light chain constant region domain, such as Ckappa;
$V_2$ represents a dab, scFv, dsscFv or dsFv;
p is 0 or 1;
q is 0 or 1; and
when p is 1 q is 0 or 1 and when q is 1 p is 0 or 1 i.e. p and q do not both represent 0.

In one embodiment the molecule comprises no more than one binding site for CD45 and no more than one binding site for CD79.

The above format is particularly useful for screening combinations of variable regions, for example in longer term assays and for therapeutic use.

In one embodiment q is 0 and p is 1.
In one embodiment q is 1 and p is 1.
In one embodiment $V_1$ is a dab and $V_2$ is a dab and together they form a single binding domain of a co-operative pair of variable regions, such as a cognate $V_H/V_L$ pair.
In one embodiment $V_H$ and $V_L$ are specific to, CD79, for example CD79a or CD79b.
In one embodiment the $V_1$ is specific to, CD79, for example CD79a.
In one embodiment the $V_2$ is specific to, CD79, for example CD79a.
In one embodiment the $V_1$ is specific to, CD79, for example CD79b.
In one embodiment the $V_2$ is specific to, CD79, for example CD79b.
In one embodiment the $V_1$ and $V_2$ together (eg as one binding domain) are specific to, CD79, for example CD79a or CD79b.
In one embodiment $V_H$ and $V_L$ are specific to, CD45.
In one embodiment the $V_1$ is specific to, CD45.
In one embodiment the $V_2$ is specific to, CD45.
In one embodiment the $V_1$ and $V_2$ together (eg as one binding domain) are specific to, CD45.

In one embodiment the molecule of the present disclosure is or comprises a fusion protein.

In one embodiment there is provided a multispecific molecule according to the present disclosure, which is a bispecific protein complex having the formula A-X:Y-B wherein:
A-X is a first fusion protein;
Y-B is a second fusion protein;
X:Y is a heterodimeric-tether;
A comprises a first binding domain specific to CD45, CD79a, CD79b or a complexed of CD79a and b;
B comprises a second binding domain specific to CD45, CD79a, CD79b or a complexed of CD79a and b;
X is a first binding partner of a binding pair;
Y is a second binding partner of the binding pair; and
: is an interaction (such as a binding interaction) between X and Y, and
wherein at least one of A or B is specific to CD45 and the other is specific to CD79a, CD79b or a complexed form thereof.

The above format is a convenient because it provides a rapid and efficient way of assembling bispecific formats that, for example can be subjected to in vitro testing in functional assays.

This may facilitate the choice of a preferred pair of variable regions, which may subsequently be incorporated into an alternative, therapeutic multispecific antibody format.

Whilst not wishing to be bound by theory different permutations of variable regions specific to CD45 combined with a range of variable regions specific to CD79 may give access to different nuances in biological function.

The invention also provides novel CD45 antibodies, for example for use in the multispecific molecules of the present invention or for incorporation into any other suitable antibody format. The invention also provides novel CD79 antibodies, for example for use in the multispecific molecules of the present invention or for incorporation into any other suitable antibody format.

BRIEF DESCRIPTION OF THE FIGURES

FIG. 1 is a bar chart of the relative potency of inhibition of phosphorylated Akt for bispecific and bivalent combinations of antibodies with specificity for CD45 and CD79b.

FIG. 2 is a bar chart of the relative potency of inhibition of phosphorylated PLCg2 for bispecific and bivalent combinations of antibodies with specificity for CD45 and CD79b.

FIG. 3 is a graph showing the titration of the effect of the bispecific combination of CD45 and CD79b on CD86 expression on anti-IgM stimulated B cells.

FIG. 4 is a graph of inhibition of phosphorylated PLCg2 for bispecific proteins with specificity for CD45 and CD79b with different V regions

FIG. 6 shows data for the antigen grid cross specificities. Antigen 2=CD79b and antigen 4=CD45. Values are percentage inhibition (negative value for activation) of phosphorlylation of Syk & represent the mean of multiple V region combinations evaluated.

FIG. 7 shows data for the antigen grid cross specificities. Antigen 2=CD79b and antigen 4=CD45. Values are percentage inhibition (negative value for activation) of PLCγ2 & represent the mean of multiple V region combinations evaluated.

FIG. 8 shows data for the antigen grid cross specificities. Antigen 2=CD79b and antigen 4=CD45 Values are percentage inhibition (negative value for activation) of AKT & represent the mean of multiple V region combinations evaluated.

DETAILED DESCRIPTION OF THE DISCLOSURE

Figure 5B:
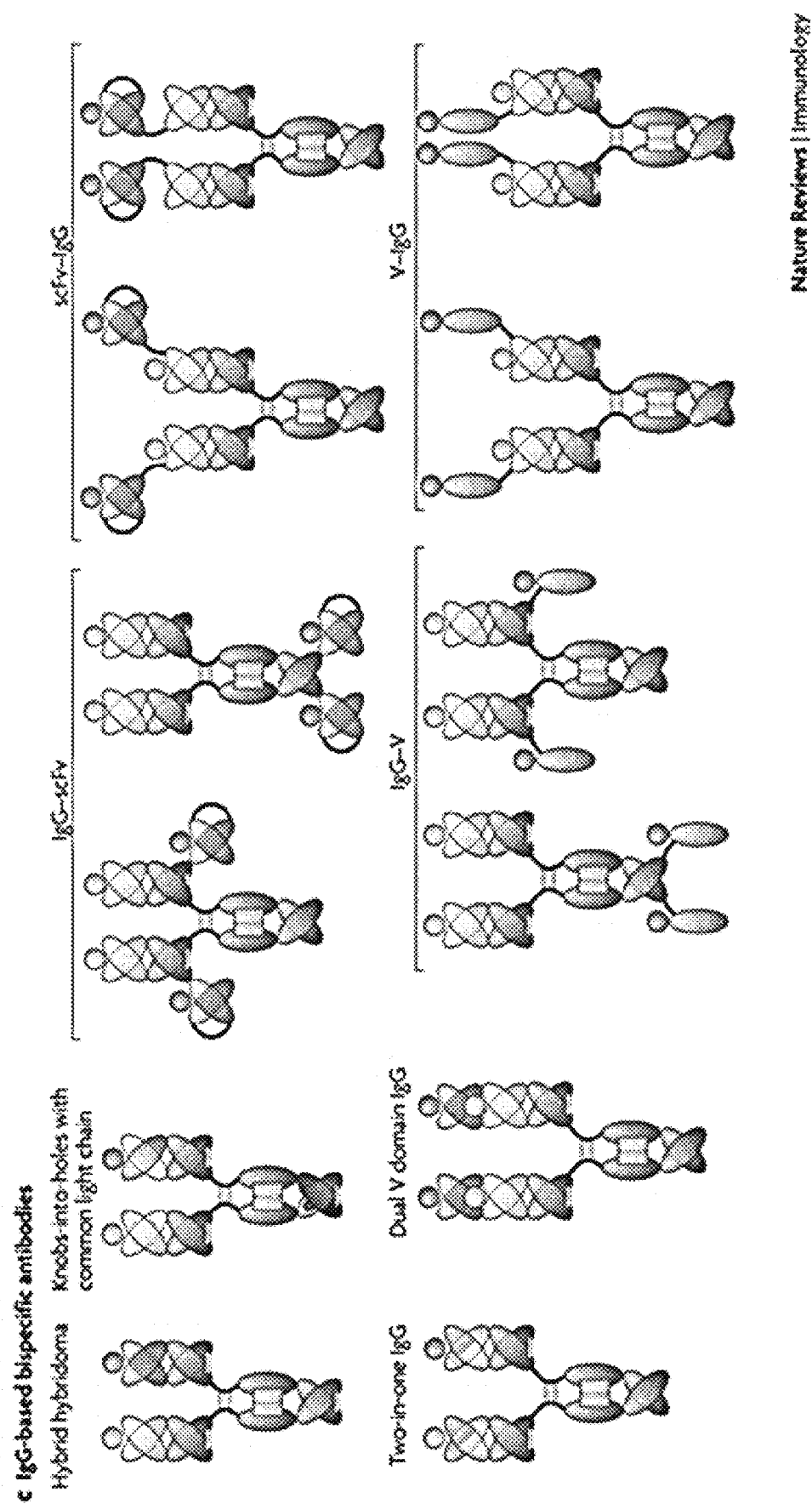
FIG. 5 is an extract from Chan and Carter Reviews Immunology vol 10, May 2010, 301 showing certain antibody formats.
Figure 9:
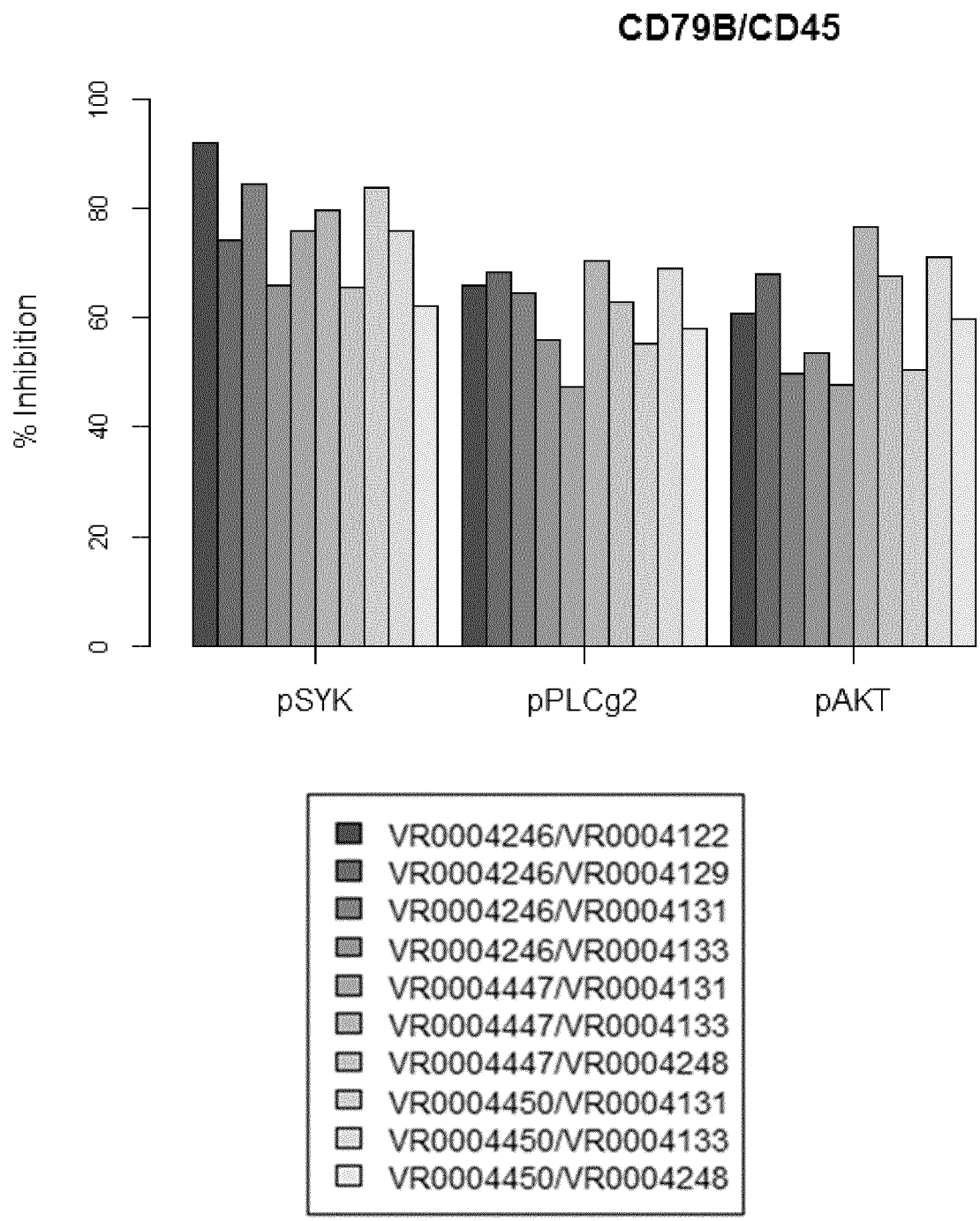
FIG. 9 shows the percentage inhibition of the phosphorlylation of Syk, PLCγ2 & AKT for each V-region combination for CD79b specificity in Fab-X combined with CD45 specificity in Fab-Y.
Figure 10:
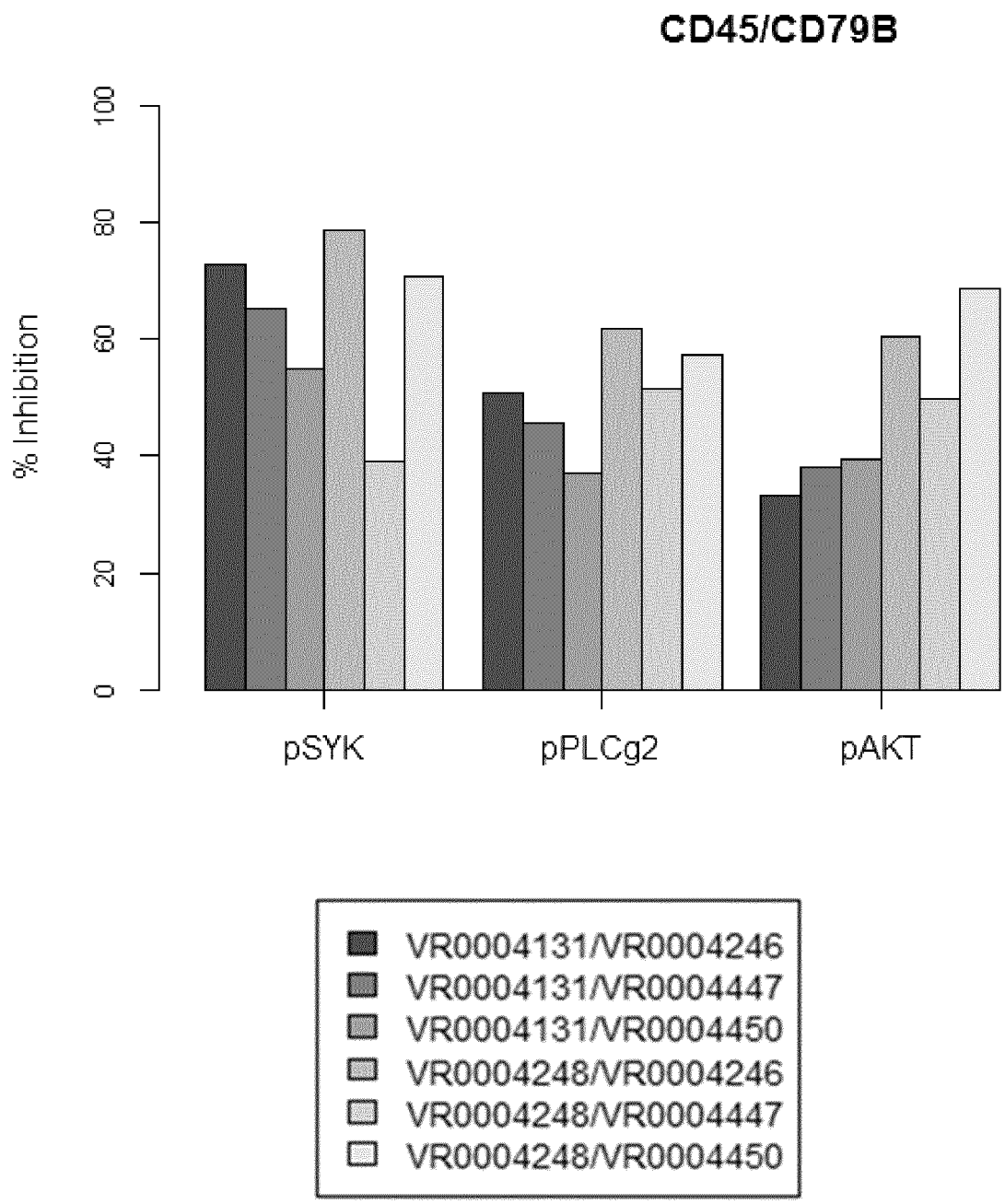
FIG. 10 shows the percentage inhibition of the phosphorlylation of Syk, PLCγ2 & AKT for each V-region combination for CD79b specificity in Fab-Y combined with CD45 specificity in Fab-X
Figure 11:
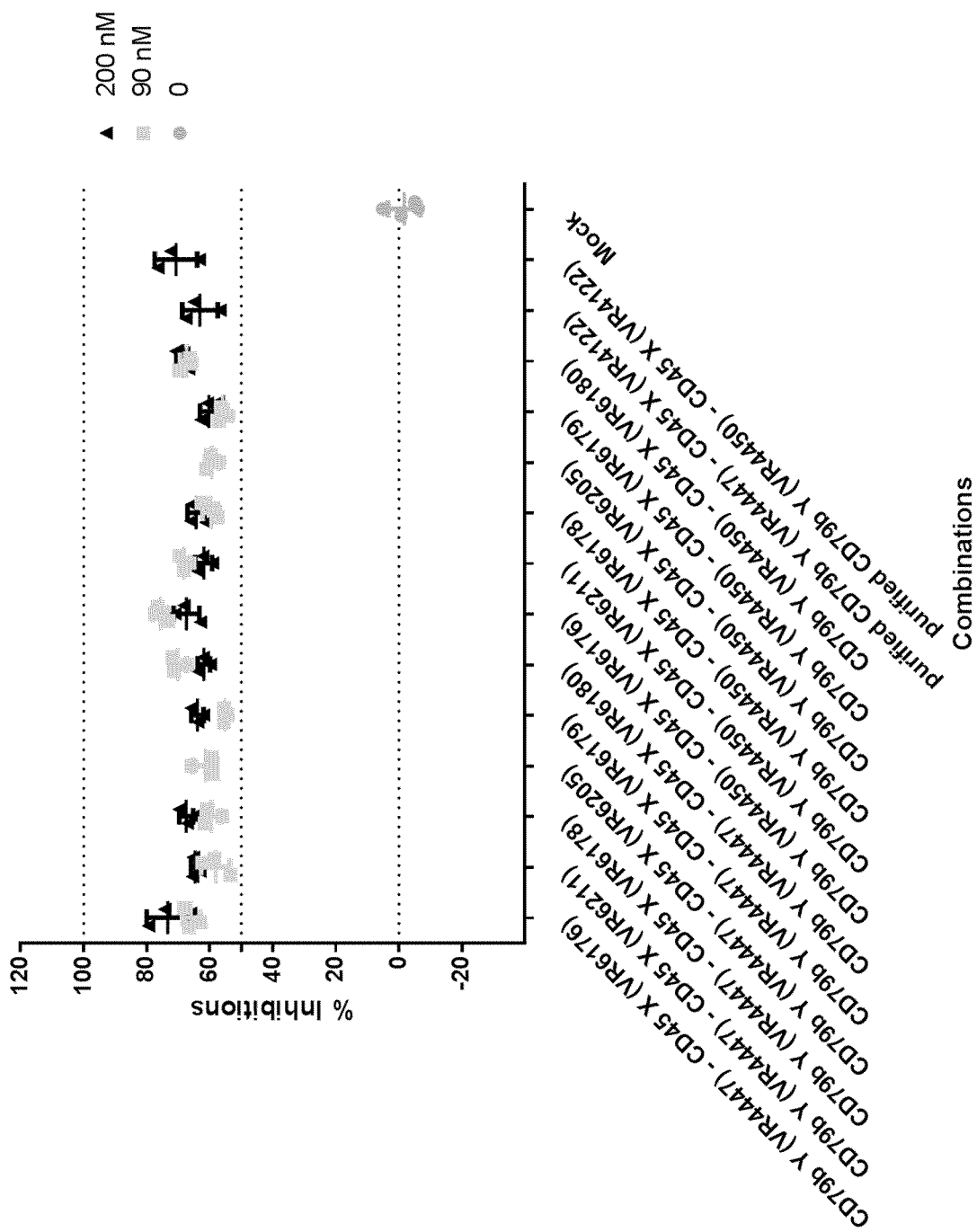
FIGS. 11 & 12 shows inhibition of PLCγ2 (+/−SD) by purified CD79b-CD45 (transiently expressed) on IgM stimulated B-cells from donor 129 & 130
Figure 12:
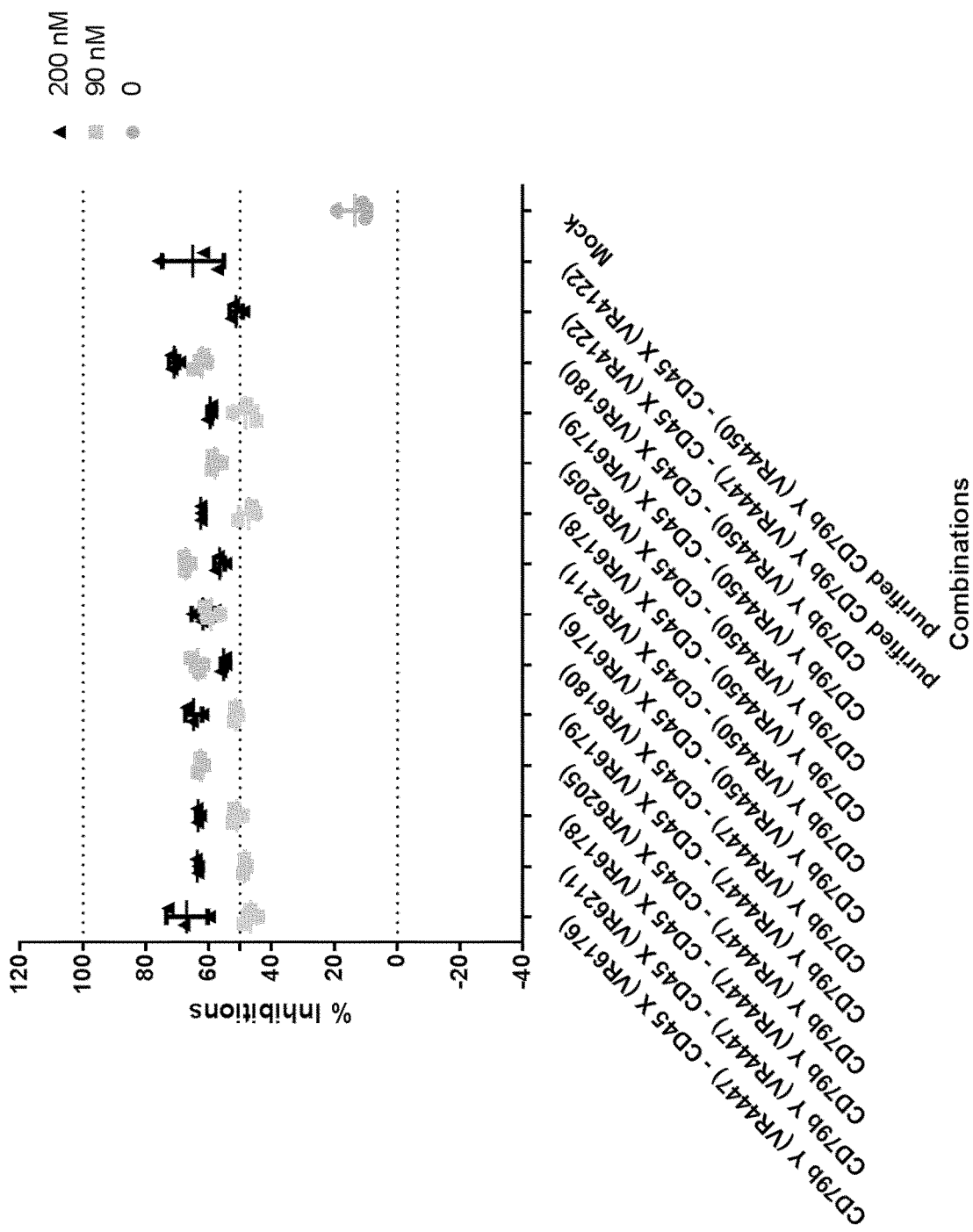
Figure 13:
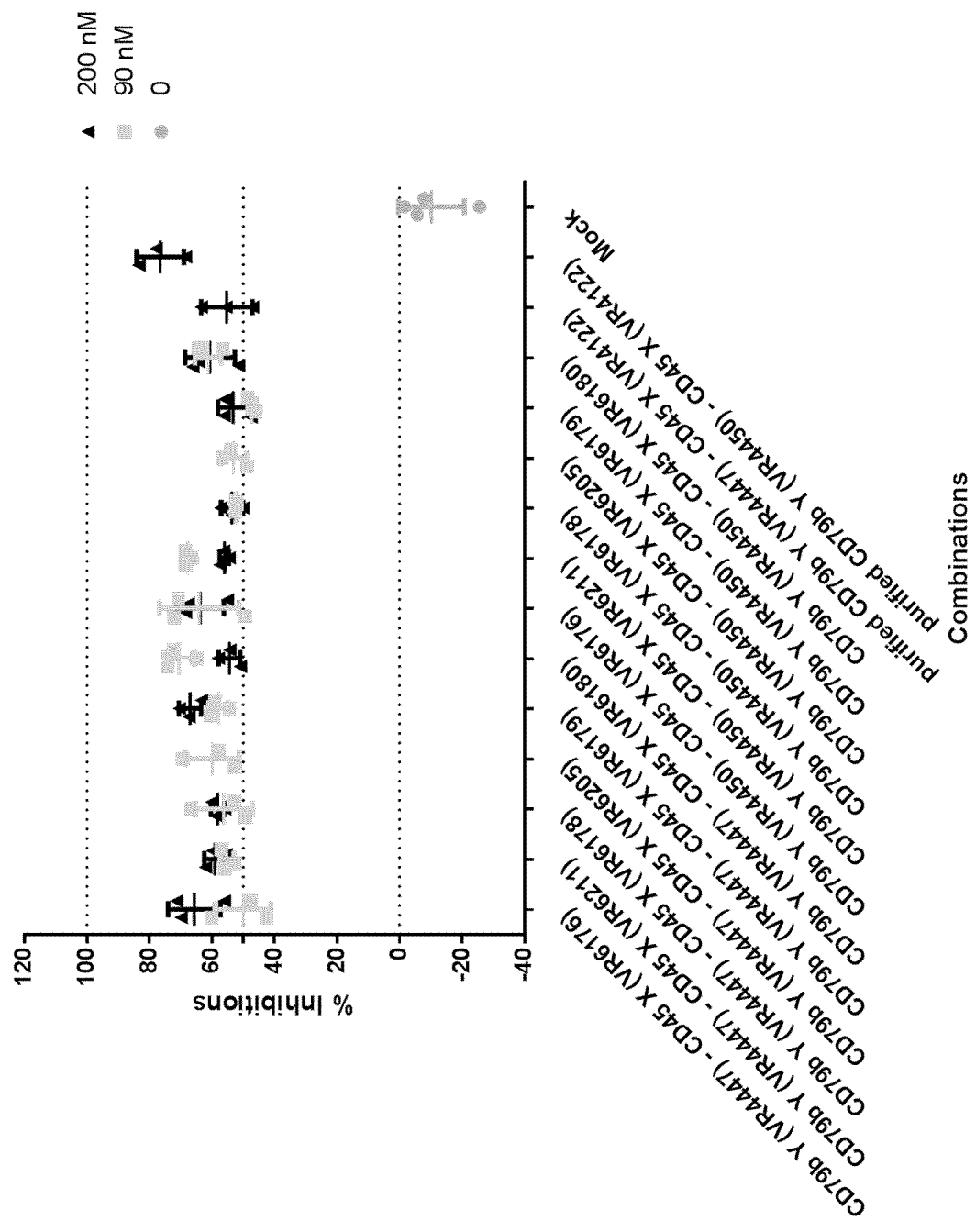
FIGS. 13 & 14 shows inhibition of p38 (+/−SD) by purified CD79b-CD45 (transiently expressed) on IgM stimulated B-cells from donor 129 & 130
Figure 14:
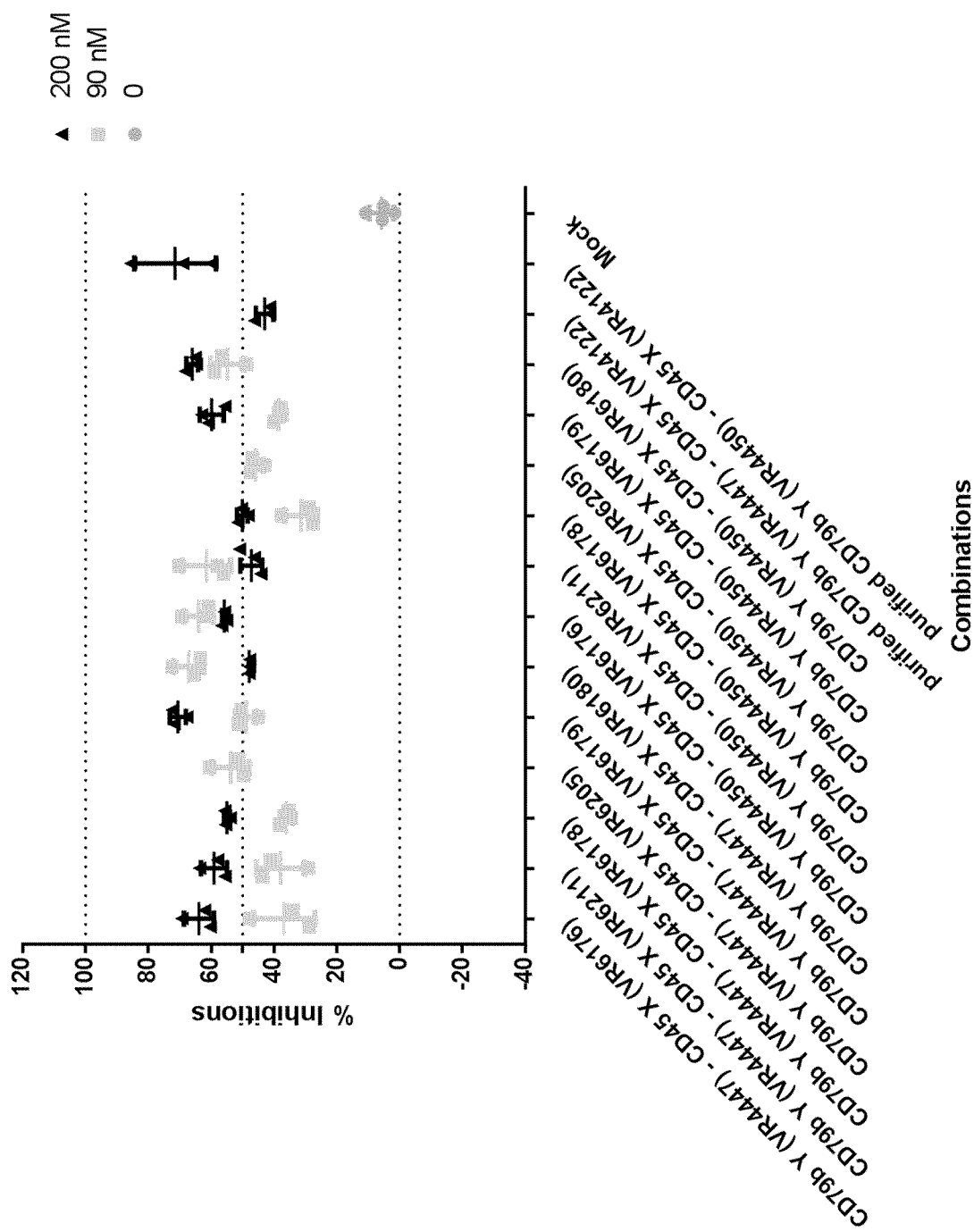
Figure 15:
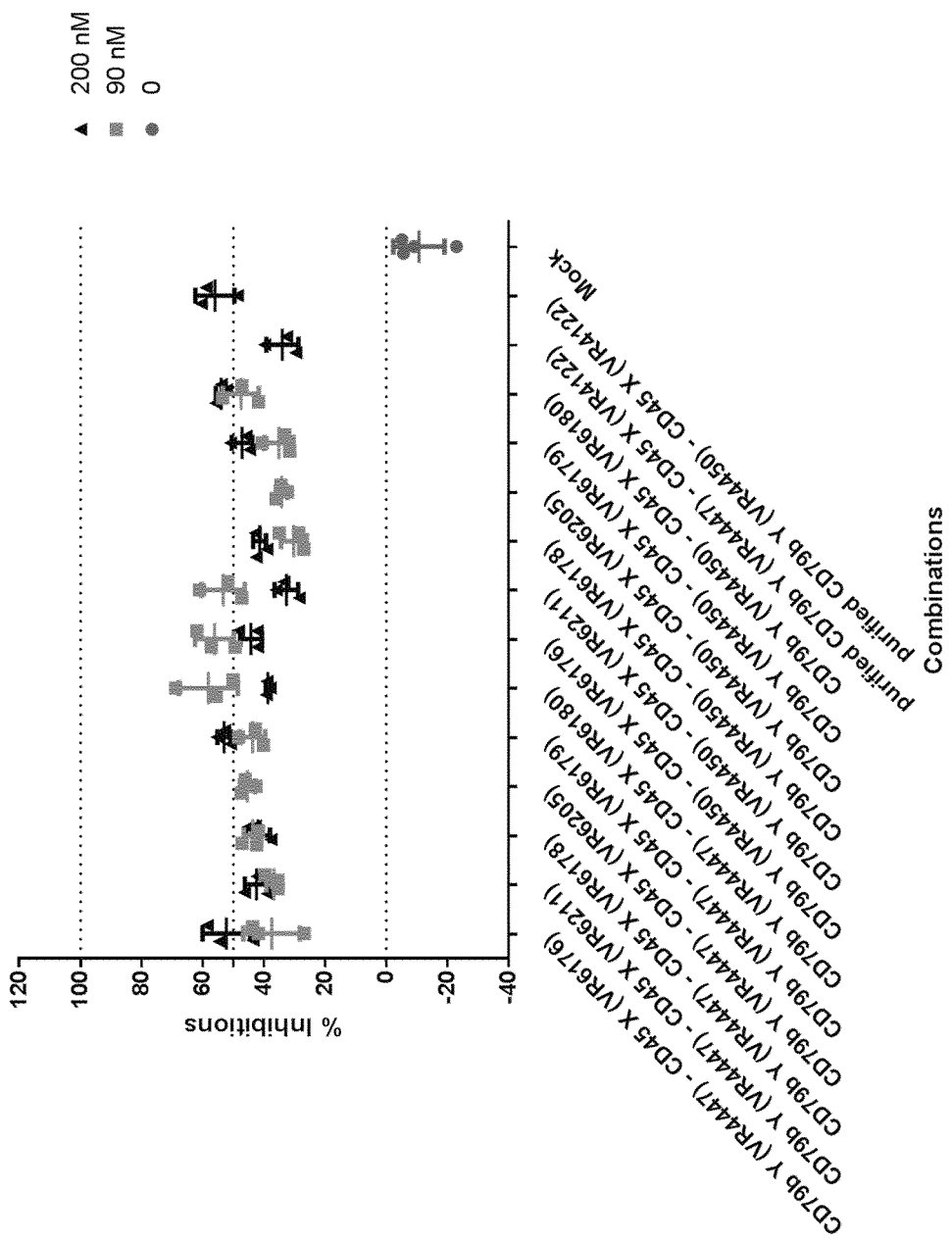
FIGS. 15 & 16 shows inhibition of Akt (+/−SD) by purified CD79b-CD45 (transiently expressed) on IgM stimulated B-cells from donor 129 & 130
Figure 16:
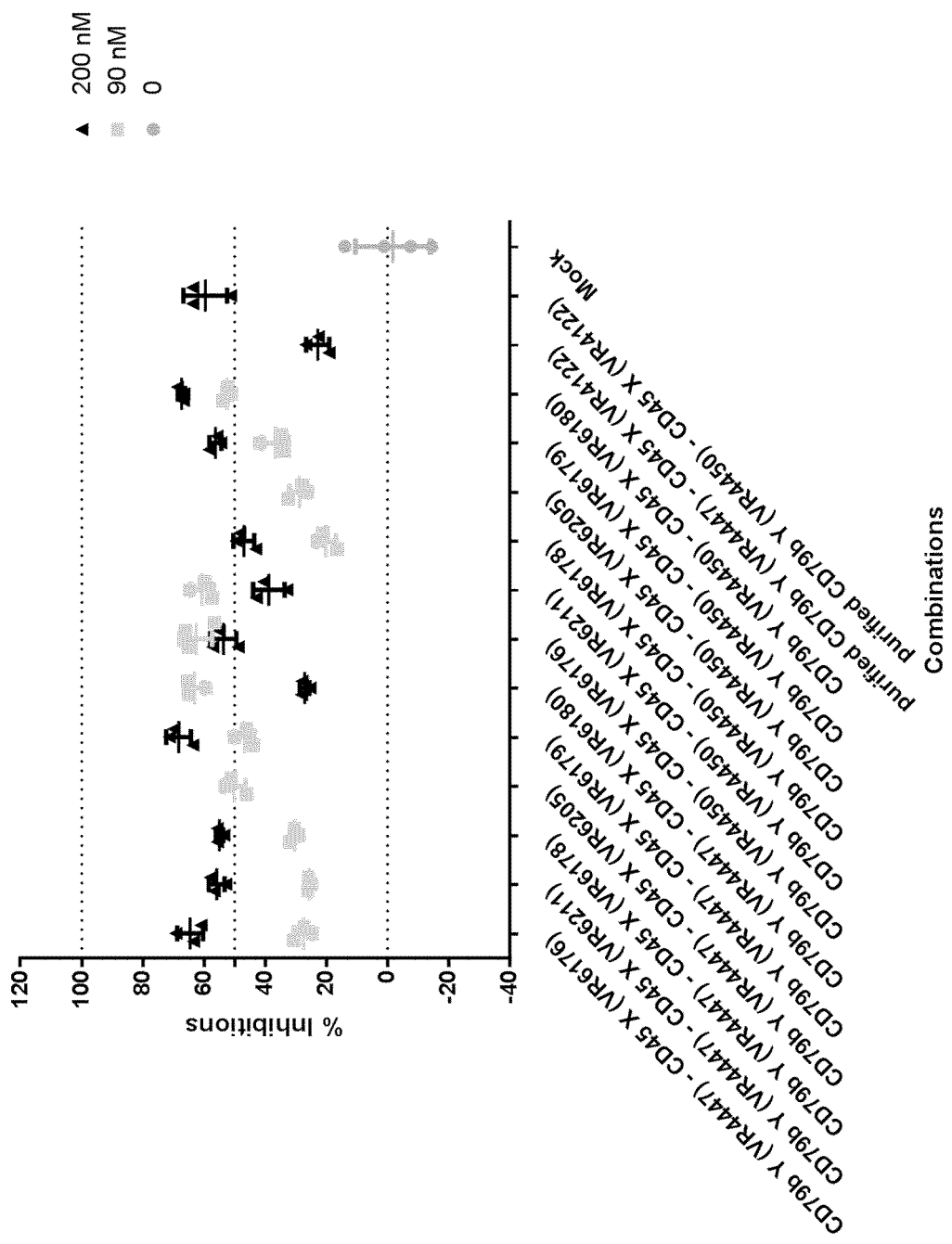

"Multispecific molecule" as employed herein refers to a molecule with the ability to specifically bind at least two distinct antigens, for example different antigens. In one embodiment the multispecific molecule is a bispecific, trispecific or tetraspecific molecule, in particular a bispecific molecule or trispecific molecule.

Thus in one aspect the disclosure extends to a molecule of a suitable format specific to at least CD45 and CD79a and to use of antibodies/fragments or combinations thereof specific to CD45 and CD79a in a multispecific molecule, such as a bispecific format or trispecific format.

Thus in one aspect the disclosure extends to a molecule of a suitable format specific to at least CD45 and CD79b and to use of antibodies/fragments or combinations thereof specific to CD45 and CD79b in a multispecific molecule, such as a bispecific format or trispecific format.

Thus in one aspect the disclosure extends to a molecule of a suitable format specific to at least CD45 and CD79a/b complex and to use of antibodies/fragments or combinations thereof specific to CD45 and CD79a/b complex in a multispecific molecule, such as a bispecific format or trispecific format.

In one embodiment the molecule of the present disclosure is trispecific, for example where the third binding domain is capable of extending the half-life of the molecule, for example by binding a serum carrier protein.

A variety of proteins exist in plasma and include thyroxine-binding protein, transthyretin, al-acid glycoprotein, transferrin, fibrinogen and albumin, or a fragment of any thereof (Bartalena & Robbins, 1993, Clinics in Lab. Med. 13:583-598; Bree et al., 1986, Clin. Pharmacokin. 11:336-342; Gitlin et al. 1964, J. Clin. Invest. 10:1938-1951; Peters, 1985, Adv Protein Chem. 37:161-245; Waldeman & Strober, 1969, Progr. Allergy, 13:1-110. In on example the third binding domain is specific to serum albumin, for example human serum albumin.

Multispecific Molecule Formats

Examples of suitable multispecific molecules are known in the art, for example as disclosed in the review "The coming of Age of Engineered Multivalent Antibodies, Nunez-Prado et al Drug Discovery Today Vol 20 Number 5 Mar. 2015, page 588-594, D. Holmes, Nature Rev Drug Disc November 2011:10; 798, Chan and Carter, Nature Reviews Immunology vol 10, May 2010, 301 incorporated herein by reference.

In one embodiment multispecific formats include those known in the art and those described herein, such as wherein the molecule format is selected from the group comprising or consisting of:

tandem sdAb, tandem sdAb-sdAb (three sdAbs);

(scFv)$_2$ (also referred to as tandem scFv), scFv-dsFv, dsscFv-dsFv (dsFv)$_2$;

diabody, dsdiabody, didsdiabody, scdiabody, dsscdiabody, didsscdiabody;

Dart antibody i.e, VL$_1$ linker VH$_2$ linker and VH$_1$ linker VL$_2$ wherein the C-terminous of VH$_1$ and VH$_2$ are joined by a disulfide bond;

BITE, dsBiTE, didsBiTE;

Di-diabody (see Nunez-Prado et al in particular molecule number 25 in FIG. 1 therein), dsdi-diabody, didsdi-diabody;

triabody, dstriabody, didstriabody, tridstriabody;

tetrabodies, dstetrabody, didstetrabody, tridstetrabody, tetradstetrabody;

tandab (see Nunez-Prado et al in particular molecule number 22 in FIG. 1 therein); dstandab, didstandab, tridstandab, tetradstandab;

[sc(Fv)$_2$]$_2$, (see Nunez-Prado et al in particular molecule number 22 in FIG. 1 therein), ds[sc(Fv)$_2$]$_2$, dids[sc(Fv)$_2$]$_2$, trids[sc(Fv)$_2$]$_2$, tetrads[sc(Fv)$_2$]$_2$, Pentabody (see Nunez-Prado et al in particular molecule number 27 in FIG. 1 therein);

Fab-scFv (also referred to as a bibody), Fab'scFv, FabdsscFv (or BYbe), Fab'dsscFv;

tribody, dstribody, didstribody (also referred to as Fab-didsscFv or TrYbe or Fab-(dsscFv)$_2$), Fab'didsscFv;

Fabdab, FabFv, Fab'dab, Fab'Fv;

Fab single linker Fv (also referred to herein as FabdsFv as disclosed in WO2014/096390), Fab' single linker Fv (also referred to herein as Fab'dsFv);

FabscFv single linker Fv, Fab'scFv single linker Fv;

FabdsscFv single linker Fv, Fab'dsscFv single linker Fv; FvFabFv, FvFab'Fv, dsFvFabFv, dsFvFab'Fv, FvFabdsFv, FvFab'dsFv, dsFvFabdsFv, dsFvFab'dsFv, FabFvFv, Fab'FvFv, FabdsFvFv, Fab'dsFvFv, FabFvdsFv, Fab'FvdsFv, FabdsFvdsFv, Fab'dsFvdsFv, diFab, diFab' including a chemically conjugated diFab', (FabscFv)$_2$, (Fab)$_2$scFvdsFv, (Fab)$_2$dsscFvdsFv, (FabdscFv)$_2$, (Fab'scFv)$_2$, (Fab')$_2$scFvdsFv, (Fab')$_2$dsscFvdsFv, (Fab'dscFv)$_2$, $V_HHC_K$ (see Nunez-Prado et al in particular molecule number 6 in FIG. 1 therein);

minibody, dsminibody, didsminibody, a miniantibody (ZIP) [see Nunez-Prado et al in particular molecule number 7 in FIG. 1 therein], dsminiantibody (ZIP) and didsminiantibody (ZIP);

tribi-minibody [see Nunez-Prado et al in particular molecule number 15 in FIG. 1 therein] dstribi-minibody, didstribi-minibody, tridstribi-minibody;

diabody-$CH_3$, dsdiabody-$CH_3$, didsdiabody-$CH_3$, scdiabody-$CH_3$, dsscdiabody-$CH_3$, didsscdiabody-$CH_3$, tandemscFv-$CH_3$, tandemdsscFv-$CH_3$, tandemdidsscFv-$CH_3$, tandemtridsscFv-$CH_3$, tandemtetradsscFv-$CH_3$, scFv-Fc (also referred to herein as a (scFvCH$_2$CH$_3$)$_2$) as described in WO2008/012543 and a single chain version thereof, dsscFvscFv-Fc, dsscFv-Fc (also referred to herein as (dsscFvCH$_2$CH$_3$)$_2$), scFv-dsFv-Fc, dsscFv-dsFv-Fc, dsFv-Fc (also referred to herein a (dsFvCH$_2$CH$_3$)$_2$), scorpion molecule (Trubion) i.e. a binding domain, linker —CH$_2$CH$_3$ binding domain as described in U.S. Pat. No. 8,409,577;

SMIP (Trubion) i.e. (scFv-CH$_2$CH$_3$)$_2$;

(dsFvCH$_2$CH$_3$)$_2$, tandem scFv-Fc, tandem dsscFvscFv-Fc, tandem dsscFv-Fc, scFv-Fc-scFv, dsscFv-Fc-scFv, scFv-Fc-dsscFv, diabody-Fc, dsdiabody-Fc, didsdiabody-Fc, triabody-Fc, dstriabody-Fc, didstriabody-Fc, tridstriabody-Fc, tetrabody-Fc, dstetrabody-Fc, didstetrabody-Fc, tridstetrabody-Fc, tetradstetrabody-Fc, dstetrabody-Fc, didstetrabody-Fc, tridstetrabody-Fc, tetradstetrabody-Fc, scdiabody-Fc, dsscdiabody, didsscdiabody;

bi or trifunctional antibody, for example with different heavy chain variable regions and common light chains for example Merus bispecific antibody format (BICLONICS) with common light chains of a fixed sequence and different heavy chains (including different CDRs) and engineered CH$_3$ domain to drive the dimerization o the different heavy chains, Duobody (i.e. wherein one full length chain in the antibody has different specificity to the other full length chain in the antibody);

a full-length antibody wherein Fab arm exchange has been employed to create a bispecific format;

bi or tri functional antibody, wherein a full-length antibody has common heavy chain and different light chains also referred to as kappa/lambda body 'or' κ/λ-body, see for example WO2012/023053 incorporated herein by reference;

Ig-scFv one, two, three or four from the C terminus of heavy or light chain, scFv-Ig one, two, three or four from the N terminus of heavy or light chain, single linker Ig-Fv, Ig-dsscFv one, two, three or four from the C terminus of heavy or light chain (with one, two, three or four disulfide bonds);

Ig-dsscFv one, two, three or four from the N terminus of heavy or light chain (with one, two, three or four disulfide bonds), Ig single linker Fv (see PCT/EP2015/064450), Ig-dab, dab-Ig, scFv-Ig, V-Ig, Ig-V, scFabFvFc, scFabdsFvFc (single linker version scFavFv), (FabFvFc)$_2$, (FabdsFvFc)$_2$, scFab'FvFc, scFab'dsFvFc, (Fab'FvFc)$_2$, (Fab'dsFvFc)$_2$ and DVDIg, which are discussed in more detail below.

In one embodiment multispecific molecule formats include those known in the art and those described herein, such as wherein the molecule format is selected from the group comprising or consisting of: diabody, scdiabody, triabody, tribody, tetrabodies, tandem scFv, FabFv, Fab'Fv, FabdsFv, Fab-scFv, Fab-dsscFv, Fab-(dsscFv)2, diFab, diFab', tandem scFv-Fc, scFv-Fc-scFv, scdiabody-Fc, scdiabody-CH$_3$, Ig-scFv, scFv-Ig, V-Ig, Ig-V, Duobody and DVDIg, which are discussed in more detail below.

In one embodiment the multispecific antibody molecule of the present disclosure does not comprise an Fc domain i.e. does not comprise a CH2 and CH3 domain, for example the molecule is selected from the group comprising a tandem scFv, scFv-dsFv, dsscFv-dsFv didsFv, diabody, dsdiabody, didsdiabody, scdiabody (also referred to as an (scFv)2), dsscdiabody, triabody, dstriabody, didstriabody, tridstriabody, tetrabodies, dstetrabody, didstetrabody, tridstetrabody, tetradstetrabody, tribody, dstribody, didstribody, Fabdab, FabFv, Fab'dab, Fab'Fv, Fab single linker Fv (as disclosed in WO2014/096390), Fab' single linker Fv, FabdsFv, Fab'dsFv, Fab-scFv (also referred to as a bibody), Fab'scFv, FabdsscFv, Fab'dsscFv, FabdidsscFv, Fab'didsscFv, FabscFv single linker Fv, Fab'scFv single linker Fv, FabdsscFvs single linker Fv, Fab'dsscFv single linker Fv, FvFabFv, FvFab'Fv, dsFvFabFv, dsFvFab'Fv, FvFabdsFv, FvFab'dsFv, dsFvFabdsFv, dsFvFab'dsFv, FabFvFv, Fab'FvFv, FabdsFvFv, Fab'dsFvFv, FabFvdsFv, Fab'FvdsFv, FabdsFvdsFv, Fab'dsFvdsFv, diFab, diFab' including a chemically conjugated diFab', (FabscFv)$_2$, (Fab)$_2$scFvdsFv, (Fab)$_2$dsscFvdsFv, (FabdscFv)$_2$, minibody, dsminibody, didsminibody, diabody-CH$_3$, dsdiabody-CH$_3$, didsdiabody-CH$_3$, scdiabody-CH$_3$, dsscdiabody-CH$_3$, didsscdiabody-CH$_3$, tandemscFv-CH$_3$, tandemdsscFv-CH$_3$, tandemdidsscFv-CH$_3$, tandemtridsscFv-CH$_3$ and tandemtetradsscFv-CH$_3$.

In one embodiment the molecule of the present disclosure does not comprise an Fc domain.

In one embodiment the molecule of the present disclosure comprises an altered Fc domain as described herein below.

Fc domain as employed herein generally refers to —(CH$_2$CH$_3$)$_2$, unless the context clearly indicates otherwise.

In one embodiment the molecule of the present disclosure does not comprise a —CH$_2$CH$_3$ fragment.

In one embodiment the molecule of the present disclosure does not comprise a CH$_2$ domain.

In one embodiment the molecule of the present disclosure does not comprise a CH$_3$ domain.

Molecule as employed herein is used in the biochemistry sense to refer to a group of atoms that form an organic, in particular proteinaceous mass, which includes a complex suitable for handling as a single entity under appropriate conditions once the complex has been formed, for example a complex formed by two or more polypeptide chains.

Molecule and construct are used interchangeably herein, unless the context indicates otherwise. Although, construct may be employed more often to refer to a polynucleotide molecule and molecule may be employed more often to refer an entity primarily comprising an amino acid sequence.

Specificity (or specific) as employed herein refers to where the partners in the interaction only recognise each other or have significantly higher affinity for each other in comparison to non-partners, for example at least 2, 3, 4, 5, 6, 7, 8, 9, 10 times higher affinity, than for example a background level of binding or binding to another unrelated protein.

A 'binding domain' as employed herein refers to a binding region, typically a polypeptide, capable of binding a target antigen, for example with sufficient affinity to characterise the domain as specific for the antigen.

Any suitable binding domains may be used in the multi-specific molecules of the present invention. These may be derived from any suitable source.

In one embodiment a biocompatible framework structure is used in a binding domain of the molecules of the present disclosure and such structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendramisat domains may be used (See for example, Nygren and Uhlen, 1997, Current Opinion in Structural Biology, 7, 463-469).

The term 'multi-specific molecules' as used herein may also include binding agents based on biological scaffolds including Adnectins, Affibodies, Darpins, Phylomers, Avimers, Aptamers, Anticalins, Tetranectins, Microbodies, Affilins and Kunitz domains.

The multispecific molecule of the present invention is typically a multispecific antibody molecule, ie. at least one or more of the binding domains of the multispecific molecule are derived from an antibody or fragment thereof.

Where the binding domain is derived from an antibody, a "binding domain or site" as employed herein is the part of the antibody that contacts the antigen. In one embodiment the binding domain contains at least one variable domain or a derivative thereof, for example a pair of variable domains or derivatives thereof, such as a cognate pair of variable domains or a derivative thereof. Typically this is a VH/VL pair.

Variable regions (also referred to herein as variable domains) generally comprise 3 CDRs and a suitable framework. In one embodiment the binding domain comprises two variable regions, a light chain variable region and a heavy chain variable region and together these elements contribute to the specificity of the binding interaction of the antibody or binding fragment.

A "cognate pair" as employed herein refers to a heavy and light chain pair of variable domains (or a derivative thereof, such as a humanised version thereof) isolated from a host as a pre-formed couple. This definition does not include variable domains isolated from a library, wherein the original pairing from a host is not retained. Cognate pairs may be advantageous because they are often affinity matured in the host and therefore may have higher affinity for the antigen to which they are specific, than a combination of variable domain pairs selected from a library, such as phage library.

A "derivative of a naturally occurring domain" as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained. Examples of modifications are those to remove glycosylation sites, GPI anchors, or solvent exposed lysines. These modifications can be achieved by replacing the relevant amino acid residues with a conservative amino acid substitution.

Other modification in the CDRs may, for example include replacing one or more cysteines with, for example a serine residue. Asn can be the substrate for deamination and this propensity can be reduced by replacing Asn and/or a neighbouring amino acid with an alternative amino acid, such as a conservative substitution. The amino acid Asp in the CDRs may be subject to isomerization. The latter can be minimized by replacing Asp and/or a neighboring amino acid with an alternative amino acid, for example a conservative substitution.

Humanised versions of a variable region are also a derivative thereof, in the context of the present specification. Humanisation may include the replacement of a non-human framework for a human framework and optionally the back-mutation of one or more residues to "donor residues". Donor residues as employed herein refers to residues found in the original variable region isolated from the host, in particular replacing a given amino acid in the human framework with the amino acid in the corresponding location in the donor framework.

In one embodiment, the binding domain or each binding domain is part of (included or incorporated in) an antibody or an antibody fragment.

In one embodiment the binding domains in the molecules of the present disclosure are in immunoglobulin/antibody molecules.

As used herein "antibody molecule" includes antibodies and binding fragments thereof.

In one embodiment the term "antibody" as used herein refers to an immunoglobulin molecule capable of specific binding to a target antigen, such as a carbohydrate, polynucleotide, lipid, polypeptide, peptide etc., via at least one antigen recognition site (also referred to as a binding site or binding domain herein), located in the variable region of the immunoglobulin molecule. "Antibody fragments" as employed herein refer to antibody binding fragments including but not limited to Fab, modified Fab, Fab', modified Fab', F(ab')2, Fv, single domain antibodies, scFv, Fv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217).

A "binding fragment" as employed herein refers to a fragment capable of binding a target peptide or antigen with sufficient affinity to characterise the fragment as specific for the peptide or antigen The methods for creating and manufacturing these antibody fragments are well known in the art (see for example Verma et al., 1998, Journal of Immunological Methods, 216:165-181). Other antibody fragments for use in the present disclosure include the Fab and Fab' fragments described in WO05/003169, WO05/003170 and WO05/003171. Multi-valent antibodies may comprise multiple specificities e.g. bispecific or may be monospecific (see for example WO92/22853, WO05/113605, WO2009/040562 and WO2010/035012).

The term "Fab fragment" as used herein refers to an antibody fragment comprising a light chain fragment comprising a $V_L$ (variable light) domain and a constant domain of a light chain ($C_L$), and a $V_H$ (variable heavy) domain and a first constant domain ($CH_1$) of a heavy chain. The Fv refers to two variable domains, for example co-operative variable domains, such as a cognate pair or affinity matured variable domains, i.e. a $V_H$ and $V_L$ pair.

Co-operative variable domains as employed herein are variable domains that complement each other and/or both contribute to antigen binding to render the Fv ($V_H/V_L$ pair) specific for the antigen in question.

"Single domain antibody" (also referred to herein as a dab and sdAb) as used herein refers to an antibody fragment consisting of a single monomeric variable antibody domain. Examples of single domain antibodies include $V_H$ or $V_L$ or $V_H H$.

Tandem-sdAb as employed herein refers to two domain antibodies connected by a linker, for example a peptide linker, in particular where the domain antibodies have specificity for different antigens.

Tandem-sdAb-sdAb as employed herein refers to three domain antibodies connected in series by two linkers, for example peptide linkers, in particular where the domain antibodies have specificity for different antigens.

dsFv as employed herein refers to an Fv with an intra-variable disulfide bond. The dsFv may be a component of a larger molecule, for example the one of the variable domains may be linked, for example via an amino acid linker to another antibody fragment/component.

$(dsFv)_2$ as employed herein refers to a dsFv with one domain linked, for example via a peptide linker or a disulfide bond (for example between, the C-terminus of two $V_H$'s) to a domain in a second dsFv, the format resembles a $(scFv)_2$ described below but each pair of variable regions comprise a intra-variable region disulfide bond.

Component as employed herein refers to a building block or portion of a multispecific molecule of the present disclosure, in particular where the component is an antibody fragment such as scFv, Fab or other fragment, in particular as described herein.

Single-chain Fv or abbreviated as "scFv", as used herein refers to an antibody fragment that comprises $V_H$ and $V_L$ antibody domains linked (for example by a peptide linker) to form a single polypeptide chain. The constant regions of the heavy and light chain are omitted in this format.

dsscFv as employed herein refers to scFv with an intra-variable region disulfide bond.

Tandem scFv (also referred to herein as a discFv or $(scFv)_2)$) as employed herein refers to two scFvs linked via a single linker such that there is a single inter-Fv linker, for example as shown in FIG. 5b.

Tandem dsscFv (also referred to herein as a scFvdsscFv or dsscFvscFv) as employed herein refers to two scFvs linked via a single linker such that there is a single inter-Fv linker, for example as shown in FIG. 5b, and wherein one of the scFv has an intravariable region disulfide bond.

Tandem didsscFv (also referred to herein as a didsscFv) as employed herein refers to two scFvs linked via a single linker such that there is a single inter-Fv linker, for example as shown in FIG. 5b, and wherein each scFv comprises an intravariable region disulfide bond.

scFv-dsFv as employed herein is a scFv linked, for example by a peptide linker, to an Fv domain which is comprised of two variable domains linked via a disulfide bond to form a dsFv. In this format the VH or VL of the scFv may be linked to the VH or VL of the dsFv.

dsscFv-dsFv as employed herein is a dsscFv linked, for example by a peptide linker, to an Fv domain which is comprised of two variable domains linked via a disulfide bond to form a dsFv. In this format the VH or VL of the dsscFv may be linked to the VH or VL of the dsFv.

Diabody as employed herein refers to two Fv pairs $V_H/V_L$ and a further $V_H/V_L$ pair which have two inter-Fv linkers, such that the $V_H$ of a first Fv is linked to the $V_L$ of the second Fv and the $V_L$ of the first Fv is linked to the $V_H$ of the second Fv.

dsDiabody as employed herein refers to a diabody comprising an intra-variable region disulfide bond.

didsDiabody as employed herein refers to a diabody comprising two intra-variable region disulfide bonds, i.e. one ds between each pair of variable regions.

Sc-diabody as employed herein refers a diabody comprising an intra-Fv linker, such that the molecule comprises three linkers and forms two normal scFvs, for example $VH_1$ linker$VL_1$ linker $VH_2$ linker $VL_2$.

dssc-diabody as employed herein refers to a sc-diabody with an intra-variable region disulfide bond.

didssc-diabody as employed herein refers to a sc-diabody with an intra-variable region disulfide bond between each pair of variable regions.

Dart as employed herein refers to $VL_1$ linker $VH_2$ linker and $VH_1$ linker $VL_2$ wherein the C-terminous of $VH_1$ and $VH_2$ are joined by a disulfide bond Paul A. Moore et al Blood, 2011; 117(17):4542-4551.

BITE as employed herein refers to a molecule comprising two pairs of variable domains in the following format; a domain from pair 1 (eg $VH_1$) connected via a linker to a domain from pair 2 (eg $VH_2$ or $VL_2$) said second domain connected by a linker to the further domain from pair 1 (eg $VL_1$) in turn connected to the remaining domain from pair two (i.e $VL_2$ or $VH_2$).

Di-diabody see Nunez-Prado et al in particular molecule number 25 in FIG. 1 therein.

Dsdi-diabody as employed herein is a di-diabody with an intra-variable region disulfide bond.

Didsdi-diabody as employed herein is a di-diabody with an intra-variable region disulfide bond between each pair of variable regions.

Triabody as employed herein refers to a format similar to the diabody comprising three Fvs and three inter-Fv linkers.

dstriabody as employed herein refers to a triabody comprising an intra-variable region disulfide bond between one of the variable domain pairs.

Didstriabody as employed herein refers to a triabody comprising two intra-variable region disulfide bonds, i.e. one ds between each of two variable domain pairs.

Tridstriabody as employed herein refers to a triabody comprising three intra-variable region disulfide bonds i.e. one ds between each pair of variable regions.

Tetrabody as employed herein refers to a format similar to the diabody comprising four Fvs and four inter-Fv linkers.

dstetrabody as employed herein refers to a tetrabody comprising an intra-variable region disulfide bond between one of the variable domain pairs.

Didstetrabody as employed herein refers to a tetrabody comprising two intra-variable region disulfide bonds, i.e. one ds between each of two variable domain pairs.

Tridstetrabody as employed herein refers to a tetrabody comprising three intra-variable region disulfide bonds i.e. one ds between each of three pairs of variable regions.

Tetradstetrabody as employed herein refers to a tetrabody comprising four intra-variable region disulfide bonds i.e. one ds between each variable domain.

Tribody (also referred to a $Fab(scFv)_2$) as employed herein refers to a Fab fragment with a first scFv appended to the C-terminal of the light chain and a second scFv appended to the C-terminal of the heavy the chain.

dstribody as employed herein refers to a tribody comprising a dsscFv in one of the two positions.

didstribody or TrYbe as employed herein refers to a tribody comprising two dsscFvs.

dsFab as employed herein refers to a Fab with an intra-variable region disulfide bond.

dsFab' as employed herein referst to a Fab' with an intra-variable region disulfide bond.

scFab is a single chain Fab fragment.

scFab' is a single chain Fab' fragment.

dsscFab is a dsFab as a single chain.

dsscFab' is a dsFab' as a single chain.

Fabdab as employed herein refers to a Fab fragment with a domain antibody appended to the heavy or light chain thereof, optionally via a linker.

Fab'dab as employed herein refers to a Fab' fragment with a domain antibody appended to the heavy or light chain thereof, optionally via a linker.

FabFv as employed herein refers to a Fab fragment with an additional variable region appended to the C-terminal of each of the following, the CH1 of the heavy chain and CL of the light chain see for example WO2009/040562. The format may be provided as a PEGylated version thereof see for example WO2011/061492, Fab'Fv as employed herein is similar to FabFv, wherein the Fab portion is replaced by a Fab'. The format may be provided as a PEGylated version thereof.

FabdsFv as employed herein refers to a FabFv wherein an intra-Fv disulfide bond stabilises the appended C-terminal variable regions, see for example WO2010/035012. The format may be provided as a PEGylated version thereof.

Fab single linker Fv and Fab' single linker as employed herein refers to a Fab or Fab' fragment linked to a variable domain, for example by a peptide linker, and said variable domain is linked to a second variable domain via an intra-variable domain disulfide bond thereby forming a dsFv, see for example WO2014/096390.

Fab-scFv (also referred to as a bibody) as employed herein is a Fab molecule with a scFv appended on the C-terminal of the light or heavy chain, optionally via a linker.

Fab'-scFv as employed herein is a Fab' molecule with a scFv appended on the C-terminal of the light or heavy chain, optionally via a linker.

FabdsscFv or BYbe as employed herein is a FabscFv with a disulfide bond between the variable regions of the single chain Fv.

Fab'dsscFv as employed herein is a Fab'scFv with a disulfide bond between the variable regions of the single chain Fv.

FabscFv-dab as employed herein refers to a Fab with a scFv appended to the C-terminal of one chain and domain antibody appended to the C-terminal of the other chain.

Fab'scFv-dab as employed herein refers to a Fab' with a scFv appended to the C-terminal of one chain and domain antibody appended to the C-terminal of the other chain.

FabdsscFv-dab as employed herein refers to a Fab with a dsscFv appended to the C-terminal of one chain and domain antibody appended to the C-terminal of the other chain.

Fab'dsscFv-dab as employed herein refers to a Fab' with a dsscFv appended to the C-terminal of one chain and domain antibody appended to the C-terminal of the other chain.

FabscFv single linker Fv as employed herein refers to a Fab single linker Fv wherein a domain of the Fv is linked to the heavy or light chain of the Fab and a scFv is linked to the other Fab chain and the domains of the Fv are connected by an intra-variable region disulfide.

FabdsscFv single linker Fv as employed herein refers to a FabscFv single linker Fv wherein the scFv comprises an intra-variable region disulfide bond.

Fab'scFv single linker Fv as employed herein refers to a Fab' single linker Fv wherein a domain of the Fv is linked to the heavy or light chain of the Fab and a scFv is linked to the other Fab chain and the domains of the Fv are connected by an intra-variable region disulfide.

Fab'dsscFv single linker Fv as employed herein refers to a Fab'scFv single linker Fv wherein the scFv comprises an intra-variable region disulfide bond.

FvFabFv as employed herein refers to a Fab with the domains of a first Fv appended to the N-terminus of the heavy and light chain of the Fab and the domains of a second Fv appended to the C-terminus of the heavy and light chain.

FvFab'Fv as employed herein refers to a Fab' with the domains of a first Fv appended to the N-terminus of the heavy and light chain of the Fab' and the domains of a second Fv appended to the C-terminus of the heavy and light chain.

dsFvFabFv as employed herein refers to a Fab with the domains of a first Fv appended to the N-terminus of the heavy and light chain of the Fab wherein the first Fv comprises an intra-variable region disulfide bond and the domains of a second Fv appended to the C-terminus of the heavy and light chain.

FvFabdsFv as employed herein refers to a Fab with the domains of a first Fv appended to the N-terminus of the heavy and light chain of the Fab and the domains of a second Fv appended to the C-terminus of the heavy and light chain and wherein the second Fv comprises an intra-variable region disulfide bond.

dsFvFab'Fv as employed herein refers to a Fab' with the domains of a first Fv appended to the N-terminus of the heavy and light chain of the Fab' wherein the first Fv comprises an intra-variable region disulfide bond and the domains of a second Fv appended to the C-terminus of the heavy and light chain.

FvFab'dsFv as employed herein refers to a Fab' with the domains of a first Fv appended to the N-terminus of the heavy and light chain of the Fab' and the domains of a second Fv appended to the C-terminus of the heavy and light chain and wherein the second Fv comprises an intra-variable region disulfide bond.

dsFvFabdsFv as employed herein refers to a Fab with the domains of a first Fv appended to the N-terminus of the heavy and light chain of the Fab wherein the first Fv comprises an intra-variable region disulfide bond and the domains of a second Fv appended to the C-terminus of the heavy and light chain and wherein the second Fv also comprises an intra-variable region disulfide bond.

dsFvFab'dsFv as employed herein refers to a Fab' with the domains of a first Fv appended to the N-terminus of the heavy and light chain of the Fab' wherein the first Fv comprises an intra-variable region disulfide bond and the domains of a second Fv appended to the C-terminus of the heavy and light chain and wherein the second Fv also comprises an intra-variable region disulfide bond.

FabFvFv as employed herein refers to a Fab fragment with two pairs of Fvs appended in series to the C-terminal of the heavy and light chain, see for example WO2011/086091.

Fab'FvFv as employed herein refers to a Fab' fragment with two pairs of Fvs appended in series to the C-terminal of the heavy and light chain, see for example WO2011/086091.

FabdsFvFv as employed herein refers to a Fab fragment with two pairs of Fvs appended in series to the C-terminal of the heavy and light chain, see for example WO2011/086091, wherein the first Fv pair attached directly to the C-terminal comprise an intra-variable region disulfide bond.

Fab'dsFvFv as employed herein refers to a Fab' fragment with two pairs of Fvs appended in series to the C-terminal of the heavy and light chain, see for example WO2011/086091, wherein the first Fv pair attached directly to the C-terminal comprise an intra-variable region disulfide bond.

FabFvdsFv as employed herein refers to a Fab fragment with two pairs of Fvs appended in series to the C-terminal of the heavy and light chain, wherein the second Fv pair at the "C"-terminal of the molecule comprise an intra-variable region disulfide bond.

Fab'FvdsFv as employed herein refers to a Fab' fragment with two pairs of Fvs appended in series to the C-terminal of the heavy and light chain, wherein the second Fv pair at the "C"-terminal of the molecule comprise an intra-variable region disulfide bond.

FabdsFvdsFv as employed herein refers to a Fab fragment with two pairs of Fvs appended in series to the C-terminal of the heavy and light chain, wherein the first and second Fv pair comprise an intra-variable region disulfide bond.

Fab'dsFvdsFv as employed herein refers to a Fab' fragment with two pairs of Fvs appended in series to the C-terminal of the heavy and light chain, wherein the first and second Fv comprise an intra-variable region disulfide bond.

DiFab as employed herein refers to two Fab molecules linked via their C-terminus of the heavy chains.

DiFab' as employed herein refers to two Fab' molecules linked via one or more disulfide bonds in the hinge region thereof.

DiFab and DiFab' molecules include chemically conjugated forms thereof.

(FabscFv)$_2$ as employed herein refers to a diFab molecule with two scFvs appended thereto, for example appended to the C-terminal of the heavy or light chain, such as the heavy chain.

(Fab'scFv)$_2$ as employed herein refers to a diFab' molecule with two scFvs appended thereto, for example appended to the C-terminal of the heavy or light chain, such as the heavy chain.

(Fab)$_2$scFvdsFv as employed herein refers to a diFab with a scFv and dsFv appended, for example one from each of the heavy chain C-terminal.

(Fab')$_2$scFvdsFv as employed herein refers to a diFab' with a scFv and dsFv appended, for example one from each of the heavy chain C-terminal.

(Fab)$_2$dsscFvdsFv, as employed herein refers to a diFab with a dsscFv and dsFv appended, for example from the heavy chain C-terminal.

(Fab')$_2$dsscFvdsFv as employed herein refers to the a diFab' with a dsscFv and dsFv appended, for example from the heavy chain C-terminal.

Minibody as employed herein refers to (VL/VH—CH$_3$)$_2$.

dsminibody as employed herein refers to (VL/VH—CH$_3$)$_2$ wherein one VL/VH comprises an intra-variable region disulfide bond.

didsminibody as employed herein refers to a (dsFv-CH$_3$)$_2$ scFv-Fc as employed herein refers to a scFv appended to the N-terminus of a CH2 domain, for example via a hinge, of constant region fragment —(CH2CH3), such that the molecule has 2 binding domains.

dsscFv-Fc as employed herein refers to a dsscFv appended to the N-terminus of a CH2 domain and a scFv appended to the N-terminus of a second CH2 domain, for example via a hinge, of constant region fragment —(CH2CH3)2, such that the molecule has 2 binding domains.

didsscFv-Fc as employed herein refers to a scFv appended to the N-terminus of a CH2 domain, for example via a hinge, of constant region fragment —(CH2CH3)2, such that the molecule has 2 binding domains Tandem scFv-Fc as employed herein refers to two tandem scFvs, wherein each one is appended in series to the N-terminus of a CH2 domain, for example via a hinge, of constant region fragment —(CH2CH3), such that the molecule has 4 binding domains.

Scdiabody-Fc as employed herein is two scdiabodies, wherein each one is appended to the N-terminus of a CH$_2$ domain, for example via a hinge, of constant region fragment —CH$_2$CH$_3$.

ScFv-Fc-scFv as employed herein refers to four scFvs, wherein one of each is appended to the N-terminus and the C-terminus of both the heavy and light chain of a —CH2CH3 fragment.

Scdiabody-CH3 as employed herein refers to two scdiabody molecules each linked, for example via a hinge to a CH3 domain.

kappa/lambda body 'or' K/λ-body is in the format of a normal IgG with two heavy chains and two light chains, wherein the two light chains are different to each other, one is a lambda light chain (VL-CL) and the other is a kappa light chain (VK-CK). The heavy chain is identical, even at the CDRs as described in WO2012/023053.

IgG-scFv as employed herein is a full length antibody with a scFv on the C-terminal of each of the heavy chains or each of the light chains.

scFv-IgG as employed herein is a full length antibody with a scFv on the N-terminal of each of the heavy chains or each of the light chains.

V-IgG as employed herein is a full length antibody with a variable domain on the N-terminal of each of the heavy chains or each of the light chains.

IgG-V as employed herein is a full length antibody with a variable domain on the C-terminal of each of the heavy chains or each of the light chains DVD-Ig (also known as dual V domain IgG) is a full length antibody with 4 additional variable domains, one on the N-terminus of each heavy and each light chain.

Duobody or 'Fab-arm exchange' as employed herein is a bispecific IgG format antibody where matched and complementary engineered amino acid changes in the constant domains (typically CH3) of two different monoclonal antibodies lead, upon mixing, to the formation of heterodimers. A heavy:light chain pair from the first antibody will, as a result of the residue engineering, prefer to associate with a heavy:light chain pair of a second antibody. See for example WO2008/119353, WO2011/131746 and WO2013/060867

Where one or more pairs of variable regions in the multispecific molecule of the present invention comprise a disulphide bond between VH and VL this may be in any suitable position such as between two of the residues listed below (unless the context indicates otherwise Kabat numbering is employed in the list below). Wherever reference is made to Kabat numbering the relevant reference is Kabat et al., 1987, in Sequences of Proteins of Immunological Interest, US Department of Health and Human Services, NIH, USA.

In one embodiment the disulfide bond is in a position selected from the group comprising:

$V_H37+V_L95C$ see for example Protein Science 6, 781-788 Zhu et al (1997);

$V_H44+V_L100$ see for example; Biochemistry 33 5451-5459 Reiter et al (1994); or Journal of Biological Chemistry Vol. 269 No. 28 pp. 18327-18331 Reiter et al (1994); or Protein Engineering, vol. 10 no. 12 pp. 1453-1459 Rajagopal et al (1997);

$V_H44+V_L105$ see for example J Biochem. 118, 825-831 Luo et al (1995);

$V_H45+V_L87$ see for example Protein Science 6, 781-788 Zhu et al (1997);

$V_H55+V_L101$ see for example FEBS Letters 377 135-139 Young et al (1995);

$V_H100+V_L50$ see for example Biochemistry 29 1362-1367 Glockshuber et al (1990);

$V_H100b+V_L49$;

$V_H98+V_L$ 46 see for example Protein Science 6, 781-788 Zhu et al (1997);

$V_H101+V_L46$;

$V_H105+V_L43$ see for example; Proc. Natl. Acad. Sci. USA Vol. 90 pp. 7538-7542 Brinkmann et al (1993); or Proteins 19, 35-47 Jung et al (1994), $V_H106+V_L57$ see for example FEBS Letters 377 135-139 Young et al (1995)

and a position corresponding thereto in variable region pair located in the molecule.

In one embodiment, the disulphide bond is formed between positions $V_H44$ and $V_L100$.

"Monospecific" as employed herein refers to the ability to bind a target antigen only once. Thus is one embodiment the multispecific molecules of the present invention are monspecific for each antigen Thus in one embodiment the binding domains of the multispecific molecules according to the present disclosure are monospecific. This is advantageous in some therapeutic applications because the molecules of the disclosure are not able to cross-link antigen via binding the target antigen more than once. Thus in one embodiment bispecific or multispecific molecules of the present disclosure are not able to cross-link by binding the same target twice in two different locations, for example on the same cell or on two different cells.

Cross-linking, in particular in relation to CD79b on the same cell or different cells can generate signals in vivo, for example which stimulate the activity of the target antigen In another embodiment, for example where the molecules of the disclosure comprise at least three binding domains then two or three binding domains (for example antibodies, fragments or a combination of an antibody and a fragment) may have different antigen specificities, for example binding to two or three different target antigens.

In one example the multispecific molecules of the present invention contain no more than one binding domain for CD22 and no more than one binding domain for CD79. Each binding domain is monospecific.

In one embodiment, each antibody or antibody fragment employed in the multi-specific molecules of the present disclosure is monovalent.

Thus in one embodiment the binding domains of the multispecific molecules of the present disclosure are monovalent.

Thus in one embodiment the binding domains of the multispecific molecules of the present disclosure are monovalent and monospecific.

In one embodiment the multispecific molecule of the present disclosure is comprised of two or more monospecific, monovalent binding domains such as Fab, Fab', scFv, VH, VL, VHH, Fv, dsFv, combined or linked in any suitable way to construct a multispecific molecule, for example as described herein above.

Constant Regions

The antibody constant region domains of a multispecific molecule of the present disclosure, if present, may be selected having regard to the proposed function of the multispecific antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required.

It will be appreciated that sequence variants of these constant region domains may also be used. For example IgG4 molecules in which the serine at position 241 has been changed to proline as described in Angal et al., 1993, Molecular Immunology, 1993, 30:105-108 may be used. Accordingly, in the embodiment where the antibody is an IgG4 antibody, the antibody may include the mutation S241P.

In one embodiment, the antibody heavy chain comprises a $CH_1$ domain and the antibody light chain comprises a CL domain, either kappa or lambda.

In one embodiment, the antibody heavy chain comprises a $CH_1$ domain, a $CH_2$ domain and a $CH_3$ domain and the antibody light chain comprises a CL domain, either kappa or lambda.

The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions (Bruhns P. et al., 2009. Specificity and affinity of human Fcgamma receptors and their polymorphic variants for human IgG subclasses. Blood. 113(16):3716-25), see also Jeffrey B. Stavenhagen, et al. *Cancer Research* 2007 Sep. 15; 67(18):8882-90.

Binding of IgG to the FcγRs or C1q depends on residues located in the hinge region and the CH2 domain. Two regions of the CH2 domain are critical for FcγRs and C1q binding, and have unique sequences in IgG2 and IgG4. Substitutions into human IgG1 of IgG2 residues at positions 233-236 and IgG4 residues at positions 327, 330 and 331 have been shown to greatly reduce ADCC and CDC (Armour K L. et al., 1999. Recombinant human IgG molecules lacking Fcgamma receptor I binding and monocyte triggering activities. Eur J Immunol. 29(8):2613-24 and Shields R L. et al., 2001. High resolution mapping of the binding site on human IgG1 for Fc gamma RI, Fc gamma RII, Fc gamma RIII, and FcRn and design of IgG1 variants with improved binding to the Fc gamma R. J Biol Chem. 276(9):6591-604). Furthermore, Idusogie et al. demonstrated that alanine substitution at different positions, including K322, significantly reduced complement activation (Idusogie E E. et al., 2000. Mapping of the C1q binding site on rituxan, a chimeric antibody with a human IgG1 Fc. J Immunol. 164(8):4178-84). Similarly, mutations in the CH2 domain of murine IgG2A were shown to reduce the binding to FcγRI, and C1q (Steurer W. et al., 1995. Ex vivo coating of islet cell allografts with murine CTLA4/Fc promotes graft tolerance. J Immunol. 155(3):1165-74).

In one embodiment the Fc region employed is mutated, in particular a mutation described herein. In one embodiment the mutation is to remove binding and/or effector function.

In one embodiment the Fc mutation is selected from the group comprising a mutation to remove binding of the Fc region, a mutation to increase or remove an effector function, a mutation to increase half-life and a combination of the same.

Some antibodies that selectively bind FcRn at pH 6.0, but not pH 7.4, exhibit a higher half-life in a variety of animal models. Several mutations located at the interface between the CH2 and CH3 domains, such as T250Q/M428L (Hinton P R. et al., 2004. Engineered human IgG antibodies with longer serum half-lives in primates. J Biol Chem. 279(8): 6213-6) and M252Y/S254T/T256E+H433K/N434F (Vaccaro C. et al., 2005. Engineering the Fc region of immunoglobulin G to modulate in vivo antibody levels. Nat Biotechnol. 23(10):1283-8), have been shown to increase the binding affinity to FcRn and the half-life of IgG1 in vivo.

However, there is not always a direct relationship between increased FcRn binding and improved half-life (Datta-Mannan A. et al., 2007. Humanized IgG1 Variants with Differential Binding Properties to the Neonatal Fc Receptor: Relationship to Pharmacokinetics in Mice and Primates. Drug Metab. Dispos. 35: 86-94).

IgG4 subclass show reduced Fc receptor (FcγRIIIa) binding, antibodies of other IgG subclasses generally show strong binding. Reduced receptor binding in these other IgG subtypes can be effected by altering, for example replacing one or more amino acids selected from the group comprising Pro238, Aps265, Asp270, Asn270 (loss of Fc carbohydrate), Pro329, Leu234, Leu235, Gly236, Gly237, Ile253, Ser254, Lys288, Thr307, Gln311, Asn434 and His435.

In one embodiment a molecule according to the present disclosure has an Fc of IgG subclass, for example IgG1, IgG2 or IgG3 wherein the Fc is mutated in one, two or all following positions S228, L234 and/or D265.

In one embodiment the mutations in the Fc region are independently selected from S228P, L234A, L235A, L235A, L235E and combinations thereof.

It may be desired to either reduce or increase the effector function of an Fc region. Antibodies that target cell-surface molecules, especially those on immune cells, abrogating effector functions is required. In some embodiments, for example for the treatment of autoimmunity, enhanced Fc binding on immune cells by increasing negative Fc receptor binding (FcgRIIb or CD32b) may be desirable see Stavenhagen J B, et al Advances in Enzyme Regulation 2007 Dec. 3 and Veri M C, et al. Arthritis Rheum, 2010 Mar. 30; 62(7):1933-43. Conversely, for antibodies intended for oncology use, increasing effector functions may improve the therapeutic activity.

Numerous mutations have been made in the CH2 domain of human IgG1 and their effect on ADCC and CDC tested in vitro (Idusogie E E. et al., 2001. Engineered antibodies with increased activity to recruit complement. J Immunol. 166 (4):2571-5). Notably, alanine substitution at position 333 was reported to increase both ADCC and CDC. Lazar et al. described a triple mutant (S239D/I332E/A330L) with a higher affinity for FcγRIIIa and a lower affinity for FcγRIIb resulting in enhanced ADCC (Lazar G A. et al., 2006. Engineered antibody Fc variants with enhanced effector function. PNAS 103(11): 4005-4010). The same mutations were used to generate an antibody with increased ADCC (Ryan M C. et al., 2007. Antibody targeting of B-cell maturation antigen on malignant plasma cells. Mol. Cancer Ther., 6: 3009-3018). Richards et al. studied a slightly different triple mutant (S239D/I332E/G236A) with improved FcγRIIIa affinity and FcγRIIa/FcγRIIb ratio that mediates enhanced phagocytosis of target cells by macrophages (Richards J O et al 2008. Optimization of antibody binding to Fcgamma RIIa enhances macrophage phagocytosis of tumor cells. Mol Cancer Ther. 7(8):2517-27).

Due to their lack of effector functions, IgG4 antibodies represent a suitable IgG subclass for receptor blocking without cell depletion. IgG4 molecules can exchange half-molecules in a dynamic process termed Fab-arm exchange. This phenomenon can occur between therapeutic antibodies and endogenous IgG4. The S228P mutation has been shown to prevent this recombination process allowing the design of less unpredictable therapeutic IgG4 antibodies (Labrijn A F. et al., 2009. Therapeutic IgG4 antibodies engage in Fab-arm exchange with endogenous human IgG4 in vivo. Nat Biotechnol. 27(8):767-71). This technology may be employed to create bispecific antibody molecules.

It will also be understood by one skilled in the art that antibodies may undergo a variety of post-translational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

Affinity

The multispecific molecules of the present invention comprise a binding domain specific to the antigen CD45 and a binding domain specific to the antigen CD79a and/or CD79b.

In one embodiment a binding domain employed in the molecules of the present disclosure is specific to CD45.

In one embodiment a binding domain employed in the molecules of the present disclosure is specific to CD79a.

In one embodiment a binding domain employed in the molecules of the present disclosure is specific to CD79b.

In one embodiment a binding domain employed in the molecules of the present disclosure is specific to CD79 complex, i.e. it recognises an epitope present in the complex and specific thereto, for example an epitope comprising an interaction between CD79a and CD79b.

CD45 (also known as PTPRC) is a known protein. CD45 is a member of the protein tyrosine phosphatase (PTP) family. PTPs are known to be signaling molecules that regulate a variety of cellular processes including cell growth, differentiation, mitotic cycle, and oncogenic transformation. This PTP contains an extracellular domain, a single transmembrane segment and two tandem intracytoplasmic catalytic domains, and thus belongs to receptor type PTP. Various isoforms of CD45 exist: CD45RA, CD45RB, CD45RC, CD45RAB, CD45RAC, CD45RBC, CD45RO, CD45R (ABC). CD45RA is located on naive T cells and CD45R0 is located on memory T cells. CD45 splice variant isoforms A, B and C are expressed differentially on human B cells. CD45 is a member of the Protein Tyrosine Phosphatase (PTP) family: Its intracellular (COOH-terminal) region contains two PTP catalytic domains, and the extracellular region is highly variable due to alternative splicing of exons 4, 5, and 6 (designated A, B, and C, respectively), plus differing levels of glycosylation. The CD45 isoforms detected are cell type-, maturation, and activation state-specific. In general the long form of the protein (A, B or C) is expressed on naïve or unactivated B cells and the mature or truncated form of CD45 (RO) is expressed on activated or mature/memory B cells.

The human sequence is available in UniProt entry number P08575 and provided herein in SEQ ID NO:143, or amino acids 24-1304 of SEQ ID NO:143, lacking the signal peptide. The murine version in UniProt entry P06800. The present disclosure relates to all forms of CD45, from any species. In one embodiment CD45 refers to the human form of the protein and natural variants and isoforms thereof.

In one embodiment the affinity of the binding domain for CD45 in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

The binding domain for CD79 may bind to CD79a and/or CD79b.

CD79a (also known as immunoglobulin alpha and B-cell antigen receptor complex-associated protein alpha chain) is a known protein. Expression of CD79a is restricted to B lymphocytes. The human sequence is available in UniProt under entry P11912 (SEQ ID NO: and without signal sequence amino acids 33-226 of SEQ ID NO: 141). The murine version is available in UniProt under entry 11911. The present disclosure relates to all forms of CD79a from any species, in particular human and any natural variants thereof. In one embodiment CD79a refers to the human form of the protein.

CD79b (also known as immunoglobulin associated beta and cluster differentiation 79B) is a known protein. Expression of CD79b is restricted to B lymphocytes. The human sequence is available in UniProt under entry P40259 (SEQ ID NO:142 and without signal sequence amino acids 29-229 of SEQ ID NO:142). The murine version in UniProt under entry P15530. The present disclosure relates to all forms of CD79b, from any species, in particular human and any natural variants thereof. In one embodiment CD79b refers to the human form of the protein.

In one embodiment the binding domain specific to CD79 binds CD79a.

In one embodiment the binding domain specific to CD79 binds CD79b.

In one embodiment the binding domain specific to CD79 binds a complex of CD79a and CD79b In one embodiment the affinity of the binding domain for CD79 in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

In one embodiment the affinity of the binding domain for CD79a in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

In one embodiment the affinity of the binding domain for CD79b in a molecule of the present disclosure is about 100 nM or stronger such as about 50 nM, 20 nM, 10 nM, 1 nM, 500 pM, 250 pM, 200 pM, 100 pM or stronger, in particular a binding affinity of 50 pM or stronger.

It will be appreciated that the affinity of the binding domain for CD45 may be the same or different from the affinity of the binding domain for CD79.

In one embodiment, the multi-specific antibody molecules of the present disclosure or antibody/fragment components thereof are processed to provide improved affinity for a target antigen or antigens. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al J. Mol. Biol., 250, 359-368, 1996), DNA shuffling (Patten et al Curr. Opin. Biotechnol., 8, 724-733, 1997), phage display (Thompson et al., J. Mol. Biol., 256, 77-88, 1996) and sexual PCR (Crameri et al Nature, 391, 288-291, 1998). Vaughan et al (supra) discusses these methods of affinity maturation.

Antibodies & Generation of the Same

Binding domains for use in the present invention may be generated by any suitable method known in the art, for example CDRs may be taken from non-human antibodies including commercially available antibodies and grafted into human frameworks or alternatively chimeric antibodies can be prepared with non-human variable regions and human constant regions etc.

Typically the binding domains for use in the present invention are binding domains derived from antibodies which bind the selected antigen, such as antibodies which bind CD45, CD79a and/or CD79b.

Examples of CD45 and CD79 antibodies are known in the art and these may be employed directly in the molecules of the present invention or screened for suitability using the methods described herein, and subsequently modified if necessary, for example humanised, using the methods described herein. Therapeutic anti-CD45 and anti-CD79 antibodies have been described in the art, for example anti-CD45 antibodies disclosed in US2011/0076270, anti-CD79b antibodies disclosed in WO2014/011521 and WO2015/021089.

Examples of CD45 antibodies include rat monoclonal YTH54, YTH25.4, mouse monoclonal from Miltenyi clone 5B1 and clone 30F11, rat monoclonal YAML568, from BD Bioscience mouse monoclonal clone 2D1 catalog No. 347460, from Novus mouse monoclonal antibody 5D3A3 catalog No. NBP2-37293, mouse monoclonal H130 catalog No. NBP1-79127, mouse monoclonal 4A8A4C7A2 catalog No. NBP1-47428, mouse monoclonal 2B11 catalog No. NBP2-32934, rat monoclonal YTH24.5 catalog No. NB100-63828, rabbit monoclonal Y321 catalog No. NB110-55701, mouse monoclonal PD7/26/16 catalog No. NB120-875, from Santa Cruz mouse monoclonal from clone B8 catalog No. sc-28369, mouse monoclonal from clone F10-89-4 catalog No. sc-52490, rabbit monoclonal from clone H-230 catalog No. sc-25590, goat monoclonal from clone N-19 catalog No. sc-1123, mouse monoclonal from clone OX1 catalog No. sc-53045, rat monoclonal (T29/33) catalog No sc-18901, rat monoclonal (YAML 501.4) catalog No. sc65344, rat monoclonal (YTH80.103) catalog No sc-59071, mouse monoclonal (35105) catalog No. sc-53201, mouse monoclonal (35-Z6) catalog No. sc-1178, mouse monoclonal (158-4D3) catalog No. sc-52386, mouse monoclonal to CD45RO (UCH-L1) catalog No. sc-1183, mouse monoclonal to CD45RO (2Q1392) catalog No. sc-70712. CD45 antibodies are also disclosed in WO2005/026210, WO02/072832 and WO2003/048327 incorporated herein by reference.

Commercially available anti-CD79a antibodies include mouse monoclonal LS-B4504 (LSBio) from clone HM57, mouse monoclonal LS-B8330, mouse monoclonal LS-C44954, rabbit monoclonal LS-B9093, mouse monoclonal LS-B8513 from clone JCB117, rabbit monoclonal LS-C210607 from clone SP18, mouse monoclonal LS-C175441 from clone 5E2, mouse monoclonal LS-C338670 from clone 3D3, mouse monoclonal LS-C88120 from clone HM47/A9, mouse monoclonal LS-C191714, mouse monoclonal LS-C87592, mouse monoclonal LS-C44955, mouse monoclonal LS-C95934, mouse monoclonal LS-C121584, mouse monoclonal LS-C121585, mouse monoclonal LS-C204347, mouse monoclonal LS-C88122, Abcam mouse monoclonal ab3121 [HM47/A9], rabbit monoclonal ab79414, and rabbit monoclonal ab133483.

Commercially available CD79b antibodies include mouse monoclonal Abcam antibody ab33295, rat monoclonal ab23826, mouse monoclonal ab103422, rabbit monoclonal ab134103, rabbit monoclonal ab134147, and rabbit monoclonal ab183343.

Such commercially available antibodies may be useful tools in the discovery of therapeutic antibodies.

The skilled person may generate antibodies for use in the multi-specific molecules of the invention using any suitable method known in the art.

Antigen polypeptides, for use in generating antibodies for example for use to immunize a host or for use in panning, such as in phage display, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The antigen polypeptide may in some instances be part of a larger protein such as a fusion protein for example fused to an affinity tag or similar. In one embodiment the host may be immunised with a cell transfected with the relevant protein or polypeptide, for example co-transfected with CD79a and CD79b.

Antibodies generated against an antigen polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al 1983, Immunology Today, 4:72) and the EBV-hybridoma technique (Cole et al Monoclonal Antibodies and Cancer Therapy, pp 77-96, Alan R Liss, Inc., 1985).

Antibodies may also be generated using single lymphocyte antibody methods by cloning and expressing immunoglobulin variable region cDNAs generated from single lymphocytes selected for the production of specific antibodies by, for example, the methods described by Babcook, J. et al 1996, Proc. Natl. Acad. Sci. USA 93(15):7843-78481; WO92/02551; WO2004/051268 and WO2004/106377.

The antibodies for use in the present disclosure can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO90/02809; WO91/10737; WO92/01047; WO92/18619; WO93/11236; WO95/15982; WO95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; 5,969,108, and WO20011/30305.

In one example the multi-specific molecules of the present disclosure are fully human, in particular one or more of the variable domains are fully human.

Fully human molecules are those in which the variable regions and the constant regions (where present) of both the heavy and the light chains are all of human origin, or substantially identical to sequences of human origin, not necessarily from the same antibody. Examples of fully human antibodies may include antibodies produced, for example by the phage display methods described above and antibodies produced by mice in which the murine immunoglobulin variable and optionally the constant region genes have been replaced by their human counterparts e.g. as described in general terms in EP0546073, U.S. Pat. Nos. 5,545,806, 5,569,825, 5,625,126, 5,633,425, 5,661,016, 5,770,429, EP 0438474 and EP0463151.

In one example the binding domains of the multi-specific molecules according to the disclosure are humanised.

Humanised (which include CDR-grafted antibodies) as employed herein refers to molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

As used herein, the term "humanised antibody molecule" refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the humanised antibody according to the present invention has a variable domain comprising human acceptor framework regions as well as one or more of the CDRs provided herein.

Examples of human frameworks which can be used in the present disclosure are KOL, NEWM, REI, EU, TUR, TEI, LAY and POM (Kabat et al supra). For example, KOL and NEWM can be used for the heavy chain, REI can be used for the light chain and EU, LAY and POM can be used for both the heavy chain and the light chain. Alternatively, human germline sequences may be used; these are available at: http://www2.mrc-lmb.cam.ac.uk/vbase/list2.php.

In a humanised antibody molecule of the present disclosure, the acceptor heavy and light chains do not necessarily need to be derived from the same antibody and may, if desired, comprise composite chains having framework regions derived from different chains.

The framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al 1998, Nature, 332, 323-324). Such changes should be kept to the minimum necessary to recover the affinity of the donor antibody. A protocol for selecting residues in the acceptor framework regions which may need to be changed is set forth in WO91/09967.

Derivatives of frameworks may have 1, 2, 3 or 4 amino acids replaced with an alternative amino acid, for example with a donor residue.

Donor residues are residues from the donor antibody, i.e. the antibody from which the CDRs were originally derived, in particular the residue in a corresponding location from the donor sequence is adopted. Donor residues may be replaced by a suitable residue derived from a human receptor framework (acceptor residues).

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one example there is provided a binding domain comprising a heavy chain variable region (VH), specific for CD79 which comprises three CDRs, wherein CDR H1 has the sequence given in SEQ ID NO: 78, CDR H2 has the sequence given in SEQ ID NO: 79, and CDR H3 has the sequence given in SEQ ID NO: 80.

In one embodiment there is provided a binding domain comprising a heavy chain variable region (VH), specific for CD79 comprising 3 heavy chain CDRs SEQ ID NO: 88 for CDRH1, SEQ ID NO: 89 for CDRH2 and SEQ ID NO: 90 for CDRH3.

In one embodiment there is provided the binding domain comprising a light chain variable region specific for CD79 comprising 3 light chain CDRs SEQ ID NO: 75 for CDRL1, SEQ ID NO: 76 for CDRL2 and SEQ ID NO: 77 for CDRL3.

In one embodiment there is provided binding domain comprising a light chain variable region specific for CD79 comprising 3 light chain CDRs SEQ ID NO: 85 for CDRL1, SEQ ID NO: 86 for CDRL2 and SEQ ID NO: 87 for CDRL3.

In one example there is provided a binding domain comprising a heavy chain variable region (VH), specific for CD79 which comprises three CDRs, wherein CDR H1 has the sequence given in SEQ ID NO: 78, CDR H2 has the sequence given in SEQ ID NO: 79, and CDR H3 has the sequence given in SEQ ID NO: 80 and a light chain variable region (VL) which comprises three CDRs, wherein CDR L1 has the sequence given in SEQ ID NO: 75, CDR L2 has the sequence given in SEQ ID NO: 76 and CDR L3 has the sequence given in SEQ ID NO: 77.

In one example there is provided a binding domain comprising a heavy chain variable region (VH), specific for CD79 which comprises three CDRs, wherein CDR H1 has the sequence given in SEQ ID NO: 88, CDR H2 has the sequence given in SEQ ID NO: 89, and CDR H3 has the sequence given in SEQ ID NO: 90 and a light chain variable region (VL) which comprises three CDRs, wherein CDR L1 has the sequence given in SEQ ID NO: 85, CDR L2 has the sequence given in SEQ ID NO: 86 and CDR L3 has the sequence given in SEQ ID NO: 87.

In one embodiment a multispecific molecule according to the present disclosure comprises a binding domain specific to CD45 which comprises 3 heavy chain CDRS selected from the group comprising SEQ ID NO: 98, 99, 100, 108, 109, 110, 118, 119, 120, 128, 129 and 130, In one embodiment a multispecific molecule according to the present disclosure comprises a binding domain specific to CD45 which comprises 3 light chain CDRS selected from the group comprising SEQ ID NO: 95, 97, 97, 105, 106, 107, 115, 116, 117, 125, 126 and 127.

In one embodiment a multispecific molecule according to the present disclosure comprises a binding domain specific to CD45 which comprises 3 heavy chain CDRS selected from the group comprising SEQ ID NO: 98, 99, 100, 108, 109, 110, 118, 119, 120, 128, 129, 130, and 3 light chain CDRS selected from the group comprising SEQ ID NO: 95, 97, 97, 105, 106, 107, 115, 116, 117, 125, 126 and 127.

In one embodiment there is provided a binding domain comprising a heavy chain variable region (VH), specific for CD45 comprising 3 heavy chain CDRs SEQ ID NO: 98 for CDRH1, SEQ ID NO: 99 for CDRH2 and SEQ ID NO: 100 for CDRH3.

In one embodiment there is provided a binding domain comprising a heavy chain variable region (VH), specific for CD45 comprising 3 heavy chain CDRs SEQ ID NO: 108 for CDRH1, SEQ ID NO: 109 for CDRH2 and SEQ ID NO: 110 for CDRH3.

In one embodiment there is provided a binding domain comprising a heavy chain variable region (VH), specific for CD45 comprising 3 heavy chain CDRs SEQ ID NO: 118 for CDRH1, SEQ ID NO: 119 for CDRH2 and SEQ ID NO: 120 for CDRH3.

In one embodiment there is provided a binding domain comprising a heavy chain variable region (VH), specific for CD45 comprising 3 heavy chain CDRs SEQ ID NO: 128 for CDRH1, SEQ ID NO: 129 for CDRH2 and SEQ ID NO: 130 for CDRH3.

In one embodiment there is provided a binding domain comprising a light chain variable region specific for CD45 comprising 3 light chain CDRs SEQ ID NO: 95 for CDRL1, SEQ ID NO: 96 for CDRL2 and SEQ ID NO: 97 for CDRL3.

In one embodiment there is provided binding domain comprising a light chain variable region specific for CD45 comprising 3 light chain CDRs SEQ ID NO: 105 for CDRL1, SEQ ID NO: 106 for CDRL2 and SEQ ID NO: 107 for CDRL3.

In one embodiment there is provided binding domain comprising a light chain variable region specific for CD45 comprising 3 light chain CDRs SEQ ID NO: 115 for CDRL1, SEQ ID NO: 116 for CDRL2 and SEQ ID NO: 117 for CDRL3.

In one embodiment there is provided a binding domain comprising a light chain variable region specific for CD45 comprising 3 light chain CDRs SEQ ID NO: 125 for CDRL1, SEQ ID NO: 126 for CDRL2 and SEQ ID NO: 127 for CDRL3.

In one example there is provided a binding domain specific to CD45 comprising a heavy chain variable region (VH), which comprises three CDRs, wherein CDR H1 has the sequence given in SEQ ID NO: 98, CDR H2 has the sequence given in SEQ ID NO: 99, and CDR H3 has the sequence given in SEQ ID NO: 100 and a light chain variable region (VL) which comprises three CDRs, wherein CDR L1 has the sequence given in SEQ ID NO: 95, CDR L2 has the sequence given in SEQ ID NO: 96 and CDR L3 has the sequence given in SEQ ID NO: 97. In one example there is provided a binding domain specific to CD45 comprising a heavy chain variable region (VH), which comprises three CDRs, wherein CDR H1 has the sequence given in SEQ ID NO: 108, CDR H2 has the sequence given in SEQ ID NO: 109, and CDR H3 has the sequence given in SEQ ID NO: 110 and a light chain variable region (VL) which comprises three CDRs, wherein CDR L1 has the sequence given in SEQ ID NO: 105, CDR L2 has the sequence given in SEQ ID NO: 106 and CDR L3 has the sequence given in SEQ ID NO: 107. In one example there is provided a binding domain specific to CD45 comprising a heavy chain variable region (VH), which comprises three CDRs, wherein CDR H1 has the sequence given in SEQ ID NO: 118, CDR H2 has the sequence given in SEQ ID NO: 119, and CDR H3 has the sequence given in SEQ ID NO: 120 and a light chain variable region (VL) which comprises three CDRs, wherein CDR L1 has the sequence given in SEQ ID NO: 115, CDR L2 has the sequence given in SEQ ID NO: 116 and CDR L3 has the sequence given in SEQ ID NO: 117. In one example there is provided a binding domain specific to CD45 comprising a heavy chain variable region (VH), which comprises three CDRs, wherein CDR H1 has the sequence given in SEQ ID NO: 128, CDR H2 has the sequence given in SEQ ID NO: 129, and CDR H3 has the sequence given in SEQ ID NO: 130 and a light chain variable region (VL) which comprises three CDRs, wherein CDR L1 has the sequence given in SEQ ID NO: 125, CDR L2 has the sequence given in SEQ ID NO: 126 and CDR L3 has the sequence given in SEQ ID NO: 127. In one example the present invention provides a multispecific molecule comprising a binding domain specific to the antigen CD79 and a binding domain specific to the antigen CD45 wherein these pairs of binding domains each comprise 6 CDRs from a pair of CD79 and CD45 antibodies, for example selected from the following pairs antibodies; 4447 and 4122, 4447 and 4129, 4447 and 4131, 4447 and 4133, 4450 and 4122, 4450 and 4129, 4450 and 4131 and 4447 and 4133.

The sequences of these CD79 antibodies (antibody 4447 and antibody 4450), including VH, VL and CDR sequences are provided herein below. The sequences of these CD45 antibodies (antibodies 4122, 4129, 4131 and 4133) including VH, VL and CDR sequences are provided herein below, and may be combined as binding domains in molecules of the present invention. In one embodiment the disclosure extends to an antibody sequence disclosed herein.

In one example there is provided a binding domain specific to albumin comprising a heavy chain variable region (VH), which comprises three CDRs, wherein CDR H1 has the sequence given in SEQ ID NO: 131, CDR H2 has the sequence given in SEQ ID NO: 132, and CDR H3 has the sequence given in SEQ ID NO: 133 and a light chain variable region (VL) which comprises three CDRs, wherein CDR L1 has the sequence given in SEQ ID NO: 134, CDR L2 has the sequence given in SEQ ID NO: 135 and CDR L3 has the sequence given in SEQ ID NO: 136.

In one example there is provided a binding domain specific to albumin comprising a heavy chain variable region (VH) having the sequence given in SEQ ID NO:137 and a light chain variable region (VL) having the sequence given in SEQ ID NO:139.

In one example there is provided a binding domain specific to albumin comprising a heavy chain variable region (VH) having the sequence given in SEQ ID NO:138 and a light chain variable region (VL) having the sequence given in SEQ ID NO:140.

In one example the binding domains are humanised.

In one example one or more CDRs provided herein may be modified to remove undesirable residues or sites, such as cysteine residues or aspartic acid (D) isomerisation sites or asparagine (N) deamidation sites. In one example an Asparagine deamidation site may be removed from one or more CDRs by mutating the asparagine residue (N) and/or a neighbouring residue to any other suitable amino acid. In one example an asparagine deamidation site such as NG or NS may be mutated, for example to NA or NT.

In one example an Aspartic acid isomerisation site may be removed from one or more CDRs by mutating the aspartic acid residue (D) and/or a neighbouring residue to any other suitable amino acid. In one example an aspartic acid isomerisation site such as DG or DS may be mutated, for example to EG, DA or DT.

For example one or more cysteine residues in any one of the CDRs may be substituted with another amino acid, such as serine.

In one example an N-glycosylation site such as NLS may be removed by mutating the asparagine residue (N) to any other suitable amino acid, for example to SLS or QLS. In one example an N-glycosylation site such as NLS may be removed by mutating the serine residue (S) to any other residue with the exception of threonine (T).

The skilled person is able to test variants of CDRs or humanised sequences in any suitable assay such as those described herein to confirm activity is maintained.

Specific binding to antigen may be tested using any suitable assay including for example ELISA or surface plasmon resonance methods such as BIACORE where binding to antigen (CD45 and/or CD79) may be measured. Such assays may use isolated natural or recombinant CD45 or CD79 (a or b) or a suitable fusion protein/polypeptide. In one example binding is measured using recombinant CD45 (SEQ ID NO: 143 or amino acids 23-1304 of SEQ ID NO:143) or CD79 such as the sequence provided in SEQ ID NO:141 and SEQ ID NO:142 and amino acids 33-226 of SEQ ID NO:141 and amino acids 29-229 of SEQ ID NO:142) by for example surface plasmon resonance, such as BIACORE. Alternatively the proteins may be expressed on a cell, such as a HEK cell and affinity measured employing a flow cytometry based affinity determination.

The antibody sequences provided by the present invention may be used to identify further antibodies and hence binding domains suitable for use in the multispecific molecules of the present invention. Antibodies which cross-block the binding of an antibody molecule according to the present invention to CD79 in particular, an antibody molecule comprising the heavy chain sequence given in SEQ ID NO:73 and the light chain sequence given in SEQ ID NO:71 or an antibody molecule comprising the heavy chain sequence given in SEQ ID NO:83 and the light chain sequence given in SEQ ID NO:81 may be similarly useful in binding CD79 and therefore similarly useful in the multispecific molecules of the present invention. Accordingly, the present invention also provides a multi-specific molecule comprising a binding domain specific to the antigen CD45 and a binding domain specific to the antigen CD79b wherein the binding domain for CD79b cross-blocks the binding of any one of the antibody molecules described herein above to CD79 and/or is cross-blocked from binding CD79 by any one of those antibodies. In one embodiment, such an antibody binds to the same epitope as an antibody described herein above.

Similarly antibodies which cross-block the binding of an antibody molecule according to the present invention to CD45, in particular, an antibody molecule comprising the heavy chain sequence given in SEQ ID NO:93 and the light chain sequence given in SEQ ID NO:91 or an antibody molecule comprising the heavy chain sequence given in SEQ ID NO:103 and the light chain sequence given in SEQ ID NO:101, or an antibody molecule comprising the heavy chain sequence given in SEQ ID NO:113 and the light chain sequence given in SEQ ID NO:111, or an antibody molecule comprising the heavy chain sequence given in SEQ ID NO:123 and the light chain sequence given in SEQ ID NO:121, or an antibody molecule comprising the heavy chain sequence given in SEQ ID NO:133 and the light chain sequence given in SEQ ID NO:131 may be similarly useful in binding CD45 and therefore similarly useful in the multispecific molecules of the present invention. Accordingly, the present invention also provides a multi-specific molecule comprising a binding domain specific to the antigen CD45 and a binding domain specific to the antigen CD79 wherein the binding domain for CD45 cross-blocks the binding of any one of the antibody molecules described herein above to CD45 and/or is cross-blocked from binding CD45 by any one of those antibodies. In one embodiment, such an antibody binds to the same epitope as an antibody described herein above. In another embodiment the cross-blocking antibody binds to an epitope which borders and/or overlaps with the epitope bound by an antibody described herein above.

In another embodiment the cross-blocking neutralising antibody binds to an epitope which borders and/or overlaps with the epitope bound by an antibody described herein above.

Cross-blocking antibodies can be identified using any suitable method in the art, for example by using competition ELISA or BIACORE assays where binding of the cross blocking antibody to antigen (CD45 and/or CD79) prevents the binding of an antibody of the present invention or vice versa. Such cross blocking assays may use isolated natural or recombinant CD45 or CD79 (a and/or b) or a suitable fusion protein/polypeptide. In one example binding and cross-blocking is measured using recombinant CD45 (SEQ ID NO: 143) or CD79.

Alternatively or in addition, the antibodies according to this aspect of the invention may be cross-blocked from binding to antigen (CD45 or CD79) by an a binding domain disclosed herein, for example comprising CDRs derived from the heavy chain variable sequence given in and the light chain sequence given in SEQ ID NO:71 and 73, 81 and 83, 91 and 93, 101 and 103, 111 and 113, and 121 and 123. Also provided therefore is a multi-specific molecule comprising a binding domain specific to the antigen CD45 and a binding domain specific to the antigen CD79b wherein the binding domain for CD79b cross-blocks the binding of any one of the antibody molecules described herein above to CD79b and/or is cross-blocked from binding CD79 by any one of those antibodies by greater than 80%, for example by greater than 85%, such as by greater than 90%, in particular by greater than 95% and optionally wherein the binding domain for CD45 cross-blocks the binding of any one of the antibody molecules described herein above to CD45 and/or is cross-blocked from binding CD45 by any one of those antibodies by greater than 80%, for example by greater than 85%, such as by greater than 90%, in particular by greater than 95%.

In one aspect, there is provided a multi-specific antibody molecule comprising or consisting of:

a) a polypeptide chain of formula (I):

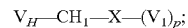

$V_H$—$CH_1$—X—$(V_1)_p$;

b) a polypeptide chain of formula (II):

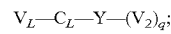

$V_L$—$C_L$—Y—$(V_2)_q$;

wherein:

$V_H$ represents a heavy chain variable domain;

$CH_1$ represents a domain of a heavy chain constant region, for example domain 1 thereof;

X represents a bond or linker, for example an amino acid linker;

Y represents a bond or linker, for example an amino acid linker;

$V_1$ represents a dab, scFv, dsscFv or dsFv;

$V_L$ represents a variable domain, for example a light chain variable domain;

$C_L$ represents a domain from a constant region, for example a light chain constant region domain, such as Ckappa;

$V_2$ represents a dab, scFv, dsscFv or dsFv;

p is 0 or 1;

q is 0 or 1; and when p is 1 q is 0 or 1 and when q is 1 p is 0 or 1 i.e. p and q do not both represent 0

In one embodiment the multispecific antibody molecule comprises no more than one binding domain for CD45 and no more than one binding domain for CD79

In one embodiment q is 0 and p is 1.

In one embodiment q is 1 and p is 1.

In one embodiment $V_1$ is a dab and $V_2$ is a dab and together they form a single binding domain of a co-operative pair of variable regions, such as a cognate VH/VL pair, which are optionally linked by a disulphide bond.

In one embodiment $V_H$ and $V_L$ are specific to, CD79, for example CD79a or CD79b.

In one embodiment the $V_1$ is specific to, CD79, for example CD79a or CD79b.

In one embodiment the $V_2$ is specific to, CD79, for example CD79a or CD79b.

In one embodiment the $V_1$ and $V_2$ together (eg as binding domain) are specific to, CD79, for example CD79a or CD79b and $V_H$ and $V_L$ are specific to, CD45.

In one embodiment the $V_1$ is specific to, CD45.

In one embodiment the $V_2$ is specific to, CD45.

In one embodiment the $V_1$ and $V_2$ together (eg as one binding domain) are specific to, CD45 and $V_H$ and $V_L$ are specific to CD79.

In one embodiment the $V_1$ is specific to CD45, $V_2$ is specific to albumin and $V_H$ and $V_L$ are specific to CD79.

In one embodiment the $V_1$ is specific to albumin, $V_2$ is specific to CD45 and $V_H$ and $V_L$ are specific to CD79.

In one embodiment the $V_1$ is specific to CD79, $V_2$ is specific to albumin and $V_H$ and $V_L$ are specific to CD45.

In one embodiment the $V_1$ is specific to albumin, $V_2$ is specific to CD79 and $V_H$ and $V_L$ are specific to CD45.

In one embodiment the $V_1$ is a dsscFv specific to CD45, $V_2$ is a dsscFv specific to albumin and $V_H$ and $V_L$ are specific to CD79.

In one embodiment the $V_1$ is a dsscFv specific to albumin, $V_2$ is a dscFv specific to CD45 and $V_H$ and $V_L$ are specific to CD79.

In one embodiment the $V_1$ is a dsscFv specific to CD79, $V_2$ is a dsscFv specific to albumin and $V_H$ and $V_L$ are specific to CD45.

In one embodiment the $V_1$ is a dsscFv specific to albumin, $V_2$ is a dsscFv specific to CD79 and $V_H$ and $V_L$ are specific to CD45.

V1, V2, VH and VL in the constructs above may each represent a binding domain and incorporate any of the sequences provided herein.

X and Y represent any suitable linker, for example X and Y may be SGGGGSGGGGS (SEQ ID NO:17).

In one embodiment, when $V_1$ and/or $V_2$ are a dab, dsFv or a dsscFv, the disulfide bond between the variable domains $V_H$ and $V_L$ of $V_1$ and/or $V_2$ is formed between positions $V_H44$ and $V_L100$.

The present disclosure also extends to novel polypeptide sequences disclosed herein and sequences at least 80% similar or identical thereto, for example 85% or greater, such 90% or greater, in particular by 95% or greater similarity or identity.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In particular in one aspect the present invention provides the CD45 and CD79 antibodies described herein in any suitable antibody format.

Accordingly in one aspect the present invention provides anti-CD45 antibodies or fragments thereof containing one or more of the binding domains described herein above comprising the CDRs provided herein and in SEQ ID NOS 95, 96, 97, 98, 99 and 100 (antibody 4122) or 105, 106, 107, 108, 109 and 110 (antibody 4129) or 115, 116, 117, 118, 119 and 120 (antibody 4131) or 125, 126, 127, 128, 129 and 130 (antibody 4133). Also provided are anti-CD79 antibodies or fragments thereof containing one or more of the binding domains described herein above comprising the CDRs provided herein and in SEQ ID NOS 75, 76, 77, 78, 79 and 80 (antibody 4447) or SEQ ID NOs 85, 86, 87, 88, 89 and 90 (antibody 4450).

Said CDRs may be incorporated into any suitable antibody framework and into any suitable antibody format. Such antibodies include whole antibodies and functionally active fragments or derivatives thereof which may be, but are not limited to, monoclonal, humanised, fully human or chimeric antibodies. Accordingly, such antibodies may comprise a complete antibody molecule having full length heavy and light chains or a fragment thereof and may be, but are not limited to Fab, modified Fab, Fab', F(ab')$_2$, Fv, single domain antibodies, scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Multi-valent antibodies may comprise multiple specificities or may be monospecific (see for example WO 92/22853 and WO05/113605). It will be appreciated that this aspect of the invention also extends to variants of these anti-CD45 and CD79 antibodies including humanised versions and modified versions, including those in which amino acids have been mutated in the CDRs to remove one or more isomerisation, deamidation, glycosylation site or cysteine residue as described herein above.

Linkers

The teaching herein of linkers in one context can equally be applied to linkers in different contexts where a linker is employed, such as in any multispecific molecule of the present invention.

In one embodiment, the linker employed in a molecule of the disclosure is an amino acid linker 50 residues or less in length, for example selected from a sequence shown in sequence 5 to 70.

TABLE 1

Hinge linker sequences

| SEQ ID NO: | SEQUENCE |
|---|---|
| 5 | DKTHTCAA |
| 6 | DKTHTCPPCPA |
| 7 | DKTHTCPPCPATCPPCPA |
| 8 | DKTHTCPPCPATCPPCPATCPPCPA |
| 9 | DKTHTCPPCPAGKPTLYNSLVMSDTAGTCY |
| 10 | DKTHTCPPCPAGKPTHVNVSVVMAEVDGTCY |
| 11 | DKTHTCCVECPPCPA |
| 12 | DKTHTCPRCPEPKSCDTPPPCPRCPA |
| 13 | DKTHTCPSCPA |

TABLE 2

Flexible linker sequences

| SEQ ID NO: | SEQUENCE |
|---|---|
| 14 | SGGGGSE |
| 15 | DKTHTS |
| 16 | (S)GGGGS |
| 17 | (S)GGGGSGGGGS |
| 18 | (S)GGGGSGGGGSGGGGS |
| 19 | (S)GGGGSGGGGSGGGGSGGGGS |
| 20 | (S)GGGGSGGGGSGGGGSGGGGSGGGGS |
| 21 | AAAGSG-GASAS |
| 22 | AAAGSG-XGGGS-GASAS |
| 23 | AAAGSG-XGGGSXGGGS-GASAS |
| 24 | AAAGSG-XGGGSXGGGSXGGGS-GASAS |
| 25 | AAAGSG-XGGGSXGGGSXGGGSXGGGS-GASAS |
| 26 | AAAGSG-XS-GASAS |
| 27 | PGGNRGTTTTRRPATTTGSSPGPTQSHY |
| 28 | ATTTGSSPGPT |
| 29 | ATTTGS |
| 30 | GS |
| 31 | EPSGPISTINSPPSKESHKSP |
| 32 | GTVAAPSVFIFPPSD |
| 33 | GGGGIAPSMVGGGGS |
| 34 | GGGGKVEGAGGGGS |
| 35 | GGGGSMKSHDGGGGS |
| 36 | GGGGNLITIVGGGGS |
| 37 | GGGGVVPSLPGGGGS |
| 38 | GGEKSIPGGGGS |
| 39 | RPLSYRPPFPFGFPSVRP |
| 40 | YPRSIYIRRRHPSPSLTT |
| 41 | TPSHLSHILPSFGLPTFN |
| 42 | RPVSPFTFPRLSNSWLPA |
| 43 | SPAAHFPRSIPRPGPIRT |
| 44 | APGPSAPSHRSLPSRAFG |
| 45 | PRNSIHFLHPLLVAPLGA |
| 46 | MPSLSGVLQVRYLSPPDL |
| 47 | SPQYPSPLTLTLPPHPSL |
| 48 | NPSLNPPSYLHRAPSRIS |
| 49 | LPWRTSLLPSLPLRRRP |
| 50 | PPLFAKGPVGLLSRSFPP |
| 51 | VPPAPVVSLRSAHARPPY |
| 52 | LRPTPPRVRSYTCCPTP- |
| 53 | PNVAHVLPLLTVPWDNLR |
| 54 | CNPLLPLCARSPAVRTFP |

(S) is optional in sequences 17 to 20.

Examples of rigid linkers include the peptide sequences GAPAPAAPAPA (SEQ ID NO:69), PPPP (SEQ ID NO:70) and PPP.

Other linkers are shown in Table 3:

| SEQ ID NO: | SEQUENCE |
|---|---|
| 55 | DLCLRDWGCLW |
| 56 | DICLPRWGCLW |
| 57 | MEDICLPRWGCLWGD |
| 58 | QRLMEDICLPRWGCLWEDDE |
| 59 | QGLIGDICLPRWGCLWGRSV |
| 60 | QGLIGDICLPRWGCLWGRSVK |
| 61 | EDICLPRWGCLWEDD |
| 62 | RLMEDICLPRWGCLWEDD |
| 63 | MEDICLPRWGCLWEDD |
| 64 | MEDICLPRWGCLWED |
| 65 | RLMEDICLARWGCLWEDD |
| 66 | EVRSFCTRWPAEKSCKPLRG |

-continued

| SEQ ID NO: | SEQUENCE |
|---|---|
| 67 | RAPESFVCYWETICFERSEQ |
| 68 | EMCYFPGICWM |

Effector Molecules

If desired a multispecific molecule for use in the present invention may be conjugated to one or more effector molecule(s). It will be appreciated that the effector molecule may comprise a single effector molecule or two or more such molecules so linked as to form a single moiety that can be attached to the multispecific molecules of the present invention. Where it is desired to obtain an antibody or multispecific molecule according to the present disclosure linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

In one embodiment the multispecific molecules of the present disclosure may comprise an effector molecule.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Functional Assays and Screening Formats

Typically suitable binding domains for use in the present invention can be identified by testing one or more binding domain pairs in a functional assay. For example a multi specific molecule comprising a binding domain specific to the antigen CD45 and a binding domain specific to the antigen CD79a and/or CD79b may be tested in one or more functional assays.

A "functional assay," as used herein, is an assay that can be used to determine one or more desired properties or activities of the protein complexes, antibody complexes or the mixture of antibodies subject to the assay conditions. Suitable functional assays may be binding assays, apoptosis assays, antibody-dependent cellular cytotoxicity (ADCC) assays, complement-dependent cytotoxicity (CDC) assays, inhibition of cell growth or proliferation (cytostatic effect) assays, cell-killing (cytotoxic effect) assays, cell-signaling assays, cytokine production assays, antibody production and isotype switching, and cellular differentiation assays.

The efficacy of multispecific antibodies according to the present disclosure can be compared to individual antibodies or mixtures of antibodies (or fragments) in such models by methods generally known to one of ordinary skill in the art.

The functional assays may be repeated a number of times as necessary to enhance the reliability of the results. Various statistical tests known to the skilled person can be employed to identify statistically significant results and thus identify multispecific molecules with biological functions.

Examples of suitable functional assays are described in the Examples herein and include measuring the ability of a multispecific molecule of the present invention to inhibit B cell activation following stimulation with anti-IgM, as measured by detecting the inhibition of markers of B cell activation such as phosphorylated Akt expression, phosphorylated P38 expression, PLCγ signalling, CD40 expression, CD71 expression and/or CD86 expression.

When establishing a functional assay for screening the skilled person can set a suitable threshold over which an identified activity is deemed a 'hit'. Where more than one functional assay is used the threshold for each assay may be set at a suitable level to establish a manageable hit rate. In one example the hit rate may be 3-5%. In one example the criteria set when searching for pairs of binding domains that inhibit B cell function may be at least 30% inhibition of at least two phospho-readouts in a B cell activation assay.

In one example a multispecific molecule of the present invention has an IC50 of less than 5 nM for inhibition of CD86 expression in anti-IgM stimulated B cells.

In one embodiment in vivo assays, such as animal models, including mouse tumor models, models of auto-immune disease, virus-infected or bacteria-infected rodent or primate models, and the like, may be employed to test molecules of the present disclosure.

An example of a suitable format for screening and discovery of binding domains is described herein below.

Screening to identify binding domains for use in the present invention may employ a bispecific protein complex.

"Bispecific protein complex" as used herein refers to a molecule comprising two proteins (A and B referred to herein as bispecific components) which are retained together by a heterodimeric-tether. In one embodiment one or both of the proteins have a binding domain, for example one or both of the proteins are antibodies or fragments thereof.

Typically the bispecific protein complex has the formula A-X:Y-B wherein:
  A-X is a first fusion protein;
  Y-B is a second fusion protein;
  X:Y is a heterodimeric-tether;
  A comprises a first binding domain;
  B comprises a second binding domain;
  X is a first binding partner of a binding pair;
  Y is a second binding partner of the binding pair; and
  : is an interaction (such as a binding interaction) between X and Y.

"Fusion proteins" as employed herein comprise a protein component, for example A or B fused to another entity, for example a binding partner X or Y (as appropriate). In embodiment the fusion protein is a translational protein expressed by a recombinant techniques from a genetic construct, for example expressed in a host from a DNA construct.

The function of the tether X:Y is to retain the proteins A and B in proximity to each other so that synergistic function of A and B can be realised.

"heterodimeric-tether" as used herein refers to a tether comprising two different binding partners X and Y which form a interaction (such as a binding) between each other which has an overall affinity that is sufficient to retain the two binding partners together. In one embodiment X and/or Y are unsuitable for forming homodimers.

Heterodimerically-tethered and heterodimeric-tether are used interchangeably herein.

In one embodiment "unsuitable for forming homodimers" as employed herein refers to formation of the heterodimers of X-Y are more preferable, for example stable, such as thermodynamically stable and/or physically stable (for example evidenced by lack of aggregation), once formed.

In one embodiment the X-Y interaction is more favourable than the X-X or Y-Y interaction. This reduces the formation of homodimers X-X or Y-Y when the fusion proteins A-X and B—Y are mixed. This also renders removal of homodimers relatively simple, for example, one purification step, such as column chromatography provides substantially pure fusion proteins and/or bispecific protein complexes according to the present disclosure.

In one embodiment a purification step is provided after expression of the fusion protein. Thus in one embodiment prior to in vitro mixing the fusion protein(s) is/are provided in substantially pure form. Substantially pure form as employed herein refers to wherein the fusion protein is in the range 85 to 100%, for example 90, 91, 92, 93, 94, 95, 96, 97, 98, 99 or 100% monomer.

In one embodiment no purification is required after the bispecific protein complex formation.

In one embodiment the ratio of fusion proteins employed in the in vitro mixing step of the present method is A-X to B-Y 0.8:1 to 3:1, such as 1.5: 1 or 2:1.

In one embodiment the ratio of fusion proteins employed in the in vitro mixing step of the present method is B-Y to A-X 0.8:1 to 3:1, such as 1.5:1 or 2:1.

In one embodiment the ratio is 1:1.

In one embodiment one (or at least one) of the binding partners is incapable of forming a homodimer, for example an amino acid sequence of the binding partner is mutated to eliminate or minimise the formation of homodimers.

In one embodiment both of the binding partners are incapable of forming a homodimer, for example one of the binding partners is a peptide and the other binding partner is a $V_{HH}$ specific to said peptide.

In one embodiment an scFv employed in the molecules of the present disclosure is incapable of forming a homodimer.

Incapable of forming homodimers as employed herein, refers to a low or zero propensity to form homodimers. Low as employed herein refers to 5% or less, such as 4, 3, 2, 1, 0.5% or less aggregate.

Small amounts of aggregate in the fusion proteins or residual in the heterodimerically-tethered bispecific protein complex generally has minimal effect on the method of the present disclosure.

In one embodiment: is a binding interaction, for example based on attractive forces such as Van der Waals forces, such as hydrogen bonding and electrostatic interactions, for example, based on antibody specificity for an antigen, such as a peptide.

In one embodiment: is a covalent bond formed from a specific chemical interaction, such as click chemistry.

In one embodiment: is not a covalent bond.

"Form the complex" as employed herein refers to an interaction, including a binding interactions or a chemical reaction, which is sufficiently specific and strong when the fusion protein components A-X and B—Y are brought into contact under appropriate conditions that the complex is assembled and the fusion proteins are retained together.

"Retained together" as employed herein refers to the holding of the components (the fusion proteins) in the proximity of each other, such that after binding the complex can be handled as if it were one molecule, and in many instances behaves and acts like a single molecule. In one embodiment the retention renders the complex suitable for use in the method disclosed herein, i.e. suitable for use in at least one functional screen.

In one embodiment the binding interaction is reversible.

Specificity when in relation to X and Y as employed herein refers where the binding partners X and Y in the interaction only recognise each other or have significantly higher affinity for each other in comparison to non-partners, for example at least 2, 3, 4, 5, 6, 7, 8, 9, 10 times higher affinity.

In one embodiment, the binding interaction between X and Y has a low dissociation constant. Examples of a low dissociation constant include $1\text{-}9\times10^{-2}$ $s^{-1}$ or less, for example $1\text{-}9\times10^{-3}$ $s^{-1}$, $1\text{-}9\times10^{-4}$ $s^{-1}$, $1\text{-}9\times10^{-5}$ $s^{-1}$, $1\text{-}9\times10^{-6}$ $s^{-1}$ or $1\text{-}9\times10^{-7}$ $s^{-1}$. Particularly suitable dissociation constants include $1\times10^{-4}$ $s^{-1}$ or less, for example $1\times10^{-5}$ $s^{-1}$, $1\times10^{-6}$ $s^{-1}$ or $1\times10^{-7}$ $s^{-1}$.

Whilst not wishing to be bound by theory it is thought that the low dissociation constant (also referred to as off rate) allows the molecules to be sufficiently stable to render the bispecific protein complex useful, in particular in functional screening assays.

In one embodiment, the affinity of X and Y for each other is 5 nM or stronger, for example 4 nM, 3 nM, 2 nM, 1 nM or stronger.

In one embodiment, the affinity of X and Y for each other is 900 pM or stronger, such as 800, 700, 600, 500, 400, 300, 200, 100 or 50 pM or stronger.

In another embodiment, the affinity of X and Y for each other is 10 pM or stronger, for example 9, 8, 7, 6 or 5 pM.

Affinity is a value calculated from the on and off rate of an interaction. The term "affinity" as used herein refers to the strength of the sum total of non-covalent interactions between a single binding site of a molecule (e.g. an antibody) and its binding partner (e.g. a peptide). The affinity of a molecule for its binding partner can generally be represented by the equilibrium dissociation constant ($K_D$). Affinity can be measured by common methods known in the art, including those described herein, such as surface plasmon resonance methods, in particular BIACORE.

In one embodiment, multiple bispecific protein complexes according to the present disclosure are tested in parallel or essentially simultaneously.

Simultaneously as employed herein refers to the where the samples/molecules/complexes are analysed in the same analysis, for example in the same "run".

In one embodiment simultaneously refers to concomitant analysis where the signal output is analysed by the instrument at essentially the same time. This signal may require deconvolution to interpret the results obtained.

Advantageously, testing multiple bispecific protein complexes allows for more efficient screening of a large number of bispecific protein complexes and the identification of new and interesting relationships. Clearly different variable regions to the target antigens of interesting CD45 and CD79 can give access to subtle nuances in biological function.

In one embodiment, the multiple bispecific protein complexes are tested by using a multiplex as defined above and subjecting the same to one or more functional assays.

The term "biological function" as used herein refers to an activity that is natural to or the purpose of the biological entity being tested, for example a natural activity of a cell, protein or similar. Ideally the presence of the function can be tested using an in vitro functional assay, including assays utilizing living mammalian cells. Natural function as employed herein includes aberrant function, such as functions associated with cancers.

A relevant "biological comparator" as employed herein refers to a suitable entity for assessing activity, in the same assay as that employed for the bispecific protein complex, to establish if there is any change or novel activity or function. Suitable comparators for A-X:Y-B may include purified protein (including recombinant proteins) in a natural form or presented in the same format as the bispecific i.e. where A and B are the same entity, such as A-X:Y-A or B-X:Y-B. Alternatively the fusion protein A-X or B-Y in an uncomplexed form may be employed as a comparator. Alternatively, multiple comparators of different formats (in particular as described herein) may be employed. The person skilled in the art is able to identify and include a suitable control/comparator based on common general knowledge or information that is found in the literature.

The term "synergistic function" as used herein refers to biological activity that is not observed or higher than observed when the first and second proteins of a bispecific protein complex of the present disclosure are not employed together, for example activity which is only observed in a bispecific form. Therefore, "synergistic" includes novel biological function.

The present disclosure provides a molecule with at least specificity to CD45 and CD79 with a novel biological function.

Novel biological function as employed herein refers to function which is not apparent or absent until the two or more synergistic entities [protein A and protein B] are brought together (as a bispecific or otherwise) or a previously unidentified function.

Higher as employed herein refers to an increase in activity including an increase from zero i.e. some activity in the bispecific where the individual uncomplexed bispecific component or components has/have no activity in the relevant functional assay, also referred to herein as new activity or novel biological function. Higher as employed herein also includes a greater than additive function in the bispecific in a relevant functional assay in comparison to the individual uncomplexed bispecific components or bivalent binding domains, for example 10, 20, 30, 40, 50, 60, 70, 80, 90, 100, 200, 300% or more increase in a relevant activity.

In one embodiment the novel synergistic function is a higher inhibitory activity.

In one embodiment the multispecific antibody molecule of the present invention has a higher inhibitory activity than the sum of the activity of a bivalent binding domain to CD45 and a bivalent binding domain to CD79a provided alone or in admixture In one embodiment, at least one of the first binding partner, X, and the second binding partner, Y, of the binding pair are independently selected from a peptide and a protein; for example the first binding partner or second binding partner is a peptide.

Suitable peptides include the group comprising GCN4, Fos/Jun (human and murine Fos have a Uniprot number P01100 and P01101 respectively and human and murine jun have a Uniprot number P05412 and P05627 respectively), human influenza hemagglutinin (HA), polyhistidine (His), green fluorescent protein (GFP) and FLAG. Other peptides are also contemplated as suitable for use in the present disclosure and particularly suitable peptides are affinity tags for protein purification because such peptides have a tendency to bind with high affinity to their respective binding partners.

The term "peptide" as used herein refers to a short polymer of amino acids linked by peptide bonds, wherein the peptide contains in the range of 2 to 100 amino acids, for example 5 to 99, such as 6 to 98, 7 to 97 or 8 to 96. In one embodiment a peptide employed in the present disclosure is an amino acid sequence of 50 amino acid residues or less, for example 40, 30, 10 or less. The peptides used in the present disclosure are of a sufficient length to be fit for purpose, for example if the peptide is a linker, it needs to be suitably long to allow the fragment which it links to perform its biological function; alternatively if the peptide is a binding partner, it must be capable of binding specifically to another entity such as an antibody.

In one embodiment, the other binding partner of the binding pair (the alternative first or second binding partner) is a protein.

Protein as employed herein refers to an amino acid sequence of 100 amino acids or more. In one embodiment a "protein" as employed herein refers to an amino acid sequence with a secondary or tertiary structure.

In one embodiment, the first protein, A, and/or second protein, B, of the bispecific protein complex is an antibody or antibody fragment. Such a bispecific protein complex may be referred to as a bispecific antibody complex.

In one embodiment each antibody or fragment employed in the bispecific antibody complex of the disclosure comprises one binding site.

The full length antibody or antibody fragment employed in the fusion proteins (A-X or B-Y) may be monospecific, multivalent or bispecific.

Advantageously, the use of two bispecific antibody or antibody fragments allows the molecules of the present disclosure, such as the bispecific antibody complex described herein to potentially be specific for up to 4 different antigens (i.e. the complex may be tetraspecific). This allows avidity type effects to be investigated.

In one embodiment, the antibody or antibody fragment employed in the molecules of the present disclosure or components thereof, such as the first fusion protein A-X is a monospecific antibody or antibody fragment, for example a Fab, Fab', scFv or similar, and in particular is specific to CD45.

In one embodiment, the antibody or antibody fragment employed in the molecules of the present disclosure or components thereof, such as the second fusion protein B-Y is a monospecific antibody or antibody fragment, for example a Fab, Fab', scFv or similar, and in particular is specific to CD79a and/or CD79b.

In one embodiment, the antibody or antibody fragment employed in the molecules of the present disclosure or components thereof, such as the second fusion protein B-Y is multivalent, that is has two or more binding domains.

In one embodiment, the antibody or antibody fragment employed in the molecules of the present disclosure or components thereof, such as the first fusion protein A-X is monovalent and the antibody or antibody fragment employed in the molecules of the present disclosure or components thereof, such as the second fusion protein B-X is monovalent.

Thus in one embodiment the binding domains of the multispecific molecules of the present disclosure are monovalent.

Thus in one embodiment the binding domains of the multispecific molecules of the present disclosure are monovalent and monospecific.

In one embodiment, the antibody or antibody fragment employed in the molecules of the present disclosure or components thereof, such as the first fusion protein A-X is monovalent and the antibody or antibody fragment employed in the molecules of the present disclosure or components thereof, such as the second fusion protein B-Y is multivalent.

In one embodiment, the antibody or antibody fragment employed in the molecules of the present disclosure or components thereof, such as the first fusion protein A-X is multivalent and the antibody or antibody fragment employed in the molecules of the present disclosure or components thereof, such as the second fusion protein B-Y is monovalent.

In one embodiment, the antibody or antibody fragment employed in the molecules of the present disclosure or components thereof, such as the first fusion protein A-X is multivalent and the antibody or antibody fragment employed in the molecules of the present disclosure or components thereof, such as the second fusion protein B-Y is multivalent.

In one embodiment, a first antibody, a second antibody or both the first and second antibody of a the molecules of the present disclosure or components thereof, such as a bispecific antibody complex may be an IgG format, for example an anti-CD45 and/or anti-CD79 antibody may be provided in an IgG format.

In one embodiment, an antibody fragment is selected from the group consisting of: a fragment antigen (Fab) fragment, a single chain variable fragment (scFv) and a single domain antibody (sdAb), such as a scFv, is employed in the first (A-X) or second fusion protein (B-Y). Advantageously, the small size of a scFv may facilitate the correct folding of the bispecific antibody complexes.

In one embodiment, the first (A), second antibody/fragment (B) or both the first and second antibody/fragment of the bispecific antibody complex of the present disclosure may be a Fab.

In one embodiment, the first, second antibody/fragment or both the first and second antibody/fragment of the bispecific antibody complex of the present disclosure is/are a Vim.

"Fusion protein" as employed in the context of a bispecific complex of the present disclosure refers to a protein, for example an antibody or antibody fragment attached to a binding partner. For convenience bispecific protein complexes of the present disclosure are referred to herein as A-X:Y-B. However, this nomenclature is not intended to limit how the fusion protein A-X and B—Y are designed because our experiments indicate that binding partners X and Y can be reversed i.e. A-Y and B-X without adversely impacting on the method. Thus A and B and X and Y are nominal labels referred to for assisting the explanation of the present technology.

"Attached" as employed herein refers to connected or joined directly or indirectly via a linker, such as a peptide linker examples of which are discussed below. Directly connected includes fused together (for example a peptide bond) or conjugated chemically.

"Binding partner" as employed herein refers to one component part of a binding pair.

In one embodiment, the affinity of the binding partners is high, 5 nM or stronger, such as 900, 800, 700, 600, 500, 400, 300 pM or stronger.

"Binding pair" as employed herein refers to two binding partners which specifically bind to each other. Examples of a binding pair include a peptide and an antibody or binding fragment specific thereto, or an enzyme and ligand, or an enzyme and an inhibitor of that enzyme.

In one embodiment, the first binding partner (X) is selected from the group comprising: a full length antibody, a Fab, a Fab', a scFv, a peptide and a sdAb, wherein examples of a sdAb include VH or VL or $V_HH$.

In one embodiment, the second partner (Y) is selected from the group comprising: a full length antibody, a Fab, a Fab', a scFv, a peptide and a sdAb, wherein examples of a sdAb include VH or VL or $V_HH$.

In one embodiment, where A is an antibody or fragment thereof the first binding partner (X) is attached to the C-terminal of the heavy or light chain of the first antibody or antibody fragment, for example, the first binding partner is attached to the C-terminal of the heavy chain of the first antibody or antibody fragment.

In another embodiment, where B is an antibody or fragment thereof the second binding partner (Y) is attached to the C-terminal of the heavy or light chain of the second antibody or antibody fragment, for example the second binding partner is attached to the C-terminal of the heavy chain of the second antibody or antibody fragment.

In one embodiment X is attached to the C-terminal of the heavy chain of the antibody or fragment (protein A) and Y is attached to the C-terminal of the antibody or fragment (protein B).

In one embodiment X is attached via a linker (such as ASGGGG or ASGGGGSG) to the C-terminal of the heavy chain of the antibody or fragment (protein A) and Y is attached via a linker (such as ASGGGG or ASGGGGSG) to the C-terminal of the antibody or fragment (protein B).

In one embodiment, the first or second binding partner (X or Y) is a peptide.

Examples of a suitable binding pair may include GCN4 (SEQ ID NO: 1) or a variant thereof and 52SR4 (SEQ ID NO:3) or a variant thereof, which is a scFv specific for GCN4.

In a one embodiment, the first binding partner (nominally X) is GCN4 (for example as shown in SEQ ID NO:1) or a variant thereof (for example without the His tag) and the second binding partner (nominally Y) is a scFv specific for GCN4 (for example as shown in SEQ ID NO:3) or a variant thereof.

In a one embodiment, the first binding partner (nominally X) is a sFv specific for GCN4 (for example as shown in SEQ ID NO:3) or a variant thereof and the second binding partner (nominally Y) is GCN4 (for example as shown in SEQ ID NO:1) or a variant thereof.

GCN4 variants include an amino acid sequence with at least 80%, 85%, 90%, 91%, 92%, 93%, 94% 95%, 96%, 97% or 98%, or 99% identity to SEQ ID NO:1. GCN4 variants also include an amino acid having at least 80%, 85%, 90%, 91%, 92%, 93%, 94%, 95%, 96%, 97%, 98%, or 99% to a sequence encoded by a nucleotide sequence SEQ ID NO:2, or a nucleotide sequence which hybridises to SEQ ID NO: 2 under stringent conditions.

A suitable scFv specific to GCN4 is 52SR4 (SEQ ID NO: 3) or a variant thereof. Variants of 52SR4 include an amino acid sequence with at least 80%, or 85%, or 90%, or 95%, or 98%, or 99% identity to SEQ ID NO: 3. 52SR4 variants also include an amino acid sequence having at least at least 80%, or 85%, or 90%, or 95%, or 98%, or 99% to a sequence encoded by a nucleotide sequence SEQ ID NO:4, or a nucleotide sequence which hybridises to SEQ ID NO: 2 under stringent conditions.

The present inventors have found that the single chain antibody 52SR4 and peptide GCN4, are a binding pair suitable for use in the bispecific protein complexes of the present disclosure.

Alternatively, any suitable antibody/fragment and antigen (such as a peptide) may be employed as X and Y.

In one embodiment, the first binding partner (X) and the second binding partner (Y) are a protein.

In one embodiment, the first binding partner (X) is an enzyme or an active fragment thereof and the second binding partner (Y) is a ligand or vice versa.

In one embodiment, the first binding partner (X) is an enzyme or an active fragment thereof and the second binding partner (Y) is an inhibitor of that enzyme or vice versa.

"Active fragment" as employed herein refers to an amino acid fragment, which is less than the whole amino acid sequence for the entity and retains essentially the same biological activity or a relevant biological activity, for example greater than 50% activity such as 60%, 70%, 80%, 85%, 90%, 91%, 92%, 93%, 94%, 95%, 96%, 97%, 98%, 99% or 100%.

In another embodiment, the first binding partner X is glutathione (GSH) and the second binding partner Y is glutathione-S-transferase (GST) or vice versa.

In another embodiment, X is Fos and Y is Jun or vice versa.

In another embodiment, X is His and Y is anti-His or vice versa.

In another embodiment, the binding pair is clamodulin binding peptide and Y is calmodulin or vice versa.

In another embodiment, X is maltose-binding protein and Y is an anti-maltose binding protein or fragment thereof or vice versa.

Other enzyme-ligand combinations are also contemplated for use in binding partners. Also suitable are affinity tags known in the art for protein purification because these have a tendency to bind with high affinity to their respective binding partners.

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST software available from NCBI (Altschul, S. F. et al., 1990, J. Mol. Biol. 215:403-410; Gish, W. & States, D. J.

1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In one embodiment, the first or second binding partner (X or Y) is a protein or peptide.

In one embodiment, the first and second fusion proteins comprise one or more peptide linkers. The linkers may be incorporated at various locations in the fusion proteins. For example, a linker may be introduced between a binding partner and the protein attached thereto.

In one embodiment, the linker is a peptide linker.

The term "peptide linker" as used herein refers to a peptide with amino acid sequences. A range of suitable peptide linkers will be known to the person of skill in the art.

In one embodiment, the peptide linker may be of synthetic origin, i.e. prepared by synthetic chemistry techniques.

In one embodiment, the binding partners of the bispecific protein complexes are joined to their respective proteins via peptide linkers.

In one embodiment the fusion proteins is a translational fusion, that is a fusion protein expressed in a host cells comprising a genetic construct from which the fusion protein is expressed.

In one embodiment the fusion protein is prepared by conjugating the A to X or B to Y optionally via a peptide linker.

In one embodiment, the peptide linker is 50 amino acids in length or less, for example 20 amino acids of less.

Generally it will be more efficient to express the fusion protein recombinantly and therefore a direct peptide bond or a peptide linker that can be expressed by a host cell may be advantageous.

In one aspect, there is provided a method of producing a bispecific protein complex of the present disclosure, comprising the steps of:
  (a) producing a first fusion protein (A-X), comprising a binding domain specific to CD45 or CD79 a and/or CD79b (A), attached to a first binding partner (X) of a binding pair;
  (b) producing a second fusion protein (B-Y), comprising a binding domain specific to CD45 or CD79a and/or CD79b (B), attached to a second binding partner (Y) of a binding pair;
    wherein at least the first fusion protein or the second fusion protein comprises a binding domain specific to CD45 and the remaining fusion protein comprises a binding domain specific to CD79a and/or CD79b, and
  (c) mixing the first (A-X) and second fusion proteins (B-Y) together prepared in step a) and b).

In particular, the heterodimerically-tethered bispecific protein complex is prepared by mixing A-X and B-Y in vitro. Thus in one embodiment the method comprises an in vitro mixing step bringing A-X and B-Y into contact.

Thus generally the fusion proteins A-X and B—Y are not co-expressed in the same cell. This is advantageous because it allows, for example 100 A-X fusion proteins and 100 A-Y fusion proteins to be expressed separately and optionally purified, and through subsequent mixing of the 200 fusion proteins in the various permutations can provide 10,000 heterodimerically-tethered bispecific protein complexes.

In contrast prior art methods require co-expression of bispecifics and thus for 10,000 complexes, 10,000 transfections, expressions and purifications are required.

The binding partners X and Y have affinity for each other and act as biological equivalent of VELCRO or a bar and magnet and hold the complex together. Advantageously, this means that the fusion proteins A-X and Y-B can be readily assembled into a bispecific protein complex simply by mixing the fusion proteins together. Thus the bispecific protein complex of the present disclosure has a modular structure which allows for two different proteins to be easily assembled in order to produce large panels of permutations of bispecific protein complexes with different combinations of antigen specificities in, for example a grid-like fashion. This allows for the efficient and systematic screening of a large number of bispecific protein complexes in order to detect additive, synergistic or novel biological function. Given X and Y are specific for each other this significantly reduces the ability to form homodimers. X and Y are collectively referred to herein as a binding pair or binding partners. In one embodiment X does not have high affinity for other Xs. In one embodiment Y does not have high affinity for other Ys. Advantageously, when X and Y do not form homodimers, this prevents the formation of undesired monospecific protein complexes, increases yield of the desired bispecific protein complexes, and removes the need for onerous purification steps to remove the monospecific protein complexes.

This rapid assembly of bispecific protein complexes, the level of yield and/or purity cannot be obtained efficiently by prior art methods, in particular prior art methods generally require extensive purification steps.

Advantageously, the X and Y components allow a multiplex comprising bispecific protein complexes made up of different permutations of fusion proteins to be assembled rapidly and easily.

In one embodiment the proteins A and B are antibodies or antibody fragments. When the antibody or antibody fragments are held together as a complex via X and Y, this forms a bispecific antibody complex.

The mixing is generally effected in conditions where the X and Y can interact. In one embodiment, the fusion proteins are incubated in cell culture media under cell culturing conditions, for example the fusion proteins are incubated for 90 minutes in a 37° C./5% $CO_2$ environment.

In one embodiment the fusions proteins of the present disclosure are mixed in an aqueous environment, for example one fusion protein may be bound to a solid surface such as a bead or a plate and the other fusion protein can be introduced thereto in an aqueous solution/suspension. The solid phase allows excess components and reagents to be washed away readily. In one embodiment neither fusion is attached a solid phase and are simply admixed in a liquid/solution/medium.

Advantageously, the method of the present disclosure can be employed to prepare complexes formed between heterogenous pairs (i.e. between the first fusion protein [A-X] and second fusion protein [B-Y]) wherein interactions between homogenous pairs (i.e. between two first fusion proteins [A-X] or two second fusion proteins [B-Y]) are minimised. Thus the present method allows large numbers of bispecific protein complexes to be prepared, with minimal or no contamination with homodimeric complexes. This level of purity and yield is not possible using the prior art methods.

In one embodiment the complexes formed require no further purification steps.

In one embodiment the complexes formed require one purification step, for example column chromatography.

In one embodiment the method further comprises at least one purification step, for example after expression of a fusion protein according to the present disclosure.

A "functional assay," as used herein, is an assay that can be used to determine one or more desired properties or activities of the protein complexes, antibody complexes or the mixture of antibodies subject to the assay conditions. Suitable functional assays may be binding assays, apoptosis assays, antibody-dependent cellular cytotoxicity (ADCC) assays, complement-dependent cytotoxicity (CDC) assays, inhibition of cell growth or proliferation (cytostatic effect) assays, cell-killing (cytotoxic effect) assays, cell-signaling assays, cytokine production assays, antibody production and isotype switching, and cellular differentiation assays, In one embodiment in vivo assays, such as animal models, including mouse tumor models, models of auto-immune disease, virus-infected or bacteria-infected rodent or primate models, and the like, may be employed to test molecules of the present disclosure.

In the context of bispecific antibody complexes, the efficacy of bispecific antibody complexes according to the present disclosure can be compared to individual antibodies or mixtures of antibodies (or fragments) in such models by methods generally known to one of ordinary skill in the art.

The functional assays may be repeated a number of times as necessary with or without different samples of a particular bispecific antibody complex to enhance the reliability of the results. Various statistical tests known to the skilled person can be employed to identify statistically significant results and thus identify bispecific antibody complexes with biological functions, and in particular to identify optimal variable region pairs for use in multispecific molecule of the present invention.

Compositions and Medical Uses

In one aspect there is provided a molecule according to the present disclosure or a component, such as a fusion protein, a heterodimerically-tethered bispecific protein complex, a composition comprising a molecule of the invention, including a fusion protein or said bispecific protein complex, a multiplex, array, library as defined herein.

In one embodiment the molecules of the present disclosure, for example an antibody described herein, a multispecific molecule and/or a bispecific protein complexes are suitable for therapeutic applications and may provide novel therapies for treating diseases. Thus in a further aspect, there is provided a molecule of the present disclosure, for example a bispecific protein complex as described above, for use in therapy. The molecules of the present disclosure including the multispecific molecules and bispecific protein complexes described herein are suitable for treating a range of diseases, such as cancer.

The molecules of the present disclosure, including the multispecific molecules and bispecific protein complexes described herein are also particularly suited for inhibiting B cell function in order to control immune and autoimmune reactions in various autoimmune diseases.

Thus, the present disclosure extends to a method of treating a disease in a patient, comprising the administration of a therapeutically effect amount of a molecule of the present disclosure, for example a multispecific molecule or bispecific protein complex of the present disclosure.

In one aspect, there is provided a pharmaceutical composition comprising one or more molecules of the present disclosure, for example a multispecific molecule of the present disclosure.

Various different components can be included in the composition, including pharmaceutically acceptable carriers, excipients and/or diluents. The composition may, optionally, comprise further molecules capable of altering the characteristics of the population of multispecific molecules of the invention thereby, for example, reducing, stabilizing, delaying, modulating and/or activating the function of the antibodies. The composition may be in solid, or liquid form and may be, inter alia, be in the form of a powder, a tablet, a solution or an aerosol.

The present invention also provides a pharmaceutical or diagnostic composition comprising an antibody molecule or a multispecific molecule of the present invention in combination with one or more of a pharmaceutically acceptable excipient, diluent or carrier. Accordingly, provided is the use of a multispecific molecule of the invention for use in the treatment and for the manufacture of a medicament for the treatment of a pathological condition or disorder.

Pathological Conditions

The pathological condition or disorder, may, for example be selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis, hypochlorhydia and cancer, including breast cancer, lung cancer, gastric cancer, ovarian cancer, hepatocellular cancer, colon cancer, pancreatic cancer, esophageal cancer, head & neck cancer, kidney, and cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof.

In one embodiment the disorder is cancer, for example Leukemia, including lyphocytic leukemia, such as acute lymphoblastic leukemia or chronic lymphocytic leukemia; or myelogenus leukemia, such as acute myelogenous leukemia or chronic myelogenous leukemia.

In one embodiment autoimmune disease includes:— Acute disseminated encephalomyelitis (adem), acute necrotizing hemorrhagic leukoencephalitis, Addison's disease, adrenal insufficiency, hypocortisolism, alopecia areata, amyloidosis, ankylosing spondylitis, spondyloarthritis, Strumpell-marie disease, anti-GBM/anti-TBM nephritis, antiphospholipid syndrome (aps), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune lymphoproliferative syndrome (ALPS), Canale-Smith syndrome, autoimmune myocarditis, autoimmune oophoritis, autoimmune pancreatitis (AIP), autoimmune polyglandular syndromes (types I, II & III), autoimmune retinopathy (AR), autoimmune thrombocytopenic purpura (ATP), autoimmune thyroid disease, autoimmune urticaria, axonal/neuronal neuropathies, balo disease, Behcet's disease, bullous pemphigoid, cardiomyopathy, Castleman disease, coeliac disease, chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid (CP), Crohn's disease, inflammatory bowel disease, colitis, enteritis, ileitis, Cogans syndrome, cold agglutinin disease, congenital heart block, Coxsackie myocarditis, crest disease, cryoglobulinemia, demyelinating neuropathies, dermatitis herpetiformis, Duhring's disease, dermatomyositis, diabetes, type I, discoid lupus erythematosus (DLE), Dressler's syndrome, endometriosis, epidermolysis bullosa (EB) and eb acquisita (EBA), eosinophilic gastroenteritis, esophagitis, eosinophilic fasciitis, schulman's syndrome, erythema nodosum, experimental allergic encephalomyelitis, Evans syndrome, fibrosing alveolitis, giant cell arteritis (temporal arteritis), giant cell myocarditis, glomerulonephritis (non-proliferative: focal segmental glomerulosclerosis and membranous glomerulonephritis, proliferative: IgA nephropathy), goodpasture's syndrome, granulomatosis with polyangiitis (GPA) (formerly called Wegener's granulomatosis), Graves' disease, Guillain-Barré syndrome, Miller Fisher syndrome, acute motor axonal neuropathy, acute motor sensory axonal neuropathy, acute panautonomic neuropathy, Bickerstaff's brainstem encephalitis, Hashimoto's encephalitis, Hashimoto's thyroiditis, hemolytic anemia, Henoch-Schonlein purpura, herpes gestationis, hypogammaglobulinemia, idiopathic pulmonary fibrosis, idiopathic thrombocytopenic purpura (ITP), IgA nephropathy (IGAN), berger's syndrome, synpharyngitic glomerulonephritis, IgA pemphigus, IgG4-related sclerosing disease, immune-regulated infertility-inclusion body myositis, insulin-dependent diabetes mellitus, interstitial cystitis, Isaac's syndrome, neuromyotonia juvenile arthritis, juvenile myositis, Kawasaki syndrome, Lambert-Eaton syndrome, leukocytoclastic vasculitis, lichen planus, lichen sclerosus, ligneous conjunctivitis, linear IgA dermatosis (LAD), pemphigoid, lupus (SLE), Lyme disease, Meniere's disease, microscopic polyangiitis (MPA), mixed connective tissue disease (MCTD), monoclonal gammaopathy, Mooren's ulcer, Mucha-Habermann disease, multiple sclerosis, myasthenia gravis, myositis, narcolepsy, neuromyelitis optica (devic's), neuromyotonia, Isaac's syndrome (acquired, paraneoplastic, hereditary), neutropenia, ocular cicatricial pemphigoid, optic neuritis, oophoritis, opsoclonus-myoclonus syndrome, orchitis, palindromic rheumatism, pandas (pediatric autoimmune neuropsychiatric disorders associated with *streptococcus*), paraneoplastic autoimmune multiorgan syndrome (PAMS), paraneoplastic cerebellar degeneration, paraneoplastic pemphigus (PNP), paroxysmal nocturnal hemoglobinuria (PNH), Parry Romberg syndrome, Parsonnage-Turner syndrome, pars planitis (peripheral uveitis), pempgigoid gestationis (PG), pemphigus vulgaris (PV), pemphigus folliaceus (PF), peripheral neuropathy, perivenous encephalomyelitis, pernicious anemia, Poems syndrome, polyarteritis *nodosa* (PAN), polymyalgia rheumatic, polymyositis, postmyocardial infarction syndrome, postpericardiotomy syndrome, progesterone dermatitis primary biliary cirrhosis, Hanot syndrome, primary sclerosing cholangitis (PSC), sclerosong cholangitis, psoriasis, psoriatic arthritis, pyoderma gangrenosum, pure red cell aplasia, Rasmussen's encephalitis, chronic focal encephalitis (CFE), Raynauds phenomenon, reactive arthritis, Reiter's syndrome, recoverin-associated retinopathy (RAR), reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, systemic sclerosis, sjogren's syndrome, sperm & testicular autoimmunity, stiff person/man syndrome, subacute bacterial endocarditis (SBE), Susac's syndrome, sympathetic ophthalmia, Takayasu's arteritis, temporal arteritis/giant cell arteritis, thromboangiitis obliterans, Buerger's disease, thrombocytopenic purpura (TTP), Tolosa-Hunt syndrome, transverse myelitis, ulcerative colitis, undifferentiated connective tissue disease (UCTD), uveitis, polymyalgia rheumatica, Takayasu's arteritis, temporal arteritis, Buerger's disease, cutaneous vasculitis, Kawasaki disease, polyarteritis *nodosa*, Behçet's syndrome, Churg-Strauss syndrome, cutaneous vasculitis, Henoch-Schönlein purpura, microscopic polyangiitis, Wegener's granulomatosis, golfer's vasculitis, vesiculobullous dermatosis, Vitiligowegener's granulomatosis (now termed granulomatosis with polyangiitis (GPA).

In one embodiment the autoimmune disease is selected from the group comprising or consisting of:—ANCA vasculitis, IgA nephropathy (Berger's), pemphigus vulgaris/bullous pemphigoid, ITP, primary biliary cirrhosis, autoimmune thyroiditis (Grave's disease), hashimoto's disease, lupus nephritis, membranous glomerulonephritis (or membranous nephropathy), APS, myasthenia gravis, neuromyelitis optica, primary Sjögren's, autoimmune neutropaenia, autoimmune pancreatitis, dermatosmyositis, autoimmune uveitis, autoimmune retinopathy, Behçet's disease, IPF, systemic sclerosis, liver fibrosis, autoimmune hepatitis, primary sclerosing cholangitis, vitiligo, goodpasture's syndrome, pulmonary alveolar proteinosis, chronic autoimmune urticarial, psoriasis, rheumatoid arthritis, psoriatic arthritis, axial spodyloarthritis, transplantation (including GvHD), asthma, COPD, giant cell arteritis, refractory autoimmune cytopaenias, Evans syndrome (autoimmune haemolytic anaemia), type I diabetes, sarcoidosis, polymyositis, ulcerative colitis, Crohn's disease, coeliac disease, Waldenstrom's macroglobulinaemia, focal segmental glomerulosclerosis, chronic Lyme disease (Lyme borreliosis), lichen planus, Stiff person syndrome, dilated cardiomyopathy, autoimmune (lymphocytic) oophoritis, epidermolysis bullosa acquisita, autoimmune atrophic gastritis, pernicious anaemia, atopic dermatitis, atherosclerosis, multiple sclerosis, Rasmussen's encephalitis, Guillain-Barré syndrome and acquired neuromyotonia, stroke.

In one embodiment the disorder is cancer, for example leukemia, for example lyphocytic leukemia, such as acute lymphoblastic leukemia or chronic lymphocytic leukemia; or myelogenus leukemia, such as acute myelogenous leukemia or chronic myelogenous leukemia; or lymphoma, such as diffuse large B cell lymphoma or Hodgkin's or non-Hodkin's lymphoma.

The present invention also provides a pharmaceutical or diagnostic composition comprising a molecule of the present disclosure, such as a multispecific molecule described herein in combination with one or more of a pharmaceutically acceptable excipient, diluent or carrier. Accordingly, provided is the use of a molecule of the present disclosure, such as a multispecific molecule as described herein for use in treatment and in the manufacture of a medicament.

The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the multispecific molecule of the present invention together with one or more of a pharmaceutically acceptable excipient, diluent or carrier.

The term "pharmaceutically acceptable excipient" as used herein refers to a pharmaceutically acceptable formulation carrier, solution or additive to enhance the desired characteristics of the compositions of the present disclosure. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent solution used for the formulation, aseptic suspension of the antibody in the sterile buffered solvent solution, and dispensing of the formulation into sterile receptacles by methods familiar to those of ordinary skill in the art.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Such carriers enable the pharmaceutical compositions to be formulated as tablets, pills, dragées, capsules, liquids, gels, syrups, slurries and suspensions, for ingestion by the patient.

The molecules of the disclosure such as a multispecific molecule described herein can be delivered dispersed in a solvent, e.g., in the form of a solution or a suspension. It can be suspended in an appropriate physiological solution, e.g., physiological saline, a pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. As mentioned supra a suspension can made, for example, from lyophilised antibody.

A thorough discussion of pharmaceutically acceptable carriers is available in Remington's Pharmaceutical Sciences (Mack Publishing Company, N.J. 1991).

The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Alternatively, the dose may be 1 to 500 mg per day such as 10 to 100, 200, 300 or 400 mg per day. Pharmaceutical compositions may be conveniently presented in unit dose forms containing a predetermined amount of an active agent of the invention.

Compositions may be administered individually to a patient or may be administered in combination (e.g. simultaneously, sequentially or separately) with other agents, drugs or hormones.

The dose at which the multispecific molecule of the present disclosure is administered depends on the nature of the condition to be treated, the extent of the inflammation present and on whether the antibody molecule is being used prophylactically or to treat an existing condition. The frequency of dose will depend on the half-life of the multispecific molecule and the duration of its effect. If the multispecific molecule has a short half-life (e.g. 2 to 10 hours) it may be necessary to give one or more doses per day. Alternatively, if the multispecific molecule has a long half-life (e.g. 2 to 15 days) it may only be necessary to give a dosage once per day, once per week or even once every 1 or 2 months.

In the present disclosure, the pH of the final formulation is not similar to the value of the isoelectric point of the multispecific molecule, for if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention.

Direct delivery of the compositions will generally be accomplished by injection, subcutaneously, intraperitoneally, intravenously or intramuscularly, or delivered to the interstitial space of a tissue. The compositions can also be administered into a specific tissue of interest. Dosage treatment may be a single dose schedule or a multiple dose schedule.

Where the product is for injection or infusion, it may take the form of a suspension, solution or emulsion in an oily or aqueous vehicle and it may contain formulatory agents, such as suspending, preservative, stabilising and/or dispersing agents. Alternatively, the multispecific molecule may be in dry form, for reconstitution before use with an appropriate sterile liquid. If the composition is to be administered by a route using the gastrointestinal tract, the composition will need to contain agents which protect the antibody from degradation but which release the bispecific protein complex once it has been absorbed from the gastrointestinal tract. A nebulisable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The term "variant" as used herein refers to peptide or protein that contains at least one amino acid sequence or nucleotide sequence alteration as compared to the amino acid or nucleotide sequence of the corresponding wild-type peptide or protein. A variant may comprise at least 80%, or 85%, or 90%, or 95%, or 98% or 99% sequence identity to the corresponding wild-type peptide or protein. However, it is possible for a variant to comprise less than 80% sequence identity, provided that the variant exhibits substantially similar function to its corresponding wild-type peptide or protein.

In one embodiment the construct of the present disclosure is at least trispecific. In this situation the further specificity may be directed to any antigen of interest, for example antigens to extend half-life such as albumin or Fc neonatal receptor (FcRn); antigens for effector function such as activating or inhibiting Fc receptors or costimulatory molecules; tissue or cell targeting antigens; or antigens to aid blood/brain barrier (BBB) transfer such as transferrin receptor or LRP1.

The disclosure also extends to compositions, such as pharmaceutical compositions comprising said novel formats with the particular antigen specificity.

In a further aspect the disclosure includes use of the formats and the compositions in treatment.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients or non-antibody ingredients such as steroids or other drug molecules.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/Kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

Agents as employed herein refers to an entity which when administered has a physiological affect.

Drug as employed herein refers to a chemical entity which at a therapeutic dose has an appropriate physiological affect.

In one embodiment the antibodies or fragments according to the present disclosure are employed with an immunosuppressant therapy, such as a steroid, in particular prednisone.

In one embodiment the antibodies or fragments according to the present disclosure are employed with Rituximab or other B cell therapies.

In one embodiment the antibodies or fragments according to the present disclosure are employed with any B cell or T cell modulating agent or immunomodulator. Examples include methotrexate, microphenyolate and azathioprine.

The dose at which the antibody molecule of the present invention is administered depends on the nature of the condition to be treated, the extent of the inflammation present and on whether the antibody molecule is being used prophylactically or to treat an existing condition. The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) and/or long lasting pharmacodynamics (PD) profile it may only be necessary to give a dosage once per day, once per week or even once every 1 or 2 months.

In one embodiment the dose is delivered bi-weekly, i.e. twice a month.

In one embodiment doses are spaced to allow anti-drug (in this case anti-antibody) responses to waine before administration of further dose.

Half life as employed herein is intended to refer to the duration of the molecule in circulation, for example in serum/plasma.

Pharmacodynamics as employed herein refers to the profile and in particular duration of the biological action of the molecule according the present disclosure.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pI of the protein is in the range 8-9 or above then a formulation pH of 7 may be appropriate. Whilst not wishing to be bound by theory it is thought that this may ultimately provide a final formulation with improved stability, for example the antibody or fragment remains in solution. In one example the pharmaceutical formulation at a pH in the range of 4.0 to 7.0 comprises: 1 to 200 mg/mL of an antibody molecule according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 1 to 5 µm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus(R) nebulizer connected to a Pari Master(R) compressor manufactured by Pari Respiratory Equipment, Inc., Richmond, Va.).

The antibody or multispecific molecule of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibodies disclosed herein may be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

In one embodiment, the molecule of the present disclosure, such as a bispecific protein complex described herein may be used to functionally alter the activity of the antigen or antigens of interest. For example, the bispecific protein complex may neutralize, antagonize or agonise the activity of said antigen or antigens, directly or indirectly.

The present disclosure also extends to a kit, comprising a molecule of the present disclosure or a component thereof. In one embodiment the kit comprises:
a) one or more fusion proteins (A-X) comprising a first antibody or antibody fragment (A) specific to CD45 or CD79a and/or CD79b attached to a first binding partner of a binding pair (X); and
b) one or more fusion proteins (B-Y) comprising a second antibody or antibody fragment (B) specific to CD45 or CD79a and/or CD79b attached to a second binding partner of the binding pair (Y), wherein the latter is specific for the first binding partner; for example wherein the first binding partner (X) is a peptide or polypeptide and the second binding (Y) partner is an antibody or antibody fragment specific thereto;
wherein Y the second binding partner is specific to the first binding partner X and the second binding partner is, for example an antibody or antibody fragment specific thereto; and the specific interaction (such as a binding interaction) of the two binding partners forms a heterodimer-tether which physically brings the two fusion proteins from a) and b) together to form a bispecific protein complex; and
wherein at least one of A or B is specific to CD45 and the other is specific to CD79a and/or CD79b, and
the fusion protein(s) is/are in a complexed or a non-complexed form.

Advantageously, the kit may comprise bispecific protein complexes of the present disclosure, or may comprise fusion proteins which are in a complexed or non-complexed form. In the former case, the bispecific protein complexes are ready for use "out of the box" which provides convenience and ease of use, whereas in the latter case, the bispecific protein complexes can be assembled according to the user's requirements by using combining different fusion proteins.

In another embodiment, the kit further comprises instructions for use.

In yet another embodiment, the kit further comprises one or more reagents for performing one or more functional assays.

In one embodiment, molecules of the present disclosure including fusion proteins, bispecific proteins complexes or compositions comprising same are provided for use as a laboratory reagent.

Further Aspects

In a further aspect, there is provided a nucleotide sequence, for example a DNA sequence encoding a construct as described herein including a multispecific molecule or a fusion protein as defined above.

In one embodiment, there is provided a nucleotide sequence, for example a DNA sequence encoding a construct as described herein including a multispecific molecule or a bispecific protein complex or an antibody according to the present disclosure.

The disclosure herein also extends to a vector comprising a nucleotide sequence as defined above.

The term "vector" as used herein refers to a nucleic acid molecule capable of transporting another nucleic acid to which it has been linked. An example of a vector is a "plasmid," which is a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell, where they are subsequently replicated along with the host genome. In the present specification, the terms "plasmid" and "vector" may be used interchangeably as a plasmid is the most commonly used form of vector.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

The term "selectable marker" as used herein refers to a protein whose expression allows one to identify cells that have been transformed or transfected with a vector containing the marker gene. A wide range of selection markers are known in the art. For example, typically the selectable marker gene confers resistance to drugs, such as G418, hygromycin or methotrexate, on a host cell into which the vector has been introduced. The selectable marker can also be a visually identifiable marker such as a fluorescent marker for example. Examples of fluorescent markers include rhodamine, FITC, TRITC, Alexa Fluors and various conjugates thereof.

Also provided is a host cell comprising one or more cloning or expression vectors comprising one or more DNA sequences encoding an antibody of the present disclosure. Any suitable host cell/vector system may be used for expression of the DNA sequences encoding the antibody molecule of the present disclosure. Bacterial, for example *E. coli*, and other microbial systems may be used or eukaryotic, for example mammalian, host cell expression systems may also be used. Suitable mammalian host cells include CHO, myeloma or hybridoma cells.

The present disclosure also provides a process for the production of a molecule according to the present disclosure or a component thereof comprising culturing a host cell containing a vector of the present disclosure under conditions suitable for leading to expression of protein from DNA encoding the molecule of the present disclosure, and isolating the molecule.

The molecules of the present disclosure including the bispecific protein complexes described herein may be used in diagnosis/detection kits. The kits may, for example comprise bispecific antibody complexes that are specific for two antigens, both of which are present on the same cell type, and wherein a positive diagnosis can only be made if both antigens are successfully detected. By using a molecule of the present disclosure such as a bispecific antibody complexes described herein rather than two separate antibodies or antibody fragments in a non-complexed form, the specificity of the detection can be greatly enhanced.

In one embodiment, the molecules of the present disclosure such as the bispecific antibody complexes are fixed on a solid surface. The solid surface may for example be a chip, or an ELISA plate.

Further provided is the use of a molecule according to the present disclosure, for example a bispecific protein complex described herein for detecting in a sample the presence of a first and a second peptide, whereby the said molecules are used as detection agents.

The molecules of the present disclosure such as the bispecific antibody complexes described herein may for example be conjugated to a fluorescent marker which facilitates the detection of bound antibody-antigen complexes. Such bispecific antibody complexes can be used for immunofluorescence microscopy. Alternatively, the bispecific antibody complexes may also be used for western blotting or ELISA.

In one embodiment, there is provided a process for purifying a molecule according to the present disclosure or a component thereof In one embodiment, there is provided a process for purifying a molecule according the present disclosure or a component thereof comprising the steps: performing anion exchange chromatography in non-binding mode such that the impurities are retained on the column and the antibody is maintained in the unbound fraction. The step may, for example be performed at a pH about 6-8.

The process may further comprise an initial capture step employing cation exchange chromatography, performed for example at a pH of about 4 to 5.

The process may further comprise of additional chromatography step(s) to ensure product and process related impurities are appropriately resolved from the product stream.

The purification process may also comprise of one or more ultra-filtration steps, such as a concentration and diafiltration step.

"Purified form" as used supra is intended to refer to at least 90% purity, such as 91, 92, 93, 94, 95, 96, 97, 98, 99% w/w or more pure.

In the context of this specification "comprising" is to be interpreted as "including".

Aspects of the disclosure comprising certain elements are also intended to extend to alternative embodiments "consisting" or "consisting essentially" of the relevant elements.

Positively recited embodiments may be employed herein as a basis for a disclaimer.

All references referred to herein are specifically incorporated by reference.

The sub-headings herein are employed to assist in structuring the specification and are not intended to be used to contruct the meaning of technical terms herein.

Sequences of the disclosure are provided herein below.

GCN4(7P14P) sequences
SEQ ID NO: 1
ASGGGRMKQLEPKVEELLPKNYHLENEVARLKKLVGERHHHHHH
wherein the amino acids in bold are optional SEQ ID NO: 2
GCTAGCGGAGGCGGAAGAATGAAACAACTTGAACCCAAGGTTGAAGAATT
GCTTCCGAAAAATTATCACTTGGAAAATGAGGTTGCCAGATTAAAGAAAT
TAGTTGGCGAACGCCATCACCATCACCATCAC 52SR4 ds scFv-sequence
SEQ ID NO: 3
DAVVTQESALTSSPGETVTLTCRSSTGAVTTSNYASWVQEKPDHLFTGLI
GGTNNRAPGVPARFSGSLIGDKAALTITGAQTEDEAIYFCVLWYSDHWVF
GCGTKLTVLGGGGSGGGGSGGGGSGGGGSDVQLQQSGPGLVAPSQSLSI
TCTVSGFLLTDYGVNWVRQSPGKCLEWLGVIWGDGITDYNSALKSRLSVT
KDNSKSQVFLKMNSLQSGDSARYYCVTGLFDYWGQGTTLTVSSAAAHHHH
HHEQKLISEEDL- SEQ ID NO: 4
GATGCGGTGGTGACCCAGGAAAGCGCGCTGACCAGCAGCCCGGGCGAAAC
CGTGACCCTGACCTGCCGCAGCAGCACCGGCGCGGTGACCACCAGCAACT
ATGCGAGCTGGGTGCAGGAAAAACCGGATCATCTGTTTACCGGCCTGATT
GGCGGCACCAACAACCGCGCGCCGGGCGTGCCGGCGCGCTTTAGCGGCAG
CCTGATTGGCGATAAAGCGGCGCTGACCATTACCGGCGCGCAGACCGAAG
ATGAAGCGATTTATTTTTGCGTGCTGTGGTATAGCGACCATTGGGTGTTT
GGCTGCGGCACCAAACTGACCGTGCTGGGTGGAGGCGGTGGCTCAGGCGG
AGGTGGCTCAGGCGGTGGCGGGTCTGGCGGCGGCGGCAGCGATGTGCAGC
TGCAGCAGAGCGGCCCGGGCCTGGTGGCGCCGAGCCAGAGCCTGAGCATT
ACCTGCACCGTGAGCGGCTTTCTCCTGACCGATTATGGCGTGAACTGGGT
GCGCCAGAGCCCGGGCAAATGCCTGGAATGGCTGGGCGTGATTTGGGGCG
ATGGCATTACCGATTATAACAGCGCGCTGAAAAGCCGCCTGAGCGTGACC
AAAGATAACAGCAAAAGCCAGGTGTTTCTGAAAATGAACAGCCTGCAGAG
CGGCGATAGCGCGCGCTATTATTGCGTGACCGGCCTGTTTGATTATTGGG
GCCAGGGCACCACCCTGACCGTGAGCAGCGCGGCCGCCCATCACCATCAC
CATCACGAACAGAAACTGATTAGCGAAGAAGATCTGTAATAG CD79b Antibodies Ab 4447
Rabbit Ab 4447 VL region
SEQ ID NO: 71
AQVLTQTPSP VSAPVGGTVT INCQASQSVV SGNYLAWLQQ
KPGQPPKQLI HSASTLASGV SSRFSGSGS
G TQFTLTISGV QCEDAATYYC LGEFSCSSHD
CNAFGGGTEV VVK Rabbit Ab 4447 VL region
SEQ ID NO: 72
gcccaagtgc tgacccagac tccgtcccct gtgtctgcac ctgtgggagg cacagtcacc atcaattgcc aggccagtca gagtgttgtt agtggcaatt acctagcctg gcttcagcag aaaccagggc agcctcccaa gcaactgatc cattctgcat ccactctggc atctggggtc tcatcgcggt tcagcggcag tggatctggg acacaattca ctctcaccat cagcggcgtg

```
cagtgtgaag atgctgccac ttactactgt ctaggcgaat ttagttgtag tagtcatgat tgtaatgctt tcggcggagg gaccgaggtg gtggtcaaa
```

Rabbit Ab 4447 VH region
```
                                     SEQ ID NO: 73
QSLEESGGRL VTPGTPLTLT CTVSGFSLSN YAVSWVRQAP
GEGLEWIGII YIETGTTWYA NWAKGRFTIS KTSTTVDLTI
TSPSTEDTAT YFCAREPYEP YDDSNIYYGM DPWGPGTLVT VSS
```

Rabbit Ab 4447 VH region
```
                                     SEQ ID NO: 74
cagtcgctgg aggagtccgg gggtcgcctg gtcacgcctg ggacacccct gacactcacc tgcaccgtct ctggattctc cctcagtaac tatgcagtaa gctgggtccg ccaggctcca ggggagggac tggaatggat cgggatcatt tatattgaaa ctggtaccac atggtacgcg aactgggcga aaggccgatt caccatctcc aaaacctcga ccacggtgga tctgacaatc accagtccgt caaccgagga cacggccacc tatttctgtg ccagagaacc ttatgaacct tatgatgata gtaatattta ctacggcatg gaccctggg gcccaggcac cctcgtcacc gtctcgagt
```

| | | |
|---|---|---|
| CDRL1 | SEQ ID NO: 75 | QASQSVVSGNYLA |
| CDRL2 | SEQ ID NO: 76 | SASTLAS |
| CDRL3 | SEQ ID NO: 77 | LGEFSCSSHDCNA |
| CDRH1 | SEQ ID NO: 78 | GFSLSNYAVS |
| CDRH2 | SEQ ID NO: 79 | IIYIETGTTWYANWAKG |
| CDRH3 | SEQ ID NO: 80 | EPYEPYDDSNIYYGMDP |

The disclosure also extends to a derivative of SEQ ID NO: 77 wherein one or both cysteine are replaced with another amino acid for example serine, in particular where the first cys is replaced by serine and the second cys remains unchanged, or the first cysteine remains unchanged and the second cysteine is replaced by serine, or where both cysteines are replaced by serine.

Ab 4450
Rabbit Ab 4450 VL region
```
                                     SEQ ID NO: 81
AIDMTQTPSP VSAAVGGTVT INCQSSQSIY NNNDLAWYQQ
KPGQPPKLLI YEASKLASGV PSRFKGSGSG TQFTLTISGV
QCDDAATYYC QGGGSGGDGI AFGGGTKVVV E
```

Rabbit Ab 4450 VL region
```
                                     SEQ ID NO: 82
gccattgata tgacccagac tccatccccc gtgtctgcag ctgtgggagg cacagtcacc atcaattgcc agtccagtca gagtatttat aataataatg acttagcctg gtatcagcag aaaccagggc agcctcccaa gctcctgatc tacgaagcat ccaaactggc atctggggtc ccatcgcggt tcaaaggcag tggatctggg acacagttca ctctcaccat cagtggcgtg cagtgtgatg atgctgccac ttactactgt cagggcggtg
```

```
gtagtggtgg tgatggcatt gctttcggcg gagggaccaa ggtggtcgtc gaa
```

Rabbit Ab 4450 VH region
```
                                     SEQ ID NO: 83
QSVEESGGRL VTPGAPLTLT CTVSGFSLNN YVMVWVRQAP
GKGLEWIGII YVSGNAYYAS WAKGRFTISR TSTTVDLKVT
SLTTEDTATY FCARDAGHSD VDVLDIWGPG TLVTVSS
```

Rabbit Ab 4450 VH region
```
                                     SEQ ID NO: 84
cagtcggtgg aggagtccgg gggtcgcctg gtcacgcctg gggcacccct gacactcacc tgcacagtct ctggattctc cctcaataac tatgtaatgg tctgggtccg ccaggctcca gggaagggc tggaatggat cggaatcatt tatgttagtg gtaatgcata ctacgcgagc tgggcaaaag gccgattcac catctccaga acctcgacca cggtggatct gaaagtgacc agtctgacaa ccgaggacac ggccacctat ttctgtgcca gagatgctgg tcatagtgat gtcgatgttt ggatatttg gggcccgggc accctcgtca ccgtctcgag t
```

| | | |
|---|---|---|
| CDRL1 | SEQ ID NO: 85 | QSSQSIYNNNDLA |
| CDRL2 | SEQ ID NO: 86 | EASKLAS |
| CDRL3 | SEQ ID NO: 87 | QGGGSGGDGIA |
| CDRH1 | SEQ ID NO: 88 | GFSLNNYVMV |
| CDRH2 | SEQ ID NO: 89 | IIYVSGNAYYASWAKG |
| CDRH3 | SEQ ID NO: 90 | DAGHSDVDVLDI |

The disclosure also extends to a derivative of SEQ ID NO: 87 wherein at least one of the amino acids in the motif DG is replaced by another amino acid, for example the motif is mutated to EG, DA or DS.

CD45 Antibodies
Ab 4122
Rabbit Ab 4122 VL region
```
                                     SEQ ID NO: 91
DIVMTQTPAS VSEPVGGTVT IMCQASQSIS NWLAWYQQKP
GQPPKLLIYQ ASKLASGVPS RFKGSGSGTE YTLTISDLEC
ADAATYYCQS YYDSGSNVFF AFGGGTKVVV E
```

Rabbit Ab 4122 VL region
```
                                     SEQ ID NO: 92
gacattgtga tgacccagac tccagcctcc gtgtctgaac ctgtgggagg cacagtcacc atcatgtgcc aggccagtca gagcattagc aattggttag cctggtatca acagaaacca gggcagcctc ccaagctcct gatctaccag gcatccaaac tggcatctgg ggtcccatcg cggttcaaag gcagtggatc tgggacagag tacactctca ccatcagcga cctggagtgt gccgatgctg ccacttacta ctgtcaaagc tattatgata gtggtagtaa tgttttttt gcttcggcg gagggaccaa ggtggtggtc gaa
```

```
Rabbit Ab 4122 VH region
                                       SEQ ID NO: 93
LSLEESGGDL VKPGASLTLT CTASGFSFSA GYWICWVRQA
PGKGLEWIAC TYAGRSGSTY YANWVNGRFT IPKTSSTTVT
LQMTSLSGAD TASYFCARGN AGVAVGALWG PGTLVTVSS Rabbit Ab 4122 VH region
                                       SEQ ID NO: 94
ctgtcgttgg aggagtccgg gggagacctg gtcaagcctg gggcatccct gacactcacc tgcacagcct ggattctc cttcagtgcc ggctattgga tatgttgggt ccgccaggct ccagggaagg ggctggagtg gatcgcatgc acttatgctg gtcgtagtgg tagcacttac tacgcgaact gggtgaatgg ccgattcacc atccccaaaa cctcgtcgac cacggtgact ctgcaaatga ccagtctgtc aggcgcggac acggccagct atttctgtgc gagaggtaat gctggtgttg ctgttggtgc cttgtggggc ccaggcaccc tggtcaccgt ctcgagt

CDRL1      SEQ ID NO: 95       QASQSISNWLA

CDRL2      SEQ ID NO: 96       QASKLAS

CDRL3      SEQ ID NO: 97       QSYYDSGSNVFFA

CDRH1      SEQ ID NO: 98       GFSFSAGYWIC

CDRH2      SEQ ID NO: 99       CTYAGRSGSTYYANWVNG

CDRH3      SEQ ID NO: 100      GNAGVAVGAL
```

The disclosure also extends to a derivative of SEQ ID NO: 97 wherein at least one of the amino acids in the motif DS is replaced by another amino acid, for example the motif is mutated to DA or DT The disclosure also extends to a derivative of SEQ ID NO: 98 wherein cysteine is replaced by another amino acid, for example serine.

The disclosure also extends to a derivative of SEQ ID NO: 99 wherein cysteine is replaced by another amino acid, for example serine.

The disclosure also extends to a derivative of SEQ ID NO: 99 wherein at least one of the amino acids in the motif NG is replaced by another amino acid, for example the motif is mutated to NA, NS or NT.

```
Ab 4129
Rabbit Ab 4129 VL region
                                       SEQ ID NO: 101
DIVMTQTPAS VEAAVGGTVT INCQASQSIS SWLSWYQQKP
GQPPKLLIYG ASNLASGVPS RFSGSGSGTQ FSLTISDLEC
ADAATYYCQS YYDSGSSVFF NFGGGTKVVV K Rabbit Ab 4129 VL region
                                       SEQ ID NO: 102
gacattgtga tgacccagac tccagcctcc gtggaggcag ctgtgggagg cacagtcacc atcaattgcc aagccagtca gagcattagc agttggttat cctggtatca gcagaaacca gggcagcctc ccaagctcct gatctatggt gcatccaatc tggcatctgg ggtcccatca cggttcagcg gcagtggatc tgggacacag ttcagtctca ccatcagcga cctggagtgt gccgatgctg ccacttacta ctgtcaaagc tattatgata
```

```
gtggtagtag tgtttttttt aatttcggcg gagggaccaa ggtggtcgtc aaa

Rabbit Ab 4129 VH region
                                       SEQ ID NO: 103
QSLEESGGDL VKPGASLTLT CTASGFSFSA GYWICWVRQA
PGKGLEWIAC IYAGSSGSTY YASWAKGRFT IPKTSSTTVT
LQMTSLTGAD TATYFCARGN AGVAVGALWG PGTLVTVSS Rabbit Ab 4129 VH region
                                       SEQ ID NO: 104
cagtcgttgg aggagtccgg gggagacctg gttaagcctg gggcatccct gacactcacc tgcacagcct ggattctc cttcagtgcc ggctattgga tatgttgggt ccgccaggct ccagggaagg ggctggagtg gatcgcatgc atttatgctg gtagtagtgg tagcacttac tacgcgagct gggcgaaagg ccgattcacc atccccaaaa cctcgtcgac cacggtgact ctgcaaatga ccagtctgac aggcgcggac acggccacct atttctgtgc gagaggtaat gctggtgttg ctgttggtgc cttgtggggc ccaggcaccc tcgtcaccgt ctcgagt

CDRL1      SEQ ID NO: 105      QASQSISSWLS

CDRL2      SEQ ID NO: 106      GASNLAS

CDRL3      SEQ ID NO: 107      QSYYDSGSSVFFN

CDRH1      SEQ ID NO: 108      GFSFSAGYWIC

CDRH2      SEQ ID NO: 109      CIYAGSSGSTYYASWAKG

CDRH3      SEQ ID NO: 110      GNAGVAVGAL
```

The disclosure also extends to a derivative of SEQ ID NO: 107 wherein at least one of the amino acids in the motif DS is replaced by another amino acid, for example the motif is mutated to DA or DT.

The disclosure also extends to a derivative of SEQ ID NO: 108 wherein cysteine is replaced by another amino acid, for example serine.

The disclosure also extends to a derivative of SEQ ID NO: 109 wherein cysteine is replaced by another amino acid, for example serine.

```
Ab 4131
Rabbit Ab 4131 VL region
                                       SEQ ID NO: 111
DIVMTQTPAS VSEPVGGSVT IKCQASQSFY NLLAWYQQKP
GQPPKLLIYD ASDLASGVPS RFKGSGSGTD FTLTISDLEC
ADAAAYYCQS ADGSSYAFGG GTEVVVK Rabbit Ab 4131 VL region
                                       SEQ ID NO: 112
gacattgtga tgacccagac tccagcctcc gtgtctgaac ctgtgggagg ctcagtcacc atcaagtgcc aggccagtca gagcttttac aacctcttag cctggtatca gcagaaacca gggcagcctc ccaaactcct gatctatgat gcatccgatc tggcatctgg ggtcccatcg cggttcaaag gcagtggatc tgggactgat ttcactctca ccatcagcga cctggagtgt
```

```
                                    gagtgtttat aataacaaca acttatcctg gtatcagcag
gccgatgctg ccgcttacta ctgtcaaagt gctgatggta
gtagttacgc tttcggcgga gggaccgagg tggtcgtcaa a
                                    aaaccagggc agcctcccaa gctcttgatc tacgatgcat
Rabbit Ab4131 VH region
                            SEQ ID NO: 113   ccaaattggc atctggggtc ccatcccggt tcaaaggcag
QEQLEESGGG LVKPEGSLTL TCTASGVSFS SSYWIYWVRQ
APGKGLEWIA CIYTGSSGST YYASWAKGRF TVSETSSTTV   tggatctggg acacagttca ctctcaccat cagcggcgtg
TLQMTSLTAA DTATYFCARA SAWTYGMDLW GPGTLVTVSS
                                    cagtgtgacg atgctgccac ttactactgt ctaggcggtt
Rabbit Ab 4131 VH region
                            SEQ ID NO: 114   attatagtag tggttggtat tttgctttcg gcggagggac
caggagcaat ggaggagtc cggggaggc ctggtcaagc
                                    caaggtggtg gtcaaa
ctgaggatc cctgacactc acctgcacag cctctggagt
                                    Rabbit Ab 4133 VH region
ctccttcagt agcagctatt ggatatactg gtccgccag                             SEQ ID NO: 123
                                    QEQLVESGGG LVQPEGSLTL TCTASGFSFS GNYYMCWVRQ
gctccaggga aggggctgga gtggatcgca tgcatttata   APGKGLEWIG CLYTGSSGST YYASWAKGRF TISKTSSTTV
                                    TLQMTSLTAA DTATYFCARD LGYEIDGYGG LWGQGTLVTV SS
ctggtagtag tggtagcact tactacgcga gctgggcgaa
                                    Rabbit Ab 4133 VH region
aggccgattc accgtctccg aaacctcgtc gaccacggtg                            SEQ ID NO: 124
                                    caggagcagc tggtggagtc cggggaggc ctggtccagc
actctgcaaa tgaccagtct gacagccgcg gacacggcca
                                    ctgagggatc cctgacacta acctgcacag cttctggatt
cctatttctg tgcgagagca agcgcttgga cctacggcat
                                    ctccttcagt ggcaactact acatgtgctg ggtccgccag
ggacctctgg ggcccgggca ccctcgtcac cgtctcgagt
                                    gctccaggga aggggctgga gtggatcgga tgcctttata
CDRL1    SEQ ID NO: 115    QASQSFYNLLA
                                    ctggtagtag tggtagcaca tattacgcga gctgggcgaa
CDRL2    SEQ ID NO: 116    DASDLAS
                                    aggccgattc accatctcca aaacctcgtc gaccacggtg
CDRL3    SEQ ID NO: 117    QSADGSSYA
                                    actctgcaaa tgaccagtct gacagccgcg gacacggcca
CDRH1    SEQ ID NO: 118    GVSFSSSYWIY
                                    cctatttctg tgcgagagat ctaggttatg aaattgatgg
CDRH2    SEQ ID NO: 119    CIYTGSSGSTYYASWAKG
                                    ttatggggc ttgtgggcc agggcacct cgtcaccgtc tcgagt
CDRH3    SEQ ID NO: 120    ASAWTYGMDL
                                    CDRL1    SEQ ID NO: 125    QASQSVYNNNNLS
```

The disclosure also extends to a derivative of SEQ ID NO: 117 wherein at least one of the amino acids in the motif DS is replaced by another amino acid, for example the motif is mutated to DA or DT.

The disclosure also extends to a derivative of SEQ ID NO: 119 wherein cysteine is replaced by another amino acid, for example serine.

```
CDRL2    SEQ ID NO: 126    DASKLAS
CDRL3    SEQ ID NO: 127    LGGYYSSGWYFA
CDRH1    SEQ ID NO: 128    GFSFSGNYYMC
CDRH2    SEQ ID NO: 129    CLYTGSSGSTYYASWAKG
CDRH3    SEQ ID NO: 130    DLGYEIDGYGGL
```

```
Ab 4133
Rabbit Ab 4133 VL region
                            SEQ ID NO: 121
AQVLTQTPSP VSAVVGGTVS ISCQASQSVY NNNNLSWYQQ
KPGQPPKLLI YDASKLASGV PSRFKGSGSG TQFTLTISGV
QCDDAATYYC LGGYYSSGWY FAFGGGTKVV VK Rabbit Ab 4133 VL region
                            SEQ ID NO: 122
gcgcaagtgc tgacccagac tccatctccc gtgtctgcag
ttgtgggagg cacagtcagc atcagttgcc aggccagtca
```

The disclosure also extends to a derivative of SEQ ID NO: 125 wherein the glycosylation site NLS is removed, for example is mutated to SLS or QLS.

The disclosure also extends to a derivative of SEQ ID NO: 128 wherein cysteine is replaced by another amino acid, for example serine.

The disclosure also extends to a derivative of SEQ ID NO: 130 wherein at least one of the amino acids in the motif DG is replaced by another amino acid, for example the motif is mutated to EG, DA or DS.

| Serum Albumin Binding Antibodies | | |
|---|---|---|
| CDRH1 dAbH1 | SEQ ID NO: 131 | Gly Ile Asp Leu Ser Asn Tyr Ala Ile Asn |
| CDRH2 dAbH1 | SEQ ID NO: 132 | Ile Ile Trp Ala Ser Gly Thr Thr Phe Tyr Ala Thr Trp Ala Lys Gly |
| CDRH3 dAbH1 | SEQ ID NO: 133 | Thr Val Pro Gly Tyr Ser Thr Ala Pro Tyr Phe Asp Leu |
| CDRL1 dAbL1 | SEQ ID NO: 134 | Gln Ser Ser Pro Ser Val Trp Ser Asn Phe Leu Ser |

| Serum Albumin Binding Antibodies |
|---|

CDRL2 dAbL1    SEQ ID NO: 135    Glu Ala Ser Lys Leu Thr Ser

CDRL3 dAbL1    SEQ ID NO: 136    Gly Gly Gly Tyr Ser Ser Ile Ser Asp Thr
                                 Thr

Heavy chain variable domain of anti-albumin antibody (no ds)
                                                           SEQ ID NO: 137
Glu Val Gln Leu Leu Glu Ser Gly Gly Gly Leu Val Gln Pro Gly Gly Ser Leu Arg
Leu Ser Cys Ala Val Ser Gly Ile Asp Leu Ser Asn Tyr Ala Ile Asn Trp Val Arg
Gln Ala Pro Gly Lys Gly Leu Glu Trp Ile Gly Ile Ile Trp Ala Ser Gly Thr Thr
Phe Tyr Ala Thr Trp Ala Lys Gly Arg Phe Thr Ile Ser Arg Asp Asn Ser Lys Asn
Thr Val Tyr Leu Gln Met Asn Ser Leu Arg Ala Glu Asp Thr Ala Val Tyr Tyr Cys
Ala Arg Thr Val Pro Gly Tyr Ser Thr Ala Pro Tyr Phe Asp Leu Trp Gly Gln Gly
Thr Leu Val Thr Val Ser Ser Heavy chain variable domain of anti-albumin antibody (ds)
                                                           SEQ ID NO: 138
Glu Val Gln Leu Leu Glu Ser Gly Gly Gly Leu Val Gln Pro Gly Gly Ser Leu Arg
Leu Ser Cys Ala Val Ser Gly Ile Asp Leu Ser Asn Tyr Ala Ile Asn Trp Val Arg
Gln Ala Pro Gly Lys Cys Leu Glu Trp Ile Gly Ile Ile Trp Ala Ser Gly Thr Thr
Phe Tyr Ala Thr Trp Ala Lys Gly Arg Phe Thr Ile Ser Arg Asp Asn Ser Lys Asn
Thr Val Tyr Leu Gln Met Asn Ser Leu Arg Ala Glu Asp Thr Ala Val Tyr Tyr Cys
Ala Arg Thr Val Pro Gly Tyr Ser Thr Ala Pro Tyr Phe Asp Leu Trp Gly Gln Gly
Thr Leu Val Thr Val Ser Ser Light chain variable domain of anti-albumin antibody (no ds)
                                                           SEQ ID NO: 139
Asp Ile Gln Met Thr Gln Ser Pro Ser Ser Val Ser Ala Ser Val Gly Asp Arg Val
Thr Ile Thr Cys Gln Ser Ser Pro Ser Val Trp Ser Asn Phe Leu Ser Trp Tyr Gln
Gln Lys Pro Gly Lys Ala Pro Lys Leu Leu Ile Tyr Glu Ala Ser Lys Leu Thr Ser
Gly Val Pro Ser Arg Phe Ser Gly Ser Gly Ser Gly Thr Asp Phe Thr Leu Thr Ile
Ser Ser Leu Gln Pro Glu Asp Phe Ala Thr Tyr Tyr Cys Gly Gly Gly Tyr Ser Ser
Ile Ser Asp Thr Thr Phe Gly Gly Gly Thr Lys Val Glu Ile Lys Arg Thr Light chain variable domain of anti-albumin antibody (ds)
                                                           SEQ ID NO: 140
Asp Ile Gln Met Thr Gln Ser Pro Ser Ser Val Ser Ala Ser Val Gly Asp Arg Val
Thr Ile Thr Cys Gln Ser Ser Pro Ser Val Trp Ser Asn Phe Leu Ser Trp Tyr Gln
Gln Lys Pro Gly Lys Ala Pro Lys Leu Leu Ile Tyr Glu Ala Ser Lys Leu Thr Ser
Gly Val Pro Ser Arg Phe Ser Gly Ser Gly Ser Gly Thr Asp Phe Thr Leu Thr Ile
Ser Ser Leu Gln Pro Glu Asp Phe Ala Thr Tyr Tyr Cys Gly Gly Gly Tyr Ser Ser
Ile Ser Asp Thr Thr Phe Gly Cys Gly Thr Lys Val Glu Ile Lys Arg Thr Human CD79a
                                                           SEQ ID NO: 141
MPGGPGVLQA LPATIFLLFL LSAVYLGPGC QALWMHKVPA SLMVSLGEDA HFQCPHNSSN
NANVTWWRVL HGNYTWPPEF LGPGEDPNGT LIIQNVNKSH GGIYVCRVQE GNESYQQSCG
TYLRVRQPPP RPFLDMGEGT KNRIITAEGI ILLFCAVVPG TLLLFRKRWQ NEKLGLDAGD
EYEDENLYEG LNLDDCSMYE DISRGLQGTY QDVGSLNIGD VQLEKP Human CD79b
                                                           SEQ ID NO: 142
MARLALSPVP SHWMVALLLL LSAEPVPAAR SEDRYRNPKG SACSRIWQSP
RFIARKRGFT VKMHCYMNSA SGNVSWLWKQ EMDENPQQLK LEKGRMEESQ
NESLATLTIQ GIRFEDNGIY FCQQKCNNTS EVYQGCGTEL RVMGFSTLAQ
LKQRNTLKDG IIMIQTLLII LFIIVPIFLL LDKDDSKAGM EEDHTYEGLD
IDQTATYEDI VTLRTGEVKW SVGEHPGQE Human CD45
                                                           SEQ ID NO: 143
MYLWLKLLAF GFAFLDTEVF VTGQSPTPSP TGLTTAKMPS VPLSSDPLPT
HTTAFSPAST FERENDFSET TTSLSPDNTS TQVSPDSLDN ASAFNTTGVS
SVQTPHLPTH ADSQTPSAGT DTQTFSGSAA NAKLNPTPGS NAISDVPGER
STASTFPTDP VSPLTTTLSL AHHSSAALPA RTSNTTITAN TSDAYLNASE
TTTLSPSGSA VISTTTIATT PSKPTCDEKY ANITVDYLYN KETKLFTAKL
NVNENVECGN NTCTNNEVHN LTECKNASVS ISHNSCTAPD KTLILDVPPG
VEKFQLHDCT QVEKADTTIC LKWKNIETFT CDTQNITYRF QCGNMIFDNK
EIKLENLEPE HEYKCDSEIL YNNHKFTNAS KIIKTDFGSP GEPQIIFCRS
EAAHQGVITW NPPQRSFHNF TLCYIKETEK DCLNLDKNLI KYDLQNLKPY
TKYVLSLHAY IIAKVQRNGS AAMCHFTTKS APPSQVWNMT VSMTSDNSMH
VKCRPPRDRN GPHERYHLEV EAGNTLVRNE SHKNCDFRVK DLQYSTDYTF
KAYFHNGDYP GEPFILHHST SYNSKALIAF LAFLIIVTSI ALLVVLYKIY
DLHKKRSCNL DEQQELVERD DEKQLMNVEP IHADILLETY KRKIADEGRL
FLAEFQSIPR VFSKFPIKEA RKPFNQNKNR YVDILPYDYN RVELSEINGD
AGSNYINASY IDGFKEPRKY IAAQGPRDET VDDFWRMIWE QKATVIVMVT
RCEEGNRNKC AEYWPSMEEG TRAFGDVVVK INQHKRCPDY IIQKLNIVNK

```
                    Serum Albumin Binding Antibodies

KEKATGREVT  HIQFTSWPDH  GVPEDPHLLL  KLRRRVNAFS  NFFSGPIVVH
CSAGVGRTGT  YIGIDAMLEG  LEAENKVDVY  GYVVKLRRQR  CLMVQVEAQY
ILIHQALVEY  NQFGETEVNL  SELHPYLHNM  KKRDPPSEPS  PLEAEFQRLP
SYRSWRTQHI  GNQEENKSKN  RNSNVIPYDY  NRVPLKHELE  MSKESEHDSD
ESSDDDSDSE  EPSKYINASF  IMSYWKPEVM  IAAQGPLKET  IGDFWQMIFQ
RKVKVIVMLT  ELKHGDQEIC  AQYWGEGKQT  YGDIEVDLKD  TDKSSTYTLR
VFELRHSKRK  DSRTVYQYQY  TNWSVEQLPA  EPKELISMIQ  VVKQKLPQKN
SSEGNKHHKS  TPLLIHCRDG  SQQTGIFCAL  LNLLESAETE  EVVDIFQVVK
ALRKARPGMV  STFEQYQFLY  DVIASTYPAQ  NGQVKKNNHQ  EDKIEFDNEV
DKVKQDANCV  NPLGAPEKLP  EAKEQAEGSE  PTSGTEGPEH  SVNGPASPAL  NQGS
```

REFERENCES

1. Ribosome display efficiently selects and evolves high-affinity antibodies in vitro from immune libraries. Hanes J, Jermutus L, Weber-Bornhauser S, Bosshard H R, Plückthun A. (1998) Proc. Natl. Acad. Sci. U.S.A. 95, 14130-14135
2. Directed in Vitro Evolution and Crystallographic Analysis of a Peptide-binding Single Chain Antibody Fragment (scFv) with Low Picomolar Affinity. Zhand C, Spinelli S, Luginbuhl B, Amstutz P, Cambillau C, Pluckthun A. (2004) J. Biol. Chem. 279, 18870-18877
3. Antigen recognition by conformational selection. Berger C, Weber-Bornhauser S, Eggenberger Y, Hanes J, Pluckthun A, Bosshard H. R. (1999) F.E.B.S. Letters 450, 149-153

EXAMPLES

The term Fab-Kd-Fab as used in the Examples describes the bispecific protein complex having the formula A-X:Y-B wherein:
 A-X is a first fusion protein;
 Y-B is a second fusion protein;
 X:Y is a heterodimeric-tether;
 A comprises a Fab fragment specific to an antigen such as CD45 or CD79;
 B comprises a Fab fragment specific to an antigen such as CD45 or CD79;
 X is a first binding partner of a binding pair such as a scFv;
 Y is a second binding partner of the binding pair such as a peptide; and
 : is an interaction (such as a binding interaction) between X and Y.

Example 1—Production of Fab-A (Fab-scFv [A-X]) and Fab-B (Fab-Peptide [B-Y]) for Functional Assays Cloning Strategy Antibody variable region DNA was generated by PCR or gene synthesis flanking restriction enzyme sites DNA sequence. These sites were HindIII and XhoI for variable heavy chains and HindIII and BsiWI for variable light chains. This makes the heavy variable region amenable to ligating into the two heavy chain vectors (pNAFH with FabB-Y and pNAFH with FabA-Xds [disulphide stabilised]) as they have complementary restriction sites. This ligates the variable region upstream (or 5') to the murine constant regions and peptide Y (GCN4) or scFv X (52SR4) creating a whole reading frame. The light chains were cloned into standard in house murine constant kappa vectors (pMmCK or pMmCK S171C) which again use the same complimentary restriction sites. The pMmCK S171C vector is used if the variable region is isolated from a rabbit. The cloning events were confirmed by sequencing using primers which flank the whole open reading frame.

Cultivating CHOS

Suspension CHOS cells were pre-adapted to CDCHO media (Invitrogen) supplemented with 2 mM (100×) glutamx. Cells were maintained in logarithmic growth phase agitated at 140 rpm on a shaker incubator (Kuner A G, Birsfelden, Switzerland) and cultured at 37° C. supplemented with 8% $CO_2$.

Electroporation Transfection

Prior to transfection, the cell numbers and viability were determined using CEDEX cell counter (Innovatis AG. Bielefeld, Germany) and required amount of cells ($2\times10^8$ cells/ml) were transferred into centrifuge conical tubes and were spun at 1400 rpm for 10 minutes. The Pelleted cells were re-suspended in sterile Earls Balanced Salts Solution and spun at 1400 rpm for further 10 minutes. Supernatant was discarded and pellets were re-suspended to desired cell density.

Vector DNA at a final concentration of 400 ug for $2\times10^8$ cells/ml mix and 800 μl was pipetted into Cuvettes (Biorad) and electroporated using in-house electroporation system.

Transfected cells were transferred directly into 1×3 L Erlenmeyer Flasks contained ProCHO 5 media enriched with 2 mM glutamx and antibiotic antimitotic (100×) solution (1 in 500) and Cells were cultured in Kuhner shaker incubator set at 37° C., 5% $CO_2$ and 140 rpm shaking. Feed supplement 2 g/L ASF (AJINOMOTO) was added at 24 hr post transfection and 0 temperature dropped to 32° C. for further 13 days culture. At day four 3 mM Sodium buryrate (n-BUTRIC ACID Sodium Salt, Sigma B-5887) was added to the culture.

On day 14, cultures were transferred to tubes and supernatant separated from the cells after centrifugation for 30 minutes at 4000 rpm. Retained supernatants were further filtered through 0.22 um SARTO BRAN P Millipore followed by 0.22 μm Gamma gold filters. Final expression levels were determined by Protein G-HPLC.

Large Scale (TOL) Purification

The Fab-A and Fab-B were purified by affinity capture using the AKTA Xpress systems and HisTrap Excel pre-packed nickel columns (GE Healthcare). The culture supernatants were 0.22 μm sterile filtered and pH adjusted to neutral, if necessary, with weak acid or base before loading onto the columns. A secondary wash step, containing 15-25 mM Imidazole, was used to displace any weakly bound host cell proteins/non-specific His binders from the nickel resin. Elution was performed with 10 mM sodium phosphate, pH7.4+1M NaCl+250 mM Imidazole and 2 ml fractions collected. One column volume into the elution the system was paused for 10 minutes to tighten the elution peak, and consequently decrease the total elution volume. The cleanest fractions were pooled and buffer exchanged into PBS (Sigma), pH7.4 and 0.22 µm filtered. Final pools were assayed by A280 Scan, SE-HPLC (G3000 method), SDS-PAGE (reduced & non-reduced) and for endotoxin using the PTS Endosafe system.

Example 2—CD45 Fab/CD79Fab Bispecific Complex but not a Mixture of CD45 and CD79 Fab or Bivalent CD79 Fab Complex Inhibits Akt Signalling Human PBMC derived from platelet apheresis cones were banked as frozen aliquots. Prior to an assay being performed, cells were thawed, washed in DMEM (Life Technologies) and allowed to acclimatise to a 37° C./5% $CO_2$ environment. During this period grids of bispecific or bivalent antibodies were created by diluting equimolar (200 nM) quantities of Fab'-A (Fab-scFv) and Fab-B (Fab-peptide) or Fab-A (Fab-peptide) and Fab-B (Fab-peptide) with antigen specificity for the cell surface proteins CD45 and CD79b in DMEM containing 10% calf serum and 2 mM glutamine. This grid is shown in Table 4.

TABLE 4

Grid of bispecific and bivalent combinations of antibodies with specificity for CD45 and CD79b.

| (A-X or Y) | (B-Y) Fab B | |
|---|---|---|
| Fab A | CD45-Y | CD79b-Y |
| CD45-X | CD45-X:Y-CD45 | CD45-X:Y-CD79b |
| CD79b-X | CD79b-X:Y-CD45 | CD79b-X:Y-CD79b |
| CD45-Y | | CD45-Y:CD79b-Y | where X is a scFv (52SR4) and Y is a peptide (GCN4)

FabA-X and FabB-Y or Fab-A-Y and Fab-B-Y were incubated together for 90 minutes (in a 37° C./5% $CO_2$ environment) before mixing with $2.5 \times 10^5$ PBMC in V bottomed 96 well plates. PBMC plus bispecific or bivalent combinations were then incubated together for a further 90 minutes. After this time B cells were activated by the addition of 200 nM of goat F(ab')2 anti-human IgM (Southern Biotechnology) for 8 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer (PBS+ 1% BSA+0.01% $NaN_3$) and washed once more. Cells were then resuspended in ice cold Perm Buffer III (BD Biosciences) for 30 minutes before being washed twice in flow buffer. Cells were then stained with a fluorescently labelled anti-CD20 antibody (BD Biosciences) and a fluorescently labelled anti-phospho Akt antibody that recognises a modified serine residue at position 473 on the protein. Plates were then resuspended and incubated for 1 hour at room temperature in the dark. After this time plates were washed a further two times and resuspended in 25 µl of flow buffer. Cellular expression of CD20 and Akt was measured using an Intellicyt HTFC flow cytometer.

Using the data analysis software package FORECYT (Intellicyt) B cells were identified as distinct from other cell populations and the geometric mean of Akt levels was calculated for each well. All data was then expressed as the percentage inhibition of the maximal response (anti-IgM only) minus the background (cells only). The relative effect of the combinations of CD45 and CD79b is shown in Table 5 (↓=inhibition, ↑=stimulation and ↔=no overall effect).

TABLE 5

Table of the relative potency of inhibition of phosphorylated Akt for bispecific & bivalent combinations of antibodies with specificity for CD45 & CD79b.

| (A-X) | (B-Y) Fab B | |
|---|---|---|
| Fab A | CD45-Y | CD79b-Y |
| CD45-X | Not Tested | Not Tested |
| CD79b-X | ↓↓ | ↔ |
| CD45-Y | Not tested | ↔ | where X is a scFv (52SR4) and Y is a peptide (GCN4).

This data is also shown in the form of a bar chart (FIG. 1): the data represents mean values and the error bars are 95% confidence intervals. The data shows that the bispecific combination of CD45 with CD79b can inhibit phospho-Akt expression in B cells stimulated with anti-IgM, whereas combining CD79b-Y with CD79b-Y, which is a mixture which cannot form a bispecific, does not.

Example 3—CD45 Fab/CD79Fab Bispecific Complex but not a Mixture of CD45 and CD79 Fab or Bivalent CD79 Fab' Complex Inhibits PLCγ2 Signalling Human PBMC derived from platelet apheresis cones were banked as frozen aliquots. Prior to an assay being performed cells were thawed, washed in DMEM (Life Technologies) and allowed to acclimatise to a 37° C./5% $CO_2$ environment. During this period grids of bispecific or bivalent antibodies were created by diluting equimolar (200 nM) quantities of Fab-a (Fab-scFv [A-X]) and Fab'-B (Fab-peptide [B-Y]) or Fab-A (Fab-peptide) and Fab-B (Fab-peptide with antigen specificity for the cell surface proteins CD45 and CD79b in DMEM containing 10% calf serum and 2 mM glutamine. This grid is shown in Table 4.

Fab'A-X and Fab'B-Y or Fab-A-Y and Fab-B-Y were incubated together for 90 minutes (in a 37° C./5% $CO_2$ environment) before mixing with $2.5 \times 10^5$ PBMC in V bottomed 96 well plates. PBMC plus bispecific or bivalent combinations were then incubated together for a further 90 minutes. After this time B cells were activated by the addition of 200 nM of goat F(ab')2 anti-human IgM (Southern Biotechnology) for 8 minutes at 37° C. The signalling reaction was then halted by adding an equal volume of Cytofix buffer (BD Biosciences). Plates were then left at room temperature for 15 minutes before centrifugation at 500 g for 5 minutes. Excess supernatant was discarded from the cell pellet which was resuspended in flow buffer and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences) and a fluorescently labelled anti-phospho PLCγ2 antibody that recognises a modified tyrosine residue at position 759 on the protein. Plates were then resuspended and incubated for 1 hour at room temperature in the dark. After this time plates were washed a further two times and resuspended in 25 µl of flow buffer. Cellular expression of CD20 and PLCg2 was measured using an Intellicyt HTFC flow cytometer.

Using the data analysis software package FORECYT (Intellicyt) B cells were identified as distinct from other cell populations and the geometric mean of PLCγ2 levels was calculated for each well. All data was then expressed as the percentage inhibition of the maximal response (anti-IgM only) minus the background (cells only). The relative effect of the combination of CD45 and CD79b is shown in Table 6 (↓=inhibition, ↑=stimulation and ⇔=no overall effect).

TABLE 6

Table of the relative potency of inhibition of phosphorylated PLCg2 for bispecific and bivalent combinations of antibodies with specificity for CD45 and CD79b.

| (A-X or Y) | (B-Y) Fab B | |
|---|---|---|
| Fab A | CD45-Y | CD79b-Y |
| CD45-X | Not Tested | Not Tested |
| CD79b-X | ↓↓↓ | ⇔ |
| CD45-Y | Not tested | ⇔ | where X is a scFv and Y is a peptide

This data can also be expressed as a bar chart (FIG. 2), the data represents mean values and the error bars are 95% confidence intervals. The data shows that the bispecific combination of CD45 with CD79b, inhibit phospho-PLCγ2 expression in B cells stimulated with anti-IgM, whereas combining CD79b-Y with CD79b-Y, which is a mixture which cannot form a bispecific, does not.

Example 4 The Bispecific CD45 and CD79b Complex can Potently Inhibit the Expression of CD86 on B Cells Human PBMC derived from platelet apheresis cones were banked as frozen aliquots. Prior to an assay being performed cells were thawed, washed in DMEM (Life Technologies) and allowed to acclimatise to a 37 degree C./5% $CO_2$ environment. During this period bispecific combinations were created by diluting equimolar (500 nM) quantities of Fab-X (Fab-scFv) and Fab-Y (Fab-peptide) with antigen specificity for the cell surface proteins CD45 and CD79b in DMEM containing 10% calf serum and 2 mM glutamine. These combinations were then diluted in 8 stepwise 1 in 2.5 dilutions to create a dose titration for this combination. Fab-X and Fab-Y were incubated together for 90 minutes (in a 37 degree C./5% CO2 environment) before adding 2.5× 105 PBMC to V bottomed 96 well plates. PBMC were then added to Fab'-X and Fab'-Y combinations and incubated together for a further 90 minutes. After this time B cells were activated by the addition of 200 nM of goat F(ab')2 anti-human IgM (Southern Biotechnology) for 24 hours at 37 degrees C. To enable detection of cell surface activation markers plates were placed on ice and washed once in ice cold flow buffer (PBS+1% BSA+0.01% NaN3). Cells were then stained with a fluorescently labelled anti-CD19 antibody (BD Biosciences) and a fluorescently labelled anti-CD86 antibody and incubated on ice for 1 hour in the dark. After this time plates were washed a further two times and resuspended in 25 ul of flow buffer. Cellular expression of CD19 and CD86 was measured using an Intellicyt HTFC flow cytometer. Using the data analysis software package FORECYT (Intellicyt) B cells were identified as distinct from other cell populations and the geometric mean of CD86 levels was calculated for each well. All data was then expressed as the percentage inhibition of the maximal response (anti-IgM only) minus the background (cells only). As can be seen in FIG. 3 a titration of the combination of CD45-X/CD79b-Y was able to inhibit anti-IgM induced CD86 expression on B cells after 24 hours. The $IC_{50}$, as extrapolated using a 4 parameter logistic curve fit using Graphpad Prism 6, was 4.7 nM (the data represents mean values and the error bars are standard deviations).

Example 5—The Inhibitory Effect of CD45 and CD79b Bispecific Protein can be Reproduced with Different Antibody V Regions Immunisation:

DNA encoding antigens CD79a and CD79b and CD45 was obtained by gene synthesis or commercial sources & cloned into an expression vector with a strong constitutive promoter. Plasmid DNA was then transfected into Rab-9 rabbit fibroblast cells (ATCC CRL-1414) using an in-house electroporation system. For CD79 immunisations, both CD79a and CD79b were co-transfected. Twenty four hours later cells were checked for antigen expression by flow cytometry & frozen in aliquots in liquid nitrogen until use. Up to 6 antigens were immunised per rabbit by either co-expression on the same cell or making mixtures of singly or multiple transfected cells. Rabbits were immunised with 3 doses of cells.

Antibody Discovery:

B cell cultures were prepared using a method similar to that described by Zubler et al. (1985). Briefly, spleen or PBMC-derived B cells from immunized rabbits were cultured at a density of approximately 2000-5000 cells per well in bar-coded 96-well tissue culture plates with 200 μl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 3% activated splenocyte culture supernatant and gamma-irradiated mutant EL4 murine thymoma cells ($5 \times 10^4$/well) for seven days at 37° C. in an atmosphere of 5% $CO_2$.

The presence of antigen-specific antibodies in B cell culture supernatants was determined using a homogeneous fluorescence-based binding assay using HEK293 cells co-transfected withCD79a and CD79b or CD45. Screening involved the transfer of 10 ul of supernatant from barcoded 96-well tissue culture plates into barcoded 384-well black-walled assay plates containing HEK293 cells transfected with target antigen (approximately 3000 cells/well) using a Matrix Platemate liquid handler. Binding was revealed with a goat anti-rabbit IgG Fcγ-specific Cy-5 conjugate (Jackson). Plates were read on an Applied Biosystems 8200 cellular detection system.

Following primary screening, positive supernatants were consolidated on 96-well bar-coded master plates using an Aviso Onyx hit-picking robot and B cells in cell culture plates frozen at −80° C. Master plates were then screened in a homogeneous fluorescence-based binding assay on HEK293 cells transfected with CD79a and CD79b or CD45 antigens or SUPERAVIDIN beads (Bangs Laboratories) coated with recombinant CD45 protein as a source of antigen. This was done in order to determine the antigen specificity for each well.

To allow recovery of antibody variable region genes from a selection of wells of interest, a deconvolution step was performed to enable identification of the antigen-specific B cells in a given well that contained a heterogeneous population of B cells. This was achieved using the Fluorescent foci method (Clargo et al., 2014.Mabs 2014 Jan. 1: 6(1) 143-159; EP1570267B1). Briefly, Immunoglobulin-secreting B cells from a positive well were mixed with either HEK293 cells transfected with target antigen or streptavidin beads (New England Biolabs) coated with biotinylated target antigen and a 1:1200 final dilution of a goat anti-rabbit Fcγ fragment-specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube. The fluorescent foci method was also used to identify antigen-specific B cells from a heterogeneous population of B cells directly from the bone marrow of immunized rabbits.

Antibody variable region genes were recovered from single cells by reverse transcription (RT)-PCR using heavy and light chain variable region-specific primers. Two rounds of PCR were performed, with the nested secondary PCR incorporating restriction sites at the 3' and 5' ends allowing cloning of the variable region into mouse Fab-X and Fab-Y (VH) or mouse kappa (VL) mammalian expression vectors. Heavy and light chain constructs for the Fab-X and Fab-Y expression vectors were co-transfected into HEK-293 cells using Fectin 293 (Life Technologies) or Expi293 cells using Expifectamine (Life Technologies) and recombinant antibody expressed in 6-well tissue culture plates in a volume of 5 ml. After 5-7 days expression, supernatants were harvested. Supernatants were tested in a homogeneous fluorescence-based binding assay on HEK293 cells transfected with antigen and SUPERAVIDIN beads (Bangs Laboratories) coated with recombinant protein or antigen transfected HEK cells. This was done to confirm the specificity of the cloned antibodies.

Production of Small Scale Fab A-X and Fab B-Y (Small Scale (50 mL) Expi293 Transfection)

The Expi293 cells were routinely sub-cultured in EXPI293 Expression Medium to a final concentration of $0.5 \times 10^6$ viable cells/mL and were incubated in an orbital shaking incubator (Multitron, Infors HT) at 120 rpm 8% $CO_2$ and 37° C.

On the day of transfection cell viability and concentration were measured using an automated Cell Counter (Vi-CELL, Beckman Coulter). To achieve a final cell concentration of $2.5 \times 10^6$ viable cells/mL the appropriate volume of cell suspension was added to a sterile 250 mL Erlenmeyer shake flask and brought up to the volume of 42.5 mL by adding fresh, pre-warmed EXPI293 Expression Medium for each 50 mL transfection.

To prepare the lipid-DNA complexes for each transfection a total of 50 μg of heavy chain and light chain plasmid DNAs were diluted in OPTI MEM I medium (LifeTechnologies) to a total volume of 2.5 mL and 135 μL of EXPIFECTAMINE 293 Reagent (LifeTechnologies) was diluted in OPTI MEM I medium to a total volume of 2.5 mL. All dilutions were mixed gently and incubate for no longer than 5 minutes at room temperature before each DNA solution was added to the respective diluted EXPIFECTAMINE 293 Reagent to obtain a total volume of 5 mL. The DNA-EXPIFECTAMINE 293 Reagent mixtures were mixed gently and incubated for 20-30 minutes at room temperature to allow the DNA-EXPIFECTAMINE 293 Reagent complexes to form.

After the DNA-EXPIFECTAMINE 293 reagent complex incubation was completed, the 5 mL of DNA-EXPIFECTAMINE 293 Reagent complex was added to each shake flask. The shake flasks were incubated in an orbital shaking incubator (Multitron, Infors HT) at 120 rpm, 8% $CO_2$ and 37° C.

Approximately 16-18 hours post-transfection, 250 μL of EXPIFECTAMINE 293 Transfection Enhancer 1 (LifeTechnologies) and 2.5 mL of EXPIFECTAMINE 293 Transfection Enhancer 2 (LifeTechnologies) were added to each shake flask.

The cell cultures were harvested 7 days post transfection. The cells were transferred into 50 mL spin tubes (Falcon) and spun down for 30 min at 4000 rpm followed by sterile filtration through a 0.22 um Stericup (Merck Millipore). The clarified and sterile filtered supernatants were stored at 4° C. Final expression levels were determined by Protein G-HPLC.

Small Scale (50 ml) Purification:

Both Fab-X and Fab-Y were purified separately by affinity capture using a small scale vacuum based purification system. Briefly, the 50 ml of culture supernatants were 0.22 μm sterile filtered before 500 μL of Ni Sepharose beads (GE Healthcare) were added. The supernatant beads mixture was then tumbled for about an hour before supernatant was removed by applying vacuum. Beads were then washed with Wash 1 (50 mM Sodium Phosphate 1 M NaCl pH 6.2) and Wash 2 (0.5 M NaCl). Elution was performed with 50 mM sodium acetate, pH4.0+1M NaCl. The eluted fractions buffer exchanged into PBS (Sigma), pH7.4 and 0.22 μm filtered. Final pools were assayed by A280 scan, SE-UPLC (BEH200 method), SDS-PAGE (reduced & non-reduced) and for endotoxin using the PTS Endosafe system.

Human PBMC derived from platelet apheresis cones were banked as frozen aliquots. Prior to an assay being performed cells were thawed, washed in RPMI 1640 (Life Technologies) and allowed to acclimatise to a 37° C./5% $CO_2$ environment. During this period combinations of bispecific, bivalent or mixtures of antibodies were created by diluting equimolar (200 nM) quantities of Fab'-X (Fab-scFv) and Fab'-Y (Fab-peptide) with antigen specificity for the cell surface proteins CD45 and CD79b in RPMI 1640 containing 10% fetal bovine serum, 50 units/mL Penicillin, 50 μg/mL Streptomycin and 2 mM L-glutamine. These combinations of 3 different CD79b Fab-Ys and 2 different CD45 Fab-Xs are shown in Table 7.

TABLE 7

Grid of bispecific proteins with specificity for CD45 and CD79b.

| (A-X) Fab A | (B-Y) Fab B | | |
|---|---|---|---|
| | CD79-Y VR4447 | CD79-Y VR4450 | CD79b-y VR4246 |
| CD45-X VR4131 | CD45-X:Y-CD79b | CD45-X:Y-CD79b | CD45-X:Y-CD79b |
| CD45X VR4248 | CD45-X:Y-CD79b | CD45-X:Y-CD79b | CD45-X:Y-CD79b | where X is a scFv (52SR4) and Y is a peptide (GCN4)

FabA-X and FabB-Y were incubated together for 60 minutes (in a 37° C./5% $CO_2$ environment) before mixing with $2.5 \times 10^5$ PBMC in V bottomed 96 well plates. PBMC plus FabA-X and/or FabB-Y combinations were then incubated together for a further 90 minutes. After this time B cells were activated by the addition of 12.5 μg/mL of goat F(ab')2 anti-human IgM (Southern Biotechnology) for 10 minutes at 37° C. The signalling reaction was then halted by adding an equal volume of Cytofix buffer (BD Biosciences). Plates were then left at room temperature for 15 minutes before centrifugation at 500×g for 5 minutes. Excess supernatant was discarded from the cell pellet which was resuspended in flow buffer (PBS+1% BSA+0.1% $NaN_3$+2 mM EDTA) and washed once more. Cells were then resuspended in ice cold Perm Buffer III (BD Biosciences) for 30 minutes before being washed twice in flow buffer.

Cells were then stained with a fluorescently labelled anti-CD20 antibody (BD Biosciences), and an anti-phospho PLCγ2 antibody that recognises a modified tyrosine residue at position 759. Plates were then resuspended and incubated for 1 hour at room temperature in the dark. After this time plates were washed a further two times and resuspended in 40 µl of flow buffer. Cellular expression of CD20 and PLCγ2 was measured using an Intellicyt HTFC flow cytometer.

Using the data analysis software package FORECYT (Intellicyt) B cells were identified as distinct from other cell populations and the geometric mean of PLCγ2 levels were calculated for each well. All data was then expressed as the percentage inhibition of the maximal response (anti-IgM only) minus the background (cells only).

As can be seen in FIG. 4 the data shows that the combination of CD45 with CD79b with different antibody V regions can inhibit phospho-PLCγ2 expression in B cells stimulated with anti-IgM.

Example 6: Grid Screening of Large Panels of Heterodimerically Tethered Protein Complexes to Identify Novel Bispecific Antibody Targets Introduction:

Following the successful validation of the bispecific format and screening method in the earlier examples the screening was expanded to a larger number of antigen pairs. A panel of antibody variable (V) region pairs to 23 different antigens expressed on B cells was generated. Using the Fab-Kd-Fab [i.e. A-X:Y-B wherein A and B are Fab fragments] format a grid of heterodimerically tethered protein complexes was formed representing multiple V region combinations of each of 315 different antigen pair combinations. These combinations were screened for their ability to modulate BCR (B cell receptor) signalling in a high through-put flow cytometry assay to select novel target pairs for intervention with a bispecific antibody.

Immunisation:

DNA encoding selected antigens was obtained by gene synthesis or commercial sources & cloned into an expression vector with a strong constitutive promoter. Plasmid DNA was then transfected into Rab-9 rabbit fibroblast cells (ATCC CRL-1414) using an in-house electroporation system. Twenty four hours later cells were checked for antigen expression by flow cytometry & frozen in aliquots in liquid nitrogen until use. Up to 6 antigens were immunised per rabbit by either co-expression on the same cell or making mixtures of singly or multiple transfected cells. Rabbits were immunised with 3 doses of cells.

Antibody Discovery:

B cell cultures were prepared using a method similar to that described by Zubler et al. (1985). Briefly, spleen or PBMC-derived B cells from immunized rabbits were cultured at a density of approximately 2000-5000 cells per well in bar-coded 96-well tissue culture plates with 200 µl/well RPMI 1640 medium (Gibco BRL) supplemented with 10% FCS (PAA laboratories ltd), 2% HEPES (Sigma Aldrich), 1% L-Glutamine (Gibco BRL), 1% penicillin/streptomycin solution (Gibco BRL), 0.1% β-mercaptoethanol (Gibco BRL), 3% activated splenocyte culture supernatant and gamma-irradiated mutant EL4 murine thymoma cells ($5\times10^4$/well) for seven days at 37° C. in an atmosphere of 5% $CO_2$.

The presence of antigen-specific antibodies in B cell culture supernatants was determined using a homogeneous fluorescence-based binding assay using HEK293 cells co-transfected with the antigens that the rabbits were immunized with. Screening involved the transfer of 10 ul of supernatant from barcoded 96-well tissue culture plates into barcoded 384-well black-walled assay plates containing HEK293 cells transfected with target antigen (approximately 3000 cells/well) using a Matrix Platemate liquid handler. Binding was revealed with a goat anti-rabbit IgG Fcγ-specific Cy-5 conjugate (Jackson). Plates were read on an Applied Biosystems 8200 cellular detection system.

Following primary screening, positive supernatants were consolidated on 96-well bar-coded master plates using an Aviso Onyx hit-picking robot and B cells in cell culture plates frozen at −80° C. Master plates were then screened in a homogeneous fluorescence-based binding assay on HEK293 cells transfected with antigens separately and SUPERAVIDIN beads (Bangs Laboratories) coated with recombinant protein as a source of antigen. This was done in order to determine the antigen specificity for each well.

To allow recovery of antibody variable region genes from a selection of wells of interest, a deconvolution step was performed to enable identification of the antigen-specific B cells in a given well that contained a heterogeneous population of B cells. This was achieved using the Fluorescent foci method (Clargo et al., 2014.Mabs 2014 Jan. 1: 6(1) 143-159; EP1570267B1). Briefly, Immunoglobulin-secreting B cells from a positive well were mixed with either HEK293 cells transfected with target antigen or streptavidin beads (New England Biolabs) coated with biotinylated target antigen and a 1:1200 final dilution of a goat anti-rabbit Fcγ fragment-specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube. The fluorescent foci method was also used to identify antigen-specific B cells from a heterogeneous population of B cells directly from the bone marrow of immunized rabbits.

Antibody variable region genes were recovered from single cells by reverse transcription (RT)-PCR using heavy and light chain variable region-specific primers. Two rounds of PCR were performed, with the nested secondary PCR incorporating restriction sites at the 3' and 5' ends allowing cloning of the variable region into mouse Fab-X and Fab-Y (VH) or mouse kappa (VL) mammalian expression vectors. Heavy and light chain constructs for the Fab-X and Fab-Y expression vectors were co-transfected into HEK-293 cells using Fectin 293 (Life Technologies) or Expi293 cells using Expifectamine (Life Technologies) and recombinant antibody expressed in 6-well tissue culture plates in a volume of 5 ml. After 5-7 days expression, supernatants were harvested. Supernatants were tested in a homogeneous fluorescence-based binding assay on HEK293 cells transfected with antigen and SUPERAVIDIN beads (Bangs Laboratories) coated with recombinant protein or antigen transfected HEK cells. This was done to confirm the specificity of the cloned antibodies.

Production of Small Scale Fab A-X and Fab B-Y (Small Scale (50 mL) Expi293 Transfection)

The Expi293 cells were routinely sub-cultured in EXPI293 Expression Medium to a final concentration of $0.5 \times 10^6$ viable cells/mL and were incubated in an orbital shaking incubator (Multitron, Infors HT) at 120 rpm 8% $CO_2$ and 37° C.

On the day of transfection cell viability and concentration were measured using an automated Cell Counter (Vi-CELL, Beckman Coulter). To achieve a final cell concentration of $2.5 \times 10^6$ viable cells/mL the appropriate volume of cell suspension was added to a sterile 250 mL Erlenmeyer shake flask and brought up to the volume of 42.5 mL by adding fresh, pre-warmed EXPI293 Expression Medium for each 50 mL transfection.

To prepare the lipid-DNA complexes for each transfection a total of 50 μg of heavy chain and light chain plasmid DNAs were diluted in OPTI-MEM I medium (LifeTechnologies) to a total volume of 2.5 mL and 135 μL of EXPIFECTAMINE 293 Reagent (LifeTechnologies) was diluted in OPTI-MEM I medium to a total volume of 2.5 mL. All dilutions were mixed gently and incubate for no longer than 5 minutes at room temperature before each DNA solution was added to the respective diluted EXPIFECTAMINE 293 Reagent to obtain a total volume of 5 mL. The DNA-EXPIFECTAMINE 293 Reagent mixtures were mixed gently and incubated for 20-30 minutes at room temperature to allow the DNA-EXPIFECTAMINE 293 Reagent complexes to form.

After the DNA-EXPIFECTAMINE 293 reagent complex incubation was completed, the 5 mL of DNA-EXPIFECTAMINE 293 Reagent complex was added to each shake flask. The shake flasks were incubated in an orbital shaking incubator (Multitron, Infors HT) at 120 rpm, 8% $CO_2$ and 37° C.

Approximately 16-18 hours post-transfection, 250 μL of EXPIFECTAMINE 293 Transfection Enhancer 1 (LifeTechnologies) and 2.5 mL of EXPIFECTAMINE 293 Transfection Enhancer 2 (LifeTechnologies) were added to each shake flask.

The cell cultures were harvested 7 days post transfection. The cells were transferred into 50 mL spin tubes (Falcon) and spun down for 30 min at 4000 rpm followed by sterile filtration through a 0.22 um Stericup (Merck Millipore). The clarified and sterile filtered supernatants were stored at 4° C. Final expression levels were determined by Protein G-HPLC.

Small Scale (50 ml) Purification:

Both Fab-X and Fab-Y were purified separately by affinity capture using a small scale vacuum based purification system. Briefly, the 50 ml of culture supernatants were 0.22 μm sterile filtered before 500 μL of Ni Sepharose beads (GE Healthcare) were added. The supernatant beads mixture was then tumbled for about an hour before supernatant was removed by applying vacuum. Beads were then washed with Wash 1 (50 mM Sodium Phosphate 1 M NaCl pH 6.2) and Wash 2 (0.5 M NaCl). Elution was performed with 50 mM sodium acetate, pH4.0+1M NaCl. The eluted fractions buffer exchanged into PBS (Sigma), pH7.4 and 0.22 μm filtered. Final pools were assayed by A280 scan, SE-UPLC (BEH200 method), SDS-PAGE (reduced & non-reduced) and for endotoxin using the PTS Endosafe system.

Screening Assays

Donor PBMCs were rapidly thawed using a water bath set to 37° C., and carefully transferred to a 50 ml Falcon tube. They were then diluted dropwise to 5 ml in assay media to minimise the osmotic shock. The cells were then diluted to 20 ml carefully before adding the final media diluent to make the volume 50 ml. The cells were then spun at 500 g for 5 minutes before removing the supernatant and resuspending the cells in 1 ml media. The cells were then counted and diluted to $1.66 \times 10^6$ cells/ml before dispensing 30 μl per well into a V-bottom TC plate giving a final assay concentration of $5.0 \times 10^4$ cells/well. The cell plate was then stored covered in a 37° C., 5% $CO_2$ incubator until they were required, giving them a minimum of 1 hour to rest.

Fab-X and Fab-Y reagents were mixed in an equimolar ratio at 5x the final assay concentration in assay media and incubated for 90 min at 37° C., 5% $CO_2$. Samples were prepared in a 96-well U-bottom polypropylene plate and covered during the incubation.

10 μl of 5x Fab-KD-Fab mixture was added to the appropriate test wells containing cells and mixed by shaking at 1000 rpm for 30 sec prior to being incubated for 90 min at 37° C., 5% $CO_2$. The cells were then stimulated with 10 μl of anti-human IgM. The final assay concentration of stimulus varied depending on the assay panel readouts, the three antibody cocktails A, B and C (detailed below) were stimulated at a final assay concentration of either 50 μg/ml (cocktail A & C) or 25 μg/ml (cocktail B). The assay plates were then gently mixed at 1000 rpm for 30 sec prior to incubation at 37° C., 5% $CO_2$ for 5 min (antibody cocktail A & C) or 2 min (antibody cocktail B). The assay was stopped by adding 150 μl ice-cold BD CytoFix to all wells and incubated for 15 min at RT. The fixed cells were then spun at 500 g for 5 min to pellet the cells and allow removal of the supernatant using a BioTek ELx405 plate washer. The pellet was re-suspended by vortexing the plate at 2400 rpm for 30 sec. The cells were then permeabilised at 4° C. by adding 100 μl ice-cold BD Cell Permeabilisation Buffer III for 30 min. The cells were then washed in 100 μl FACS buffer and spun at 500 g for 5 min. Supernatant was again removed by the ELx405 before using it to rapidly dispense 200 μl FACS Buffer to wash away any residual permeabilisation buffer. Cells were again spun at 500 g and the supernatant removed by inversion. During the preceding spin step the antibody cocktail was prepared in FACS Buffer and kept shielded from the light. The cells were then re-suspended by vortexing (2400 RPM, 30 sec) before 20 μl of antibody cocktail was added to all wells and the plate shaken for 30 sec at 1000 rpm. The cells were then incubated for 60 min at RT in the dark. The cells were then washed twice in 200 μl FACS buffer with a 500 g spin and supernatant removed after each step. Finally the cells were re-suspended by vortexing for 30 sec at 2400 rpm before adding a final 20 μl FACS buffer. The plate(s) were then read on the Intellicyt HTFC/iQue instrument.

FACS Buffer=PBS+1% BSA+0.05% NaN3+2 mM EDTA

Antibody Cocktail A=1:2 CD20 PerCp-Cy5.5 (BD Biosciences)+1:5 PLCγ2 AF88+1:10 Akt AF647+1:50 ERK1/2 PE (diluted in FACS buffer).

Antibody Cocktail B=1:2 CD20 PerCp-Cy5.5 (BD Biosciences)+1:5 Syk PE+1:5 BLNK AF647 (diluted in FACS buffer)

Antibody Cocktail C=1:5 CD20 PerCp-Cy5.5 (Biolegend)+1:5 PLCγ2 AF488+1:10 Akt AF647+1:5 Syk PE (diluted in FACS buffer)

| Reagent | Supplier | Catalogue number |
| --- | --- | --- |
| Anti-human IgM | Southern Biotech | 2022-14 |
| CytoFix | BD Biosciences | 554655 |
| Perm Buffer III | BD Biosciences | 558050 |
| Anti Akt (pS473) AF647 | BD Biosciences | 561670 |
| Anti SYK (pY348) PE | BD Biosciences | 558529 |
| Anti PLCγ2 (pY759) AF488 | BD Biosciences | 558507 |
| Anti-BLNK(pY84) AF647 | BD Biosciences | 558443 |
| Anti ERK1/2 (pT202/pY204) PE | BD Biosciences | 561991 |

-continued

| Reagent | Supplier | Catalogue number |
|---|---|---|
| Anti-human CD20 PerCp-Cy5.5 | BD Biosciences | 558021 |
| Anti-human CD20 AF488 | BD Biosciences | 558056 |
| Anti-human CD20 PerCp-Cy5.5 | Biolegend | 340508 |
| Phosphate Buffer Saline (PBS) | Fisher Scientific | 10562765 |
| RPMI 1640 | Life Technologies | 31870 |
| Foetal Calf Serum (FCS) | Life Technologies | 16140 |
| Glutamax | Life Technologies | 35050 |
| Penicillin/Streptomycin (P/S) | Life Technologies | 15070 |
| EDTA | Sigma | 03690 |
| Sodium Azide (NaN3) | Sigma | S2002 |
| Bovine Serum Albumon (BSA) | Sigma | A1470 |

Fab-X+Fab-Y combinations were screened with either antibody cocktail A and B or C alone. All screens were conducted on cone cells from 2 different blood donors. Data was captured and evaluated using commercially available software tools. A total of 2500 Fab-X+Fab-Y combinations were screened to 315 different antigen combinations.

Results

The percentage inhibition of the induction of phosphorylation of BCR signalling cascade proteins by each Fab-Kd-Fab [i.e. A-X:Y-B where A and B are Fab fragments] combination was calculated, in this example looking for new combinations of antigens that inhibit B cell function, the criteria for a positive combination was set as at least 30% inhibition of at least two phospho-readouts by at least one combination of V regions. According to this threshold 11 new antigen pair combinations out of 315 examined met the required criteria. This represents a 3.5% hit rate demonstrating the importance of screening large numbers of combinations to find those of desired activity and how rare the activity of the combination of CD79b and CD45 is.

FIGS. 6-8 show the data for the antigen grid cross specificities. Values are percentage inhibition (negative value for activation) of phosphorlylation of Syk, PLCγ2 & AKT respectively and represent the mean of multiple V-region combinations evaluated. 315 different antigen combinations were tested and as can be seen the effect on BCR signalling by different combinations of antibody varied significantly from strong inhibition e.g. antigen 2 (CD79b) on Fab-X combined with antigen 4 (CD45) on Fab-Y (70.4% inhibition of phospho Syk FIG. 6) to activation e.g antigen 6 on X and antigen 11 on Y (minus 118.10% phospho Syk FIG. 6). Each data point representing the mean % values represented in FIGS. 6-8 is shown for antigen combination 2 (CD79b) on Fab-X and antigen 4 (CD45) on Fab-Y in FIG. 9. In this case, 10 different combinations of different antibody V regions were evaluated. The same antigen combination but in alternative orientation, i.e. antigen 2 (CD79b) on Fab-Y and antigen 4 (CD45) on Fab-X is shown in FIG. 10. In this case, 6 different combinations of different antibody V regions were evaluated. Again, all V regions show inhibition but optimal V region combinations can be identified and selected using the method.

Example 7—Screening of Transiently Expressed V-Regions to Antigen CD45 as Fab-X with Purified Anti-CD79b Fab-Y in Heterodimerically Tethered Protein Complexes to Select Optimal Anti-CD45 Antibody V-Regions Introduction:

New V-regions to CD45 that inhibit B cell signalling as a bispecific antibody in combination with CD79b specific V regions were identified using grid screening of heterodimerically tethered protein complexes. The CD45 V regions were expressed transiently as Fab-X and combined with purified anti-CD79b Fab-Y. The inhibition of activation of B cell signalling was measured to select the most potent anti-CD45 and anti-CD79b V regions. The preparation of antigen expressing cells and immunisation of rabbits was carried out in the same way as described in Example 6.

Antibody Discovery:

B cell cultures were prepared in the same way as described in Example 6. The screening of antigen-specific antibodies in B cell culture supernatants and the deconvolution step for identification of antigen specific B cells was determined in the same way as Example 6.

Antibody variable region genes were recovered from single cells by reverse transcription (RT)-PCR using heavy and light chain variable region-specific primers. Two rounds of PCR were performed, with the nested 2° PCR incorporating restriction sites at the 3' and 5' ends allowing cloning of the variable region into mouse Fab-X and mouse kappa (VL) mammalian expression vector. These vectors were then co-transfected in HEK-293 cells using 293Fectin (Life Technologies) or in Expi293 cells using Expifectamine (Life Technologies) and left to express for 6 days. Supernatants were tested in a homogeneous fluorescence-based binding assay on HEK293 cells transfected with antigen and SUPERAVIDIN beads (Bangs Laboratories) coated with recombinant protein or antigen transfected HEK cells. This was done to confirm the specificity of the cloned antibodies.

In addition to the Fab-X transient supernatants, negative control Mock supernatants were prepared in the same way using an irrelevant control DNA.

The expression levels of Fab-X were determined by Protein G-HPLC.

Production of Purified Fab-X and Fab-Y:

Purified Fab-X and Fab-Y was prepared using the same method described in Example 6.

PhosFlow Assay:

CD79b-specific Fab-Y and CD45-specific Fab-X, either purified or in transient supernatant, were incubated together for 60 minutes (in a 37° C. & 5% $CO_2$ environment) at equimolar concentration of 200 nM and 90 nM. A mock supernatant was also included neat. In V-bottomed 96 well plates, $5.0\times10^4$ PBMC were added to wells, to which were added titrated Fab-X and Fab-Y combinations or mock supernatant. The combinations and cells were then incubated together for a further 90 minutes. After this time B cells were activated by the addition of 25 μg/mL of goat $F(ab')_2$ anti-human IgM (Southern Biotechnology) for 15 minutes at 37° C. plus 5% $CO_2$. The signalling reaction was then halted by adding an equal volume of Cytofix buffer (BD Biosciences). Plates were then left at room temperature for 15 minutes before centrifugation at 500×g for 5 minutes. Excess supernatant was discarded from the cell pellet which was resuspended in FACS buffer (PBS+1% BSA+0.01% NaN3+2 mM EDTA) and washed once more. Cells were then resuspended in ice cold Perm Buffer III (BD Biosciences) for 30 minutes before being washed twice in flow buffer. Cells were then stained as described in Example 6, except that instead of 3 different antibody cocktails, only one cocktail was used with the same assay concentrations and incubation conditions as described for antibody cocktail A in Example 6.

Antibody Cocktail=1:3 CD20 PerCp-Cy5.5+1:5 PLCγ2 AF88+1:10 Akt AF647+1:5 p38 MAPK PE (diluted in FACS buffer).

Results

As can be seen in FIGS. 11 to 16, the data shows that the combination of different transiently expressed antigen CD45 V regions in Fab-X with 2 different purified antigen CD79b V regions (VR447 and VR4450) in Fab-Y can inhibit B cell activation (as measured by inhibition of PLCγ2, p38 and Akt) to different levels and screening in a bispecific format therefore facilitates selection of optimal V region combinations. Combinations with transient Fab-X are compared to a reference combination with a purified CD45 Fab-X (VR4122).

Example 8—Effect of Co-Targeting the Antigen CD79b Plus Antigen CD45 on Memory B Cell Function Using Molecularly Linked Bispecific Bybes with or without Further Addition of an Anti-Albumin Introduction:

To check that targeting CD79b/CD45 has a functional effect on B cells in long term culture, IgG production from B cells in a mixed PBMC culture was measured. The measurement of specific antibodies to the recall antigen tetanus toxoid provides a read out of memory B cell function.

Antigen CD79b specificity (VR4447) and antigen CD45 specificity (VR4248 and VR4133) were generated in a BYbe format with or without addition of an anti-albumin fragment (VR0645). The anti-albumin antibody fragment was fused to the light chain of the antigen CD45 Fab of the BYbe format as described in Example 8.

Description of constructs used in this experiment.

| Construct Name | Fab Specificity | Heavy Chain scFv | Light Chain sFv |
| --- | --- | --- | --- |
| VR4447/VR4248 BYbe | Antigen CD79b | Antigen CD45 | None |
| VR4447/VR4248/VR645 BYbe/Albumin | Antigen CD79b | Antigen CD45 | Albumin |
| VR4447/VR4133 BYbe | Antigen CD79b | Antigen CD45 | None |
| VR4447/VR4133/VR645 BYbe/Albumin | Antigen CD79b | Antigen CD45 | Albumin |

Methods

Purification of BYbes with/without Anti-Albumin Additional Specificity

The BYbe (Fab-dsscFv [scFv off C-terminus of Fab heavy chain]) and BYbe with anti-albimin (Fab-2xdsscFv [scFvs off C-terminus of Fab heavy chain and light chain]) formats were purified as follows. Clarified cell culture supernatants from standard expiHEK or CHO expression were 0.22 um sterile filtered. The filtered supernatants were loaded at 2 ml/min onto 50 ml GammabindPlus Sepharose XK26 columns (GE Healthcare) equilibrated in PBS pH7.4 (Sigma Aldrich Chemicals). After loading the columns were washed with PBS pH7.4 and then eluted with 0.1M Glycine/HCl. pH 2.7. The elution was followed by absorbance at 280 nm, the elution peak collected, and then neutralised with 1/25th volume of 2 M Tris/HCl pH8.5. The neutralised samples were concentrated using Amicon Ultra-15 concentrators with either a 10 kDa or 30 kDa molecular weight cut off membrane and centrifugation at 4000×g in a swing out rotor. Concentrated samples were applied to either a XK16/60 or XK26/60 Superdex 200 column (GE Healthcare) equilibrated in PBS, pH7.4. The columns were developed with an isocratic gradient of PBS, pH7.4 at either 1 ml/min or 2.6 ml/min respectively. Fractions were collected and analysed by size exclusion chromatography on a TSK gel G3000SWXL; 5 µm, 7.8×300 mm column developed with an isocratic gradient of 0.2 M phosphate, pH 7.0 at 1 ml/min, with detection by absorbance at 280 nm. Selected monomer fractions were pooled and concentrated to >1 mg/ml using an Amicon Ultra-15 concentrator with a 10 kDa or 30 kDa molecular weight cut off membrane and centrifugation at 4000×g in a swing out rotor. Final samples were assayed; for concentration by A280 Scanning UV-visible spectrophotometer (Cary 50Bio); for % monomer by size exclusion chromatography on a TSK gel G3000SWXL; 5 µm, 7.8×300 mm column developed with an isocratic gradient of 0.2 M phosphate, pH7.0 at 1 ml/min, with detection by absorbance at 280 nm; by reducing and non-reducing SDS-PAGE run on 4-20% Tris-Glycine 1.5 mm gels (Novex) at 50 mA (per gel) for 53 minutes; and for endotoxin by Charles River's ENDOSAFE Portable Test System with Limulus Amebocyte Lysate (LAL) test cartridges.

Activation of B Cells and Measurement of Tetanus Toxoid Specific IgG

Human PBMCs were stimulated with 500 ng/ml CD40L, 1 ug/ml CpG and 50 ng/ml IL-21 in 1640 media plus 10% foetal bovine serum and 2 mM Glutamax (R10 medium) for 6 days. Constructs of purified protein were added at a final concentration of 100 nM at day 0 and remained in the culture medium for the duration of the assay. After 6 days the supernatants were harvested and the amount of tetanus toxoid specific IgG was detected by ELISA.

Briefly, Maxisorp half-well ELISA plates (Nunc) were coated with 10 ug/ml tetanus toxoid in PBS overnight at 4° C. The plates were then blocked in 5% Milk—in PBS containing 0.05% Tween 20 for 2 hours. The supernatants were diluted and then added for 2 hours at room temperature. The plates were washed with PBS-0.05% Tween20 and tetanus bound antibody was detected using a peroxidase-goat anti-human IgG(H+L) diluted to 1 ug/ml in 5% milk-PBS 0.05% Tween 20. Plates were developed using TMB substrate solution (KPL) and absorbance was measured at 450 nM using a Synergy 2 micro-plate reader (Biotek). Data was exported to Excel and percentage inhibition was calculated relative to cells cultured without test antibodies. The data was then imported into Graphpad PRISM and plotted as bar charts.

Figure 17:
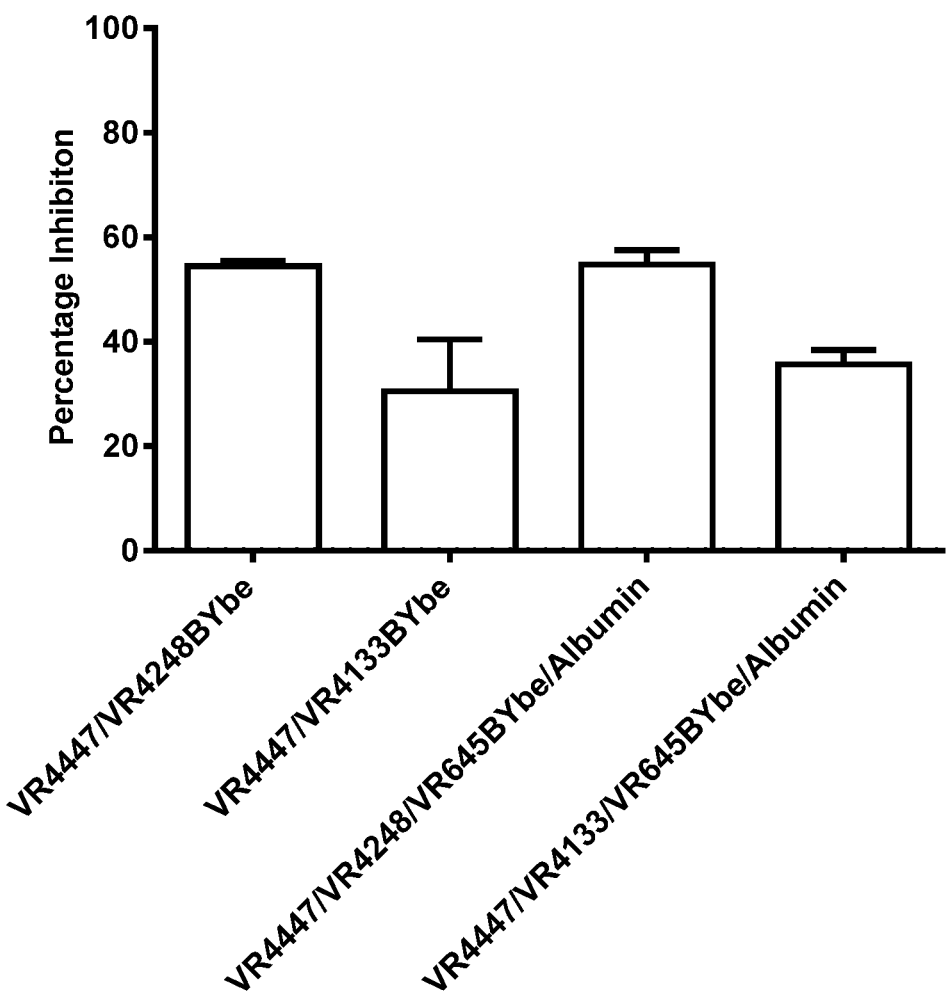
FIG. 17 shows the inhibition of tetanus toxoid IgG production from PBMCs cultured with different multispecific molecules

FIG. 17 shows the inhibition of tetanus toxoid IgG production from PBMCs cultured with VR4447/VR4248 BYbe, VR4447/VR4133 BYbe, VR4447/VR4248/VR645 BYbe/Albumin and VR4447/VR4133/VR645 BYbe/Albumin. Data shown is from a single donor.

The invention claimed is:
1. An antibody comprising a binding domain specific to antigen CD45 and a binding domain specific to antigen-CD79b,
wherein the binding domain specific to the antigen CD45 comprises:
3 heavy chain CDRs comprising SEQ ID NO: 128 for CDRH1, SEQ ID NO: 129 for CDRH2 and SEQ ID NO: 130 for CDRH3 and 3 light chain CDRs comprising SEQ ID NO: 125 for CDRL1, SEQ ID NO: 126 for CDRL2 and SEQ ID NO: 127 for CDRL3; and
wherein the binding domain specific to the antigen CD79b comprises:
3 heavy chain CDRs comprising SEQ ID NO: 88 for CDRH1, SEQ ID NO: 89 for CDRH2 and SEQ ID NO: 90 for CDRH3 and 3 light chain CDRs comprising SEQ ID NO: 85 for CDRL1, SEQ ID NO: 86 for CDRL2 and SEQ ID NO: 87, for CDRL3.

2. The antibody according to claim 1, wherein the antibody is bispecific or trispecific.

3. The antibody according to claim 1, wherein the antibody is a fusion protein.

4. The antibody according to claim 1, wherein the antibody format is selected from diabody, scdiabody, triabody, tandem scFv, FabFv, Fab'Fv, FabdsFv, Fab-scFv, Fab-dsscFv, Fab-(dsscFv)2 diFab, diFab', tribody, tandem scFv-Fc, scFv-Fc-scFv, scdiabody-Fc, scdiabody-CH3, Ig-scFv, scFv-Ig, V-Ig, and Ig-V.

5. The antibody according to claim 1, wherein each binding domain is monospecific.

6. The antibody according to claim 1, wherein the antibody comprises no more than one binding domain which is specific to CD45 and no more than one binding domain which is specific to CD79b.

7. The antibody according to claim 1, wherein the binding domain which is specific to CD45 and the binding domain which is specific to CD79b are independently selected from a Fab, scFv, Fv, dsFv and dsscFv.

8. The antibody according to claim 1, wherein the binding domains are humanised.

9. The antibody according to claim 1, which further comprises a binding domain specific to serum albumin.

10. A composition comprising one or more multispecific antibodies as defined in claim 1.

11. A nucleotide sequence encoding a multispecific molecule an antibody as defined in claim 1.

12. A vector comprising a nucleotide sequence defined in claim 11.

* * * * *

UNITED STATES PATENT AND TRADEMARK OFFICE
CERTIFICATE OF CORRECTION

PATENT NO. : 10,774,152 B2
APPLICATION NO. : 15/326499
DATED : September 15, 2020
INVENTOR(S) : Helene Margaret Finney et al.

Page 1 of 1

It is certified that error appears in the above-identified patent and that said Letters Patent is hereby corrected as shown below:

In the Claims

Column 159, Lines 25-26 (Claim 10): "multispecific antibodies" should be replaced with
--antibodies--

Column 159, Lines 27-28 (Claim 11): "a multispecific molecule an antibody" should be replaced with
--an antibody--

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 143

<210> SEQ ID NO 1
<211> LENGTH: 44
<212> TYPE: PRT

<213> ORGANISM: Artificial Sequence
<220> FEATURE:
<223> OTHER INFORMATION: GCN4(7P14P) sequence

<400> SEQUENCE: 1

```
Ala Ser Gly Gly Gly Arg Met Lys Gln Leu Glu Pro Lys Val Glu Glu
1               5                   10                  15

Leu Leu Pro Lys Asn Tyr His Leu Glu Asn Glu Val Ala Arg Leu Lys
            20                  25                  30

Lys Leu Val Gly Glu Arg His His His His His His
        35                  40
```

<210> SEQ ID NO 2
<211> LENGTH: 132
<212> TYPE: DNA
<213> ORGANISM: Artificial Sequence
<220> FEATURE:
<223> OTHER INFORMATION: GCN4(7P14P) sequence

<400> SEQUENCE: 2

```
gctagcggag gcggaagaat gaaacaactt gaacccaagg ttgaagaatt gcttccgaaa      60
aattatcact ggaaaatga ggttgccaga ttaaagaaat tagttggcga acgccatcac     120
catcaccatc ac                                                        132
```

<210> SEQ ID NO 3
<211> LENGTH: 262
<212> TYPE: PRT
<213> ORGANISM: Artificial Sequence
<220> FEATURE:
<223> OTHER INFORMATION: 52SR4 ds scFv sequence

<400> SEQUENCE: 3

```
Asp Ala Val Val Thr Gln Glu Ser Ala Leu Thr Ser Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
            35                  40                  45

Leu Ile Gly Gly Thr Asn Asn Arg Ala Pro Gly Val Pro Ala Arg Phe
50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Val Leu Trp Tyr Ser Asp
                85                  90                  95

His Trp Val Phe Gly Cys Gly Thr Lys Leu Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Asp Val Gln Leu Gln Gln Ser Gly Pro Gly Leu Val Ala Pro
    130                 135                 140

Ser Gln Ser Leu Ser Ile Thr Cys Thr Val Ser Gly Phe Leu Leu Thr
145                 150                 155                 160

Asp Tyr Gly Val Asn Trp Val Arg Gln Ser Pro Gly Lys Cys Leu Glu
                165                 170                 175

Trp Leu Gly Val Ile Trp Gly Asp Gly Ile Thr Asp Tyr Asn Ser Ala
            180                 185                 190

Leu Lys Ser Arg Leu Ser Val Thr Lys Asp Asn Ser Lys Ser Gln Val
        195                 200                 205
```

```
Phe Leu Lys Met Asn Ser Leu Gln Ser Gly Asp Ser Ala Arg Tyr Tyr
    210                 215                 220

Cys Val Thr Gly Leu Phe Asp Tyr Trp Gly Gln Gly Thr Thr Leu Thr
225                 230                 235                 240

Val Ser Ser Ala Ala Ala His His His His His His Glu Gln Lys Leu
                245                 250                 255

Ile Ser Glu Glu Asp Leu
            260

<210> SEQ ID NO 4
<211> LENGTH: 792
<212> TYPE: DNA
<213> ORGANISM: Artificial Sequence
<220> FEATURE:
<223> OTHER INFORMATION: 52SR4 ds scFv sequence

<400> SEQUENCE: 4
gatgcggtgg tgacccagga aagcgcgctg accagcagcc cgggcgaaac cgtgaccctg      60
acctgccgca gcagcaccgg cgcggtgacc accagcaact atgcgagctg ggtgcaggaa     120
aaaccggatc atctgtttac cggcctgatt ggcggcacca caaccgcgc gccgggcgtg     180 ccggcgcgct ttagcggcag cctgattggc gataaagcgg cgctgaccat taccggcgcg     240
cagaccgaag atgaagcgat ttattttttgc gtgctgtggt atagcgacca ttgggtgttt     300
ggctgcggca ccaaactgac cgtgctgggt ggaggcggtg gctcaggcgg aggtggctca     360
ggcggtggcg gtctggcgg cggcggcagc gatgtgcagc tgcagcagag cggcccgggc     420
ctggtggcgc gagccagag cctgagcatt acctgcaccg tgagcggctt ctctcctgacc     480 gattatggcg tgaactgggt cgccagagc ccgggcaaat gcctggaatg gctgggcgtg     540
atttggggcg atggcattac cgattataac agcgcgctga aaagccgcct gagcgtgacc     600
aaagataaca gcaaaagcca ggtgtttctg aaaatgaaca gcctgcagag cggcgatagc     660
gcgcgctatt attgcgtgac cggcctgttt gattattggg gccagggcac cacccctgacc     720 gtgagcagcg cggccgccca tcaccatcac catcacgaac agaaactgat tagcgaagaa     780
gatctgtaat ag                                                        792

<210> SEQ ID NO 5
<211> LENGTH: 8
<212> TYPE: PRT
<213> ORGANISM: Artificial Sequence
<220> FEATURE:
<223> OTHER INFORMATION: Hinge linker

<400> SEQUENCE: 5

Asp Lys Thr His Thr Cys Ala Ala
1               5

<210> SEQ ID NO 6
<211> LENGTH: 11
<212> TYPE: PRT
<213> ORGANISM: Artificial Sequence
<220> FEATURE:
<223> OTHER INFORMATION: Hinge linker

<400> SEQUENCE: 6

Asp Lys Thr His Thr Cys Pro Pro Cys Pro Ala
1               5                   10

<210> SEQ ID NO 7
```

```
<211> LENGTH: 18
<212> TYPE: PRT
<213> ORGANISM: Artificial Sequence
<220> FEATURE:
<223> OTHER INFORMATION: Hinge linker

<400> SEQUENCE: 7

Asp Lys Thr His Thr Cys Pro Pro Cys Pro Ala Thr Cys Pro Pro Cys
1               5                   10                  15

Pro Ala

<210> SEQ ID NO 8
<211> LENGTH: 25
<212> TYPE: PRT
<213> ORGANISM: Artificial Sequence
<220> FEATURE:
<223> OTHER INFORMATION: Hinge linker

<400> SEQUENCE: 8

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 9
<211> LENGTH: 30
<212> TYPE: PRT
<213> ORGANISM: Artificial Sequence
<220> FEATURE:
<223> OTHER INFORMATION: Hinge linker

<400> SEQUENCE: 9

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Hinge linker

<400> SEQUENCE: 10

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 11
<211> LENGTH: 15
<212> TYPE: PRT
<213> ORGANISM: Artificial Sequence
<220> FEATURE:
<223> OTHER INFORMATION: Hinge linker

<400> SEQUENCE: 11

Asp Lys Thr His Thr Cys Cys Val Glu Cys Pro Pro Cys Pro Ala
1               5                   10                  15

<210> SEQ ID NO 12
<211> LENGTH: 26
<212> TYPE: PRT
<213> ORGANISM: Artificial Sequence
```

```
<220> FEATURE:
<223> OTHER INFORMATION: Hinge linker

<400> SEQUENCE: 12

Asp Lys Thr His Thr Cys Pro Arg Cys Pro Glu Pro Lys Ser Cys Asp
1               5                   10                  15
Thr Pro Pro Pro Cys Pro Arg Cys Pro Ala
            20                  25

<210> SEQ ID NO 13
<211> LENGTH: 11
<212> TYPE: PRT
<213> ORGANISM: Artificial Sequence
<220> FEATURE:
<223> OTHER INFORMATION: Hinge linker

<400> SEQUENCE: 13

Asp Lys Thr His Thr Cys Pro Ser Cys Pro Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Flexible linker

<400> SEQUENCE: 14

Ser Gly Gly Gly Gly Ser Glu
1               5

<210> SEQ ID NO 15
<211> LENGTH: 6
<212> TYPE: PRT
<213> ORGANISM: Artificial Sequence
<220> FEATURE:
<223> OTHER INFORMATION: Flexible linker

<400> SEQUENCE: 15

Asp Lys Thr His Thr Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Flexible linker

<400> SEQUENCE: 16

Ser Gly Gly Gly Gly Ser
1               5

<210> SEQ ID NO 17
<211> LENGTH: 11
<212> TYPE: PRT
<213> ORGANISM: Artificial Sequence
<220> FEATURE:
<223> OTHER INFORMATION: Flexible linker

<400> SEQUENCE: 17

Ser Gly Gly Gly Gly Ser Gly Gly Gly Gly Ser
1               5                   10

<210> SEQ ID NO 18
<211> LENGTH: 16
```

```
<212> TYPE: PRT
<213> ORGANISM: Artificial Sequence
<220> FEATURE:
<223> OTHER INFORMATION: Flexible linker

<400> SEQUENCE: 18

Ser Gly Gly Gly Gly Ser Gly Gly Gly Gly Ser Gly Gly Gly Gly Ser
1               5                   10                  15

<210> SEQ ID NO 19
<211> LENGTH: 21
<212> TYPE: PRT
<213> ORGANISM: Artificial Sequence
<220> FEATURE:
<223> OTHER INFORMATION: Flexible linker

<400> SEQUENCE: 19

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 20
<211> LENGTH: 26
<212> TYPE: PRT
<213> ORGANISM: Artificial Sequence
<220> FEATURE:
<223> OTHER INFORMATION: Flexible linker

<400> SEQUENCE: 20

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 21
<211> LENGTH: 11
<212> TYPE: PRT
<213> ORGANISM: Artificial Sequence
<220> FEATURE:
<223> OTHER INFORMATION: Flexible linker

<400> SEQUENCE: 21

Ala Ala Ala Gly Ser Gly Gly Ala Ser Ala Ser
1               5                   10

<210> SEQ ID NO 22
<211> LENGTH: 16
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be naturally occuring amino acid

<400> SEQUENCE: 22

Ala Ala Ala Gly Ser Gly Xaa Gly Gly Gly Ser Gly Ala Ser Ala Ser
1               5                   10                  15

<210> SEQ ID NO 23
<211> LENGTH: 21
<212> TYPE: PRT
<213> ORGANISM: Artificial Sequence
<220> FEATURE:
<223> OTHER INFORMATION: Flexible linker
```

```
<220> FEATURE:
<221> NAME/KEY: misc_feature
<222> LOCATION: (7)..(7)
<223> OTHER INFORMATION: Xaa can be naturally occuring amino acid
<220> FEATURE:
<221> NAME/KEY: misc_feature
<222> LOCATION: (12)..(12)
<223> OTHER INFORMATION: Xaa can be naturally occuring amino acid

<400> SEQUENCE: 23

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 24
<211> LENGTH: 26
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be naturally occuring amino acid
<220> FEATURE:
<221> NAME/KEY: misc_feature
<222> LOCATION: (12)..(12)
<223> OTHER INFORMATION: Xaa can be naturally occuring amino acid
<220> FEATURE:
<221> NAME/KEY: misc_feature
<222> LOCATION: (17)..(17)
<223> OTHER INFORMATION: Xaa can be naturally occuring amino acid

<400> SEQUENCE: 24

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 25
<211> LENGTH: 31
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be naturally occuring amino acid
<220> FEATURE:
<221> NAME/KEY: misc_feature
<222> LOCATION: (12)..(12)
<223> OTHER INFORMATION: Xaa can be naturally occuring amino acid
<220> FEATURE:
<221> NAME/KEY: misc_feature
<222> LOCATION: (17)..(17)
<223> OTHER INFORMATION: Xaa can be naturally occuring amino acid
<220> FEATURE:
<221> NAME/KEY: misc_feature
<222> LOCATION: (22)..(22)
<223> OTHER INFORMATION: Xaa can be naturally occuring amino acid

<400> SEQUENCE: 25

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 26
```

```
<211> LENGTH: 13
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be naturally occuring amino acid

<400> SEQUENCE: 26

Ala Ala Ala Gly Ser Gly Xaa Ser Gly Ala Ser Ala Ser
1               5                   10

<210> SEQ ID NO 27
<211> LENGTH: 28
<212> TYPE: PRT
<213> ORGANISM: Artificial Sequence
<220> FEATURE:
<223> OTHER INFORMATION: Flexible linker

<400> SEQUENCE: 27

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
            20                  25

<210> SEQ ID NO 28
<211> LENGTH: 11
<212> TYPE: PRT
<213> ORGANISM: Artificial Sequence
<220> FEATURE:
<223> OTHER INFORMATION: Flexible linker

<400> SEQUENCE: 28

Ala Thr Thr Thr Gly Ser Ser Pro Gly Pro Thr
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Flexible linker

<400> SEQUENCE: 29

Ala Thr Thr Thr Gly Ser
1               5

<210> SEQ ID NO 30

<400> SEQUENCE: 30

000

<210> SEQ ID NO 31
<211> LENGTH: 21
<212> TYPE: PRT
<213> ORGANISM: Artificial Sequence
<220> FEATURE:
<223> OTHER INFORMATION: Flexible linker

<400> SEQUENCE: 31

Glu Pro Ser Gly Pro Ile Ser Thr Ile Asn Ser Pro Ser Lys Glu
1               5                   10                  15

Ser His Lys Ser Pro
            20
```

<210> SEQ ID NO 32
<211> LENGTH: 15
<212> TYPE: PRT
<213> ORGANISM: Artificial Sequence
<220> FEATURE:
<223> OTHER INFORMATION: Flexible linker

<400> SEQUENCE: 32

Gly Thr Val Ala Ala Pro Ser Val Phe Ile Phe Pro Pro Ser Asp
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Flexible linker

<400> SEQUENCE: 33

Gly Gly Gly Gly Ile Ala Pro Ser Met Val Gly Gly Gly Gly Ser
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Flexible linker

<400> SEQUENCE: 34

Gly Gly Gly Gly Lys Val Glu Gly Ala Gly Gly Gly Gly Gly Ser
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Flexible linker

<400> SEQUENCE: 35

Gly Gly Gly Gly Ser Met Lys Ser His Asp Gly Gly Gly Gly Ser
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Flexible linker

<400> SEQUENCE: 36

Gly Gly Gly Gly Asn Leu Ile Thr Ile Val Gly Gly Gly Gly Ser
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Flexible linker

<400> SEQUENCE: 37

Gly Gly Gly Gly Val Val Pro Ser Leu Pro Gly Gly Gly Gly Ser
1               5                   10                  15

```
<210> SEQ ID NO 38
<211> LENGTH: 12
<212> TYPE: PRT
<213> ORGANISM: Artificial Sequence
<220> FEATURE:
<223> OTHER INFORMATION: Flexible linker

<400> SEQUENCE: 38

Gly Gly Glu Lys Ser Ile Pro Gly Gly Gly Gly Ser
1               5                   10

<210> SEQ ID NO 39
<211> LENGTH: 18
<212> TYPE: PRT
<213> ORGANISM: Artificial Sequence
<220> FEATURE:
<223> OTHER INFORMATION: Flexible linker

<400> SEQUENCE: 39

Arg Pro Leu Ser Tyr Arg Pro Pro Phe Pro Phe Gly Phe Pro Ser Val
1               5                   10                  15

Arg Pro

<210> SEQ ID NO 40
<211> LENGTH: 18
<212> TYPE: PRT
<213> ORGANISM: Artificial Sequence
<220> FEATURE:
<223> OTHER INFORMATION: Flexible linker

<400> SEQUENCE: 40

Tyr Pro Arg Ser Ile Tyr Ile Arg Arg Arg His Pro Ser Pro Ser Leu
1               5                   10                  15

Thr Thr

<210> SEQ ID NO 41
<211> LENGTH: 18
<212> TYPE: PRT
<213> ORGANISM: Artificial Sequence
<220> FEATURE:
<223> OTHER INFORMATION: Flexible linker

<400> SEQUENCE: 41

Thr Pro Ser His Leu Ser His Ile Leu Pro Ser Phe Gly Leu Pro Thr
1               5                   10                  15

Phe Asn

<210> SEQ ID NO 42
<211> LENGTH: 18
<212> TYPE: PRT
<213> ORGANISM: Artificial Sequence
<220> FEATURE:
<223> OTHER INFORMATION: Flexible linker

<400> SEQUENCE: 42

Arg Pro Val Ser Pro Phe Thr Phe Pro Arg Leu Ser Asn Ser Trp Leu
1               5                   10                  15

Pro Ala

<210> SEQ ID NO 43
<211> LENGTH: 18
<212> TYPE: PRT
<213> ORGANISM: Artificial Sequence
<220> FEATURE:
```

<223> OTHER INFORMATION: Flexible linker

<400> SEQUENCE: 43

Ser Pro Ala Ala His Phe Pro Arg Ser Ile Pro Arg Pro Gly Pro Ile
1               5                   10                  15

Arg Thr

<210> SEQ ID NO 44
<211> LENGTH: 18
<212> TYPE: PRT
<213> ORGANISM: Artificial Sequence
<220> FEATURE:
<223> OTHER INFORMATION: Flexible linker

<400> SEQUENCE: 44

Ala Pro Gly Pro Ser Ala Pro Ser His Arg Ser Leu Pro Ser Arg Ala
1               5                   10                  15

Phe Gly

<210> SEQ ID NO 45
<211> LENGTH: 18
<212> TYPE: PRT
<213> ORGANISM: Artificial Sequence
<220> FEATURE:
<223> OTHER INFORMATION: Flexible linker

<400> SEQUENCE: 45

Pro Arg Asn Ser Ile His Phe Leu His Pro Leu Leu Val Ala Pro Leu
1               5                   10                  15

Gly Ala

<210> SEQ ID NO 46
<211> LENGTH: 18
<212> TYPE: PRT
<213> ORGANISM: Artificial Sequence
<220> FEATURE:
<223> OTHER INFORMATION: Flexible linker

<400> SEQUENCE: 46

Met Pro Ser Leu Ser Gly Val Leu Gln Val Arg Tyr Leu Ser Pro Pro
1               5                   10                  15

Asp Leu

<210> SEQ ID NO 47
<211> LENGTH: 18
<212> TYPE: PRT
<213> ORGANISM: Artificial Sequence
<220> FEATURE:
<223> OTHER INFORMATION: Flexible linker

<400> SEQUENCE: 47

Ser Pro Gln Tyr Pro Ser Pro Leu Thr Leu Thr Leu Pro Pro His Pro
1               5                   10                  15

Ser Leu

<210> SEQ ID NO 48
<211> LENGTH: 18
<212> TYPE: PRT
<213> ORGANISM: Artificial Sequence
<220> FEATURE:
<223> OTHER INFORMATION: Flexible linker

<400> SEQUENCE: 48

Asn Pro Ser Leu Asn Pro Pro Ser Tyr Leu His Arg Ala Pro Ser Arg
1               5                   10                  15

Ile Ser

<210> SEQ ID NO 49
<211> LENGTH: 17
<212> TYPE: PRT
<213> ORGANISM: Artificial Sequence
<220> FEATURE:
<223> OTHER INFORMATION: Flexible linker

<400> SEQUENCE: 49

Leu Pro Trp Arg Thr Ser Leu Leu Pro Ser Leu Pro Leu Arg Arg Arg
1               5                   10                  15

Pro

<210> SEQ ID NO 50
<211> LENGTH: 18
<212> TYPE: PRT
<213> ORGANISM: Artificial Sequence
<220> FEATURE:
<223> OTHER INFORMATION: Flexible linker

<400> SEQUENCE: 50

Pro Pro Leu Phe Ala Lys Gly Pro Val Gly Leu Leu Ser Arg Ser Phe
1               5                   10                  15

Pro Pro

<210> SEQ ID NO 51
<211> LENGTH: 18
<212> TYPE: PRT
<213> ORGANISM: Artificial Sequence
<220> FEATURE:
<223> OTHER INFORMATION: Flexible linker

<400> SEQUENCE: 51

Val Pro Pro Ala Pro Val Val Ser Leu Arg Ser Ala His Ala Arg Pro
1               5                   10                  15

Pro Tyr

<210> SEQ ID NO 52
<211> LENGTH: 17
<212> TYPE: PRT
<213> ORGANISM: Artificial Sequence
<220> FEATURE:
<223> OTHER INFORMATION: Flexible linker

<400> SEQUENCE: 52

Leu Arg Pro Thr Pro Pro Arg Val Arg Ser Tyr Thr Cys Cys Pro Thr
1               5                   10                  15

Pro

<210> SEQ ID NO 53
<211> LENGTH: 18
<212> TYPE: PRT
<213> ORGANISM: Artificial Sequence
<220> FEATURE:
<223> OTHER INFORMATION: Flexible linker

<400> SEQUENCE: 53

Pro Asn Val Ala His Val Leu Pro Leu Leu Thr Val Pro Trp Asp Asn
1               5                   10                  15

Leu Arg

<210> SEQ ID NO 54
<211> LENGTH: 18
<212> TYPE: PRT
<213> ORGANISM: Artificial Sequence
<220> FEATURE:
<223> OTHER INFORMATION: Flexible linker

<400> SEQUENCE: 54

Cys Asn Pro Leu Leu Pro Leu Cys Ala Arg Ser Pro Ala Val Arg Thr
1               5                   10                  15

Phe Pro

<210> SEQ ID NO 55
<211> LENGTH: 11
<212> TYPE: PRT
<213> ORGANISM: Artificial Sequence
<220> FEATURE:
<223> OTHER INFORMATION: albumin binding peptide

<400> SEQUENCE: 55

Asp Leu Cys Leu Arg Asp Trp Gly Cys Leu Trp
1               5                   10

<210> SEQ ID NO 56
<211> LENGTH: 11
<212> TYPE: PRT
<213> ORGANISM: Artificial Sequence
<220> FEATURE:
<223> OTHER INFORMATION: albumin binding peptide

<400> SEQUENCE: 56

Asp Ile Cys Leu Pro Arg Trp Gly Cys Leu Trp
1               5                   10

<210> SEQ ID NO 57
<211> LENGTH: 15
<212> TYPE: PRT
<213> ORGANISM: Artificial Sequence
<220> FEATURE:
<223> OTHER INFORMATION: albumin binding peptide

<400> SEQUENCE: 57

Met Glu Asp Ile Cys Leu Pro Arg Trp Gly Cys Leu Trp Gly Asp
1               5                   10                  15

<210> SEQ ID NO 58
<211> LENGTH: 20
<212> TYPE: PRT
<213> ORGANISM: Artificial Sequence
<220> FEATURE:
<223> OTHER INFORMATION: albumin binding peptide

<400> SEQUENCE: 58

Gln Arg Leu Met Glu Asp Ile Cys Leu Pro Arg Trp Gly Cys Leu Trp
1               5                   10                  15

Glu Asp Asp Glu
            20

<210> SEQ ID NO 59
<211> LENGTH: 20
<212> TYPE: PRT
<213> ORGANISM: Artificial Sequence
<220> FEATURE:
<223> OTHER INFORMATION: albumin binding peptide

```
<400> SEQUENCE: 59

Gln Gly Leu Ile Gly Asp Ile Cys Leu Pro Arg Trp Gly Cys Leu Trp
1               5                   10                  15

Gly Arg Ser Val
            20

<210> SEQ ID NO 60
<211> LENGTH: 21
<212> TYPE: PRT
<213> ORGANISM: Artificial Sequence
<220> FEATURE:
<223> OTHER INFORMATION: albumin binding peptide

<400> SEQUENCE: 60

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 61
<211> LENGTH: 15
<212> TYPE: PRT
<213> ORGANISM: Artificial Sequence
<220> FEATURE:
<223> OTHER INFORMATION: albumin binding peptide

<400> SEQUENCE: 61

Glu Asp Ile Cys Leu Pro Arg Trp Gly Cys Leu Trp Glu Asp Asp
1               5                   10                  15

<210> SEQ ID NO 62
<211> LENGTH: 18
<212> TYPE: PRT
<213> ORGANISM: Artificial Sequence
<220> FEATURE:
<223> OTHER INFORMATION: albumin binding peptide

<400> SEQUENCE: 62

Arg Leu Met Glu Asp Ile Cys Leu Pro Arg Trp Gly Cys Leu Trp Glu
1               5                   10                  15

Asp Asp

<210> SEQ ID NO 63
<211> LENGTH: 16
<212> TYPE: PRT
<213> ORGANISM: Artificial Sequence
<220> FEATURE:
<223> OTHER INFORMATION: albumin binding peptide

<400> SEQUENCE: 63

Met Glu Asp Ile Cys Leu Pro Arg Trp Gly Cys Leu Trp Glu Asp Asp
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: albumin binding peptide

<400> SEQUENCE: 64

Met Glu Asp Ile Cys Leu Pro Arg Trp Gly Cys Leu Trp Glu Asp
1               5                   10                  15
```

```
<210> SEQ ID NO 65
<211> LENGTH: 18
<212> TYPE: PRT
<213> ORGANISM: Artificial Sequence
<220> FEATURE:
<223> OTHER INFORMATION: albumin binding peptide

<400> SEQUENCE: 65

Arg Leu Met Glu Asp Ile Cys Leu Ala Arg Trp Gly Cys Leu Trp Glu
1               5                   10                  15

Asp Asp

<210> SEQ ID NO 66
<211> LENGTH: 20
<212> TYPE: PRT
<213> ORGANISM: Artificial Sequence
<220> FEATURE:
<223> OTHER INFORMATION: albumin binding peptide

<400> SEQUENCE: 66

Glu Val Arg Ser Phe Cys Thr Arg Trp Pro Ala Glu Lys Ser Cys Lys
1               5                   10                  15

Pro Leu Arg Gly
            20

<210> SEQ ID NO 67
<211> LENGTH: 20
<212> TYPE: PRT
<213> ORGANISM: Artificial Sequence
<220> FEATURE:
<223> OTHER INFORMATION: albumin binding peptide

<400> SEQUENCE: 67

Arg Ala Pro Glu Ser Phe Val Cys Tyr Trp Glu Thr Ile Cys Phe Glu
1               5                   10                  15

Arg Ser Glu Gln
            20

<210> SEQ ID NO 68
<211> LENGTH: 11
<212> TYPE: PRT
<213> ORGANISM: Artificial Sequence
<220> FEATURE:
<223> OTHER INFORMATION: albumin binding peptide

<400> SEQUENCE: 68

Glu Met Cys Tyr Phe Pro Gly Ile Cys Trp Met
1               5                   10

<210> SEQ ID NO 69
<211> LENGTH: 11
<212> TYPE: PRT
<213> ORGANISM: Artificial Sequence
<220> FEATURE:
<223> OTHER INFORMATION: rigid linkers

<400> SEQUENCE: 69

Gly Ala Pro Ala Pro Ala Ala Pro Ala Pro Ala
1               5                   10

<210> SEQ ID NO 70
<211> LENGTH: 4
<212> TYPE: PRT
<213> ORGANISM: Artificial Sequence
<220> FEATURE:
<223> OTHER INFORMATION: rigid linker
```

<400> SEQUENCE: 70

Pro Pro Pro Pro
1

<210> SEQ ID NO 71
<211> LENGTH: 113
<212> TYPE: PRT
<213> ORGANISM: Artificial Sequence
<220> FEATURE:
<223> OTHER INFORMATION: Rabbit Ab 4447 VL region

<400> SEQUENCE: 71

Ala Gln Val Leu Thr Gln Thr Pro Ser Pro Val Ser Ala Pro Val Gly
1               5                   10                  15

Gly Thr Val Thr Ile Asn Cys Gln Ala Ser Gln Ser Val Val Ser Gly
            20                  25                  30

Asn Tyr Leu Ala Trp Leu Gln Gln Lys Pro Gly Gln Pro Pro Lys Gln
        35                  40                  45

Leu Ile His Ser Ala Ser Thr Leu Ala Ser Gly Val Ser Ser Arg Phe
    50                  55                  60

Ser Gly Ser Gly Ser Gly Thr Gln Phe Thr Leu Thr Ile Ser Gly Val
65                  70                  75                  80

Gln Cys Glu Asp Ala Ala Thr Tyr Tyr Cys Leu Gly Glu Phe Ser Cys
                85                  90                  95

Ser Ser His Asp Cys Asn Ala Phe Gly Gly Gly Thr Glu Val Val Val
            100                 105                 110

Lys

<210> SEQ ID NO 72
<211> LENGTH: 339
<212> TYPE: DNA
<213> ORGANISM: Artificial Sequence
<220> FEATURE:
<223> OTHER INFORMATION: Rabbit Ab 4447 VL region

<400> SEQUENCE: 72
gcccaagtgc tgacccagac tccgtcccct gtgtctgcac ctgtgggagg cacagtcacc    60
atcaattgcc aggccagtca gagtgttgtt agtggcaatt acctagcctg gcttcagcag   120
aaaccagggc agcctcccaa gcaactgatc cattctgcat ccactctggc atctggggtc   180
tcatcgcggt tcagcggcag tggatctggg acacaattca ctctcaccat cagcggcgtg   240
cagtgtgaag atgctgccac ttactactgt ctaggcgaat ttagttgtag tagtcatgat   300
tgtaatgctt tcggcggagg gaccgaggtg gtggtcaaa                          339

<210> SEQ ID NO 73
<211> LENGTH: 123
<212> TYPE: PRT
<213> ORGANISM: Artificial Sequence
<220> FEATURE:
<223> OTHER INFORMATION: Rabbit Ab 4447 VH region

<400> SEQUENCE: 73

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Ala
            20                  25                  30

Val Ser Trp Val Arg Gln Ala Pro Gly Glu Gly Leu Glu Trp Ile Gly
        35                  40                  45

```
Ile Ile Tyr Ile Glu Thr Gly Thr Thr Trp Tyr Ala Asn Trp Ala Lys
 50                  55                  60
Gly Arg Phe Thr Ile Ser Lys Thr Ser Thr Val Asp Leu Thr Ile
 65                  70                  75                  80
Thr Ser Pro Ser Thr Glu Asp Thr Ala Thr Tyr Phe Cys Ala Arg Glu
                 85                  90                  95
Pro Tyr Glu Pro Tyr Asp Asp Ser Asn Ile Tyr Tyr Gly Met Asp Pro
                100                 105                 110
Trp Gly Pro Gly Thr Leu Val Thr Val Ser Ser
            115                 120
```

```
<210> SEQ ID NO 74
<211> LENGTH: 369
<212> TYPE: DNA
<213> ORGANISM: Artificial Sequence
<220> FEATURE:
<223> OTHER INFORMATION: Rabbit Ab 4447 VH region

<400> SEQUENCE: 74
cagtcgctgg aggagtccgg gggtcgcctg gtcacgcctg gacacccct gacactcacc     60 tgcaccgtct ctggattctc cctcagtaac tatgcagtaa gctgggtccg ccaggctcca   120
ggggagggac tggaatggat cgggatcatt tatattgaaa ctggtaccac atggtacgcg   180
aactgggcga aaggccgatt caccatctcc aaaacctcga ccacggtgga tctgacaatc   240
accagtccgt caaccgagga cacggccacc tatttctgtg ccagagaacc ttatgaacct   300
tatgatgata gtaatattta ctacggcatg gaccctggg gcccaggcac cctcgtcacc   360
gtctcgagt                                                           369
```

```
<210> SEQ ID NO 75
<211> LENGTH: 13
<212> TYPE: PRT
<213> ORGANISM: Artificial Sequence
<220> FEATURE:
<223> OTHER INFORMATION: CDRL1

<400> SEQUENCE: 75

Gln Ala Ser Gln Ser Val Val Ser Gly Asn Tyr Leu Ala
 1               5                  10
```

```
<210> SEQ ID NO 76
<211> LENGTH: 7
<212> TYPE: PRT
<213> ORGANISM: Artificial Sequence
<220> FEATURE:
<223> OTHER INFORMATION: CDRL2

<400> SEQUENCE: 76

Ser Ala Ser Thr Leu Ala Ser
 1               5
```

```
<210> SEQ ID NO 77
<211> LENGTH: 13
<212> TYPE: PRT
<213> ORGANISM: Artificial Sequence
<220> FEATURE:
<223> OTHER INFORMATION: CDRL3

<400> SEQUENCE: 77

Leu Gly Glu Phe Ser Cys Ser Ser His Asp Cys Asn Ala
 1               5                  10
```

<210> SEQ ID NO 78
<211> LENGTH: 10
<212> TYPE: PRT
<213> ORGANISM: Artificial Sequence
<220> FEATURE:
<223> OTHER INFORMATION: CDRH1

<400> SEQUENCE: 78

Gly Phe Ser Leu Ser Asn Tyr Ala Val Ser
1               5                   10

<210> SEQ ID NO 79
<211> LENGTH: 17
<212> TYPE: PRT
<213> ORGANISM: Artificial Sequence
<220> FEATURE:
<223> OTHER INFORMATION: CDRH2

<400> SEQUENCE: 79

Ile Ile Tyr Ile Glu Thr Gly Thr Thr Trp Tyr Ala Asn Trp Ala Lys
1               5                   10                  15

Gly

<210> SEQ ID NO 80
<211> LENGTH: 17
<212> TYPE: PRT
<213> ORGANISM: Artificial Sequence
<220> FEATURE:
<223> OTHER INFORMATION: CDRH3

<400> SEQUENCE: 80

Glu Pro Tyr Glu Pro Tyr Asp Asp Ser Asn Ile Tyr Tyr Gly Met Asp
1               5                   10                  15

Pro

<210> SEQ ID NO 81
<211> LENGTH: 111
<212> TYPE: PRT
<213> ORGANISM: Artificial Sequence
<220> FEATURE:
<223> OTHER INFORMATION: Rabbit Ab 4450 VL region

<400> SEQUENCE: 81

Ala Ile Asp Met Thr Gln Thr Pro Ser Pro Val Ser Ala Ala Val Gly
1               5                   10                  15

Gly Thr Val Thr Ile Asn Cys Gln Ser Ser Gln Ser Ile Tyr Asn Asn
            20                  25                  30

Asn Asp Leu Ala Trp Tyr Gln Gln Lys Pro Gly Gln Pro Pro Lys Leu
        35                  40                  45

Leu Ile Tyr Glu Ala Ser Lys Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Gly Gly Ser Gly
                85                  90                  95

Gly Asp Gly Ile Ala Phe Gly Gly Gly Thr Lys Val Val Val Glu
            100                 105                 110

<210> SEQ ID NO 82
<211> LENGTH: 333
<212> TYPE: DNA
<213> ORGANISM: Artificial Sequence
<220> FEATURE:
<223> OTHER INFORMATION: Rabbit Ab 4450 VL region

<400> SEQUENCE: 82

```
gccattgata tgacccagac tccatccccc gtgtctgcag ctgtgggagg cacagtcacc      60
atcaattgcc agtccagtca gagtatttat aataataatg acttagcctg gtatcagcag     120
aaaccagggc agcctcccaa gctcctgatc tacgaagcat ccaaactggc atctggggtc     180
ccatcgcggt tcaaaggcag tggatctggg acacagttca ctctcaccat cagtggcgtg     240
cagtgtgatg atgctgccac ttactactgt cagggcggtg gtagtggtgg tgatggcatt     300
gctttcggcg agggaccaa ggtggtcgtc gaa                                    333
```

<210> SEQ ID NO 83
<211> LENGTH: 117
<212> TYPE: PRT
<213> ORGANISM: Artificial Sequence
<220> FEATURE:
<223> OTHER INFORMATION: Rabbit Ab 4450 VH region

<400> SEQUENCE: 83

```
Gln Ser Val Glu Glu Ser Gly Gly Arg Leu Val Thr Pro Gly Ala Pro
1               5                   10                  15

Leu Thr Leu Thr Cys Thr Val Ser Gly Phe Ser Leu Asn Asn Tyr Val
            20                  25                  30

Met Val Trp Val Arg Gln Ala Pro Gly Lys Gly Leu Glu Trp Ile Gly
        35                  40                  45

Ile Ile Tyr Val Ser Gly Asn Ala Tyr Tyr Ala Ser Trp Ala Lys Gly
    50                  55                  60

Arg Phe Thr Ile Ser Arg Thr Ser Thr Val Asp Leu Lys Val Thr
65                  70                  75                  80

Ser Leu Thr Thr Glu Asp Thr Ala Thr Tyr Phe Cys Ala Arg Asp Ala
            85                  90                  95

Gly His Ser Asp Val Asp Val Leu Asp Ile Trp Gly Pro Gly Thr Leu
            100                 105                 110

Val Thr Val Ser Ser
        115
```

<210> SEQ ID NO 84
<211> LENGTH: 351
<212> TYPE: DNA
<213> ORGANISM: Artificial Sequence
<220> FEATURE:
<223> OTHER INFORMATION: Rabbit Ab 4450 VH region

<400> SEQUENCE: 84

```
cagtcggtgg aggagtccgg gggtcgcctg gtcacgcctg ggcacccct gacactcacc       60 tgcacagtct ctggattctc cctcaataac tatgtaatgg tctgggtccg ccaggctcca     120
gggaaggggc tggaatggat cggaatcatt tatgttagtg gtaatgcata ctacgcgagc     180
tgggcaaaag gccgattcac catctccaga acctcgacca cggtggatct gaaagtgacc     240
agtctgacaa ccgaggacac ggccacctat ttctgtgcca gagatgctgg tcatagtgat     300
gtcgatgttt tggatatttg gggcccgggc accctcgtca ccgtctcgag t              351
```

<210> SEQ ID NO 85
<211> LENGTH: 13
<212> TYPE: PRT
<213> ORGANISM: Artificial Sequence
<220> FEATURE:

<223> OTHER INFORMATION: CDRL1

<400> SEQUENCE: 85

Gln Ser Ser Gln Ser Ile Tyr Asn Asn Asn Asp Leu Ala
1               5                   10

<210> SEQ ID NO 86
<211> LENGTH: 7
<212> TYPE: PRT
<213> ORGANISM: Artificial Sequence
<220> FEATURE:
<223> OTHER INFORMATION: CDRL2

<400> SEQUENCE: 86

Glu Ala Ser Lys Leu Ala Ser
1               5

<210> SEQ ID NO 87
<211> LENGTH: 11
<212> TYPE: PRT
<213> ORGANISM: Artificial Sequence
<220> FEATURE:
<223> OTHER INFORMATION: CDRL3

<400> SEQUENCE: 87

Gln Gly Gly Gly Ser Gly Gly Asp Gly Ile Ala
1               5                   10

<210> SEQ ID NO 88
<211> LENGTH: 10
<212> TYPE: PRT
<213> ORGANISM: Artificial Sequence
<220> FEATURE:
<223> OTHER INFORMATION: CDRH1

<400> SEQUENCE: 88

Gly Phe Ser Leu Asn Asn Tyr Val Met Val
1               5                   10

<210> SEQ ID NO 89
<211> LENGTH: 16
<212> TYPE: PRT
<213> ORGANISM: Artificial Sequence
<220> FEATURE:
<223> OTHER INFORMATION: CDRH2

<400> SEQUENCE: 89

Ile Ile Tyr Val Ser Gly Asn Ala Tyr Tyr Ala Ser Trp Ala Lys Gly
1               5                   10                  15

<210> SEQ ID NO 90
<211> LENGTH: 12
<212> TYPE: PRT
<213> ORGANISM: Artificial Sequence
<220> FEATURE:
<223> OTHER INFORMATION: CDRH3

<400> SEQUENCE: 90

Asp Ala Gly His Ser Asp Val Asp Val Leu Asp Ile
1               5                   10

<210> SEQ ID NO 91
<211> LENGTH: 111
<212> TYPE: PRT
<213> ORGANISM: Artificial Sequence
<220> FEATURE:
<223> OTHER INFORMATION: Rabbit Ab 4122 VL region

<400> SEQUENCE: 91

Asp Ile Val Met Thr Gln Thr Pro Ala Ser Val Ser Glu Pro Val Gly
1               5                   10                  15

Gly Thr Val Thr Ile Met Cys Gln Ala Ser Gln Ser Ile Ser Asn Trp
            20                  25                  30

Leu Ala Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Tyr Tyr Asp Ser Gly Ser
                85                  90                  95

Asn Val Phe Phe Ala Phe Gly Gly Gly Thr Lys Val Val Val Glu
            100                 105                 110

<210> SEQ ID NO 92
<211> LENGTH: 333
<212> TYPE: DNA
<213> ORGANISM: Artificial Sequence
<220> FEATURE:
<223> OTHER INFORMATION: Rabbit Ab 4122 VL region

<400> SEQUENCE: 92
gacattgtga tgacccagac tccagcctcc gtgtctgaac ctgtgggagg cacagtcacc      60
atcatgtgcc aggccagtca gagcattagc aattggttag cctggtatca acagaaacca    120
gggcagcctc ccaagctcct gatctaccag gcatccaaac tggcatctgg ggtcccatcg    180
cggttcaaag gcagtggatc tgggacagag tacactctca ccatcagcga cctggagtgt    240
gccgatgctg ccacttacta ctgtcaaagc tattatgata gtggtagtaa tgttttttt     300
gctttcggcg agggaccaa ggtggtggtc gaa                                  333

<210> SEQ ID NO 93
<211> LENGTH: 119
<212> TYPE: PRT
<213> ORGANISM: Artificial Sequence
<220> FEATURE:
<223> OTHER INFORMATION: Rabbit Ab 4122 VH region

<400> SEQUENCE: 93

Leu Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ala Gly Tyr
            20                  25                  30

Trp Ile Cys Trp Val Arg Gln Ala Pro Gly Lys Gly Leu Glu Trp Ile
        35                  40                  45

Ala Cys Thr Tyr Ala Gly Arg Ser Gly Ser Thr Tyr Tyr Ala Asn Trp
    50                  55                  60

Val Asn Gly Arg Phe Thr Ile Pro Lys Thr Ser Ser Thr Thr Val Thr
65                  70                  75                  80

Leu Gln Met Thr Ser Leu Ser Gly Ala Asp Thr Ala Ser Tyr Phe Cys
                85                  90                  95

Ala Arg Gly Asn Ala Gly Val Ala Val Gly Ala Leu Trp Gly Pro Gly
            100                 105                 110

Thr Leu Val Thr Val Ser Ser
            115

<210> SEQ ID NO 94
<211> LENGTH: 357
<212> TYPE: DNA
<213> ORGANISM: Artificial Sequence
<220> FEATURE:
<223> OTHER INFORMATION: Rabbit Ab 4122 VH region

<400> SEQUENCE: 94

```
ctgtcgttgg aggagtccgg gggagacctg gtcaagcctg gggcatccct gacactcacc      60
tgcacagcct ctggattctc cttcagtgcc ggctattgga tatgttgggt ccgccaggct     120
ccagggaagg ggctggagtg gatcgcatgc acttatgctg gtcgtagtgg tagcacttac     180
tacgcgaact gggtgaatgg ccgattcacc atccccaaaa cctcgtcgac cacggtgact     240
ctgcaaatga ccagtctgtc aggcgcggac acggccagct atttctgtgc gagaggtaat     300
gctggtgttg ctgttggtgc cttgtggggc ccaggcaccc tggtcaccgt ctcgagt       357
```

<210> SEQ ID NO 95
<211> LENGTH: 11
<212> TYPE: PRT
<213> ORGANISM: Artificial Sequence
<220> FEATURE:
<223> OTHER INFORMATION: CDRL1

<400> SEQUENCE: 95

Gln Ala Ser Gln Ser Ile Ser Asn Trp Leu Ala
1               5                   10

<210> SEQ ID NO 96
<211> LENGTH: 7
<212> TYPE: PRT
<213> ORGANISM: Artificial Sequence
<220> FEATURE:
<223> OTHER INFORMATION: CDRL2

<400> SEQUENCE: 96

Gln Ala Ser Lys Leu Ala Ser
1               5

<210> SEQ ID NO 97
<211> LENGTH: 13
<212> TYPE: PRT
<213> ORGANISM: Artificial Sequence
<220> FEATURE:
<223> OTHER INFORMATION: CDRL3

<400> SEQUENCE: 97

Gln Ser Tyr Tyr Asp Ser Gly Ser Asn Val Phe Phe Ala
1               5                   10

<210> SEQ ID NO 98
<211> LENGTH: 11
<212> TYPE: PRT
<213> ORGANISM: Artificial Sequence
<220> FEATURE:
<223> OTHER INFORMATION: CDRH1

<400> SEQUENCE: 98

Gly Phe Ser Phe Ser Ala Gly Tyr Trp Ile Cys
1               5                   10

<210> SEQ ID NO 99
<211> LENGTH: 18
<212> TYPE: PRT

```
<213> ORGANISM: Artificial Sequence
<220> FEATURE:
<223> OTHER INFORMATION: CDRH2

<400> SEQUENCE: 99

Cys Thr Tyr Ala Gly Arg Ser Gly Ser Thr Tyr Tyr Ala Asn Trp Val
1               5                   10                  15

Asn Gly

<210> SEQ ID NO 100
<211> LENGTH: 10
<212> TYPE: PRT
<213> ORGANISM: Artificial Sequence
<220> FEATURE:
<223> OTHER INFORMATION: CDRH3

<400> SEQUENCE: 100

Gly Asn Ala Gly Val Ala Val Gly Ala Leu
1               5                   10

<210> SEQ ID NO 101
<211> LENGTH: 111
<212> TYPE: PRT
<213> ORGANISM: Artificial Sequence
<220> FEATURE:
<223> OTHER INFORMATION: Rabbit Ab 4129 VL region

<400> SEQUENCE: 101

Asp Ile Val Met Thr Gln Thr Pro Ala Ser Val Glu Ala Ala Val Gly
1               5                   10                  15

Gly Thr Val Thr Ile Asn Cys Gln Ala Ser Gln Ser Ile Ser Ser Trp
            20                  25                  30

Leu Ser Trp Tyr Gln Gln Lys Pro Gly Gln Pro Pro Lys Leu Leu Ile
        35                  40                  45

Tyr Gly Ala Ser Asn Leu Ala Ser Gly Val Pro Ser Arg Phe Ser Gly
    50                  55                  60

Ser Gly Ser Gly Thr Gln Phe Ser Leu Thr Ile Ser Asp Leu Glu Cys
65                  70                  75                  80

Ala Asp Ala Ala Thr Tyr Tyr Cys Gln Ser Tyr Tyr Asp Ser Gly Ser
                85                  90                  95

Ser Val Phe Phe Asn Phe Gly Gly Gly Thr Lys Val Val Val Lys
                100                 105                 110

<210> SEQ ID NO 102
<211> LENGTH: 333
<212> TYPE: DNA
<213> ORGANISM: Artificial Sequence
<220> FEATURE:
<223> OTHER INFORMATION: Rabbit Ab 4129 VL region

<400> SEQUENCE: 102
gacattgtga tgacccagac tccagcctcc gtggaggcag ctgtgggagg cacagtcacc     60
atcaattgcc aagccagtca gagcattagc agttggttat cctggtatca gcagaaacca    120
gggcagcctc ccaagctcct gatctatggt gcatccaatc tggcatctgg ggtcccatca    180
cggttcagcg gcagtggatc tgggacacag ttcagtctca ccatcagcga cctggagtgt    240
gccgatgctg ccacttacta ctgtcaaagc tattatgata gtggtagtag tgttttttt     300 aatttcggcg gagggaccaa ggtggtcgtc aaa                                 333

<210> SEQ ID NO 103
```

```
<211> LENGTH: 119
<212> TYPE: PRT
<213> ORGANISM: Artificial Sequence
<220> FEATURE:
<223> OTHER INFORMATION: Rabbit Ab 4129 VH region

<400> SEQUENCE: 103

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ala Gly Tyr
            20                  25                  30

Trp Ile Cys Trp Val Arg Gln Ala Pro Gly Lys Gly Leu Glu Trp Ile
        35                  40                  45

Ala Cys Ile Tyr Ala Gly Ser Ser Gly Ser Thr Tyr Tyr Ala Ser Trp
    50                  55                  60

Ala Lys Gly Arg Phe Thr Ile Pro Lys Thr Ser Ser Thr Thr Val Thr
65                  70                  75                  80

Leu Gln Met Thr Ser Leu Thr Gly Ala Asp Thr Ala Thr Tyr Phe Cys
                85                  90                  95

Ala Arg Gly Asn Ala Gly Val Ala Val Gly Ala Leu Trp Gly Pro Gly
            100                 105                 110

Thr Leu Val Thr Val Ser Ser
        115

<210> SEQ ID NO 104
<211> LENGTH: 357
<212> TYPE: DNA
<213> ORGANISM: Artificial Sequence
<220> FEATURE:
<223> OTHER INFORMATION: Rabbit Ab 4129 VH region

<400> SEQUENCE: 104
cagtcgttgg aggagtccgg gggagacctg gttaagcctg ggcatccct gacactcacc      60
tgcacagcct ctggattctc cttcagtgcc ggctattgga tatgttgggt ccgccaggct    120
ccagggaagg ggctggagtg gatcgcatgc atttatgctg gtagtagtgg tagcacttac    180
tacgcgagct gggcgaaagg ccgattcacc atccccaaaa cctcgtcgac cacggtgact    240
ctgcaaatga ccagtctgac aggcgcggac acggccacct atttctgtgc gagaggtaat    300
gctggtgttg ctgttggtgc cttgtggggc ccaggcaccc tcgtcaccgt ctcgagt       357

<210> SEQ ID NO 105
<211> LENGTH: 11
<212> TYPE: PRT
<213> ORGANISM: Artificial Sequence
<220> FEATURE:
<223> OTHER INFORMATION: CDRL1

<400> SEQUENCE: 105

Gln Ala Ser Gln Ser Ile Ser Ser Trp Leu Ser
1               5                   10

<210> SEQ ID NO 106
<211> LENGTH: 7
<212> TYPE: PRT
<213> ORGANISM: Artificial Sequence
<220> FEATURE:
<223> OTHER INFORMATION: CDRL2

<400> SEQUENCE: 106

Gly Ala Ser Asn Leu Ala Ser
1               5
```

<210> SEQ ID NO 107
<211> LENGTH: 13
<212> TYPE: PRT
<213> ORGANISM: Artificial Sequence
<220> FEATURE:
<223> OTHER INFORMATION: CDRL3

<400> SEQUENCE: 107

Gln Ser Tyr Tyr Asp Ser Gly Ser Ser Val Phe Phe Asn
1               5                   10

<210> SEQ ID NO 108
<211> LENGTH: 11
<212> TYPE: PRT
<213> ORGANISM: Artificial Sequence
<220> FEATURE:
<223> OTHER INFORMATION: CDRH1

<400> SEQUENCE: 108

Gly Phe Ser Phe Ser Ala Gly Tyr Trp Ile Cys
1               5                   10

<210> SEQ ID NO 109
<211> LENGTH: 18
<212> TYPE: PRT
<213> ORGANISM: Artificial Sequence
<220> FEATURE:
<223> OTHER INFORMATION: CDRH2

<400> SEQUENCE: 109

Cys Ile Tyr Ala Gly Ser Ser Gly Ser Thr Tyr Tyr Ala Ser Trp Ala
1               5                   10                  15

Lys Gly

<210> SEQ ID NO 110
<211> LENGTH: 10
<212> TYPE: PRT
<213> ORGANISM: Artificial Sequence
<220> FEATURE:
<223> OTHER INFORMATION: CDRH3

<400> SEQUENCE: 110

Gly Asn Ala Gly Val Ala Val Gly Ala Leu
1               5                   10

<210> SEQ ID NO 111
<211> LENGTH: 107
<212> TYPE: PRT
<213> ORGANISM: Artificial Sequence
<220> FEATURE:
<223> OTHER INFORMATION: Rabbit Ab 4131 VL region

<400> SEQUENCE: 111

Asp Ile Val Met Thr Gln Thr Pro Ala Ser Val Ser Glu Pro Val Gly
1               5                   10                  15

Gly Ser Val Thr Ile Lys Cys Gln Ala Ser Gln Ser Phe Tyr Asn Leu
                20                  25                  30

Leu Ala Trp Tyr Gln Gln Lys Pro Gly Gln Pro Pro Lys Leu Leu Ile
            35                  40                  45

Tyr Asp Ala Ser Asp Leu Ala Ser Gly Val Pro Ser Arg Phe Lys Gly
        50                  55                  60

Ser Gly Ser Gly Thr Asp Phe Thr Leu Thr Ile Ser Asp Leu Glu Cys
65                  70                  75                  80

Ala Asp Ala Ala Ala Tyr Tyr Cys Gln Ser Ala Asp Gly Ser Ser Tyr
            85                  90                  95

Ala Phe Gly Gly Gly Thr Glu Val Val Val Lys
            100                 105

<210> SEQ ID NO 112
<211> LENGTH: 321
<212> TYPE: DNA
<213> ORGANISM: Artificial Sequence
<220> FEATURE:
<223> OTHER INFORMATION: Rabbit Ab 4131 VL region

<400> SEQUENCE: 112
gacattgtga tgacccagac tccagcctcc gtgtctgaac ctgtgggagg ctcagtcacc    60
atcaagtgcc aggccagtca gagcttttac aacctcttag cctggtatca gcagaaacca   120
gggcagcctc ccaaactcct gatctatgat gcatccgatc tggcatctgg ggtcccatcg   180
cggttcaaag cagtggatc tgggactgat ttcactctca ccatcagcga cctggagtgt    240
gccgatgctg ccgcttacta ctgtcaaagt gctgatggta gtagttacgc tttcggcgga   300
gggaccgagg tggtcgtcaa a                                              321

<210> SEQ ID NO 113
<211> LENGTH: 120
<212> TYPE: PRT
<213> ORGANISM: Artificial Sequence
<220> FEATURE:
<223> OTHER INFORMATION: Rabbit Ab 4131 VH region

<400> SEQUENCE: 113

Gln Glu Gln Leu Glu Glu Ser Gly Gly Gly Leu Val Lys Pro Glu Gly
1               5                   10                  15

Ser Leu Thr Leu Thr Cys Thr Ala Ser Gly Val Ser Phe Ser Ser Ser
            20                  25                  30

Tyr Trp Ile Tyr Trp Val Arg Gln Ala Pro Gly Lys Gly Leu Glu Trp
        35                  40                  45

Ile Ala Cys Ile Tyr Thr Gly Ser Ser Gly Ser Thr Tyr Tyr Ala Ser
    50                  55                  60

Trp Ala Lys Gly Arg Phe Thr Val Ser Glu Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Ala Ser Ala Trp Thr Tyr Gly Met Asp Leu Trp Gly Pro
            100                 105                 110

Gly Thr Leu Val Thr Val Ser Ser
        115                 120

<210> SEQ ID NO 114
<211> LENGTH: 360
<212> TYPE: DNA
<213> ORGANISM: Artificial Sequence
<220> FEATURE:
<223> OTHER INFORMATION: Rabbit Ab 4131 VH region

<400> SEQUENCE: 114
caggagcaat ggaggagtc cggggagggc ctggtcaagc ctgagggatc cctgacactc     60
acctgcacag cctctggagt ctccttcagt agcagctatt ggatatactg ggtccgccag   120
gctccaggga aggggctgga gtggatcgca tgcatttata ctggtagtag tggtagcact   180

```
tactacgcga gctgggcgaa aggccgattc accgtctccg aaacctcgtc gaccacggtg    240
actctgcaaa tgaccagtct gacagccgcg gacacggcca cctatttctg tgcgagagca    300
agcgcttgga cctacggcat ggacctctgg ggcccgggca ccctcgtcac cgtctcgagt    360
```

<210> SEQ ID NO 115
<211> LENGTH: 11
<212> TYPE: PRT
<213> ORGANISM: Artificial Sequence
<220> FEATURE:
<223> OTHER INFORMATION: CDRL1

<400> SEQUENCE: 115

Gln Ala Ser Gln Ser Phe Tyr Asn Leu Leu Ala
1               5                   10

<210> SEQ ID NO 116
<211> LENGTH: 7
<212> TYPE: PRT
<213> ORGANISM: Artificial Sequence
<220> FEATURE:
<223> OTHER INFORMATION: CDRL2

<400> SEQUENCE: 116

Asp Ala Ser Asp Leu Ala Ser
1               5

<210> SEQ ID NO 117
<211> LENGTH: 9
<212> TYPE: PRT
<213> ORGANISM: Artificial Sequence
<220> FEATURE:
<223> OTHER INFORMATION: CDRL3

<400> SEQUENCE: 117

Gln Ser Ala Asp Gly Ser Ser Tyr Ala
1               5

<210> SEQ ID NO 118
<211> LENGTH: 11
<212> TYPE: PRT
<213> ORGANISM: Artificial Sequence
<220> FEATURE:
<223> OTHER INFORMATION: CDRH1

<400> SEQUENCE: 118

Gly Val Ser Phe Ser Ser Ser Tyr Trp Ile Tyr
1               5                   10

<210> SEQ ID NO 119
<211> LENGTH: 18
<212> TYPE: PRT
<213> ORGANISM: Artificial Sequence
<220> FEATURE:
<223> OTHER INFORMATION: CDRH2

<400> SEQUENCE: 119

Cys Ile Tyr Thr Gly Ser Ser Gly Ser Thr Tyr Tyr Ala Ser Trp Ala
1               5                   10                  15

Lys Gly

<210> SEQ ID NO 120
<211> LENGTH: 10
<212> TYPE: PRT
<213> ORGANISM: Artificial Sequence
<220> FEATURE:

<223> OTHER INFORMATION: CDRH3

<400> SEQUENCE: 120

Ala Ser Ala Trp Thr Tyr Gly Met Asp Leu
1               5                   10

<210> SEQ ID NO 121
<211> LENGTH: 112
<212> TYPE: PRT
<213> ORGANISM: Artificial Sequence
<220> FEATURE:
<223> OTHER INFORMATION: Rabbit Ab 4133 VL region

<400> SEQUENCE: 121

Ala Gln Val Leu Thr Gln Thr Pro Ser Pro Val Ser Ala Val Val Gly
1               5                   10                  15

Gly Thr Val Ser Ile Ser Cys Gln Ala Ser Gln Ser Val Tyr Asn Asn
                20                  25                  30

Asn Asn Leu Ser Trp Tyr Gln Gln Lys Pro Gly Gln Pro Pro Lys Leu
            35                  40                  45

Leu Ile Tyr Asp Ala Ser Lys Leu Ala Ser Gly Val Pro Ser Arg Phe
        50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Tyr Ser
                85                  90                  95

Ser Gly Trp Tyr Phe Ala Phe Gly Gly Gly Thr Lys Val Val Val Lys
            100                 105                 110

<210> SEQ ID NO 122
<211> LENGTH: 336
<212> TYPE: DNA
<213> ORGANISM: Artificial Sequence
<220> FEATURE:
<223> OTHER INFORMATION: Rabbit Ab 4133 VL region

<400> SEQUENCE: 122
gcgcaagtgc tgacccagac tccatctccc gtgtctgcag ttgtgggagg cacagtcagc     60
atcagttgcc aggccagtca gagtgtttat aataacaaca acttatcctg gtatcagcag    120
aaaccagggc agcctcccaa gctcttgatc tacgatgcat ccaaattggc atctggggtc    180
ccatcccggt tcaaaggcag tggatctggg acacagttca ctctcaccat cagcggcgtg    240
cagtgtgacg atgctgccac ttactactgt ctaggcggtt attatagtag tggttggtat    300
tttgctttcg gcggagggac caaggtggtg gtcaaa                              336

<210> SEQ ID NO 123
<211> LENGTH: 122
<212> TYPE: PRT
<213> ORGANISM: Artificial Sequence
<220> FEATURE:
<223> OTHER INFORMATION: Rabbit Ab 4133 VH region

<400> SEQUENCE: 123

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Gly Asn
                20                  25                  30

Tyr Tyr Met Cys Trp Val Arg Gln Ala Pro Gly Lys Gly Leu Glu Trp
            35                  40                  45

```
Ile Gly Cys Leu Tyr Thr Gly Ser Ser Gly Ser Thr Tyr Tyr Ala Ser
 50                  55                  60

Trp Ala Lys Gly Arg Phe Thr Ile Ser Lys Thr Ser Ser Thr Thr Val
 65                  70                  75                  80

Thr Leu Gln Met Thr Ser Leu Thr Ala Ala Asp Thr Ala Thr Tyr Phe
                 85                  90                  95

Cys Ala Arg Asp Leu Gly Tyr Glu Ile Asp Gly Tyr Gly Gly Leu Trp
             100                 105                 110

Gly Gln Gly Thr Leu Val Thr Val Ser Ser
             115                 120

<210> SEQ ID NO 124
<211> LENGTH: 366
<212> TYPE: DNA
<213> ORGANISM: Artificial Sequence
<220> FEATURE:
<223> OTHER INFORMATION: Rabbit Ab 4133 VH region

<400> SEQUENCE: 124
caggagcagc tggtggagtc cggggagggc ctggtccagc ctgagggatc cctgacacta    60
acctgcacag cttctggatt ctccttcagt ggcaactact acatgtgctg ggtccgccag   120
gctccaggga aggggctgga gtggatcgga tgcctttata ctggtagtag tggtagcaca   180
tattacgcga gctgggcgaa aggccgattc accatctcca aaacctcgtc gaccacggtg   240
actctgcaaa tgaccagtct gacagccgcg gacacggcca cctatttctg tgcgagagat   300
ctaggttatg aaattgatgg ttatgggggc ttgtggggcc agggcaccct cgtcaccgtc   360
tcgagt                                                              366

<210> SEQ ID NO 125
<211> LENGTH: 13
<212> TYPE: PRT
<213> ORGANISM: Artificial Sequence
<220> FEATURE:
<223> OTHER INFORMATION: CDRL1

<400> SEQUENCE: 125

Gln Ala Ser Gln Ser Val Tyr Asn Asn Asn Asn Leu Ser
 1                5                  10

<210> SEQ ID NO 126
<211> LENGTH: 7
<212> TYPE: PRT
<213> ORGANISM: Artificial Sequence
<220> FEATURE:
<223> OTHER INFORMATION: CDRL2

<400> SEQUENCE: 126

Asp Ala Ser Lys Leu Ala Ser
 1                5

<210> SEQ ID NO 127
<211> LENGTH: 12
<212> TYPE: PRT
<213> ORGANISM: Artificial Sequence
<220> FEATURE:
<223> OTHER INFORMATION: CDRL3

<400> SEQUENCE: 127

Leu Gly Gly Tyr Tyr Ser Ser Gly Trp Tyr Phe Ala
 1                5                  10
```

```
<210> SEQ ID NO 128
<211> LENGTH: 11
<212> TYPE: PRT
<213> ORGANISM: Artificial Sequence
<220> FEATURE:
<223> OTHER INFORMATION: CDRH1

<400> SEQUENCE: 128

Gly Phe Ser Phe Ser Gly Asn Tyr Tyr Met Cys
1               5                   10

<210> SEQ ID NO 129
<211> LENGTH: 18
<212> TYPE: PRT
<213> ORGANISM: Artificial Sequence
<220> FEATURE:
<223> OTHER INFORMATION: CDRH2

<400> SEQUENCE: 129

Cys Leu Tyr Thr Gly Ser Ser Gly Ser Thr Tyr Tyr Ala Ser Trp Ala
1               5                   10                  15

Lys Gly

<210> SEQ ID NO 130
<211> LENGTH: 12
<212> TYPE: PRT
<213> ORGANISM: Artificial Sequence
<220> FEATURE:
<223> OTHER INFORMATION: CDRH3

<400> SEQUENCE: 130

Asp Leu Gly Tyr Glu Ile Asp Gly Tyr Gly Gly Leu
1               5                   10

<210> SEQ ID NO 131
<211> LENGTH: 10
<212> TYPE: PRT
<213> ORGANISM: Artificial Sequence
<220> FEATURE:
<223> OTHER INFORMATION: CDRH1 dAbH1

<400> SEQUENCE: 131

Gly Ile Asp Leu Ser Asn Tyr Ala Ile Asn
1               5                   10

<210> SEQ ID NO 132
<211> LENGTH: 16
<212> TYPE: PRT
<213> ORGANISM: Artificial Sequence
<220> FEATURE:
<223> OTHER INFORMATION: CDRH2 dAbH1

<400> SEQUENCE: 132

Ile Ile Trp Ala Ser Gly Thr Thr Phe Tyr Ala Thr Trp Ala Lys Gly
1               5                   10                  15

<210> SEQ ID NO 133
<211> LENGTH: 13
<212> TYPE: PRT
<213> ORGANISM: Artificial Sequence
<220> FEATURE:
<223> OTHER INFORMATION: CDRH3 dAbH1

<400> SEQUENCE: 133

Thr Val Pro Gly Tyr Ser Thr Ala Pro Tyr Phe Asp Leu
1               5                   10
```

```
<210> SEQ ID NO 134
<211> LENGTH: 12
<212> TYPE: PRT
<213> ORGANISM: Artificial Sequence
<220> FEATURE:
<223> OTHER INFORMATION: CDRL1 dAbL1

<400> SEQUENCE: 134

Gln Ser Ser Pro Ser Val Trp Ser Asn Phe Leu Ser
1               5                   10

<210> SEQ ID NO 135
<211> LENGTH: 7
<212> TYPE: PRT
<213> ORGANISM: Artificial Sequence
<220> FEATURE:
<223> OTHER INFORMATION: CDRL2 dAbL1

<400> SEQUENCE: 135

Glu Ala Ser Lys Leu Thr Ser
1               5

<210> SEQ ID NO 136
<211> LENGTH: 11
<212> TYPE: PRT
<213> ORGANISM: Artificial Sequence
<220> FEATURE:
<223> OTHER INFORMATION: CDRL3 dAbL1

<400> SEQUENCE: 136

Gly Gly Gly Tyr Ser Ser Ile Ser Asp Thr Thr
1               5                   10

<210> SEQ ID NO 137
<211> LENGTH: 121
<212> TYPE: PRT
<213> ORGANISM: Artificial Sequence
<220> FEATURE:
<223> OTHER INFORMATION: Heavy chain variable domain of anti-albumin
      antibody (no ds)

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 138
<211> LENGTH: 121
<212> TYPE: PRT
<213> ORGANISM: Artificial Sequence
```

<220> FEATURE:
<223> OTHER INFORMATION: Heavy chain variable domain of anti-albumin antibody (ds)

<400> SEQUENCE: 138

```
Glu Val Gln Leu Leu Glu Ser Gly Gly Gly Leu Val Gln Pro Gly Gly
1               5                   10                  15
Ser Leu Arg Leu Ser Cys Ala Val Ser Gly Ile Asp Leu Ser Asn Tyr
            20                  25                  30
Ala Ile Asn Trp Val Arg Gln Ala Pro Gly Lys Cys Leu Glu Trp Ile
        35                  40                  45
Gly Ile Ile Trp Ala Ser Gly Thr Thr Phe Tyr Ala Thr Trp Ala Lys
    50                  55                  60
Gly Arg Phe Thr Ile Ser Arg Asp Asn Ser Lys Asn Thr Val Tyr Leu
65                  70                  75                  80
Gln Met Asn Ser Leu Arg Ala Glu Asp Thr Ala Val Tyr Tyr Cys Ala
                85                  90                  95
Arg Thr Val Pro Gly Tyr Ser Thr Ala Pro Tyr Phe Asp Leu Trp Gly
            100                 105                 110
Gln Gly Thr Leu Val Thr Val Ser Ser
        115                 120
```

<210> SEQ ID NO 139
<211> LENGTH: 112
<212> TYPE: PRT
<213> ORGANISM: Artificial Sequence
<220> FEATURE:
<223> OTHER INFORMATION: Light chain variable domain of anti-albumin antibody (no ds)

<400> SEQUENCE: 139

```
Asp Ile Gln Met Thr Gln Ser Pro Ser Ser Val Ser Ala Ser Val Gly
1               5                   10                  15
Asp Arg Val Thr Ile Thr Cys Gln Ser Ser Pro Ser Val Trp Ser Asn
            20                  25                  30
Phe Leu Ser Trp Tyr Gln Gln Lys Pro Gly Lys Ala Pro Lys Leu Leu
        35                  40                  45
Ile Tyr Glu Ala Ser Lys Leu Thr Ser Gly Val Pro Ser Arg Phe Ser
    50                  55                  60
Gly Ser Gly Ser Gly Thr Asp Phe Thr Leu Thr Ile Ser Ser Leu Gln
65                  70                  75                  80
Pro Glu Asp Phe Ala Thr Tyr Tyr Cys Gly Gly Tyr Ser Ser Ile
                85                  90                  95
Ser Asp Thr Thr Phe Gly Gly Gly Thr Lys Val Glu Ile Lys Arg Thr
            100                 105                 110
```

<210> SEQ ID NO 140
<211> LENGTH: 112
<212> TYPE: PRT
<213> ORGANISM: Artificial Sequence
<220> FEATURE:
<223> OTHER INFORMATION: Light chain variable domain of anti-albumin antibody (ds)

<400> SEQUENCE: 140

```
Asp Ile Gln Met Thr Gln Ser Pro Ser Ser Val Ser Ala Ser Val Gly
1               5                   10                  15
Asp Arg Val Thr Ile Thr Cys Gln Ser Ser Pro Ser Val Trp Ser Asn
            20                  25                  30
```

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Cys Gly Thr Tyr Val Glu Ile Lys Arg Thr
                100                 105                 110

<210> SEQ ID NO 141
<211> LENGTH: 226
<212> TYPE: PRT
<213> ORGANISM: Artificial Sequence
<220> FEATURE:
<223> OTHER INFORMATION: Human CD79a

<400> SEQUENCE: 141

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
                20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Asn Ala Asn Val
50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
                100                 105                 110

Glu Ser Tyr Gln Gln Ser Cys Gly Thr Tyr Leu Arg Val Arg Gln Pro
                115                 120                 125

Pro Pro Arg Pro Phe Leu Asp Met Gly Glu Gly Thr Lys Asn Arg Ile
        130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
                180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
        210                 215                 220

Lys Pro
225

<210> SEQ ID NO 142
<211> LENGTH: 229
<212> TYPE: PRT
<213> ORGANISM: Artificial Sequence
<220> FEATURE:
<223> OTHER INFORMATION: Human CD79b

<400> SEQUENCE: 142

Met Ala Arg Leu Ala Leu Ser Pro Val Pro Ser His Trp Met Val Ala
1               5                   10                  15

Leu Leu Leu Leu Leu Ser Ala Glu Pro Val Pro Ala Ala Arg Ser Glu
                20                  25                  30

Asp Arg Tyr Arg Asn Pro Lys Gly Ser Ala Cys Ser Arg Ile Trp Gln
            35                  40                  45

Ser Pro Arg Phe Ile Ala Arg Lys Arg Gly Phe Thr Val Lys Met His
    50                  55                  60

Cys Tyr Met Asn Ser Ala Ser Gly Asn Val Ser Trp Leu Trp Lys Gln
65                  70                  75                  80

Glu Met Asp Glu Asn Pro Gln Gln Leu Lys Leu Glu Lys Gly Arg Met
                85                  90                  95

Glu Glu Ser Gln Asn Glu Ser Leu Ala Thr Leu Thr Ile Gln Gly Ile
                100                 105                 110

Arg Phe Glu Asp Asn Gly Ile Tyr Phe Cys Gln Gln Lys Cys Asn Asn
            115                 120                 125

Thr Ser Glu Val Tyr Gln Gly Cys Gly Thr Glu Leu Arg Val Met Gly
    130                 135                 140

Phe Ser Thr Leu Ala Gln Leu Lys Gln Arg Asn Thr Leu Lys Asp Gly
145                 150                 155                 160

Ile Ile Met Ile Gln Thr Leu Leu Ile Ile Leu Phe Ile Ile Val Pro
                165                 170                 175

Ile Phe Leu Leu Leu Asp Lys Asp Asp Ser Lys Ala Gly Met Glu Glu
                180                 185                 190

Asp His Thr Tyr Glu Gly Leu Asp Ile Asp Gln Thr Ala Thr Tyr Glu
            195                 200                 205

Asp Ile Val Thr Leu Arg Thr Gly Glu Val Lys Trp Ser Val Gly Glu
    210                 215                 220

His Pro Gly Gln Glu
225

<210> SEQ ID NO 143
<211> LENGTH: 1304
<212> TYPE: PRT
<213> ORGANISM: Artificial Sequence
<220> FEATURE:
<223> OTHER INFORMATION: Human CD45

<400> SEQUENCE: 143

Met Tyr Leu Trp Leu Lys Leu Leu Ala Phe Gly Phe Ala Phe Leu Asp
1               5                   10                  15

Thr Glu Val Phe Val Thr Gly Gln Ser Pro Thr Pro Ser Pro Thr Gly
                20                  25                  30

Leu Thr Thr Ala Lys Met Pro Ser Val Pro Leu Ser Ser Asp Pro Leu
            35                  40                  45

Pro Thr His Thr Thr Ala Phe Ser Pro Ala Ser Thr Phe Glu Arg Glu
    50                  55                  60

Asn Asp Phe Ser Glu Thr Thr Thr Ser Leu Ser Pro Asp Asn Thr Ser
65                  70                  75                  80

Thr Gln Val Ser Pro Asp Ser Leu Asp Asn Ala Ser Ala Phe Asn Thr
                85                  90                  95

Thr Gly Val Ser Ser Val Gln Thr Pro His Leu Pro Thr His Ala Asp
            100                 105                 110

Ser Gln Thr Pro Ser Ala Gly Thr Asp Thr Gln Thr Phe Ser Gly Ser
    115                 120                 125

```
Ala Ala Asn Ala Lys Leu Asn Pro Thr Pro Gly Ser Asn Ala Ile Ser
        130                 135                 140

Asp Val Pro Gly Glu Arg Ser Thr Ala Ser Thr Phe Pro Thr Asp Pro
145                 150                 155                 160

Val Ser Pro Leu Thr Thr Thr Leu Ser Leu Ala His His Ser Ser Ala
                165                 170                 175

Ala Leu Pro Ala Arg Thr Ser Asn Thr Thr Ile Thr Ala Asn Thr Ser
                180                 185                 190

Asp Ala Tyr Leu Asn Ala Ser Glu Thr Thr Thr Leu Ser Pro Ser Gly
                195                 200                 205

Ser Ala Val Ile Ser Thr Thr Thr Ile Ala Thr Thr Pro Ser Lys Pro
210                 215                 220

Thr Cys Asp Glu Lys Tyr Ala Asn Ile Thr Val Asp Tyr Leu Tyr Asn
225                 230                 235                 240

Lys Glu Thr Lys Leu Phe Thr Ala Lys Leu Asn Val Asn Glu Asn Val
                245                 250                 255

Glu Cys Gly Asn Asn Thr Cys Thr Asn Asn Glu Val His Asn Leu Thr
                260                 265                 270

Glu Cys Lys Asn Ala Ser Val Ser Ile Ser His Asn Ser Cys Thr Ala
                275                 280                 285

Pro Asp Lys Thr Leu Ile Leu Asp Val Pro Pro Gly Val Glu Lys Phe
                290                 295                 300

Gln Leu His Asp Cys Thr Gln Val Glu Lys Ala Asp Thr Thr Ile Cys
305                 310                 315                 320

Leu Lys Trp Lys Asn Ile Glu Thr Phe Thr Cys Asp Thr Gln Asn Ile
                325                 330                 335

Thr Tyr Arg Phe Gln Cys Gly Asn Met Ile Phe Asp Asn Lys Glu Ile
                340                 345                 350

Lys Leu Glu Asn Leu Glu Pro Glu His Glu Tyr Lys Cys Asp Ser Glu
                355                 360                 365

Ile Leu Tyr Asn Asn His Lys Phe Thr Asn Ala Ser Lys Ile Ile Lys
                370                 375                 380

Thr Asp Phe Gly Ser Pro Gly Glu Pro Gln Ile Ile Phe Cys Arg Ser
385                 390                 395                 400

Glu Ala Ala His Gln Gly Val Ile Thr Trp Asn Pro Pro Gln Arg Ser
                405                 410                 415

Phe His Asn Phe Thr Leu Cys Tyr Ile Lys Glu Thr Glu Lys Asp Cys
                420                 425                 430

Leu Asn Leu Asp Lys Asn Leu Ile Lys Tyr Asp Leu Gln Asn Leu Lys
                435                 440                 445

Pro Tyr Thr Lys Tyr Val Leu Ser Leu His Ala Tyr Ile Ile Ala Lys
                450                 455                 460

Val Gln Arg Asn Gly Ser Ala Ala Met Cys His Phe Thr Thr Lys Ser
465                 470                 475                 480

Ala Pro Pro Ser Gln Val Trp Asn Met Thr Val Ser Met Thr Ser Asp
                485                 490                 495

Asn Ser Met His Val Lys Cys Arg Pro Pro Arg Asp Arg Asn Gly Pro
                500                 505                 510

His Glu Arg Tyr His Leu Glu Val Glu Ala Gly Asn Thr Leu Val Arg
                515                 520                 525

Asn Glu Ser His Lys Asn Cys Asp Phe Arg Val Lys Asp Leu Gln Tyr
                530                 535                 540
```

```
Ser Thr Asp Tyr Thr Phe Lys Ala Tyr Phe His Asn Gly Asp Tyr Pro
545                 550                 555                 560

Gly Glu Pro Phe Ile Leu His His Ser Thr Ser Tyr Asn Ser Lys Ala
            565                 570                 575

Leu Ile Ala Phe Leu Ala Phe Leu Ile Ile Val Thr Ser Ile Ala Leu
            580                 585                 590

Leu Val Val Leu Tyr Lys Ile Tyr Asp Leu His Lys Lys Arg Ser Cys
        595                 600                 605

Asn Leu Asp Glu Gln Gln Leu Val Glu Arg Asp Asp Glu Lys Gln
        610                 615                 620

Leu Met Asn Val Glu Pro Ile His Ala Asp Ile Leu Leu Glu Thr Tyr
625                 630                 635                 640

Lys Arg Lys Ile Ala Asp Glu Gly Arg Leu Phe Leu Ala Glu Phe Gln
                645                 650                 655

Ser Ile Pro Arg Val Phe Ser Lys Phe Pro Ile Lys Glu Ala Arg Lys
            660                 665                 670

Pro Phe Asn Gln Asn Lys Asn Arg Tyr Val Asp Ile Leu Pro Tyr Asp
        675                 680                 685

Tyr Asn Arg Val Glu Leu Ser Glu Ile Asn Gly Asp Ala Gly Ser Asn
690                 695                 700

Tyr Ile Asn Ala Ser Tyr Ile Asp Gly Phe Lys Glu Pro Arg Lys Tyr
705                 710                 715                 720

Ile Ala Ala Gln Gly Pro Arg Asp Glu Thr Val Asp Asp Phe Trp Arg
                725                 730                 735

Met Ile Trp Glu Gln Lys Ala Thr Val Ile Val Met Val Thr Arg Cys
            740                 745                 750

Glu Glu Gly Asn Arg Asn Lys Cys Ala Glu Tyr Trp Pro Ser Met Glu
            755                 760                 765

Glu Gly Thr Arg Ala Phe Gly Asp Val Val Lys Ile Asn Gln His
        770                 775                 780

Lys Arg Cys Pro Asp Tyr Ile Ile Gln Lys Leu Asn Ile Val Asn Lys
785                 790                 795                 800

Lys Glu Lys Ala Thr Gly Arg Glu Val Thr His Ile Gln Phe Thr Ser
            805                 810                 815

Trp Pro Asp His Gly Val Pro Glu Asp Pro His Leu Leu Lys Leu
            820                 825                 830

Arg Arg Arg Val Asn Ala Phe Ser Asn Phe Phe Ser Gly Pro Ile Val
        835                 840                 845

Val His Cys Ser Ala Gly Val Gly Arg Thr Gly Thr Tyr Ile Gly Ile
850                 855                 860

Asp Ala Met Leu Glu Gly Leu Glu Ala Glu Asn Lys Val Asp Val Tyr
865                 870                 875                 880

Gly Tyr Val Val Lys Leu Arg Arg Gln Arg Cys Leu Met Val Gln Val
                885                 890                 895

Glu Ala Gln Tyr Ile Leu Ile His Gln Ala Leu Val Glu Tyr Asn Gln
            900                 905                 910

Phe Gly Glu Thr Glu Val Asn Leu Ser Glu Leu His Pro Tyr Leu His
            915                 920                 925

Asn Met Lys Lys Arg Asp Pro Pro Ser Glu Pro Ser Pro Leu Glu Ala
            930                 935                 940

Glu Phe Gln Arg Leu Pro Ser Tyr Arg Ser Trp Arg Thr Gln His Ile
945                 950                 955                 960

Gly Asn Gln Glu Glu Asn Lys Ser Lys Asn Arg Asn Ser Asn Val Ile
```

-continued

```
                965                 970                 975
Pro Tyr Asp Tyr Asn Arg Val Pro Leu Lys His Glu Leu Glu Met Ser
            980                 985                 990
Lys Glu Ser Glu His Asp Ser Asp Glu Ser Ser Asp Asp Asp Ser Asp
        995                 1000                1005
Ser Glu Glu Pro Ser Lys Tyr Ile Asn Ala Ser Phe Ile Met Ser
    1010                1015                1020
Tyr Trp Lys Pro Glu Val Met Ile Ala Ala Gln Gly Pro Leu Lys
    1025                1030                1035
Glu Thr Ile Gly Asp Phe Trp Gln Met Ile Phe Gln Arg Lys Val
    1040                1045                1050
Lys Val Ile Val Met Leu Thr Glu Leu Lys His Gly Asp Gln Glu
    1055                1060                1065
Ile Cys Ala Gln Tyr Trp Gly Glu Gly Lys Gln Thr Tyr Gly Asp
    1070                1075                1080
Ile Glu Val Asp Leu Lys Asp Thr Asp Lys Ser Ser Thr Tyr Thr
    1085                1090                1095
Leu Arg Val Phe Glu Leu Arg His Ser Lys Arg Lys Asp Ser Arg
    1100                1105                1110
Thr Val Tyr Gln Tyr Gln Tyr Thr Asn Trp Ser Val Glu Gln Leu
    1115                1120                1125
Pro Ala Glu Pro Lys Glu Leu Ile Ser Met Ile Gln Val Val Lys
    1130                1135                1140
Gln Lys Leu Pro Gln Lys Asn Ser Ser Glu Gly Asn Lys His His
    1145                1150                1155
Lys Ser Thr Pro Leu Leu Ile His Cys Arg Asp Gly Ser Gln Gln
    1160                1165                1170
Thr Gly Ile Phe Cys Ala Leu Leu Asn Leu Leu Glu Ser Ala Glu
    1175                1180                1185
Thr Glu Glu Val Val Asp Ile Phe Gln Val Val Lys Ala Leu Arg
    1190                1195                1200
Lys Ala Arg Pro Gly Met Val Ser Thr Phe Glu Gln Tyr Gln Phe
    1205                1210                1215
Leu Tyr Asp Val Ile Ala Ser Thr Tyr Pro Ala Gln Asn Gly Gln
    1220                1225                1230
Val Lys Lys Asn Asn His Gln Glu Asp Lys Ile Glu Phe Asp Asn
    1235                1240                1245
Glu Val Asp Lys Val Lys Gln Asp Ala Asn Cys Val Asn Pro Leu
    1250                1255                1260
Gly Ala Pro Glu Lys Leu Pro Glu Ala Lys Glu Gln Ala Glu Gly
    1265                1270                1275
Ser Glu Pro Thr Ser Gly Thr Glu Gly Pro Glu His Ser Val Asn
    1280                1285                1290
Gly Pro Ala Ser Pro Ala Leu Asn Gln Gly Ser
    1295                1300
```